(12) United States Patent
Ghosh

(10) Patent No.: US 10,358,467 B2
(45) Date of Patent: Jul. 23, 2019

(54) THERAPEUTIC TARGETS FOR CANCER PROGRESSION

(71) Applicant: The Regents of the University of California, Oakland, CA (US)

(72) Inventor: Pradipta Ghosh, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 193 days.

(21) Appl. No.: 15/178,480

(22) Filed: Jun. 9, 2016

(65) Prior Publication Data

US 2016/0362464 A1    Dec. 15, 2016

Related U.S. Application Data

(60) Provisional application No. 62/172,996, filed on Jun. 9, 2015.

(51) Int. Cl.
| | | |
|---|---|---|
| *C07K 14/47* | (2006.01) | |
| *C07K 16/18* | (2006.01) | |
| *C12N 15/113* | (2010.01) | |
| *C12Q 1/6886* | (2018.01) | |

(52) U.S. Cl.
CPC .......... *C07K 14/4703* (2013.01); *C07K 16/18* (2013.01); *C12N 15/113* (2013.01); *C12Q 1/6886* (2013.01); *C07K 2317/76* (2013.01); *C12Q 2600/106* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

PUBLICATIONS

Oshita et al, Genes to Cells, 2003, vol. 8, pp. 1005-1017 (Year: 2003).*

* cited by examiner

*Primary Examiner* — Karen A. Canella
(74) *Attorney, Agent, or Firm* — Eversheds Sutherland (US) LLP

(57) ABSTRACT

The invention provides DAPLE as a novel regulator of G protein activity and its diagnostic and therapeutic use in cancer.

15 Claims, 39 Drawing Sheets
(34 of 39 Drawing Sheet(s) Filed in Color)
Specification includes a Sequence Listing.

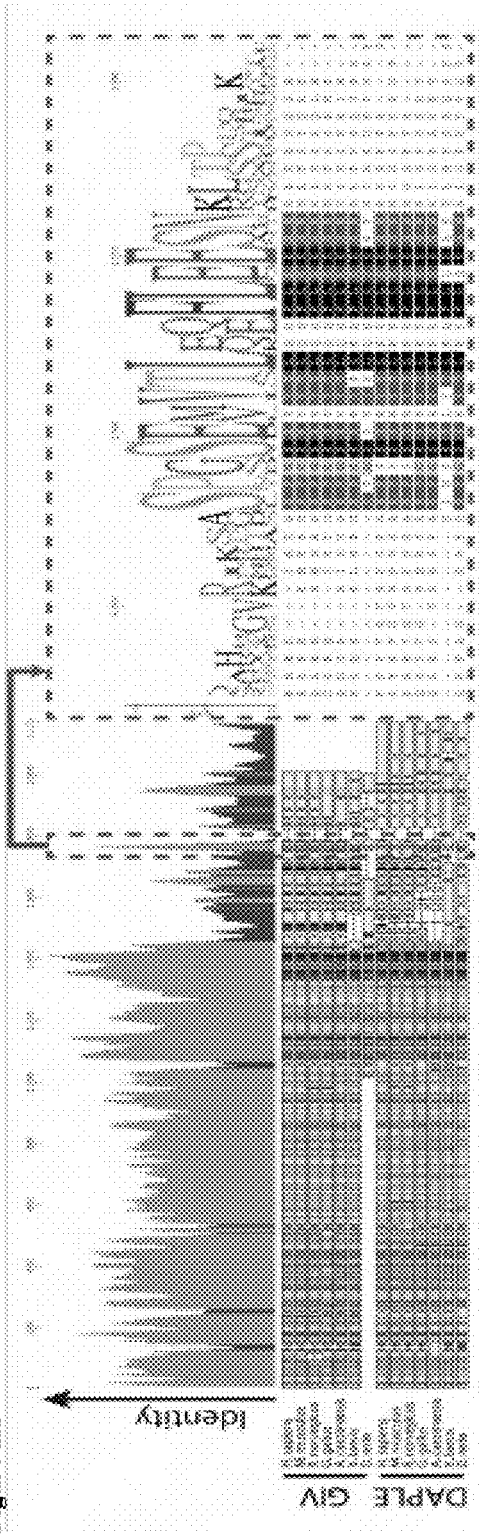
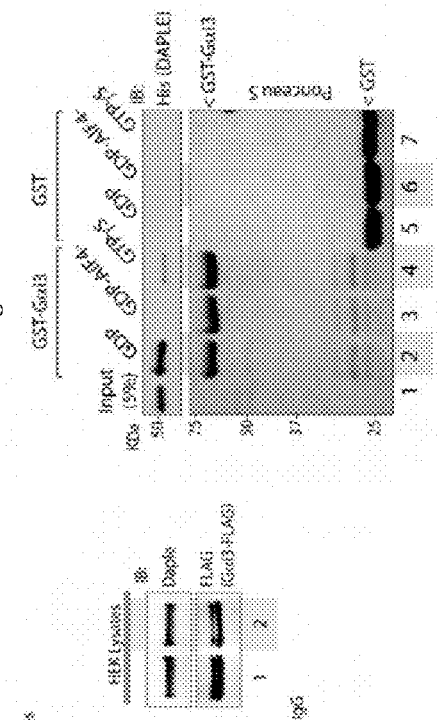
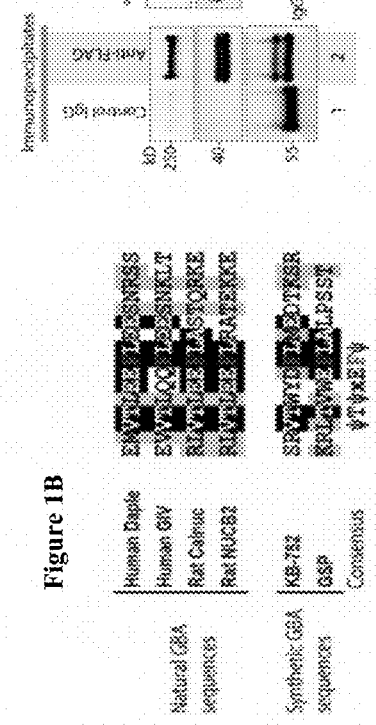
Figure 1A
Figure 1B
Figure 1C
Figure 1D

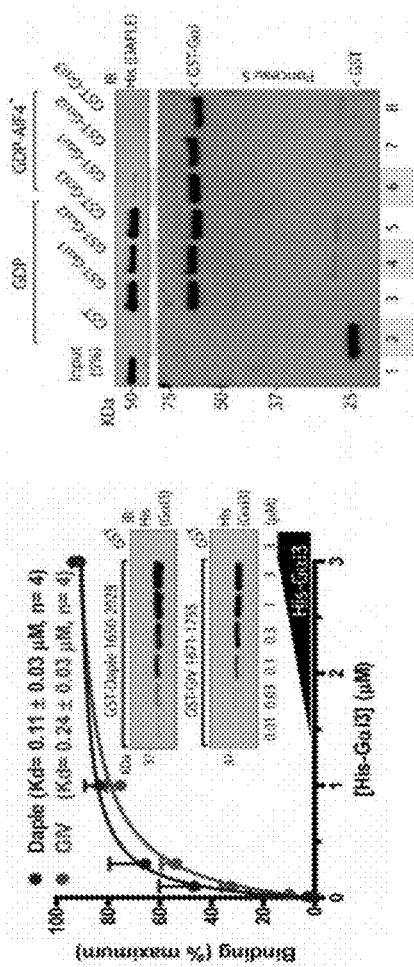
Figure 1E
Figure 1F
Figure 1G
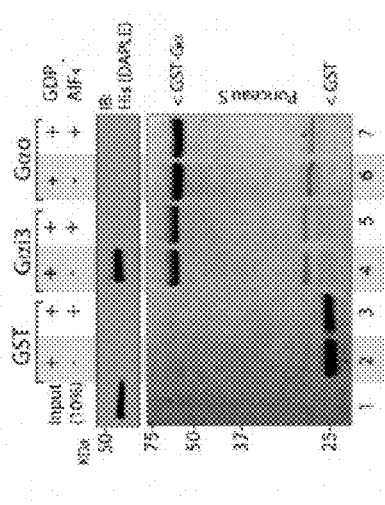
Figure 1H
Figure 1I

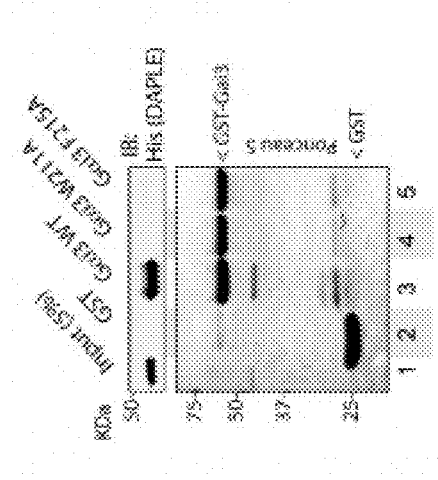
Figure 2B
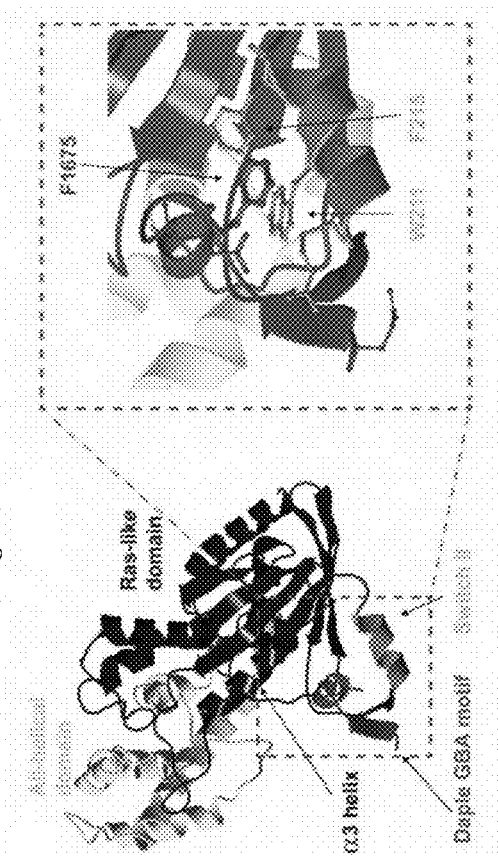
Figure 2A
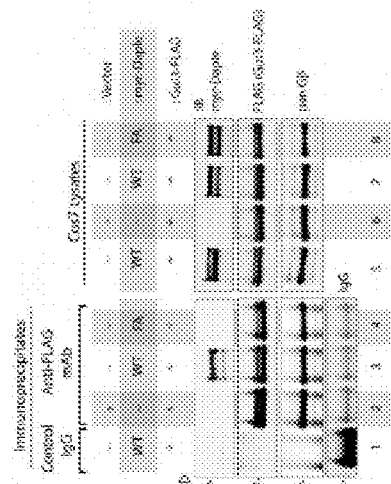
Figure 2E
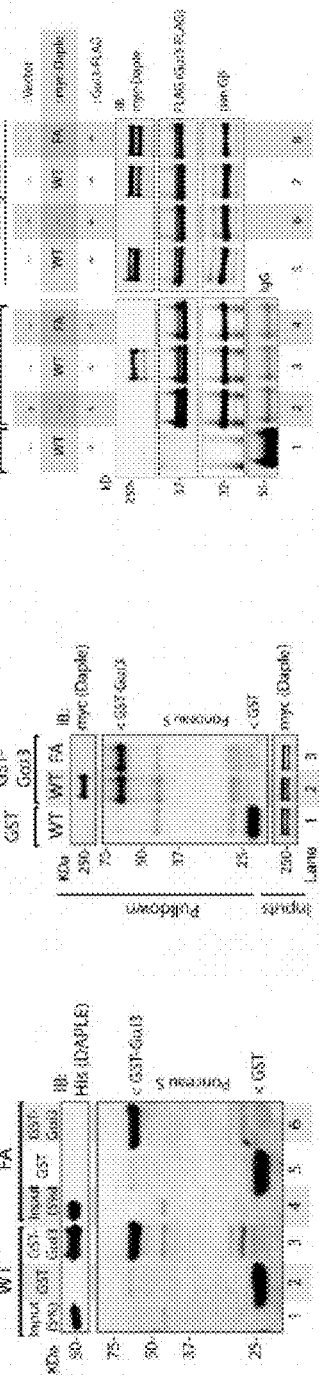
Figure 2D
Figure 2C

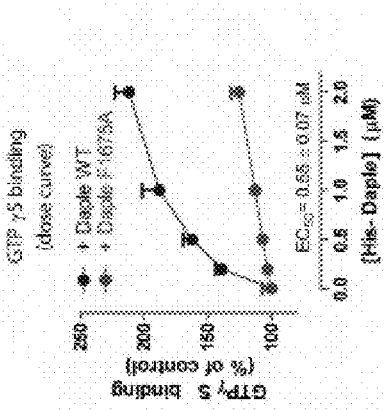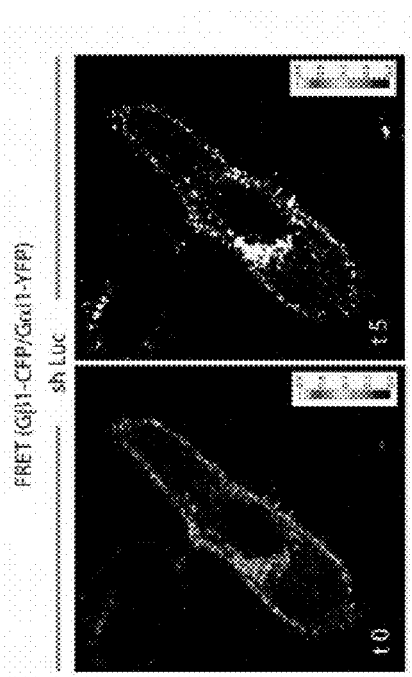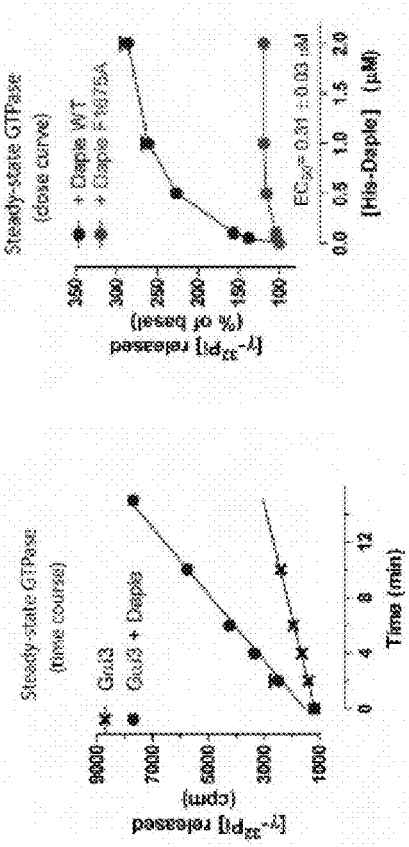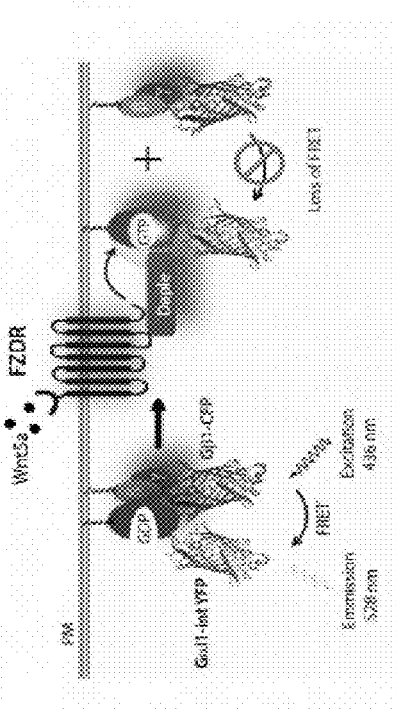
Figure 2F
Figure 2G
Figure 2H
Figure 2I
Figure 2J

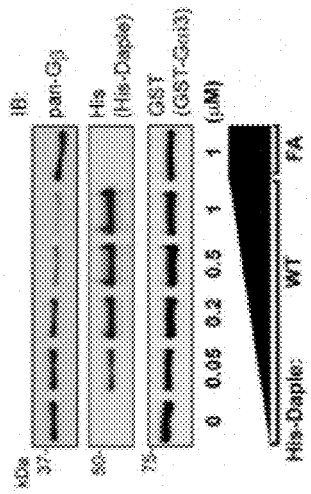
Figure 3A
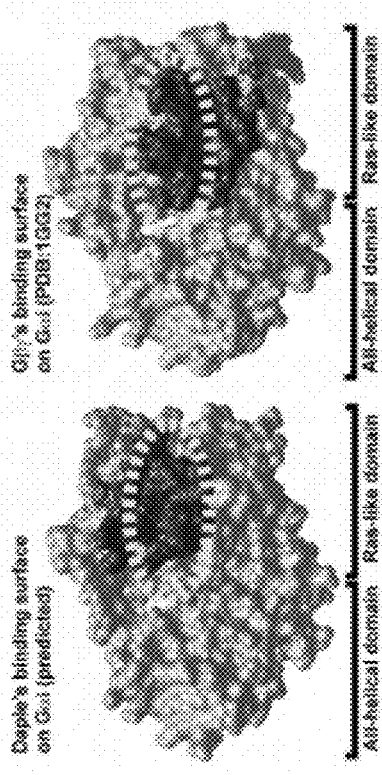
Figure 3B
Figure 3C
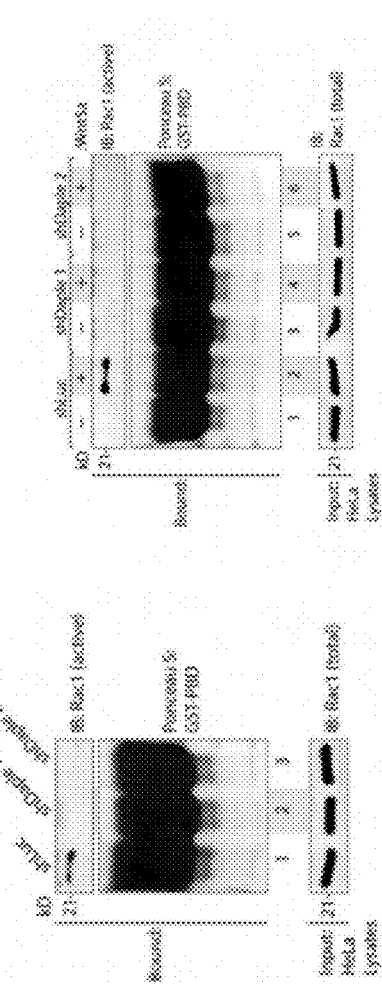
Figure 3D
Figure 3E
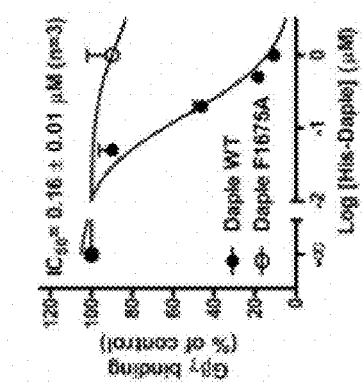

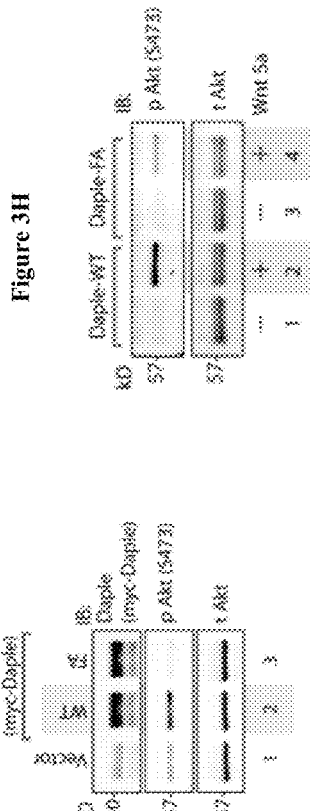
Figure 3H
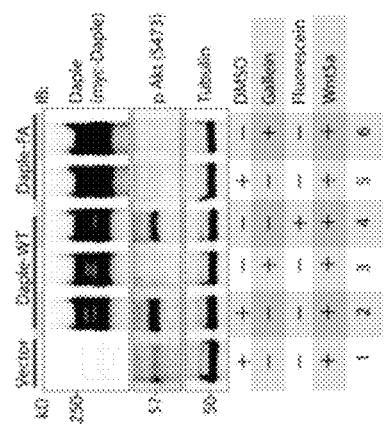
Figure 3G
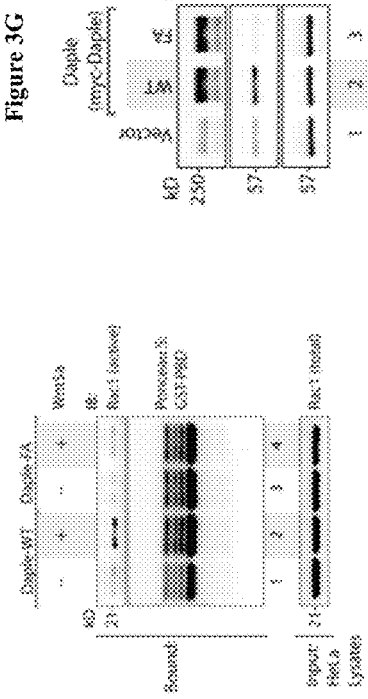
Figure 3F
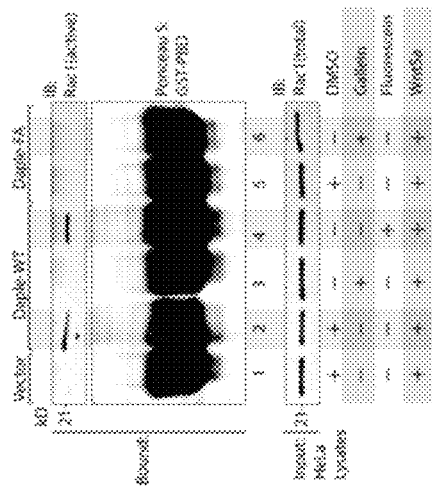
Figure 3J
Figure 3I

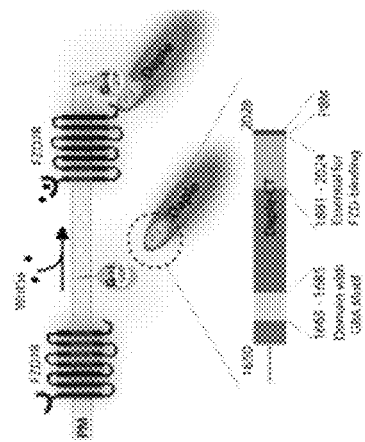
Figure 4I
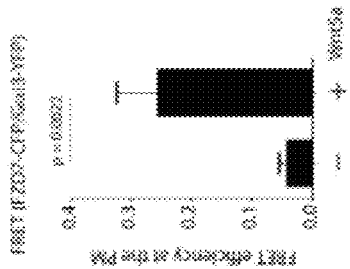
Figure 4L
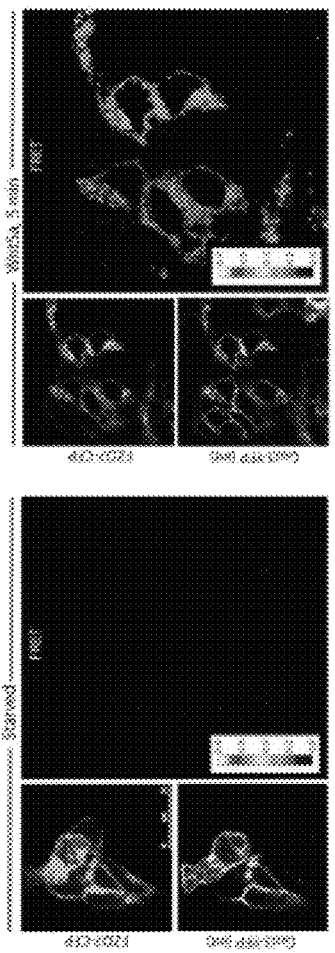
Figure 4H
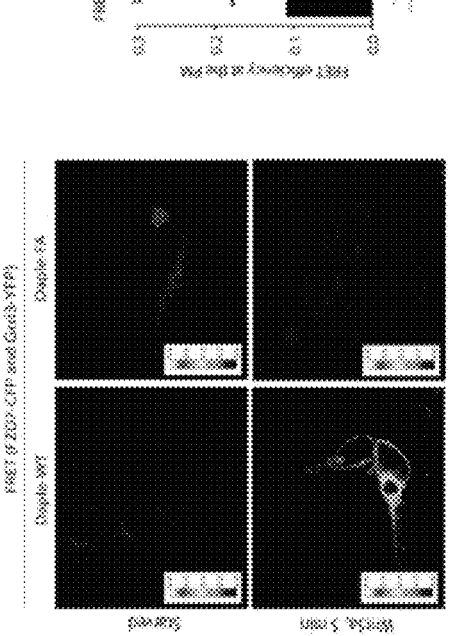
Figure 4K
Figure 4J

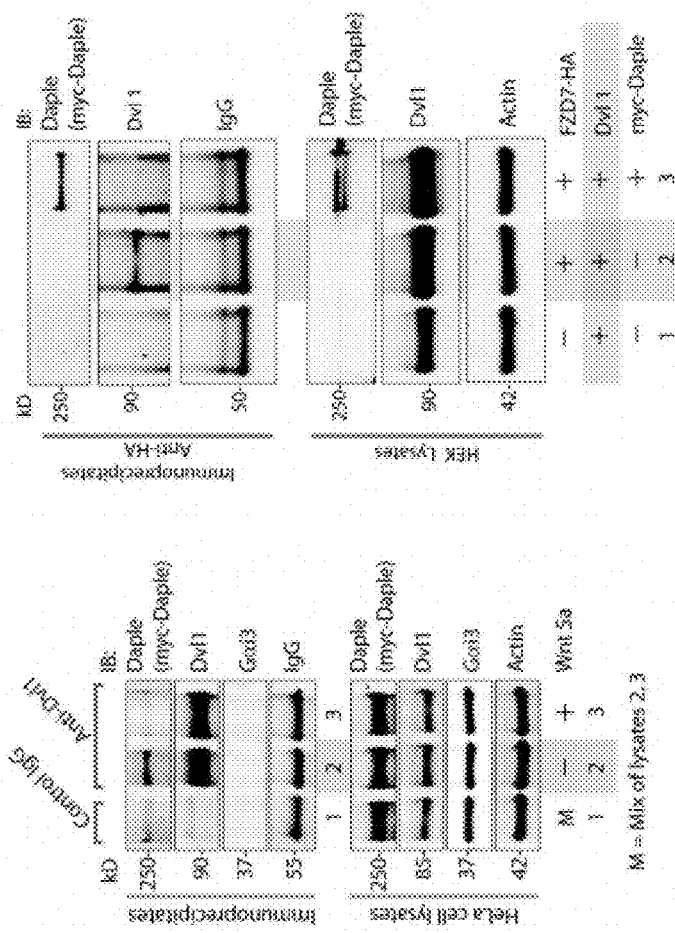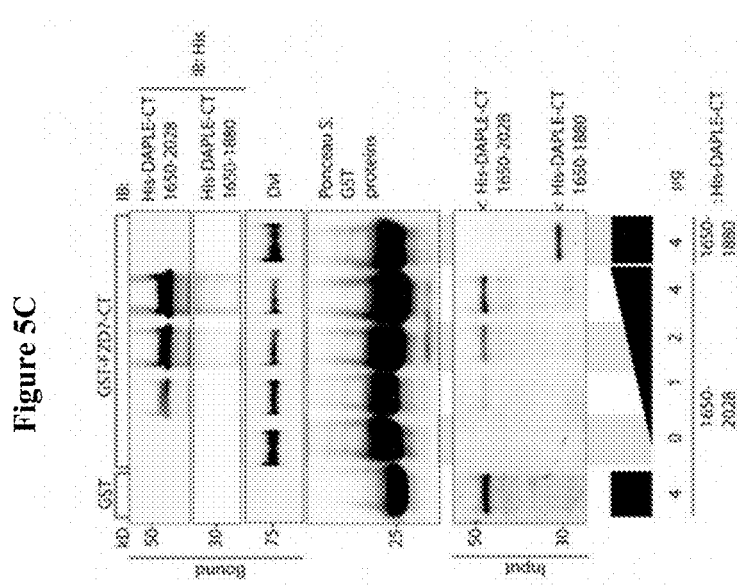
Figure 5C
Figure 5B
Figure 5A

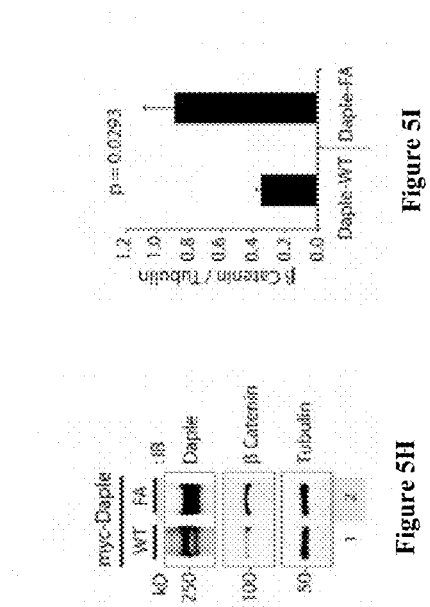
Figure 5E
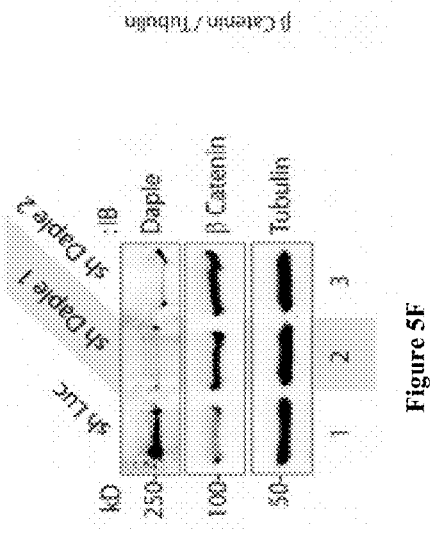
Figure 5I
Figure 5H
Figure 5G
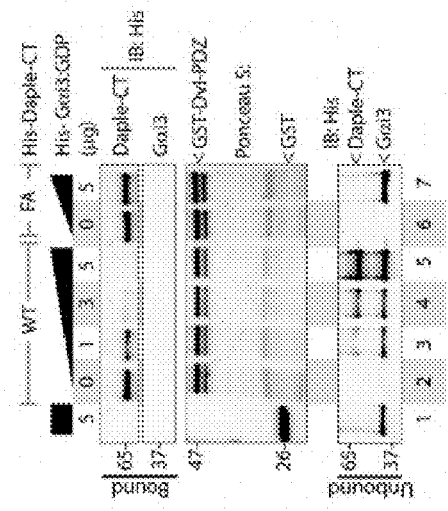
Figure 5D
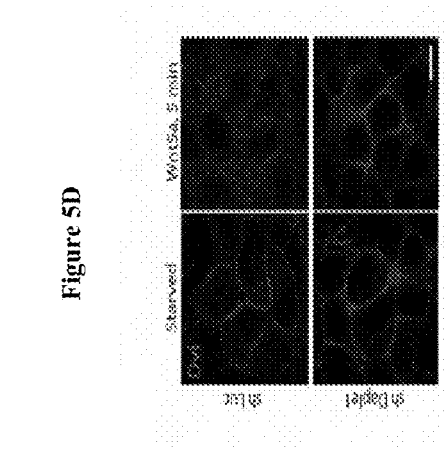
Figure 5F

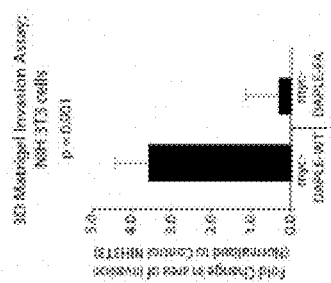
Figure 6C
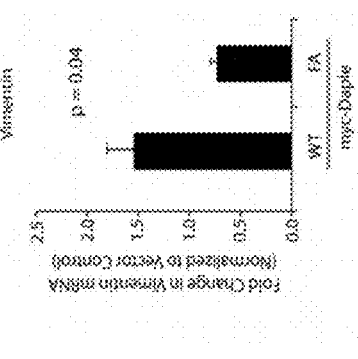
Figure 6E
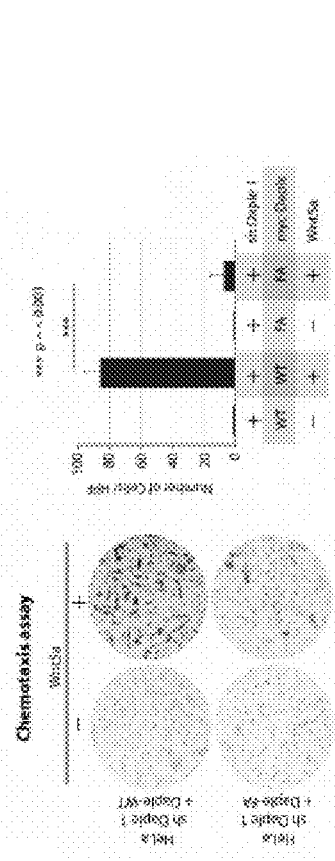
Figure 6A
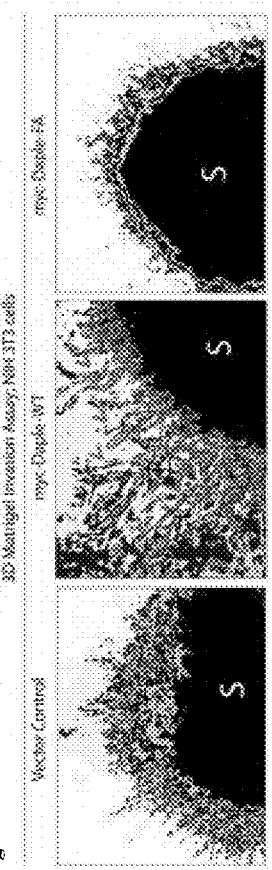
Figure 6B
Figure 6D Figure 7A
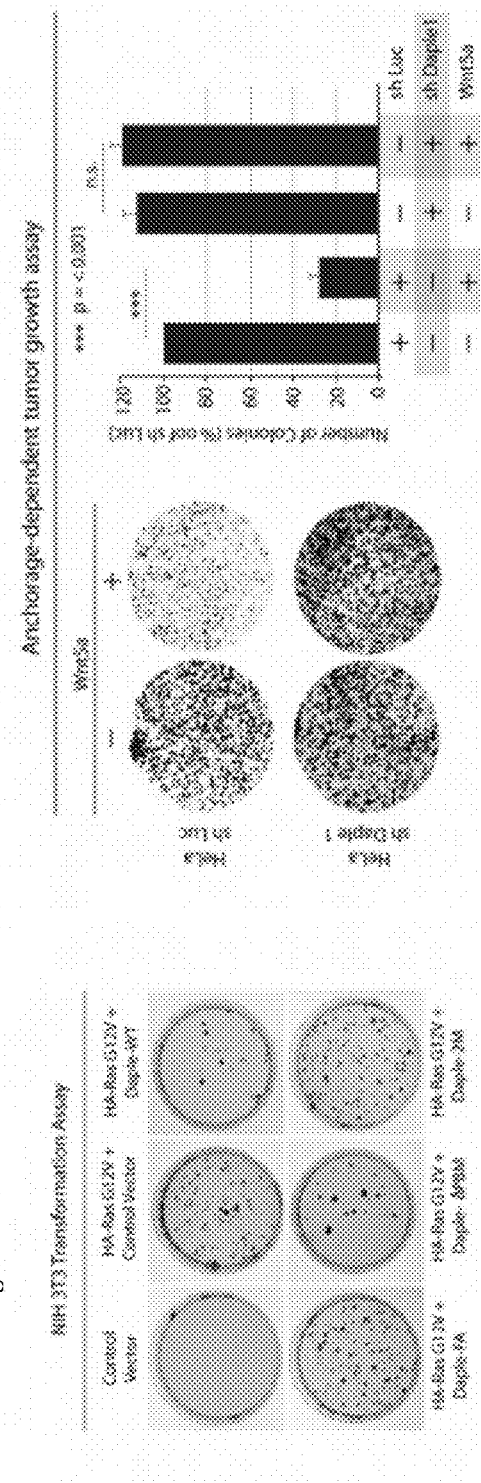
Figure 7B
Figure 7C
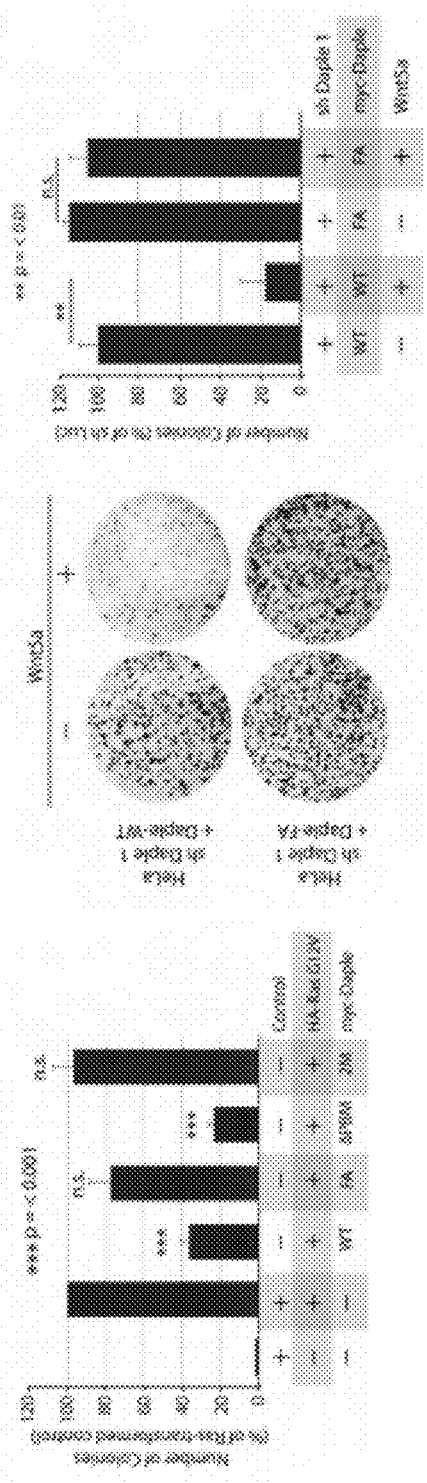

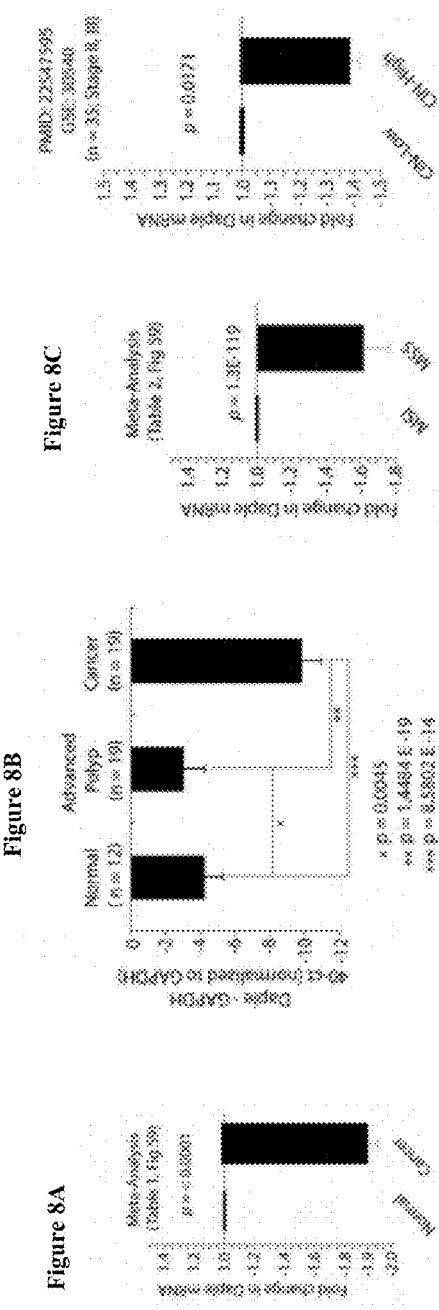

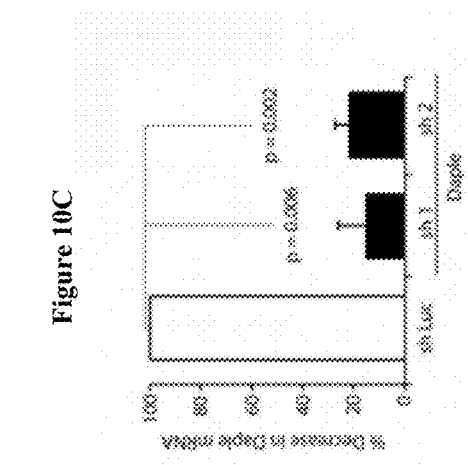
Figure 10C
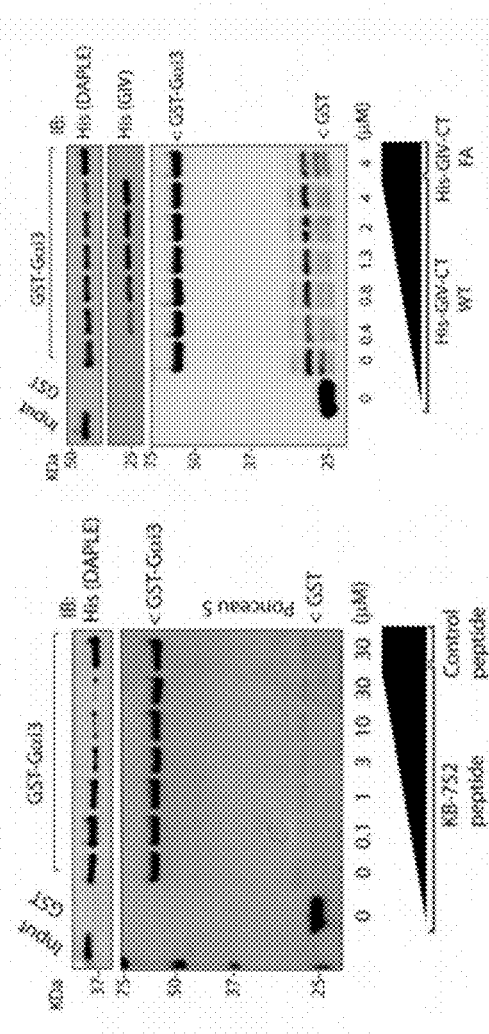
Figure 10B
Figure 10A
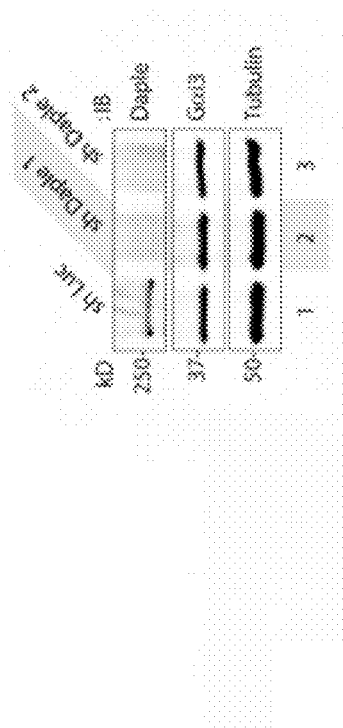
Figure 10D

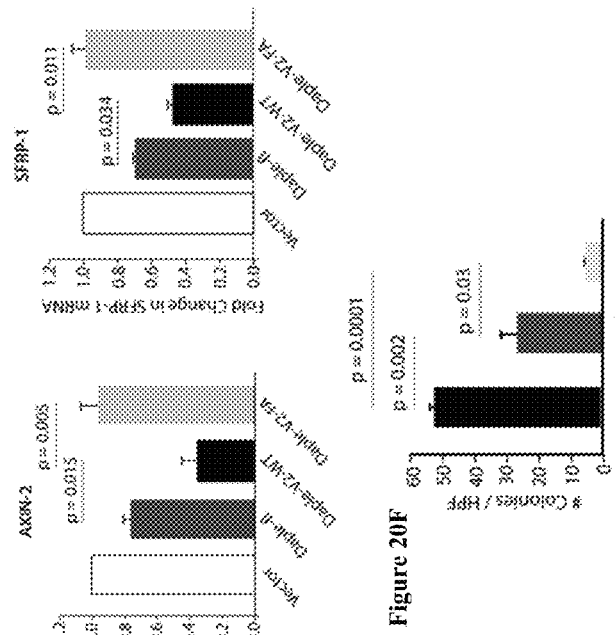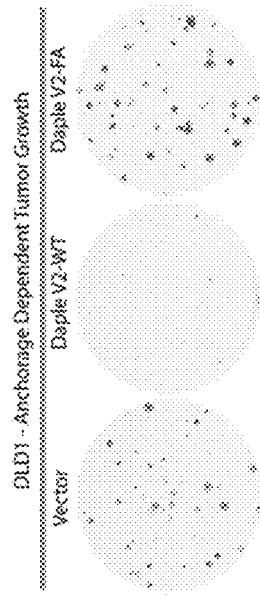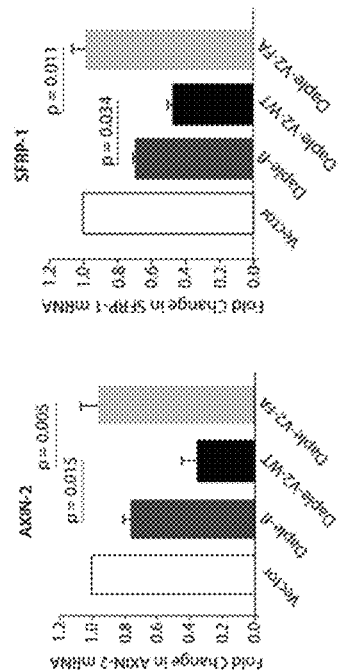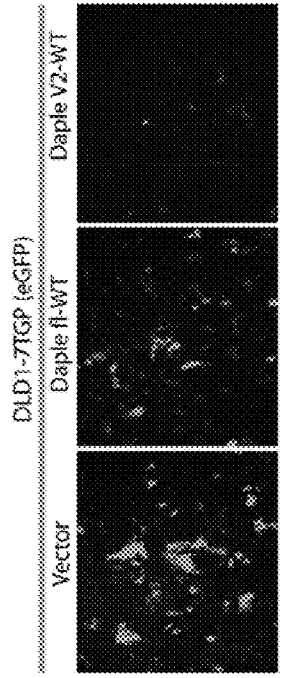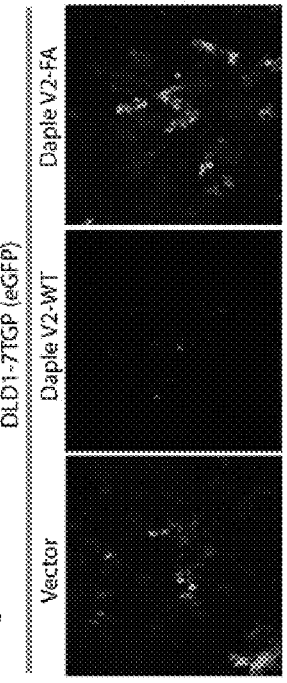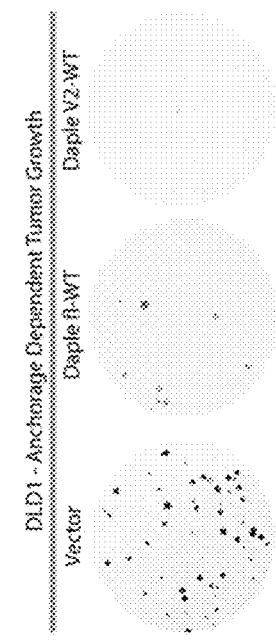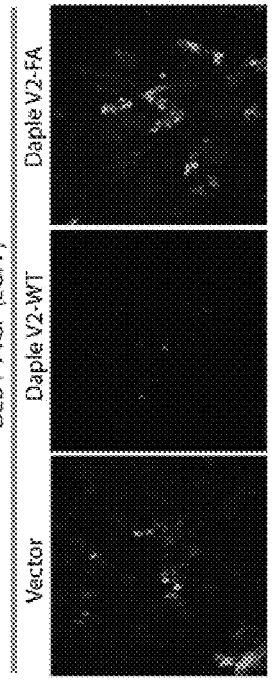

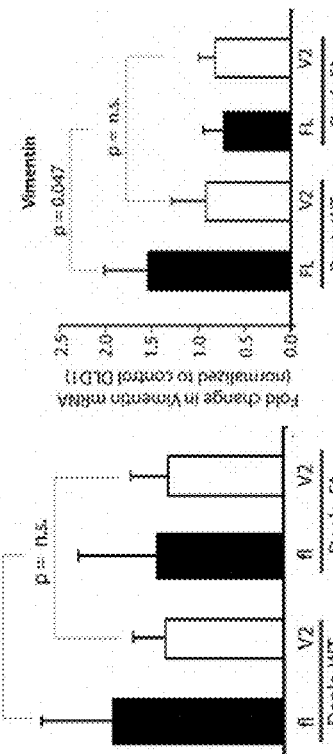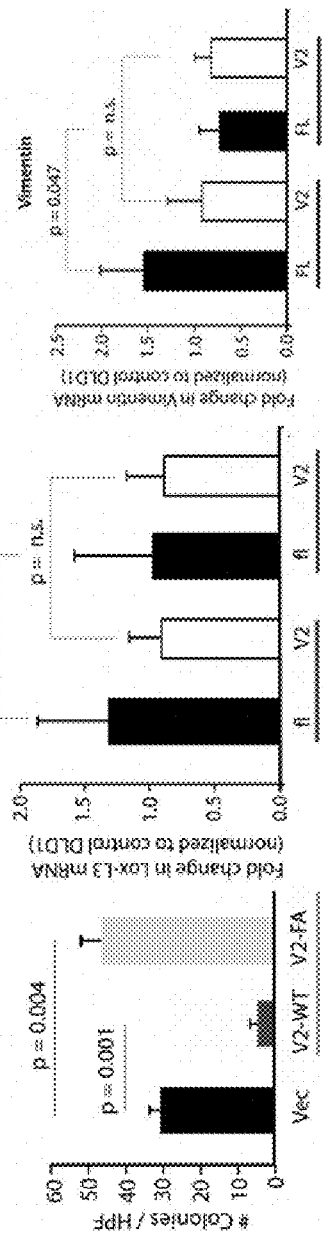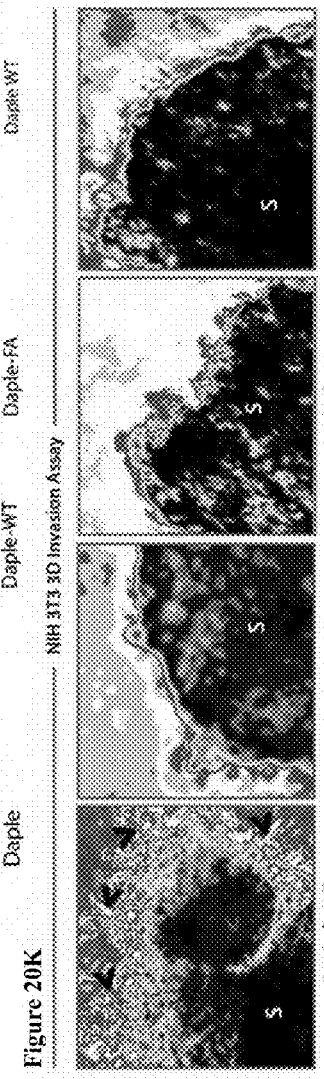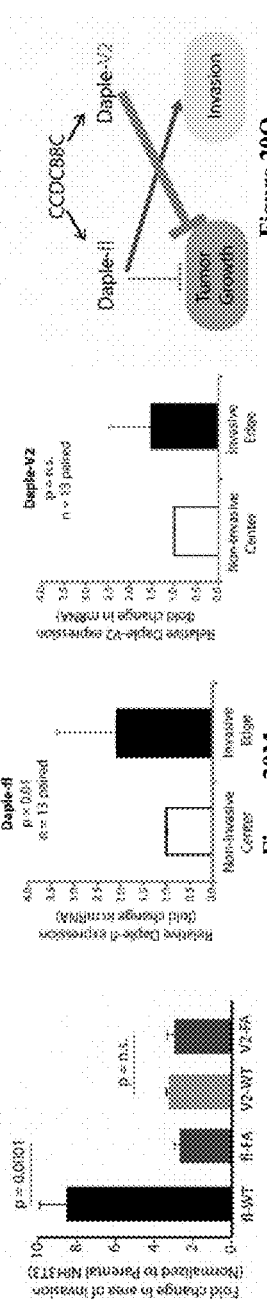
Figure 20H Figure 20I Figure 20J
Figure 20K
Figure 20L Figure 20M Figure 20N Figure 20O

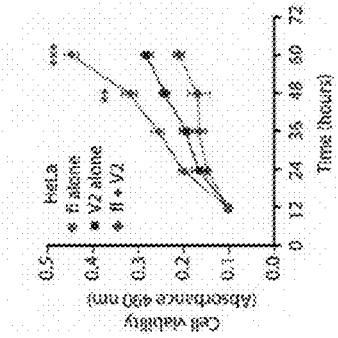
Figure 23A
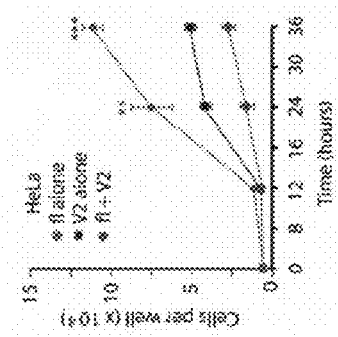
Figure 23B
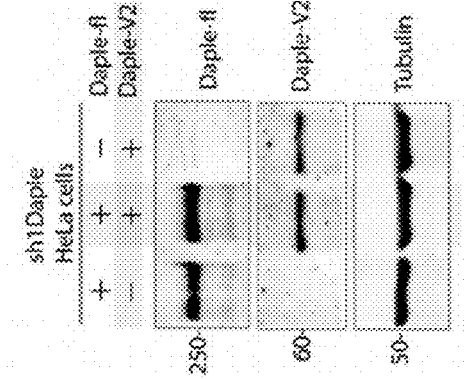
Figure 23D
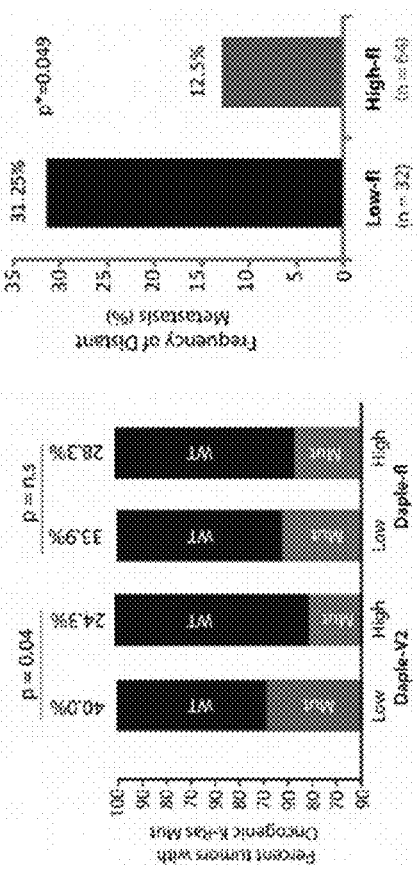
Figure 23C
Figure 23E
Figure 23F

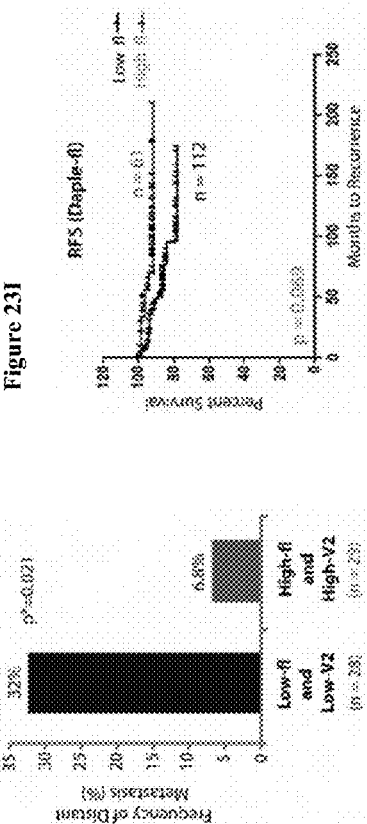
Figure 23G
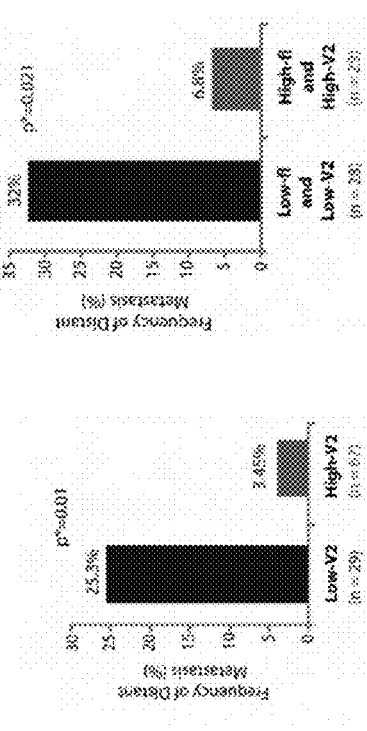
Figure 23H
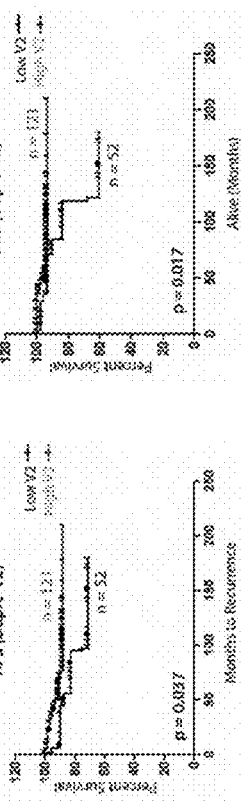
Figure 23J
Figure 23I
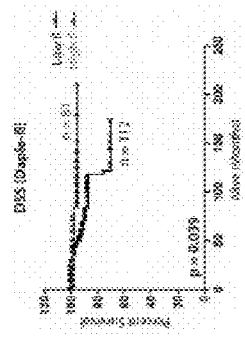
Figure 23K
Figure 23L
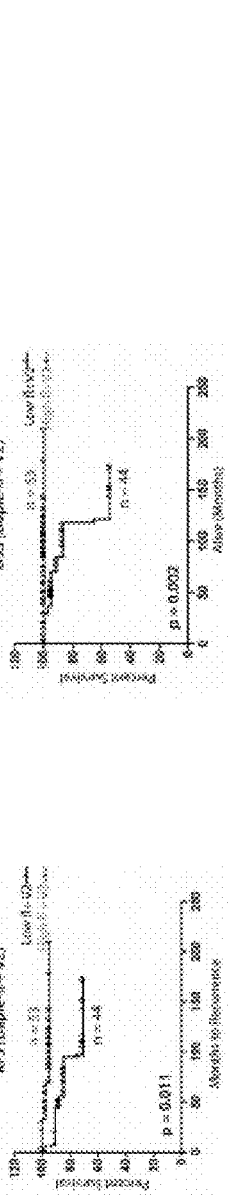
Figure 23M
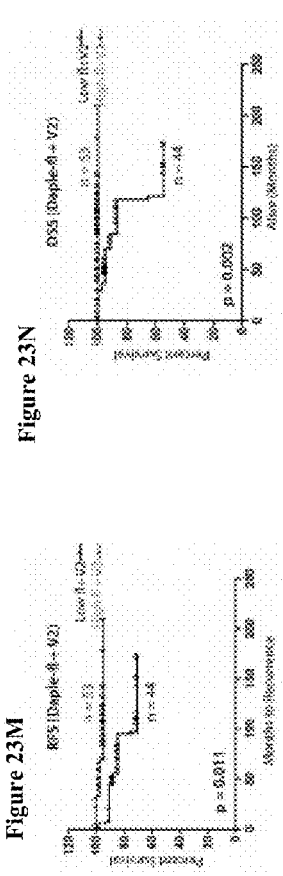
Figure 23N

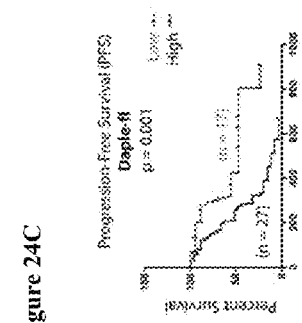
Figure 24A
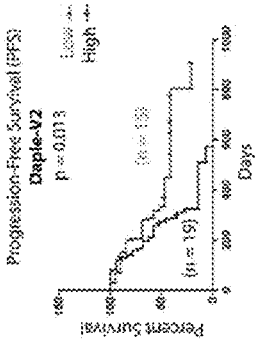
Figure 24B
Figure 24C
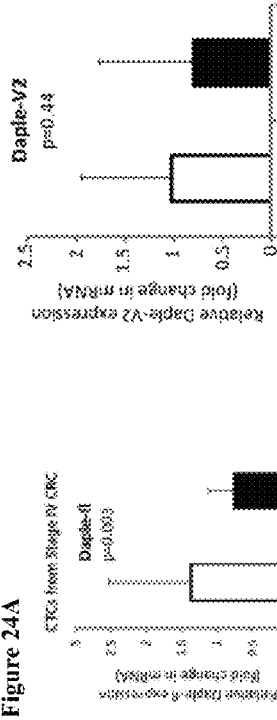
Figure 24D
Figure 24E
Figure 24F
Figure 24G
Figure 24H

SEQUENCE LISTING

<160> NUMBER OF SEQ ID NOS: 49

<210> SEQ ID NO 1
<211> LENGTH: 7573
<212> TYPE: DNA
<213> ORGANISM: Homo sapiens

<400> SEQUENCE: 1

```
gcggaacgtg ggctcgcgcg ccccgccttt gtctcccggg cgcgagccgc cgcagccccg      60
cgcccgctgc tcgctgcgga gccgttttgt gccgcggcgc gggggaacgg ggacgcgggg     120
cggggggcgc ggagccggcg ggcgcagcct cagcatggac gtgacagtct cggagctcct     180
ggagctcttc ctgcagagcc cgctggtgac ctgggtgaaa acttttggcc cgtttggaag     240
cggcagccag gacaacctga ctatgtacat ggatttagtg gacggcatct ttttgaacca     300
```

```
aattatgctg caaatagatc ccaggcccac aaatcaacgc atcaataagc acgtcaacaa    360
tgatgtgaac cttcgcattc agaatttgac catcttggtg agaaacatta agacctacta    420
ccaggaagtt ctccagcagc tgattgtaat gaatttgccc aatgttttga tgattggcag    480
agacccactg tctgggaaga gcatggagga aatcaagaag gtgctgctgc tggtgctggg    540
ctgtgctgtc cagtgtgaga ggaaagagga gttcattgaa agaatcaaac agctggacat    600
tgagacccag gctggcatcg tggcccatat ccaggaggtg actcacaacc aagagaacgt    660
gtttgacctg cagtggctgg agctgcccga cgtggctccg gaggagctgg aggccctgtc    720
gaggagcatg gtgctccacc tgcggaggct catcgaccag cgggacgagt gcaccgagct    780
gatcgtggac ctcactcagg aacgggacta cctgcaggca cagcatccac ccagccccat    840
caagtcctcc agcgccgact ccactcccag ccccaccagc agcctctcta gcgaagacaa    900
gcagcacctg gccgtagagc tggccgacac caaggccagg ctgcggcgcg tcaggcagga    960
gctggaggat aagacagagc agcttgtgga caccagacat gaggtggacc agctggtgct   1020
ggaactgcag aaagttaagc aggagaacat ccagctagcg gcagacgccc ggtctgctcg   1080
tgcctatcga gacgagctgg attccctgcg ggagaaggcg aaccgcgtgg agaggctgga   1140
gctggagctg acccgctgca aggagaagct gcacgacgtg gacttctaca aggcccgcat   1200
ggaggagctg agagaagata atatcatttt aattgaaacc aaggccatgc tggaggaaca   1260
gctgactgct gtccgggccc ggggcgataa agtccatgag ctggaaaagg agaacctgca   1320
gctgaaatcc aagcttcacg acctggaatt ggaccgggac acagataaga acgaattga   1380
ggagctgctg gaagaaaaca tggtccttga gattgcacag aagcagagca tgaacgaatc   1440
tgcccacctt ggctgggagc tggagcagct gtccaagaac gcagacttgt cagacgcctc   1500
caggaagtcg tttgtgtttg agctgaacga atgtgcgtcc agccgcatcc tgaagctgga   1560
gaaggagaat cagagcctcc agagcaccat ccaggggctg cgggacgcgt ccctggtgtt   1620
ggaggagagc ggcctcaagt gcggggagct ggagaaggaa aaccaccagc tcagcaagaa   1680
gattgaaaag ttacaaaccc agctggagag agaaaagcag agcaaccaag atctggagac   1740
cctcagtgag gagctgatca gagagaagga gcagctgcag agtgacatgg agaccctgaa   1800
ggctgacaaa gccaggcaga tcaaggacct tgagcaggaa aaggaccacc tcaaccgagc   1860
catgtggtcg ctgcgggaga ggtcgcaggt cagcagtgag gcccgcatga agacgtggaa   1920
gaaggagaac aaagccctcc accagacggt gacggaggcc aatggcaagc tcagccagtt   1980
ggagtttgag aagcggcagc tgcacaggga cttggagcag gccaaggaga gggggagcg   2040
ggcagagaag ctggagaggg agctacagcg actccaggag gagaacggga ggctggccag   2100
gaaggtgacc tccctggaga cagccaccga gaaagtcgag gccctggagc atgagagcca   2160
gggcctgcag ctggagaacc ggactctgag gaagtctctg gacaccttgc agaacgtgtc   2220
cctgcagctt gagggcctgg agcgtgacaa caagcagctg acgcagagaa cctggagct   2280
gcgcaggctg gtgagacca tgcgcttcac cagcaccaag ctggcacaga tggagaggga   2340
gaaccagcag ctggagcgtg agaaggagga gctgaggaag aacgtggatc tgctcaaggc   2400
gctgggcaag aagtcagagc gcctggagct cagctaccag agcgtgagcg ctgagaacct   2460
ccggctgcag cagagcctgg agagcagcag ccacaagacg cagaccttgg agagtgagct   2520
gggcgagctg gaggctgagc gccaggcgct gcggcgggac ctggaggccc tccggctggc   2580
caatgcacag ttggaggggg ccgagaagga caggaaggcc ctggagcagg aggtggccca   2640
gctcgagaag gataagaagc tgctggagaa ggaggccaag cggctgtggc agcaggtgga   2700
```

```
gctcaaggat gcagtcttgg acgatagcac tgccaaactg tccgccgttg agaaggagag    2760
ccgcgcgctg gacaaggagc tggcccgctg cagggacgca gccggcaagc tgaaggagct    2820
ggagaaggac aaccgggacc tcaccaagca agtcaccgtg catgcaagga cactgacaac    2880
tctgagggag gacctggtgc tcgagaagct gaagagccag cagctcagca gtgagctgga    2940
caagctgagc caggaactgg agaaggtcgg cctcaacagg gagctgctgt tgcaggagga    3000
cgacagcggc agtgacacaa aatacaagat tttggagggc agaaatgaat cagcattaaa    3060
aacaacacta gccatgaaag aagaaaagat tgtgctctta gaagcacaga tggaagagaa    3120
agcgagccta aatcgccagt tagagagtga gctgcagatg ctaaagaagg agtgtgagac    3180
cctcaggcag aaccagggag aggggcagca cttgcagaac tctttcaagc accctgcggg    3240
gaagacagcc gccagtcacc aggggaagga ggcctggggg cccggccata aggaagccac    3300
catggagctt ctccgagtga aggaccgggc catcgagctg gagcggaata atgcagctct    3360
gcaggctgag aagcagctgc taaaggaaca gctgcagcac ctggagaccc agaacgtgac    3420
cttcagcagc cagatcttga cactgcagaa acagagcgcc ttcctgcagg agcacaacac    3480
cacactgcag acccagaccg ccaagctgca ggtggagaac tccacgctga gttcccagag    3540
cgcagcgctc accgcgcagt acacgctgct gcagaaccac cacacggcca aggagacgga    3600
gaacgaaagc ctgcagaggc agcaggagca acttacagcg gcctacgagg ccctgctgca    3660
ggaccacgag cacctgggca cgctgcacga gcggcaatcg gccgagtacg aggccctcat    3720
ccgccagcac agctgcctaa agacactgca tcggaatctg gagctggagc acaaggagct    3780
cggggagagg cacggtgaca tgctgaagcg caaggcggag ctggaggagc gggagaaggt    3840
cttgaccact gagcgagagg cgctgcagca ggagcagagg acaaacgccc tcgccatggg    3900
cgagaaccag aggctgcggg gcgagctgga cagggtcaat ttcctgcacc accagctgaa    3960
gggggagtac gaggagctgc acgcccacac caaggagctg aaaacctcac tgaacaacgc    4020
gcagctggag ctcaaccgct ggcaggcccg cttcgacgag ctgaaggagc agcaccagac    4080
catggacatc tcgctgacca agctggacaa ccactgtgag ctgctctccc gtctcaaggg    4140
gaacttggag gaagaaaatc atcacctcct gagccagatc cagctgttga gccagcagaa    4200
ccagatgctt ctggagcaga acatggagaa caaggagcag taccatgagg agcagaagca    4260
gtacatagac aaattaaatg ccttacgaag acataaggaa aagctggaag aaaaaatcat    4320
ggatcaatac aagttctatg atcctcctcc aaagaagaag aaccactgga ttggagccaa    4380
agccttagtc aaactcatca accaaagaa agagggttcg agggaacgct aaaatccac     4440 cgtggacagc cctccctggc agctggagtc ctcagacccc gcctcgccgg cggcctctca    4500
gccgctcaga tcacaggccg agaaccccga caccccgca ctgggctcca actgtgcaga     4560
agagcgcgac gcccacaacg ggtctgtggg gaaaggccct ggggatctaa aaccaaagcg    4620
aggctcccca cacagaggca gccttgaccg cacagatgcc tccaccgatc tggccatgag    4680
gtcctggccc tcggagctgg gctcccggac ttgctcaact tcagccacca ctacagcccc    4740
ttccaactcc accccatcg cccggcaccc aggccgcacc aaaggctata actcagatga     4800
caacctctgt gagccatccc tggagtttga ggtcccaac cacaggcagt acgtgtcgcg     4860
gccaagtagc ttagagagca gtagaaacac atccagcaac agctcacctc ttaacctaaa    4920
aggctcctcc gagcagctcc atggccggtc tgagagcttc agcagcgaag acctgatccc    4980
cagcagggac ctggccactt tgccccggga agccagcaca ccgggacgca acgccctcgg    5040
```

```
ccgccacgag tacccottgc ctcggaacgg gcctctccca caggagggtg cccagaagag   5100
gggcacagcc cctccctacg tcggagtgcg gccctgctcg gcctccccca gcagtgagat   5160
ggtcaccttg gaggagttcc tggaggagag caaccgcagc tcccccaccc atgacactcc   5220
cagttgccgg gatgacctgc tgagtgacta cttccgaaag gccagcgatc ccccagccat   5280
cggaggccaa ccaggaccac ctgccaagaa agaaggggcc aagatgccca ccaactttgt   5340
ggcccccacc gtcaaaatgg ccgcccccac ctcggagggg aggccgctga agcccgggca   5400
gtacgtaaag ccaaacttca gactgactga ggccgaggcc ccacccagcg tggccccgag   5460
acaggcccag cctccccaga gcctgtctct gggcagaccc cggcaggctc cggtgccccc   5520
agcttcccat gcacctgcca gccgcagtgc ctccttgagc cgggccttca gcctggcctc   5580
agctgacctt ctccgggcca gcgggccaga ggcctgcaaa caggagtccc ctcagaagct   5640
gggggctcct gaggccttag ggggcagaga gacaggcagc cacaccctgc aaagcccgc   5700 accccccagc tcccatagcc tggcccggga gcggacccca cttgtgggaa aggctggcag   5760
ctcctgtcag ggcccaggtc cccgcagccg gccgctggac acgaggcgct tctccctggc   5820
tcccccaaag gaggagaggc tggcccccct gcatcagtct gccacagccc ccgccattgc   5880
cactgcaggt gctggtgctg ctgctgctgg cagtggcagc aactcccagc tcctgcactt   5940
ctcacctgct gcagccccgg ctgccaggac caagcccaag gcgcccccac gctcagggga   6000
ggtggccacc atcaccctg tccgggcagg gctcagcctc tcagagggag acggggtccc   6060
ggggcagggc tgcagtgagg ggcttccggc caagagccca ggtcggtctc ccgatttggc   6120
tccccacctc ggccgggccc tggaggactg cagtcgaggg agcgtctcaa agagcagtcc   6180
ggcctccccg gagcccggcg gggatccgca gaccgtgtgg tatgagtacg gctgtgtgtg   6240
actgtctcgt ggttgagctc gcaaacctga aaactactga cgcgccttcc gactctcacg   6300
gccttttctc ttgcttgcct gcggtgccag gagagggttt ggaatgagga aaggggttcc   6360
cacgcatttc tgctgtttgt tctgtgaatg gaaacactgt gccaagcccc aagaggatta   6420
cgcttccagg tgtgtaacgt gttttctgtg tctgccgctt ccagcagctg atatctttgg   6480
aacaaataat ccacgtcagc atggggacca attaggatgc aatgacaaac tgacttcccc   6540
caaagcagac actactccag tatgtcccag tagaacactc atttgcaatg tgttgagctc   6600
cgttaagcac acacacactc acacaacagg cttacgaggc tcaggcctgg cgggtcagaa   6660
agcccactcc ctctcccaag gccactggat cccaggagaa gcccagactg gcgatactac   6720
aaaggtctcc agggcctggc agaccccaga gtcaggcctg ctgttaaaaa gtgagagtgc   6780
tgctgttcca ttcctggggt cccaagcact tccctttacc ccaggaccca gggcagcctg   6840
cagggcagct ggcggtggcc ttggccattt gcccccagcc tccagctggc tcctgagctc   6900
tgcaccaggg ggtttgggga ccacacaggc acctgccttc ctagatttcc ctggctcact   6960
tttctgcaaa cactggatct gccaggcctg gggattgggg ggcaggaaag aggcccccat   7020 ccagcccct ccaggccagt gtgcacagtg caccgagggg tcatccgcac agagcgaggt   7080
gcaagctcga tgtgtaacct ggctgcggca cccgacatcc ccggtctcgg ggtgttgatt   7140
tatttctgaa taacttttg ggtatagaaa ccaattttt ttaatatatg acatgtatat   7200
gtacacactc atgtgaaata tgtatacttt gggggatct atttatgttc cagtgggagt   7260
cactctcttc tgtcgggaat cttatctgct gctttgtgtc tttggtcaga ttcctgacaa   7320 tttagttttcc tgttgtaaag gtgcttttcc tggggtgaac taaacctatt gattttttt   7380 ttttaagatt ttttttcct tttgatttaa tatactgaga aagaaatggg agacttttga   7440
```

```
atgttaacaa gatccatttt aggagtgttt ggggttgtgt attaaatagc cattcattct    7500
ggaactcaag gacaggactg taataaaatg gaatggaacc gaaaaaaaaa aaaaaaaaaa    7560
aaaaaaaaaa aaa                                                      7573
```

<210> SEQ ID NO 2
<211> LENGTH: 2028
<212> TYPE: PRT
<213> ORGANISM: Homo sapiens

<400> SEQUENCE: 2

```
Met Asp Val Thr Val Ser Glu Leu Leu Glu Leu Phe Leu Gln Ser Pro
1               5                   10                  15

Leu Val Thr Trp Val Lys Thr Phe Gly Pro Phe Gly Ser Gly Ser Gln
            20                  25                  30

Asp Asn Leu Thr Met Tyr Met Asp Leu Val Asp Gly Ile Phe Leu Asn
        35                  40                  45

Gln Ile Met Leu Gln Ile Asp Pro Arg Pro Thr Asn Gln Arg Ile Asn
    50                  55                  60

Lys His Val Asn Asn Asp Val Asn Leu Arg Ile Gln Asn Leu Thr Ile
65                  70                  75                  80

Leu Val Arg Asn Ile Lys Thr Tyr Tyr Gln Glu Val Leu Gln Gln Leu
                85                  90                  95

Ile Val Met Asn Leu Pro Asn Val Leu Met Ile Gly Arg Asp Pro Leu
            100                 105                 110

Ser Gly Lys Ser Met Glu Glu Ile Lys Lys Val Leu Leu Leu Val Leu
        115                 120                 125

Gly Cys Ala Val Gln Cys Glu Arg Lys Glu Glu Phe Ile Glu Arg Ile
    130                 135                 140

Lys Gln Leu Asp Ile Glu Thr Gln Ala Gly Ile Val Ala His Ile Gln
145                 150                 155                 160

Glu Val Thr His Asn Gln Glu Asn Val Phe Asp Leu Gln Trp Leu Glu
                165                 170                 175

Leu Pro Asp Val Ala Pro Glu Glu Leu Glu Ala Leu Ser Arg Ser Met
            180                 185                 190

Val Leu His Leu Arg Arg Leu Ile Asp Gln Arg Asp Glu Cys Thr Glu
        195                 200                 205

Leu Ile Val Asp Leu Thr Gln Glu Arg Asp Tyr Leu Gln Ala Gln His
    210                 215                 220

Pro Pro Ser Pro Ile Lys Ser Ser Ala Asp Ser Thr Pro Ser Pro
225                 230                 235                 240

Thr Ser Ser Leu Ser Ser Glu Asp Lys Gln His Leu Ala Val Glu Leu
                245                 250                 255

Ala Asp Thr Lys Ala Arg Leu Arg Arg Val Arg Gln Glu Leu Glu Asp
            260                 265                 270

Lys Thr Glu Gln Leu Val Asp Thr Arg His Glu Val Asp Gln Leu Val
        275                 280                 285

Leu Glu Leu Gln Lys Val Lys Gln Glu Asn Ile Gln Leu Ala Ala Asp
    290                 295                 300

Ala Arg Ser Ala Arg Ala Tyr Arg Asp Glu Leu Asp Ser Leu Arg Glu
305                 310                 315                 320

Lys Ala Asn Arg Val Glu Arg Leu Glu Leu Glu Leu Thr Arg Cys Lys
                325                 330                 335

Glu Lys Leu His Asp Val Asp Phe Tyr Lys Ala Arg Met Glu Glu Leu
```

```
              340             345             350
Arg Glu Asp Asn Ile Ile Leu Ile Glu Thr Lys Ala Met Leu Glu Glu
            355             360             365

Gln Leu Thr Ala Ala Arg Ala Arg Gly Asp Lys Val His Glu Leu Glu
            370             375             380

Lys Glu Asn Leu Gln Leu Lys Ser Lys Leu His Asp Leu Glu Leu Asp
385             390             395             400

Arg Asp Thr Asp Lys Lys Arg Ile Glu Glu Leu Leu Glu Glu Asn Met
                405             410             415

Val Leu Glu Ile Ala Gln Lys Gln Ser Met Asn Glu Ser Ala His Leu
            420             425             430

Gly Trp Glu Leu Glu Gln Leu Ser Lys Asn Ala Asp Leu Ser Asp Ala
            435             440             445

Ser Arg Lys Ser Phe Val Phe Glu Leu Asn Glu Cys Ala Ser Ser Arg
450             455             460

Ile Leu Lys Leu Glu Lys Glu Asn Gln Ser Leu Gln Ser Thr Ile Gln
465             470             475             480

Gly Leu Arg Asp Ala Ser Leu Val Leu Glu Glu Ser Gly Leu Lys Cys
            485             490             495

Gly Glu Leu Glu Lys Glu Asn His Gln Leu Ser Lys Lys Ile Glu Lys
            500             505             510

Leu Gln Thr Gln Leu Glu Arg Glu Lys Gln Ser Asn Gln Asp Leu Glu
            515             520             525

Thr Leu Ser Glu Glu Leu Ile Arg Gly Lys Glu Gln Leu Gln Ser Asp
            530             535             540

Met Glu Thr Leu Lys Ala Asp Lys Ala Arg Gln Ile Lys Asp Leu Glu
545             550             555             560

Gln Glu Lys Asp His Leu Asn Arg Ala Met Trp Ser Leu Arg Glu Arg
                565             570             575

Ser Gln Val Ser Ser Glu Ala Arg Met Lys Asp Val Glu Lys Glu Asn
            580             585             590

Lys Ala Leu His Gln Thr Val Thr Glu Ala Asn Gly Lys Leu Ser Gln
            595             600             605

Leu Glu Phe Glu Lys Arg Gln Leu His Arg Asp Leu Glu Gln Ala Lys
            610             615             620

Glu Lys Gly Glu Arg Ala Glu Lys Leu Glu Arg Glu Leu Gln Arg Leu
625             630             635             640

Gln Glu Glu Asn Gly Arg Leu Ala Arg Lys Val Thr Ser Leu Glu Thr
                645             650             655

Ala Thr Glu Lys Val Glu Ala Leu Glu His Glu Ser Gln Gly Leu Gln
            660             665             670

Leu Glu Asn Arg Thr Leu Arg Lys Ser Leu Asp Thr Leu Gln Asn Val
            675             680             685

Ser Leu Gln Leu Glu Gly Leu Glu Arg Asp Asn Lys Gln Leu Asp Ala
            690             695             700

Glu Asn Leu Glu Leu Arg Arg Leu Val Glu Thr Met Arg Phe Thr Ser
705             710             715             720

Thr Lys Leu Ala Gln Met Glu Arg Glu Asn Gln Gln Leu Glu Arg Glu
                725             730             735

Lys Glu Glu Leu Arg Lys Asn Val Asp Leu Leu Lys Ala Leu Gly Lys
            740             745             750

Lys Ser Glu Arg Leu Glu Leu Ser Tyr Gln Ser Val Ser Ala Glu Asn
            755             760             765
```

```
Leu Arg Leu Gln Gln Ser Leu Glu Ser Ser His Lys Thr Gln Thr
        770                 775                 780

Leu Glu Ser Glu Leu Gly Glu Leu Glu Ala Glu Arg Gln Ala Leu Arg
785                 790                 795                 800

Arg Asp Leu Glu Ala Leu Arg Leu Ala Asn Ala Gln Leu Glu Gly Ala
                805                 810                 815

Glu Lys Asp Arg Lys Ala Leu Glu Gln Glu Val Ala Gln Leu Glu Lys
                820                 825                 830

Asp Lys Lys Leu Leu Glu Lys Glu Ala Lys Arg Leu Trp Gln Gln Val
                835                 840                 845

Glu Leu Lys Asp Ala Val Leu Asp Asp Ser Thr Ala Lys Leu Ser Ala
        850                 855                 860

Val Glu Lys Glu Ser Arg Ala Leu Asp Lys Glu Leu Ala Arg Cys Arg
865                 870                 875                 880

Asp Ala Ala Gly Lys Leu Lys Glu Leu Glu Lys Asp Asn Arg Asp Leu
                885                 890                 895

Thr Lys Gln Val Thr Val His Ala Arg Thr Leu Thr Leu Arg Glu
        900                 905                 910

Asp Leu Val Leu Glu Lys Leu Lys Ser Gln Gln Leu Ser Ser Glu Leu
        915                 920                 925

Asp Lys Leu Ser Gln Glu Leu Glu Lys Val Gly Leu Asn Arg Glu Leu
        930                 935                 940

Leu Leu Gln Glu Asp Asp Ser Gly Ser Asp Thr Lys Tyr Lys Ile Leu
945                 950                 955                 960

Glu Gly Arg Asn Glu Ser Ala Leu Lys Thr Thr Leu Ala Met Lys Glu
                965                 970                 975

Glu Lys Ile Val Leu Leu Glu Ala Gln Met Glu Glu Lys Ala Ser Leu
                980                 985                 990

Asn Arg Gln Leu Glu Ser Glu Leu Gln Met Leu Lys Lys Glu Cys Glu
        995                 1000                1005

Thr Leu Arg Gln Asn Gln Gly Glu Gly Gln His Leu Gln Asn Ser
        1010                1015                1020

Phe Lys His Pro Ala Gly Lys Thr Ala Ala Ser His Gln Gly Lys
        1025                1030                1035

Glu Ala Trp Gly Pro Gly His Lys Glu Ala Thr Met Glu Leu Leu
        1040                1045                1050

Arg Val Lys Asp Arg Ala Ile Glu Leu Glu Arg Asn Asn Ala Ala
        1055                1060                1065

Leu Gln Ala Glu Lys Gln Leu Leu Lys Glu Gln Leu Gln His Leu
        1070                1075                1080

Glu Thr Gln Asn Val Thr Phe Ser Ser Gln Ile Leu Thr Leu Gln
        1085                1090                1095

Lys Gln Ser Ala Phe Leu Gln Glu His Asn Thr Thr Leu Gln Thr
        1100                1105                1110

Gln Thr Ala Lys Leu Gln Val Glu Asn Ser Thr Leu Ser Ser Gln
        1115                1120                1125

Ser Ala Ala Leu Thr Ala Gln Tyr Thr Leu Leu Gln Asn His His
        1130                1135                1140

Thr Ala Lys Glu Thr Glu Asn Glu Ser Leu Gln Arg Gln Gln Glu
        1145                1150                1155

Gln Leu Thr Ala Ala Tyr Glu Ala Leu Leu Gln Asp His Glu His
        1160                1165                1170
```

```
Leu Gly Thr Leu His Glu Arg Gln Ser Ala Glu Tyr Glu Ala Leu
    1175                1180                1185

Ile Arg Gln His Ser Cys Leu Lys Thr Leu His Arg Asn Leu Glu
    1190                1195                1200

Leu Glu His Lys Glu Leu Gly Glu Arg His Gly Asp Met Leu Lys
    1205                1210                1215

Arg Lys Ala Glu Leu Glu Arg Glu Lys Val Leu Thr Thr Glu
    1220                1225                1230

Arg Glu Ala Leu Gln Gln Glu Gln Arg Thr Asn Ala Leu Ala Met
    1235                1240                1245

Gly Glu Asn Gln Arg Leu Arg Gly Glu Leu Asp Arg Val Asn Phe
    1250                1255                1260

Leu His His Gln Leu Lys Gly Glu Tyr Glu Leu His Ala His
    1265                1270                1275

Thr Lys Glu Leu Lys Thr Ser Leu Asn Asn Ala Gln Leu Glu Leu
    1280                1285                1290

Asn Arg Trp Gln Ala Arg Phe Asp Glu Leu Lys Glu Gln His Gln
    1295                1300                1305

Thr Met Asp Ile Ser Leu Thr Lys Leu Asp Asn His Cys Glu Leu
    1310                1315                1320

Leu Ser Arg Leu Lys Gly Asn Leu Glu Glu Asn His His Leu
    1325                1330                1335

Leu Ser Gln Ile Gln Leu Leu Ser Gln Gln Asn Gln Met Leu Leu
    1340                1345                1350

Glu Gln Asn Met Glu Asn Lys Glu Gln Tyr His Glu Glu Gln Lys
    1355                1360                1365

Gln Tyr Ile Asp Lys Leu Asn Ala Leu Arg Arg His Lys Glu Lys
    1370                1375                1380

Leu Glu Glu Lys Ile Met Asp Gln Tyr Lys Phe Tyr Asp Pro Pro
    1385                1390                1395

Pro Lys Lys Lys Asn His Trp Ile Gly Ala Lys Ala Leu Val Lys
    1400                1405                1410

Leu Ile Lys Pro Lys Lys Glu Gly Ser Arg Glu Arg Leu Lys Ser
    1415                1420                1425

Thr Val Asp Ser Pro Pro Trp Gln Leu Glu Ser Ser Asp Pro Ala
    1430                1435                1440

Ser Pro Ala Ala Ser Gln Pro Leu Arg Ser Gln Ala Glu Asn Pro
    1445                1450                1455

Asp Thr Pro Ala Leu Gly Ser Asn Cys Ala Glu Glu Arg Asp Ala
    1460                1465                1470

His Asn Gly Ser Val Gly Lys Gly Pro Gly Asp Leu Lys Pro Lys
    1475                1480                1485

Arg Gly Ser Pro His Arg Gly Ser Leu Asp Arg Thr Asp Ala Ser
    1490                1495                1500

Thr Asp Leu Ala Met Arg Ser Trp Pro Ser Glu Leu Gly Ser Arg
    1505                1510                1515

Thr Cys Ser Thr Ser Ala Thr Thr Ala Pro Ser Asn Ser Thr
    1520                1525                1530

Pro Ile Ala Arg His Pro Gly Arg Thr Lys Gly Tyr Asn Ser Asp
    1535                1540                1545

Asp Asn Leu Cys Glu Pro Ser Leu Glu Phe Glu Val Pro Asn His
    1550                1555                1560

Arg Gln Tyr Val Ser Arg Pro Ser Ser Leu Glu Ser Ser Arg Asn
```

```
            1565                1570                1575

Thr Ser Ser Asn Ser Ser Pro Leu Asn Leu Lys Gly Ser Ser Glu
        1580                1585                1590

Gln Leu His Gly Arg Ser Glu Ser Phe Ser Ser Glu Asp Leu Ile
        1595                1600                1605

Pro Ser Arg Asp Leu Ala Thr Leu Pro Arg Glu Ala Ser Thr Pro
        1610                1615                1620

Gly Arg Asn Ala Leu Gly Arg His Glu Tyr Pro Leu Pro Arg Asn
        1625                1630                1635

Gly Pro Leu Pro Gln Glu Gly Ala Gln Lys Arg Gly Thr Ala Pro
        1640                1645                1650

Pro Tyr Val Gly Val Arg Pro Cys Ser Ala Ser Pro Ser Ser Glu
        1655                1660                1665

Met Val Thr Leu Glu Glu Phe Leu Glu Glu Ser Asn Arg Ser Ser
        1670                1675                1680

Pro Thr His Asp Thr Pro Ser Cys Arg Asp Asp Leu Leu Ser Asp
        1685                1690                1695

Tyr Phe Arg Lys Ala Ser Asp Pro Pro Ala Ile Gly Gly Gln Pro
        1700                1705                1710

Gly Pro Pro Ala Lys Lys Glu Gly Ala Lys Met Pro Thr Asn Phe
        1715                1720                1725

Val Ala Pro Thr Val Lys Met Ala Ala Pro Thr Ser Glu Gly Arg
        1730                1735                1740

Pro Leu Lys Pro Gly Gln Tyr Val Lys Pro Asn Phe Arg Leu Thr
        1745                1750                1755

Glu Ala Glu Ala Pro Pro Ser Val Ala Pro Arg Gln Ala Gln Pro
        1760                1765                1770

Pro Gln Ser Leu Ser Leu Gly Arg Pro Arg Gln Ala Pro Val Pro
        1775                1780                1785

Pro Ala Ser His Ala Pro Ala Ser Arg Ser Ala Ser Leu Ser Arg
        1790                1795                1800

Ala Phe Ser Leu Ala Ser Ala Asp Leu Leu Arg Ala Ser Gly Pro
        1805                1810                1815

Glu Ala Cys Lys Gln Glu Ser Pro Gln Lys Leu Gly Ala Pro Glu
        1820                1825                1830

Ala Leu Gly Gly Arg Glu Thr Gly Ser His Thr Leu Gln Ser Pro
        1835                1840                1845

Ala Pro Pro Ser Ser His Ser Leu Ala Arg Glu Arg Thr Pro Leu
        1850                1855                1860

Val Gly Lys Ala Gly Ser Ser Cys Gln Gly Pro Gly Pro Arg Ser
        1865                1870                1875

Arg Pro Leu Asp Thr Arg Arg Phe Ser Leu Ala Pro Pro Lys Glu
        1880                1885                1890

Glu Arg Leu Ala Pro Leu His Gln Ser Ala Thr Ala Pro Ala Ile
        1895                1900                1905

Ala Thr Ala Gly Ala Gly Ala Ala Ala Ala Gly Ser Gly Ser Asn
        1910                1915                1920

Ser Gln Leu Leu His Phe Ser Pro Ala Ala Ala Pro Ala Ala Arg
        1925                1930                1935

Thr Lys Pro Lys Ala Pro Pro Arg Ser Gly Glu Val Ala Thr Ile
        1940                1945                1950

Thr Pro Val Arg Ala Gly Leu Ser Leu Ser Glu Gly Asp Gly Val
        1955                1960                1965
```

```
Pro Gly Gln Gly Cys Ser Glu Gly Leu Pro Ala Lys Ser Pro Gly
    1970            1975                1980

Arg Ser Pro Asp Leu Ala Pro His Leu Gly Arg Ala Leu Glu Asp
    1985            1990                1995

Cys Ser Arg Gly Ser Val Ser Lys Ser Ser Pro Ala Ser Pro Glu
    2000            2005                2010

Pro Gly Gly Asp Pro Gln Thr Val Trp Tyr Glu Tyr Gly Cys Val
    2015            2020                2025

<210> SEQ ID NO 3
<211> LENGTH: 19
<212> TYPE: DNA
<213> ORGANISM: Homo sapiens

<400> SEQUENCE: 3
gtagaacact catttgcaa                                            19

<210> SEQ ID NO 4
<211> LENGTH: 19
<212> TYPE: DNA
<213> ORGANISM: Homo sapiens

<400> SEQUENCE: 4
gcacctgcct tcctagatt                                            19

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgtagaacac tcatttgcaa ttcaagagat tgcaaatgag tgttctactt ttttc      55

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcgagaaaaa agtagaacac tcatttgcaa tctcttgaat tgcaaatgag tgttctaca   59

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgcacctgcc ttcctagatt ttcaagagaa atctaggaag gcaggtgctt ttttc       55

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 8
tcgagaaaaa agcacctgcc ttcctagatt tctcttgaaa atctaggaag gcaggtgca      59

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgacatggag accctgaagg ctga                                            24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tttcatgcgg gcctcactgc tga                                             23

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcagttgtag gcaagctgcg acgt                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aagccagagg ctggtaccta gaac                                            24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgggtgcta tccacctgag                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gagtcggatc ctggtctctg                                                          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagagaactt tgccgttgaa                                                          20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gtgatgctga gaagtttcgt                                                          20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gagtttgcac tgaggatgaa aa                                                       22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcttcttctt cttggggaca                                                          20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gagtggactt gtgccgactt ca                                                       22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 20
ggtggctggt gcaaagacat ag                                              22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttgcagcctt ctcagccaa                                                  19

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggaggcaaaa gcaaatcact g                                               21

<210> SEQ ID NO 23
<211> LENGTH: 552
<212> TYPE: PRT
<213> ORGANISM: Homo sapiens

<400> SEQUENCE: 23
```

Met Ser Val Leu Ser Pro Gly Asp Leu Lys Pro Lys Arg Gly Ser Pro
1               5                   10                  15

His Arg Gly Ser Leu Asp Arg Thr Asp Ala Ser Thr Asp Leu Ala Met
            20                  25                  30

Arg Ser Trp Pro Ser Glu Leu Gly Ser Arg Thr Cys Ser Thr Ser Ala
        35                  40                  45

Thr Thr Thr Ala Pro Ser Asn Ser Thr Pro Ile Ala Arg His Pro Gly
    50                  55                  60

Arg Thr Lys Gly Tyr Asn Ser Asp Asp Asn Leu Cys Glu Pro Ser Leu
65                  70                  75                  80

Glu Phe Glu Val Pro Asn His Arg Gln Tyr Val Ser Arg Pro Ser Ser
                85                  90                  95

Leu Glu Ser Ser Arg Asn Thr Ser Ser Asn Ser Ser Pro Leu Asn Leu
            100                 105                 110

Lys Gly Ser Ser Glu Gln Leu His Gly Arg Ser Glu Ser Phe Ser Ser
        115                 120                 125

Glu Asp Leu Ile Pro Ser Arg Asp Leu Ala Thr Pro Arg Glu Ala
    130                 135                 140

Ser Thr Pro Gly Arg Asn Ala Leu Gly Arg His Glu Tyr Pro Leu Pro
145                 150                 155                 160

Arg Asn Gly Pro Leu Pro Gln Glu Gly Ala Gln Lys Arg Gly Thr Ala
                165                 170                 175

Pro Pro Tyr Val Gly Val Arg Pro Cys Ser Ala Ser Pro Ser Ser Glu
            180                 185                 190

Met Val Thr Leu Glu Glu Phe Leu Glu Glu Ser Asn Arg Ser Ser Pro
        195                 200                 205

Thr His Asp Thr Pro Ser Cys Arg Asp Asp Leu Leu Ser Asp Tyr Phe
    210                 215                 220

```
Arg Lys Ala Ser Asp Pro Pro Ala Ile Gly Gly Gln Pro Gly Pro Pro
225                 230                 235                 240

Ala Lys Lys Glu Gly Ala Lys Met Pro Thr Asn Phe Val Ala Pro Thr
            245                 250                 255

Val Lys Met Ala Ala Pro Thr Ser Glu Gly Arg Pro Leu Lys Pro Gly
        260                 265                 270

Gln Tyr Val Lys Pro Asn Phe Arg Leu Thr Glu Ala Glu Ala Pro Pro
    275                 280                 285

Ser Val Ala Pro Arg Gln Ala Gln Pro Gln Ser Leu Ser Leu Gly
290                 295                 300

Arg Pro Arg Gln Ala Pro Val Pro Pro Ala Ser His Ala Pro Ala Ser
305                 310                 315                 320

Arg Ser Ala Ser Leu Ser Arg Ala Phe Ser Leu Ala Ser Ala Asp Leu
                325                 330                 335

Leu Arg Ala Ser Gly Pro Glu Ala Cys Lys Gln Glu Ser Pro Gln Lys
            340                 345                 350

Leu Gly Ala Pro Glu Ala Leu Gly Gly Arg Glu Thr Gly Ser His Thr
        355                 360                 365

Leu Gln Ser Pro Ala Pro Ser Ser His Ser Leu Ala Arg Glu Arg
370                 375                 380

Thr Pro Leu Val Gly Lys Ala Gly Ser Ser Cys Gln Gly Pro Gly Pro
385                 390                 395                 400

Arg Ser Arg Pro Leu Asp Thr Arg Arg Phe Ser Leu Ala Pro Pro Lys
                405                 410                 415

Glu Glu Arg Leu Ala Pro Leu His Gln Ser Ala Thr Ala Pro Ala Ile
            420                 425                 430

Ala Thr Ala Gly Ala Gly Ala Ala Ala Gly Ser Gly Ser Asn Ser
        435                 440                 445

Gln Leu Leu His Phe Ser Pro Ala Ala Pro Ala Ala Arg Thr Lys
450                 455                 460

Pro Lys Ala Pro Pro Arg Ser Gly Glu Val Ala Thr Ile Thr Pro Val
465                 470                 475                 480

Arg Ala Gly Leu Ser Leu Ser Glu Gly Asp Gly Val Pro Gly Gln Gly
                485                 490                 495

Cys Ser Glu Gly Leu Pro Ala Lys Ser Pro Gly Arg Ser Pro Asp Leu
            500                 505                 510

Ala Pro His Leu Gly Arg Ala Leu Glu Asp Cys Ser Arg Gly Ser Val
        515                 520                 525

Ser Lys Ser Ser Pro Ala Ser Pro Glu Pro Gly Gly Asp Pro Gln Thr
    530                 535                 540

Val Trp Tyr Glu Tyr Gly Cys Val
545                 550

<210> SEQ ID NO 24
<211> LENGTH: 506
<212> TYPE: PRT
<213> ORGANISM: Homo sapiens

<400> SEQUENCE: 24

Met Ser Val Leu Ser Pro Gly Asp Leu Lys Pro Lys Arg Gly Ser Pro
1               5                   10                  15

His Arg Gly Ser Leu Asp Arg Thr Asp Ala Ser Thr Asp Leu Ala Met
            20                  25                  30

Arg Ser Trp Pro Ser Glu Leu Gly Ser Arg Thr Cys Ser Thr Ser Ala
```

```
             35                  40                  45
Thr Thr Thr Ala Pro Ser Asn Ser Thr Pro Ile Ala Arg His Pro Gly
             50                  55                  60
Arg Thr Lys Gly Tyr Asn Ser Asp Asp Asn Leu Cys Glu Pro Ser Leu
 65                  70                  75                  80
Glu Phe Glu Val Pro Asn His Arg Gln Tyr Val Ser Arg Pro Ser Ser
                     85                  90                  95
Leu Glu Ser Ser Arg Asn Thr Ser Ser Asn Ser Ser Pro Leu Asn Leu
                100                 105                 110
Lys Gly Ser Ser Glu Gln Leu His Gly Arg Ser Glu Ser Phe Ser Ser
                115                 120                 125
Glu Asp Leu Ile Pro Ser Arg Asp Leu Ala Thr Leu Pro Arg Glu Ala
            130                 135                 140
Ser Thr Pro Gly Arg Asn Ala Leu Gly Arg His Glu Tyr Pro Leu Pro
145                 150                 155                 160
Arg Asn Gly Pro Leu Pro Gln Glu Gly Ala Gln Lys Arg Gly Thr Ala
                    165                 170                 175
Pro Pro Tyr Val Gly Val Arg Pro Cys Ser Ala Ser Pro Ser Ser Glu
                180                 185                 190
Met Val Thr Leu Glu Glu Phe Leu Glu Glu Ser Asn Arg Ser Ser Pro
                195                 200                 205
Thr His Asp Thr Pro Ser Cys Arg Asp Asp Leu Leu Ser Asp Tyr Phe
            210                 215                 220
Arg Lys Ala Ser Asp Pro Ala Ile Gly Gly Gln Pro Gly Pro Pro
225                 230                 235                 240
Ala Lys Lys Glu Gly Ala Lys Met Pro Thr Asn Phe Val Ala Pro Thr
                    245                 250                 255
Val Lys Met Ala Ala Pro Thr Ser Glu Gly Arg Pro Leu Lys Pro Gly
                260                 265                 270
Gln Tyr Val Lys Pro Asn Phe Arg Leu Thr Glu Ala Glu Ala Pro Pro
                275                 280                 285
Ser Val Ala Pro Arg Gln Ala Gln Pro Pro Gln Ser Leu Ser Leu Gly
            290                 295                 300
Arg Pro Arg Gln Ala Pro Glu Ala Leu Gly Gly Arg Glu Thr Gly Ser
305                 310                 315                 320
His Thr Leu Gln Ser Pro Ala Pro Pro Ser His Ser Leu Ala Arg
                    325                 330                 335
Glu Arg Thr Pro Leu Val Gly Lys Ala Gly Ser Ser Cys Gln Gly Pro
                340                 345                 350
Gly Pro Arg Ser Arg Pro Leu Asp Thr Arg Arg Phe Ser Leu Ala Pro
            355                 360                 365
Pro Lys Glu Glu Arg Leu Ala Pro Leu His Gln Ser Ala Thr Ala Pro
370                 375                 380
Ala Ile Ala Thr Ala Gly Ala Gly Ala Ala Ala Gly Ser Gly Ser
385                 390                 395                 400
Asn Ser Gln Leu Leu His Phe Ser Pro Ala Ala Pro Ala Ala Arg
                405                 410                 415
Thr Lys Pro Lys Ala Pro Pro Arg Ser Gly Glu Val Ala Thr Ile Thr
                420                 425                 430
Pro Val Arg Ala Gly Leu Ser Leu Ser Glu Gly Asp Gly Val Pro Gly
            435                 440                 445
Gln Gly Cys Ser Glu Gly Leu Pro Ala Lys Ser Pro Gly Arg Ser Pro
            450                 455                 460
```

```
Asp Leu Ala Pro His Leu Gly Arg Ala Leu Glu Asp Cys Ser Arg Gly
465                 470                 475                 480

Ser Val Ser Lys Ser Ser Pro Ala Ser Pro Glu Pro Gly Gly Asp Pro
            485                 490                 495

Gln Thr Val Trp Tyr Glu Tyr Gly Cys Val
        500                 505

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cagtagaaca ctcatttgca a                                            21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aggcacctgc cttcctagat t                                            21

<210> SEQ ID NO 27
<211> LENGTH: 32
<212> TYPE: PRT
<213> ORGANISM: Homo sapiens

<400> SEQUENCE: 27

Ser Pro Ser Ser Glu Met Val Thr Leu Glu Glu Phe Leu Glu Ser
1               5                   10                  15

Asn Arg Ser Ser Pro Thr His Asp Thr Pro Ser Cys Arg Asp Asp Leu
            20                  25                  30

<210> SEQ ID NO 28
<211> LENGTH: 144
<212> TYPE: PRT
<213> ORGANISM: Homo sapiens

<400> SEQUENCE: 28

Leu Asp Thr Arg Arg Phe Ser Leu Ala Pro Lys Glu Glu Arg Leu
1               5                   10                  15

Ala Pro Leu His Gln Ser Ala Thr Ala Pro Ala Ile Ala Thr Ala Gly
            20                  25                  30

Ala Gly Ala Ala Ala Gly Ser Gly Ser Asn Ser Gln Leu Leu His
        35                  40                  45

Phe Ser Pro Ala Ala Ala Pro Ala Ala Arg Thr Lys Pro Lys Ala Pro
    50                  55                  60

Pro Arg Ser Gly Glu Val Ala Thr Ile Thr Pro Val Arg Ala Gly Leu
65                  70                  75                  80

Ser Leu Ser Glu Gly Asp Gly Val Pro Gly Gln Gly Cys Ser Glu Gly
                85                  90                  95

Leu Pro Ala Lys Ser Pro Gly Arg Ser Pro Asp Leu Ala Pro His Leu
            100                 105                 110
```

```
Gly Arg Ala Leu Glu Asp Cys Ser Arg Gly Ser Val Ser Lys Ser Ser
            115                 120                 125

Pro Ala Ser Pro Glu Pro Gly Gly Asp Pro Gln Thr Val Trp Tyr Glu
        130                 135                 140

<210> SEQ ID NO 29
<211> LENGTH: 4
<212> TYPE: PRT
<213> ORGANISM: Homo sapiens

<400> SEQUENCE: 29

Tyr Gly Cys Val
1

<210> SEQ ID NO 30
<211> LENGTH: 33
<212> TYPE: PRT
<213> ORGANISM: Homo sapiens

<400> SEQUENCE: 30

Arg His His Lys Ile Lys Thr Gly Ser Pro Gly Ser Glu Val Val Thr
1               5                   10                  15

Leu Gln Gln Phe Leu Glu Glu Ser Asn Lys Leu Thr Ser Val Gln Ile
            20                  25                  30

Lys

<210> SEQ ID NO 31
<211> LENGTH: 34
<212> TYPE: PRT
<213> ORGANISM: Mus musculus

<400> SEQUENCE: 31

Arg Ala His His Lys Met Lys Ala Gly Ser Pro Gly Ser Glu Val Val
1               5                   10                  15

Thr Leu Gln Gln Phe Leu Glu Glu Ser Asn Lys Leu Thr Ser Ile Gln
            20                  25                  30

Leu Lys

<210> SEQ ID NO 32
<211> LENGTH: 34
<212> TYPE: PRT
<213> ORGANISM: Rattus norvegicus

<400> SEQUENCE: 32

Gln Ala His His Lys Met Asn Ala Gly Ser Pro Gly Ser Glu Val Val
1               5                   10                  15

Thr Leu Gln Gln Phe Leu Glu Glu Ser Asn Lys Leu Thr Ser Ile Gln
            20                  25                  30

Leu Lys

<210> SEQ ID NO 33
<211> LENGTH: 33
<212> TYPE: PRT
<213> ORGANISM: Gallus gallus

<400> SEQUENCE: 33

Cys Gly Arg Gln Ile Lys Thr Asp Ser Pro Gly Ser Glu Val Val Thr
1               5                   10                  15

Leu Gln Gln Phe Leu Glu Glu Ser Asn Lys Ser Thr Ser Ser Glu Met
            20                  25                  30
```

Lys

<210> SEQ ID NO 34
<211> LENGTH: 34
<212> TYPE: PRT
<213> ORGANISM: Anolis carolinensis

<400> SEQUENCE: 34

Gln Gly Thr Arg Arg Ile Lys Thr Asp Ser Pro Gly Ser Glu Val Val
1               5                   10                  15

Thr Leu Gln Gln Phe Leu Glu Glu Ser Asn Thr Val Thr Ser Thr Glu
            20                  25                  30

Ile Lys

<210> SEQ ID NO 35
<211> LENGTH: 35
<212> TYPE: PRT
<213> ORGANISM: Xenopus laevis

<400> SEQUENCE: 35

Ser Leu Gln Ser Lys Leu Met Pro Gly Ser Pro Gly Ser Glu Met Val
1               5                   10                  15

Ser Leu Lys Gln Phe Leu Glu Glu Ser Asn Lys Leu Thr Val Ser Gln
            20                  25                  30

Ile Arg Ser
        35

<210> SEQ ID NO 36
<211> LENGTH: 27
<212> TYPE: PRT
<213> ORGANISM: Danio rerio

<400> SEQUENCE: 36

Ser Thr Gly Ser Asp Val Val Ser Leu Gln Gln Phe Leu Glu Glu Asn
1               5                   10                  15

Thr His Thr Ala Glu Asp Pro Pro Ser Ala Pro
            20                  25

<210> SEQ ID NO 37
<211> LENGTH: 35
<212> TYPE: PRT
<213> ORGANISM: Homo sapiens

<400> SEQUENCE: 37

Pro Pro Tyr Val Gly Val Arg Pro Cys Ser Ala Ser Pro Ser Ser Glu
1               5                   10                  15

Met Val Thr Leu Glu Glu Phe Leu Glu Glu Ser Asn Arg Ser Ser Pro
            20                  25                  30

Thr His Asp
        35

<210> SEQ ID NO 38
<211> LENGTH: 37
<212> TYPE: PRT
<213> ORGANISM: Mus musculus

<400> SEQUENCE: 38

Ser Thr His Thr Gly Val Arg Pro His Ser Ala Ser Pro Ser Ser Glu
1               5                   10                  15

Met Val Thr Leu Glu Glu Phe Leu Glu Glu Ser Asn Arg Gly Gly Ser
            20                  25                  30

Pro Thr His Asp Thr
        35

<210> SEQ ID NO 39
<211> LENGTH: 34
<212> TYPE: PRT
<213> ORGANISM: Rattus norvegicus

<400> SEQUENCE: 39

Ser Ala His Thr Gly Val Arg Pro His Ser Ala Ser Pro Ser Ser Glu
1               5                   10                  15

Met Val Thr Leu Glu Glu Phe Leu Glu Glu Ser Asn Arg Gly Ser Pro
            20                  25                  30

Thr His

<210> SEQ ID NO 40
<211> LENGTH: 35
<212> TYPE: PRT
<213> ORGANISM: Gallus gallus

<400> SEQUENCE: 40

Gln Ser Tyr Val Gly Arg Gln Arg Ser Ala Ser Pro Gly Ser Glu Met
1               5                   10                  15

Val Thr Leu Glu Glu Phe Leu Glu Glu Ser Asn Arg Leu Ser Pro Pro
            20                  25                  30

Ser Asp Thr
        35

<210> SEQ ID NO 41
<211> LENGTH: 35
<212> TYPE: PRT
<213> ORGANISM: Anolis carolinensis

<400> SEQUENCE: 41

Gln Ala Arg Ser Val Arg His Arg Pro Ala Ser Pro Gly Ser Glu Met
1               5                   10                  15

Val Thr Leu Glu Glu Phe Leu Glu Glu Ser Asn Lys Leu Ser Pro Ala
            20                  25                  30

Asn Glu Thr
        35

<210> SEQ ID NO 42
<211> LENGTH: 28
<212> TYPE: PRT
<213> ORGANISM: Xenopus laevis

<400> SEQUENCE: 42

Ser Leu Asn Asp Ser Glu Leu Ile Thr Leu His Gln Phe Leu Leu Glu
1               5                   10                  15

Ala Glu Thr Leu Asn Pro Ser Ser Gln Ser Pro Ser
            20                  25

<210> SEQ ID NO 43
<211> LENGTH: 35
<212> TYPE: PRT
<213> ORGANISM: Danio rerio

<400> SEQUENCE: 43

Gln Arg Pro Ala Ser Arg Arg Pro Ser Ser Pro Gly Ser Glu Met Val
1               5                   10                  15

Thr Leu Glu Glu Phe Leu Gln Glu Ser Asn Ala Leu Ser Pro Pro Thr
                20                  25                  30

Val Gln Thr
        35

<210> SEQ ID NO 44
<211> LENGTH: 16
<212> TYPE: PRT
<213> ORGANISM: Homo sapiens

<400> SEQUENCE: 44

Glu Met Val Thr Leu Glu Glu Phe Leu Glu Glu Ser Asn Arg Ser Ser
1               5                   10                  15

<210> SEQ ID NO 45
<211> LENGTH: 16
<212> TYPE: PRT
<213> ORGANISM: Homo sapiens

<400> SEQUENCE: 45

Glu Val Val Thr Leu Gln Gln Phe Leu Glu Glu Ser Asn Lys Leu Thr
1               5                   10                  15

<210> SEQ ID NO 46
<211> LENGTH: 16
<212> TYPE: PRT
<213> ORGANISM: Rattus norvegicus

<400> SEQUENCE: 46

Arg Leu Val Thr Leu Glu Glu Phe Leu Ala Ser Thr Gln Arg Lys Glu
1               5                   10                  15

<210> SEQ ID NO 47
<211> LENGTH: 16
<212> TYPE: PRT
<213> ORGANISM: Rattus norvegicus

<400> SEQUENCE: 47

Arg Leu Val Thr Leu Glu Glu Phe Leu Arg Ala Thr Glu Lys Lys Glu
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Arg Val Thr Trp Tyr Asp Phe Leu Met Glu Asp Thr Lys Ser Arg
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Arg Leu Thr Val Trp Glu Phe Leu Ala Leu Pro Ser Ser Thr
1               5                   10                  15

THERAPEUTIC TARGETS FOR CANCER PROGRESSION

CROSS-REFERENCE TO RELATED APPLICATIONS

This application claims priority to U.S. Provisional Application Ser. No. 62/172,996, filed Jun. 9, 2015, which is herein incorporated by reference in its entirety.

STATEMENT REGARDING FEDERALLY SPONSORED RESEARCH

Research and development leading to certain aspects of the present invention were supported, in part, by Grant Nos. R01CA160911, R01CA100768, R01GM108733, HL091061, R01CA72851 and P30 NS047101, all awarded by the National Institutes of Health. Accordingly, the U.S. government may have certain rights in the invention.

SEQUENCE LISTING

The instant application contains a sequence listing which has been submitted in ASCII format via EFS-Web and is hereby incorporated by reference in its entirety. Said ASCII copy, created on Jun. 7, 2016, is named 247106.000038_SL.txt and is 50,167 bytes in size.

FIELD OF THE INVENTION

The invention relates generally to G protein signaling regulators and diagnostic and therapeutic targets for cancer progression, as well as to methods of predicting cancer progression.

BACKGROUND OF THE INVENTION

The Wnt signaling pathway plays a crucial role in embryonic development, in tissue regeneration and in many other cellular processes including cell fate, adhesion, polarity, migration, and proliferation. Dysregulated expression of components within the Wnt pathway triggers many diseases, and most importantly, heralds cancer (Klaus & Birchmeier, 2008).

Of the multiple known Wnt proteins, some preferentially trigger the well-characterized canonical pathway, which enhances the stability, nuclear localization and activity of β-catenin, and the downstream activation of genes targeted by the TCF/LEF transcription machinery. Other Wnts, e.g., Wnt5a deviate from this canonical paradigm, and trigger so-called non-canonical pathways (Kuhl et al, 2000; Niehrs, 2001; Winklbauer et al, 2001). Among other events, these non-canonical pathways induce the elevation of intracellular $Ca^{2+}$ and activation of the small G proteins RhoA and Rac1, which regulate polarized cell movements and the planar polarity of epithelial cells (Kuhl et al, 2000; Mayor & Theveneau, 2014; Sheldahl et al, 1999). Of critical importance, non-canonical Wnt signaling antagonizes the canonical Wnt pathway (Ishitani et al, 2003; Olson & Gibo, 1998; Tones et al, 1996), although it is unclear how this occurs. Despite the lack of molecular mechanisms, dysregulation of the non-canonical Wnt pathway is widely believed to drive cancer via a two-faceted mechanism (McDonald & Silver, 2009)—1) non-canonical Wnt signaling suppresses tumorigenesis by antagonizing the canonical β-catenin/TCF/LEF pathway, and inhibition of non-canonical Wnt signaling heralds neoplastic transformation (Grumolato et al, 2010; Ishitani et al, 2003; Medrek et al, 2009); 2) hyperactivation of non-canonical Wnt signaling enhances cancer invasion/metastasis by activation of Rac1 and remodeling of the actin cytoskeleton (Yamamoto et al, 2009) and by upregulating CamKII and PKC (Dissanayake et al, 2007; Weeraratna et al, 2002). Little is known as to how such dysregulation of non-canonical Wnt signaling, i.e., early inhibition and late hyperactivation is orchestrated during cancer progression.

Non-canonical Wnt signaling is initiated by the binding of Wnt ligands to receptors of the Frizzled (FZDR) family. These receptors belong to the G protein-coupled receptor (GPCR) superfamily, which classically activate trimeric G proteins. However, the interplay between FZDR and G proteins in Wnt signaling is very controversial—on one hand, there is a wealth of evidence indicating that trimeric G proteins regulate Wnt signaling (Katanaev et al, 2005; Koval et al, 2011; Liu et al, 2005; Malbon, 2004; Schulte & Bryja, 2007). On the other hand, definitive evidence for the direct activation of trimeric G proteins by FZDR's is elusive. The experimental difficulties and controversies in the field have led to provocative speculations that FZDRs may not bind G proteins directly, but do so indirectly via other intermediates within the Wnt signaling pathway (Schulte & Bryja, 2007), but such intermediate 'linker' molecules have not been identified. Recent advances in the field of trimeric G protein signaling have important implications in this regard. It has become increasingly clear that the activity of trimeric G proteins is regulated by a plethora of accessory proteins (Bumer & Lanier, 2014; Sato et al, 2006; Siderovski & Willard, 2005) beyond classical activation by GPCRs. Among these accessory proteins, a subset of proteins called non-receptor Guanine nucleotide Exchange Factors (GEFs) are uniquely positioned to fulfill the role of an intermediate to trigger G protein signaling upon Wnt stimulation because they are cytoplasmic factors capable of activating G proteins (Garcia-Marcos et al, 2009; Garcia-Marcos et al, 2011b; Lanier, 2004; Lee & Dohlman, 2008; Natochin et al, 2005; Oner et al, 2013; Tall et al, 2003).

There is no single cytosolic target interface at the crossroads of RTKs and Wnt receptors. There is no single target described in any G protein pathway that modulates β-Catenin signaling either. Further, there is no current tool that is useful in studying the endogenous Wnt receptor protein in cells/tissues.

SUMMARY OF THE INVENTION

The invention provides a discovery and characterization of DAPLE (also known as KIAA1509 or ccdc88c), a novel non-receptor GEF for trimeric G proteins (Gi1/2/3), that works synergistically with the Wnt pathway receptors (e.g., Frizzled) to enhance PI3K and β-Catenin signals to trigger oncogenesis. Multiple cancers depend on aberrant enhancement of Wnt→β-Catenin axis of signaling to continue along the path of oncogenic progression. In certain embodiments, the invention provides that DAPLE enhances PI3K-Akt/β-Catenin signaling downstream of Wnt receptors as well as receptor tyrosine kinases (growth factor RTKs) via its GEF function. In this regard, the molecular mechanisms are identical to what has been previously described for its closely related family member, GIV/Girdin/ccdc88a.

It is well known that multiple receptors cross-talk to aberrantly process signaling during oncogenesis. It is also well known that growth factor receptors and Wnt pathway receptors potentiate each other during early stages of oncogenesis. Blocking individual receptors are not logical therapeutic options because Wnt and growth factors are required for normal physiologic cell division and growth. The uniqueness of DAPLE (ccdc88c) lies in the fact that this happens to be working at the cross-roads of the two different classes of receptors, Wnt and growth factor RTKs, works through a defined interface (DAPLE's binding to a specific class of G proteins, activation the latter through the GEF function), enhancing two signaling cascades of uptomost importance to early tumor initiation and progression (PI3K-Akt and β-Catenin).

The invention further provides that DAPLE links to multiple cancers/tumors associated with Wnt signaling abnormalities. The invention provides the first description of a molecular interface (between DAPLE and Gi) and a detailed mechanism that only allows modulation of the aberrant signaling downstream of the signals initiated by the cross-talks between the Wnt-RTK pathways.

In one aspect, the invention provides a method for inhibiting growth, self-renewal, and/or metastatic behavior of a cancer cell comprising selectively inhibiting expression or function of the full-length isoform of DAPLE (DAPLE-fl) in said cancer cell. In one embodiment, the cancer cell is a circulating tumor cell (CTC). In one embodiment, the cancer cell is a cancer initiating stem cell (CISC). In one embodiment, the cancer cell is a metastatic cancer cell. In one embodiment, selective inhibition of expression or function of DAPLE-fl is achieved by exposing said cancer cell to an effective amount of a DAPLE-fl inhibitor. In one embodiment, the cancer cell is characterized by Wnt signaling disturbances.

In another aspect, the invention provides a method for treating a cancer in a subject in need thereof, said method comprising selectively inhibiting expression or function of the full-length isoform of DAPLE (DAPLE-fl) in cancer cells of said subject. In one embodiment, the cancer is a metastatic cancer. In a related aspect, the invention provides a method for inhibiting and/or preventing cancer metastasis and/or recurrence in a subject in need thereof, comprising selectively inhibiting expression or function of the full-length isoform of DAPLE (DAPLE-fl) in cancer cells of said subject. In one embodiment of these two methods, the expression or function of DAPLE-fl is inhibited in circulating tumor cells (CTCs). In one embodiment, the expression or function of DAPLE-fl is inhibited in cancer initiating stem cell (CISC). In one embodiment, the selective inhibition of expression or function of DAPLE-fl is achieved by exposing said cancer cells to an effective amount of a DAPLE-fl inhibitor. In one embodiment, the cancer is characterized by Wnt signaling disturbances. In one embodiment, the cancer is leukemia. In one embodiment, the cancer is selected from the group consisting of gastric cancer, small bowel cancer, colon cancer, and colorectal cancer.

In one embodiment on any of the above methods involving a DAPLE-fl inhibitor, the DAPLE-fl inhibitor interacts with a region within the unique N-terminal region of DAPLE-fl or a nucleotide sequence encoding the unique N-terminal region of DAPLE-fl which is not present in the short isoform of DAPLE (DAPLE-V2). In one specific embodiment, the DAPLE-fl inhibitor interacts with a region within amino acids 1-1476 of human DAPLE-fl (SEQ ID NO: 2) or a nucleotide sequence encoding said region. In one specific embodiment, the DAPLE-fl inhibitor is selected from the group consisting of a nucleic acid-based molecule, an antibody, a peptide, and a small molecule. In one specific embodiment, the DAPLE-fl inhibitor is selected from the group consisting of interfering RNA (RNAi) molecules, dsRNA, RNA polymerase III transcribed DNAs, and antisense nucleic acids. In one specific embodiment, said RNAi molecule is shRNA or siRNA. In one specific embodiment, said shRNA comprises a nucleic acid sequence CAGTAGAACACTCATTTGCAA (SEQ ID NO: 25) or AGGCACCTGCCTTCCTAGATT (SEQ ID NO: 26). In one specific embodiment, the DAPLE-fl inhibitor is selected from the group consisting of methods which involve the use of Clustered Regularly Interspaced Short Palindromic Repeats (CRISPR)/Cas9 gene systems, methods which involve the use of zinc finger nucleases (ZFNs), and methods which involve the use of transcription activator-like effector nucleases (TALENs). In one specific embodiment, the DAPLE-fl inhibitor is an antibody.

In another aspect, the invention provides a method for inhibiting growth, self-renewal, or tumorigenicity of a cancer cell comprising selectively increasing expression or function of the short isoform of DAPLE (DAPLE-V2) in said cancer cell. In a related aspect, the invention provides a method for inhibiting progression of an adenoma cell to a cancer cell comprising selectively increasing expression or function of the short isoform of DAPLE (DAPLE-V2) in said adenoma cell. In one embodiment of these two methods, selective increase in expression or function of DAPLE-V2 is achieved by overexpression of DAPLE-V2 in said cell. In one specific embodiment, overexpression of DAPLE-V2 is achieved by introducing in said cell an expression vector encoding DAPLE-V2. In one specific embodiment, selective increase in expression or function of DAPLE-V2 is achieved by exposing said cell to an effective amount of a DAPLE activator that selectively increases expression or function of DAPLE-V2 in said cell. In one embodiment, the cell is characterized by Wnt signaling disturbances.

In a further aspect, the invention provides a method for treating a cancer in a subject in need thereof, comprising selectively increasing expression or function of the short isoform of DAPLE (DAPLE-V2) in cancer cells of said subject. In a related aspect, the invention provides a method for inhibiting progression of an adenoma to a cancer in a subject in need thereof comprising selectively increasing expression or function of the short isoform of DAPLE (DAPLE-V2) in adenoma cells of said subject. In one embodiment of these two methods, selective increase in expression or function of DAPLE-V2 is achieved by overexpression of DAPLE-V2 in said cells. In one specific embodiment, overexpression of DAPLE-V2 is achieved by introducing in said cells an expression vector encoding DAPLE-V2. In one specific embodiment, selective increase in expression or function of DAPLE-V2 is achieved by exposing said cells to an effective amount of a DAPLE activator that selectively increases expression or function of DAPLE-V2 in said cells. In one specific embodiment, the cancer is characterized by Wnt signaling disturbances. In one specific embodiment, the cancer is leukemia. In one specific embodiment, the cancer is selected from the group consisting of gastric cancer, small bowel cancer, colon cancer, and colorectal cancer.

In one embodiment of any of the above methods involving a DAPLE activator, the DAPLE-V2 activator interacts with a region within the unique N-terminal region of DAPLE-V2 or a nucleotide sequence encoding the unique N-terminal region of DAPLE-V2 which is not present in the full-length isoform of DAPLE (DAPLE-fl). In one specific embodiment, the DAPLE-V2 activator interacts with a region within amino acids 1-5 of human DAPLE-V2 (SEQ ID NO: 23) or a nucleotide sequence encoding said region.

In a separate aspect, the invention provides a method for determining whether a subject diagnosed with an adenoma is at an increased risk for progression of said adenoma to a cancer, said method comprising: (a) determining the expression level of the short isoform of DAPLE (DAPLE-V2) in adenoma cells of the subject, (b) comparing the expression level determined in step (a) to a control level, and (c) determining that the subject is at an increased risk for progression of said adenoma to a cancer if the expression level of DAPLE-V2 isoform is decreased in adenoma cells of the subject as compared to the control level. In a related aspect, the invention provides a method for determining whether a subject diagnosed with an adenoma is at an increased risk for progression of said adenoma to a cancer, said method comprising: (a) determining the expression level of the full-length isoform of DAPLE (DAPLE-fl) and the expression level of the short isoform of DAPLE (DAPLE-V2) in adenoma cells of the subject, (b) comparing the expression levels determined in step (a) to corresponding control levels, and (c) determining that the subject is at an increased risk for progression of said adenoma to a cancer if the expression levels of both DAPLE-fl and DAPLE-V2 isoforms are decreased in adenoma cells of the subject as compared to the corresponding control levels. In one embodiment of these two methods, the control is a predetermined standard. In another embodiment, the control is the expression level of the DAPLE-fl or DAPLE-V2 in corresponding normal cells of the same tissue origin from the same subject. In one embodiment, the method further comprises one or more of the following steps: (d) detecting nuclear β-Catenin; (e) detecting KRAS gene mutation; (f) detecting BRAF gene mutation; (g) detecting Daple gene copy loss; (h) detecting p53 gene loss or mutation.

In another aspect, the invention provides a method for determining whether a subject diagnosed with a cancer is at an increased risk for metastasis and/or recurrence of said cancer, the method comprising: (a) determining an expression level of the full-length isoform of DAPLE (DAPLE-fl) in cancer cells of the subject, (b) comparing the expression level of the DAPLE-fl isoform determined in step (a) to a control level, and (c) determining that the subject is at an increased risk for metastasis and/or recurrence of said cancer if the expression level of DAPLE-fl isoform in cancer cells of the subject is increased as compared to the control level. In one embodiment, the control is a predetermined standard. In another embodiment, the control is the expression level of DAPLE-fl in the primary tumor. In one embodiment, the expression level of DAPLE-fl is determined in circulating tumor cells (CTCs) of the subject. In one embodiment, the expression level of DAPLE-fl is determined in cancer-initiating stem cells (CISCs) of the subject. In one embodiment, the method further comprises one or more of the following steps: (d) detecting nuclear β-Catenin; (e) detecting KRAS gene mutation; (f) detecting BRAF gene mutation; (g) detecting Daple gene copy loss; (h) detecting p53 gene loss or mutation.

In one embodiment of any of the above diagnostic methods, the method comprises isolating cells from the subject prior to determination of the expression level of the DAPLE isoform(s). In one embodiment of any of the above diagnostic methods, the method further comprises administering a relevant cancer treatment to the subject.

In one embodiment of any of the above methods involving subjects, the subject is human.

In another aspect, the invention provides a method for identifying an inhibitor of the full-length isoform of DAPLE (DAPLE-fl) for treatment of a cancer, comprising: (a) determining the expression level or a function of DAPLE-fl in a DAPLE-fl-expressing cancer cell, (b) contacting a candidate compound with said DAPLE-fl-expressing cancer cell, (c) determining the expression level or the function of DAPLE-fl in said cancer cell after the exposure to the compound, and (d) comparing the expression levels or functions measured in steps (a) and (c), wherein a decrease of expression level or function of DAPLE-fl, as compared with said level or function prior to the compound exposure, indicates that said agent is a DAPLE-fl inhibitor. In one embodiment, the method further comprises determining the effect of the compound on the expression level or a function of the short isoform of DAPLE (DAPLE-V2) in said cancer cell to ensure that the compound does not inhibit the expression or the function of DAPLE-V2.

In another aspect, the invention provides a method for identifying an activator of the short isoform of DAPLE (DAPLE-V2) for treatment of a cancer, comprising: (a) determining the expression level or a function of DAPLE-V2 in a DAPLE-V2-expressing cancer cell, (b) contacting a candidate compound with said DAPLE-V2-expressing cancer cell, (c) determining the expression level or the function of DAPLE-V2 in said cancer cell after the exposure to the compound, and (d) comparing the expression levels or functions measured in steps (a) and (c), wherein an increase of expression level or the function of DAPLE-V2, as compared with said level or function prior to the compound exposure, indicates that said agent is a DAPLE-V2 activator. In one embodiment, the method further comprises determining the effect of the compound on the expression level or a function of the full-length isoform of DAPLE (DAPLE-fl) in said cancer cell to ensure that the compound does not increase the expression or the function of DAPLE-fl.

In another aspect, the invention provides a pharmaceutical composition comprising a selective inhibitor of expression or a function of the full-length isoform of DAPLE (DAPLE-fl) in a cancer cell, wherein said inhibitor does not inhibit expression or a function of the short isoform of DAPLE (DAPLE-V2). In one embodiment, the DAPLE-fl inhibitor interacts with a region within the unique N-terminal region of DAPLE-fl or a nucleotide sequence encoding the unique N-terminal region of DAPLE-fl which is not present in DAPLE-V2. In one specific embodiment, the DAPLE-fl inhibitor interacts with a region within amino acids 1-1476 of human DAPLE-fl (SEQ ID NO: 2) or a nucleotide sequence encoding said region. In one embodiment, the DAPLE-fl inhibitor is selected from the group consisting of a nucleic acid-based molecule, an antibody, a peptide, and a small molecule. In one embodiment, the DAPLE-fl inhibitor is selected from the group consisting of interfering RNA (RNAi) molecules, dsRNA, RNA polymerase III transcribed DNAs, and antisense nucleic acids. In one specific embodiment, RNAi molecule is shRNA or siRNA. In one embodiment, shRNA comprises a nucleic acid sequence CAGTAGAACACTCATTTGCAA (SEQ ID NO: 25) or AGGCACCTGCCTTCCTAGATT (SEQ ID NO: 26). In one embodiment, the DAPLE-fl inhibitor is selected from the group consisting of methods which involve the use of Clustered Regularly Interspaced Short Palindromic Repeats (CRISPR)/Cas9 gene systems, methods which involve the use of zinc finger nucleases (ZFNs), and methods which involve the use of transcription activator-like effector nucleases (TALENs).

In another aspect, the invention provides a pharmaceutical composition comprising a selective activator of expression or a function of the short isoform of DAPLE (DAPLE-V2) in an adenoma or cancer cell, wherein said activator does not increase expression or a function of the full-length isoform of DAPLE (DAPLE-fl). In one embodiment, the DAPLE-V2 activator interacts with a region within the unique N-terminal region of DAPLE-V2 or a nucleotide sequence encoding the unique N-terminal region of DAPLE-V2 which is not present in DAPLE-fl. In one specific embodiment, the DAPLE-V2 activator interacts with a region within amino acids 1-5 of human DAPLE-V2 (SEQ ID NO: 23) or a nucleotide sequence encoding said region.

In a further aspect, the invention provides a vector encoding the full-length isoform of DAPLE (DAPLE-fl). In one embodiment, DAPLE-fl consists of the sequence SEQ ID NO: 2. In yet another aspect, the invention provides a vector encoding the short isoform of DAPLE (DAPLE-V2). In one embodiment, DAPLE-V2 consists of the sequence SEQ ID NO: 23. In one embodiment of any of the vectors of the invention, the DAPLE sequence is operably linked to a promoter. In one embodiment of any of the vectors of the invention, the vector is an expression vector. In one embodiment of any of the vectors of the invention, the vector is a retroviral vector or a lentiviral vector or an adenoviral vector.

These and other aspects of the present invention will be apparent to those of ordinary skill in the art in the following description, claims and drawings.

DESCRIPTION OF THE DRAWINGS

The patent or application file contains at least one drawing executed in color. Copies of this patent or patent application publication with color drawing(s) will be provided by the office upon request and payment of the necessary fee.

FIGS. 1A-1L DAPLE contains a Ga-Binding and Activating (GBA) motif. (A) Phylogenetic sequence analysis reveals a conserved motif in DAPLE similar to GIV's GBA motif within an otherwise highly divergent C-terminal domain. Sequences of GIV and DAPLE from different species were aligned and the degree of identity at each position plotted. A high degree of identity is observed in the N-terminal region (<~aa 1,400) whereas the C-terminal domain (>aa 1,400) is highly divergent. The peak of highest identity (red box) within the C-terminal domain corresponds to the GBA motif (enlarged on the right). FIG. 1A contains SEQ ID NOs: 30-43, respectively. (B) DAPLE's putative GBA motif is similar to known GBA sequences. Alignment of the putative GBA motif of DAPLE with the natural GBA sequences of GIV, Calnuc and NUCB2 and the synthetic GBA sequences of KB-752 and GSP peptides. Consensus is shown below (ψ=hydrophobic, x=any). FIG. 2A contains SEQ ID NOs: 44-49, respectively. (C) Full-length DAPLE binds to Gαi3 in cells. Equal aliquots of lysates of HEK293 cells expressing Gαi3-FLAG were incubated with anti-FLAG mAb or control IgG and protein G beads. Immune complexes were analyzed for DAPLE and Gαi3 (FLAG) by immunoblotting (IB). Gβ was monitored as positive Gαi3-binding control. (D) Purified DAPLE binds directly to inactive but not active Gαi3. Purified, recombinant GST-Gαi3 preloaded with GDP (inactive), GDP+AlF$_4^-$ (active) or GTPγS (active) and immobilized on glutathione-agarose beads was incubated with purified His-DAPLE-CT (aa 1650-2028, containing the putative GBA motif) as indicated. Resin-bound proteins were eluted, separated by SDS-PAGE and analyzed by Ponceau S-staining and immunoblotting (IB) with the indicated antibodies. No binding to GST alone was detected. (E) Full-length DAPLE expressed in cells binds preferentially to inactive versus active Gαi3. Purified, recombinant GST-Gαi3 preloaded with GDP (inactive) or GDP+AlF$_4^-$ (active) and immobilized on glutathione-agarose beads was incubated with cell lysates of Cos7 cells expressing full-length myc-DAPLE as indicated. Bound proteins were analyzed for DAPLE (myc) and Gβ by immunoblotting (IB) as in D. Binding of Gβ to inactive but not active Gαi3 was used as positive control. No binding of myc-DAPLE or Gβ to GST alone was detected. (F) DAPLE and GIV bind to Gαi3 with comparable submicromolar affinities. Insert, Purified GST-DAPLE-CT and GST-GIV (aa 1671-1755, containing the GBA motif) immobilized on glutathione-agarose beads were incubated with increasing amounts (0.01-3 μM) of purified His-Gαi3 (GDP-loaded) and binding analyzed by immunoblotting as described in (D). No binding to GST alone was detected at the highest His-Gαi3 concentration tested. Graph, Gαi3 binding was quantified by measuring band intensities and data fitted to a single-site binding hyperbola (DAPLE=BLUE, GIV=RED) to determine the equilibrium dissociation constants (Kd). Mean±S.E.M of 4 independent experiments. (G) DAPLE binds to all three Gαi subunits. Binding of His-DAPLE-CT to GST-fused Gαi1, Gαi2 or Gαi3 in the inactive or active conformations was analyzed exactly as described in (D). (H) DAPLE selectively binds to Gαi, but not Gαo. Binding of His-DAPLE-CT to GST-fused Gαi3 or Gαo in the inactive or active conformations was analyzed exactly as described in (D). (I) DAPLE binds to Gαi3 mutants that do not bind to other GBA proteins. Table summarizing the binding properties of Gαi3 K248M and W258F mutants to DAPLE (FIG. 9) and GIV or Calnuc (Garcia-Marcos et al, 2010; Garcia-Marcos et al, 2011b).

FIGS. 2A-2N. DAPLE binds and activates Gαi3 in vitro and in vivo via its GBA motif. (A) Prediction of molecular contacts critical for the DAPLE-Gαi interaction. Homology-based model of DAPLE's GBA motif (Red) bound to Gαi3 (green=Switch II, blue=ras-like domain, yellow, all-helical domain) with an enlarged section depicting a putative hydrophobic contact between DAPLE's F1675 and Gαi3's W211/F215. (B) Mutation of residues in the SWII region of Gαi3 disrupts DAPLE binding. Binding of His-DAPLE-CT to GST-Gαi3 WT, W211A or F215A was analyzed exactly as described in FIG. 1D. (C) Mutation of DAPLE F1675 to A abrogates Gαi3 binding. Binding of His-DAPLE-CT WT or F1675A (FA) to GST-Gαi3 was analyzed exactly as described in FIG. 1D. (D) F1675A mutation disrupts binding of full-length DAPLE expressed in cells to Gαi3. Myc-DAPLE WT or F1675A (FA) was expressed in Cos7 and binding to GST-Gαi3 analyzed exactly as described in FIG. 1E. (E) Binding of full-length DAPLE to Gαi3 in cells is abolished upon F1675A mutation. Lysates of Cos7 cells expressing Gαi3-FLAG and myc-DAPLE-WT or F1675A (FA) were incubated with Anti-FLAG mAb and subsequently with protein G beads. Immune complexes were analyzed for DAPLE (myc) and Gαi3 (FLAG) by immunoblotting (IB). Gβ was monitored as positive Gαi3-binding control. (F) DAPLE accelerates the rate of Gαi3 steady-state GTPase activity. The steady-state GTPase activity of His-Gαi3 alone (black) or in the presence of 2 μM His-DAPLE-CT (blue) was determined by measuring the production of [$^{32}$P]Pi at different time points as described in "Methods". One experiment representative of 3 is shown. (G) DAPLE WT but not F1675A (FA) accelerates the rate of Gαi3 steady-state GTPase activity in a dose-dependent manner. The steady-state GTPase activity of His-Gαi3 was determined in the presence of increasing concentrations (0-2 μM) of His-DAPLE-CT WT (blue) or His-DAPLE-CT FA (red) by measuring the production of [$^{32}$P]Pi at 15 min. Mean±S.E.M of 5 independent experiments. (H) DAPLE WT but not F1675A dose-dependently accelerates the rate of GTPγS binding to Gαi3. GTPγ$^{35}$S binding to His-Gαi3 at 15 min was determined in the presence of increasing concentrations (0-2 µM) of His-DAPLE-CT WT (blue) or His-DAPLE-CT FA (red). Mean±S.E.M of 4 independent experiments. (I) Schematic for the Gαi1-intYFP and Gβ1-CFP constructs used as paired FRET probes in J, K and L. (J-L) Heterotrimers of Gi1 (Gαi1 and Gβ1γ2) are dissociated at the PM in control (J, sh Luc), but not DAPLE-depleted (K, shDAPLE 1) HeLa cells after Wnt5a stimulation. Control (Left) or DAPLE-depleted (Right) HeLa cells (shDAPLE 1 described in FIGS. 10A & 10B) cotransfected with Gαi1-intYFP, Gβ1-CFP and Gγ2 were maintained overnight in 0.2% FBS and subsequently stimulated with 0.1 mg/ml Wnt5a and analyzed for FRET by confocal microscopy. Representative freeze-frame images from live-cell movies are shown, which display intensities of acceptor emission due to FRET in each pixel. Activation of Gi, as determined by the loss of interaction (i.e., FRET) between Gαi1 and Gβ1γ2 was observed exclusively after ligand stimulation (compare t0 and t5) in control (J), but not in DAPLE-depleted HeLa cells (K). (L) Bar graphs display differences between FRET intensities observed in control vs DAPLE-depleted cells in (J,K). Error bars representing mean+/−S.D. of 5 randomly chosen ROIs at the PM per cell, from 4-5 cells per experiment, from 3 independent experiments. (M) HeLa cells expressing DAPLE-WT, but not DAPLE-F1675A activate Gαi3 in response to Wnt5a stimulation, as determined by immunoprecipitation with conformationally-sensitive anti-Gαi:GTP antibodies. DAPLE-depleted HeLa cells transiently transfected with myc-DAPLE WT or F1675A (FA) were serum-starved and treated (+) or not (−) with 0.1 mg/ml Wnt5a for 20 min were subjected to immuoprecipitation with antibodies that selectively recognize active Gαi subunits in their GTP-bound state. Immune complexes (top) and lysates (bottom) were analyzed for active Gαi3:GTP and total Gαi3 by immunoblotting (IB). (N) HeLa cells expressing DAPLE-WT, but not DAPLE-F1675A inhibit cAMP in response to Wnt5a stimulation, as determined by radioimmunoassay (RIA). HeLa cells transiently transfected with myc-DAPLE WT or F1675A (FA) incubated with forskolin and PDE inhibitors for 10 min, treated (+) or not (−) with 0.1 mg/ml Wnt5a for 20 min and cAMP levels quantified as detailed in "Materials and Methods". Mean±S.D. of 3 independent experiments.

FIGS. 3A-3J. DAPLE's GBA motif triggers the release of 'free' Gβγ subunits, which in turn enhance Rac1 and PI3K-Akt signaling. (A) DAPLE's GBA motif and Gβγ subunits are predicted to dock onto an overlapping binding site on Gαi. Binding areas (in red) for DAPLE (left) or Gβγ (right) on Gαi (solid grey) were extracted from a homology-based model of DAPLE-Gαi3 and the crystal structure of the Gαi1·Gβγ complex (PBD: 1GG2), respectively. (B, C) DAPLE displaces Gβγ subunits from Gαi3 via its GEF motif. GST-Gαi3·Gβγ preformed complexes immobilized on glutathione beads were incubated with increasing concentrations of His-DAPLE-CT WT or F1675A (FA). Bound proteins were analyzed by immunoblotting (B) and Gβγ binding data fitted to a single-site competition curve (C). Mean±S.E.M. of 3 independent experiments. (D, E) Activation of Rac1 is impaired in DAPLE-depleted HeLa cells. Control (shLuc) or two clones of DAPLE-depleted HeLa cell lines (shDAPLE 1 and 2) (described in FIGS. 10A & 10B) were incubated in 2% serum media (D) or starved and treated (+) or not (β) with Wnt5a (0.1 mg/ml) for 5 min (E) and analyzed for Rac1 activation by pulldown assays using GST-PBD. (F) Activation of Rac1 is impaired in cells expressing DAPLE-F1675A (FA) mutant compared to those expressing DAPLE-WT. DAPLE-depleted (shDAPLE 1) HeLa cells transiently transfected with myc-DAPLE-WT or FA were starved and stimulated with Wnt5a and analyzed for Rac1 activation as in E. (G, H) DAPLE's GBA motif is required for activation of PI3K-Akt signaling in HeLa cells, as determined by phosphorylation of Akt at 5473. DAPLE-depleted (shDAPLE 1) HeLa cells transiently transfected with myc-DAPLE WT or F1675A (FA) were incubated in a 2% serum media (G) or in a 0.2% serum media overnight and treated (+) or not (−) with 0.1 mg/ml Wnt5a for 5 min (H) prior to lysis. Equal aliquots of whole cell lysates were analyzed for Akt phosphorylation (pAkt S473) by immunoblotting (IB). (I,J) Inhibition of Gβγ signaling impairs DAPLE-dependent activation of Rac1 and Akt. DAPLE-depleted (shDAPLE 1) HeLa cells transiently transfected with myc-DAPLE WT were treated with DMSO, 10 µM of the Gβγ inhibitor gallein or its inactive analog fluorescein for 6 h, as indicated, and analyzed for Rac1 (I) or Akt (J) activation by immunoblotting or pulldown assays, respectively.

FIGS. 4A-4L. The C-terminus of DAPLE directly binds ligand-activated Frizzled receptors (FZDRs) and triggers the assembly of FZDR-Gαi complexes at the PM. (A) DAPLE and Gαi3 coimmunoprecipitate with FZD7R after Wnt5a stimulation. HeLa cells cotransfected with myc-DAPLE WT and HA-FZD7 were starved and stimulated with Wnt5a as in 3G. Equal aliquots of lysates (bottom) were then incubated with Anti-HA mAb and subsequently with protein G beads. Immune complexes (top) were analyzed for myc (myc-DAPLE) and endogenous Gαi3 by immunoblotting (IB). (B) DAPLE is recruited to the plasma membrane after Wnt5a stimulation, where it colocalizes with FZD7R. HEK293 cells expressing FZD7-CFP were grown on coverslips coated with Poly-D-Lysine, starved for 24 h (0% FBS) and treated with 0.1 mg/ml Wnt5a as in 4A. Cells were fixed and stained for DAPLE and analyzed by confocal microscopy. (C) The C-terminal region (1650-2028 aa) is sufficient for DAPLE to bind FZD7R. Lysates of Cos7 cells expressing full-lenght myc-DAPLE-WT or myc-DAPLE-CT (1650-2028 aa) were incubated with recombinant GST-FZD7-CT immobilized on glutathione-agarose beads in pulldown assays. Bound DAPLE (myc) was analyzed by immunoblotting (IB). (D) DAPLE directly binds FZD7R and the extreme C-terminus (1881-2028) is essential for the interaction. His-DAPLE-CT (1650-2028 aa) or a shorter fragment of DAPLE-CT (1650-1880 aa) was incubated in pulldown assays with immobilized GST-FZD7-CT exactly as above. Bound DAPLE-CT (His) was analyzed by immunoblotting (IB). (E) DAPLE's GBA motif is required for enhanced binding of Gαi3 to cytoplasmic tails of FZD7R in vitro. His-Gαi3 preloaded with GDP was incubated with immobilized GST-FZD7-CT, either alone (lane 2) or in the presence of His-DAPLE-CT (1650-2028 aa) WT (lane 3) or FA (lane 4) in pulldown assays as described in D. Bound Gαi3 and DAPLE-CT were detected by immunoblotting (IB). (F) DAPLE's GBA motif is essential for the coimmunoprecipitation of Gαi3 with ligand-activated FZD7Rs. HeLa cells cotransfected with HA-FZD7 and myc-DAPLE-WT or FA were starved and subsequently stimulated with Wnt5a prior to lysis as in A. Equal aliquots of lysates (bottom) were incubated with anti-HA antibodies, and subsequently with protein G beads. Immune complexes were analyzed for the presence of Gαi3 by immunoblotting (IB). (G-I) Wnt5a stimulates formation of FZD7R-Gαi3 complexes at the PM in HEK293T cells. (G) Schematic of the FRET probes used in H. (H) HEK293 cells were cotransfected with FZD7-CFP and Gαi3-YFP, starved and subsequently stimulated with Wnt5a and analyzed for FRET using confocal microscopy. Image panels display CFP, YFP and intensities of acceptor emission due to FRET in each pixel. FRET was observed after Wnt5a stimulation (right). (I) Bar graphs display FRET efficiency observed at the PM in starved vs Wnt5a stimulated cells in H. Error bars represent mean±S.D. The analysis represents 5 randomly chosen ROIs at the PM per cell, from 4-5 cells per experiment, from 3 independent experiments. (J,K) DAPLE's GBA motif is essential for the assembly of FZD7R-Gαi3 complexes at the PM. HEK293T cells were cotransfected with FZD7-CFP, Gαi3-YFP and myc-DAPLE (WT or FA), starved, and subsequently stimulated with Wnt5a prior to fixation. Fixed cells were stained for DAPLE (632 nm, see FIGS. 12A-12C) and analyzed for FRET using confocal microscope. Image panels display the intensities of acceptor emission due to FRET in each pixel. FRET was observed in cells expressing DAPLE-WT, but not in cells expressing DAPLE-FA. (K) Bar graphs display the FRET efficacy observed in DAPLE WT vs DAPLE FA cells before (−) and after (+) Wnt5a stimulation. Error bars representing mean±S.D. The analysis was done exactly as in H, I. (L) Schematic summary. Upon stimulation with Wnt5a, DAPLE's C-terminus enables the formation of FZD7R-DAPLE-Gαi3 complexes at the PM. Two distinct interaction modules present in-tandem within the C-terminus of DAPLE, the GBA motif and the FZD-binding domain are essential for the formation of such complexes.

FIGS. 5A-5M. DAPLE competes with Dv1 for binding to FZD7R and inhibits the canonical β-catenin/TCF/LEF signaling pathway via the GBA motif. (A) Dv1-DAPLE complexes are disrupted upon Wnt5a stimulation. HeLa cells cotransfected with myc-DAPLE-WT and Dv1 were incubated in a 0.2% serum media overnight, and treated (+) or not (−) with 0.1 mg/ml Wnt5a for 5 min prior to lysis. Equal aliquots of lysates (bottom) were incubated in the presence of anti-Dv1 mAb, and subsequently with protein G beads. Immune complexes (top) were analyzed for DAPLE (myc), Dv1 and Gαi3 by immunoblotting (IB). (B) Dv1 and DAPLE compete for recruitment to FZD7 receptor in cells. Equal aliquots of lysates of HEK293 cells cotransfected with FZD7-HA with Dv1 and/or myc-DAPLE-WT were incubated with anti-HA mAb and subsequently with protein G beads. Immune complexes were analyzed for DAPLE and Dv1 by immunoblotting (IB). (C) DAPLE can displace Dv1 bound to the cytoplasmic tail of FZD7R in vitro. Dv1 expressed in HEK cells was pre-bound to GST or GST-FZD7CT, and subsequently incubated with increasing amounts of recombinant His-DAPLE-CT proteins as indicated. Bound proteins were analyzed for DAPLE (His) and Dv1 by immunoblotting (IB). (D) DAPLE is required for the ligand-stimulated dissociation of Dv1 from the PM. Control (sh Luc) and DAPLE-depleted (sh DAPLE 1) Hela cells coexpressing Dv1 and FZD7R were starved and stimulated with Wnt5a prior to fixation as in 4B. Fixed cells were stained for Dv1 (green) and nucleus (DAPI; blue) and analyzed by confocal microsocpy. Bar=10 μM. (E) Gαi competes with Dv1 for binding to DAPLE in vitro. Equal aliquots of GST or GST-Dv1-PDZ (immobilized on glutathione beads) and DAPLE-CT (WT or FA) recombinant proteins were incubated with increasing amounts of purified His-Gαi3 as indicated. Bound (top) and unbound (supernatant; lower) proteins were analyzed for DAPLE-CT and Gαi3 (His) by immunoblotting (IB). GST and GST-Dv1-PDZ was visualized by ponceau staining. (F) Depletion of DAPLE increases the levels of β-catenin. Whole cell lysates of control (shLuc) and DAPLE-depleted (shDAPLE 1 and 2) HeLa cells were analyzed for β-catenin by immunoblotting (IB). (G) Bar graphs display quantification of β-catenin in F. Error bars represent mean±S.D of 3 independent experiments. (H) DAPLE's GBA motif is required for suppression of β-catenin expression/stability. Whole cell lysates from HeLa cells transfected with myc-DAPLE-WT or FA were analyzed for β-catenin expression by immunoblotting (IB). Two biological replicates are shown. (I) Bar graphs display quantification of β-catenin in H. Error bars represent mean±S.D of 3 independent experiments. (J,K,L) DAPLE's GBA motif is required for suppression of Wnt target genes. HeLa cells transfected with myc-DAPLE-WT or FA were analyzed for SFRP-1, OPN, AXIN-2 mRNA by qPCR. Results were normalized internally to mRNA levels of the housekeeping gene, GAPDH. Bar graphs display the fold change in each RNA (Y axis) in cells expressing DAPLE-FA normalized to the expression in cells expressing DAPLE-WT. Error bars represent mean±S.D of 3 independent experiments. (M) Schematic of working model. (From left to right) In the absence of Wnt5a ligand, Dv1 remains at the PM complexed to inactive Frizzled receptors (FZD7R), whereas DAPLE remains in the cytosol in complex with cytosolic Dv1, and Gαi/βγ trimers at the PM are largely inactive. Upon ligand stimulation, Dv1-DAPLE complexes dissociate and DAPLE is recruited to the cytoplasmic tails of activated receptors, Dv1 is displaced from the receptor tail by DAPLE, DAPLE favors the assembly of receptor-Gαi complexes and triggers the activation of Gαi within these complexes. Activated Gαi and Gβγ subunits trigger signaling via their respective downstream intermediates (Rac1, PI3K and cAMP). Another major consequence of these signaling events is suppression of the canonical β-catenin/TCF/LEF signaling pathway which regulates the transcription of Wnt target genes.

FIGS. 6A-6E. DAPLE enhances cell migration and invasion via its GBA motif. (A) DAPLE WT, but not FA triggers chemotactic migration towards Wnt5a. DAPLE-depleted HeLa cells (sh DAPLE 1) stably expressing DAPLE-WT or DAPLE-FA were analyzed for their ability to migrate towards Wnt5a (+) or vehicle control (−) in transwell assays. Cells were allowed to migrate for 24 h, fixed and stained with Giemsa. The number of migrating cells was averaged from 20 field-of view images per experiment. Data are presented as mean±SEM; n=3. HPF=high power field. Lysates of cells used in this assay were analyzed for DAPLE expression by immunoblotting (IB; see FIG. 15C). (B, C) DAPLE WT, but not FA triggers cell invasion. Spheroids (S) of NIH3T3 cells expressing vector control, myc-DAPLE-WT or FA were analyzed for their ability to invade matrigel in response to serum stimulation using a Cultrex-3D Spheroid Invasion Kit (Trevigen). An increase of invading cells (arrowheads; B) was noted only from the edge of tumor spheroids formed by cells expressing myc-DAPLE-WT, but not FA. Area of invasion was quantified using ImageJ (as shown with interrupted line in FIG. 15D). (C) Bar graphs display area of invasion observed in DAPLE WT and DAPLE FA expressing cells. Error bars representing mean±S.D of 3 independent experiments. (D,E) DAPLE-WT, but not DAPLE-FA enhances the expression of genes that trigger EMT. mRNA expression of the EMT markers, LOXL3 and Vimentin were analyzed by qPCR. Results were normalized internally to mRNA levels of the housekeeping gene, GAPDH. Bar graphs display the fold changes in each RNA (Y axis) normalized to the expression in cells expressing vector control. Error bars represent mean±S.E.M of 3 independent experiments.

FIGS. 7A-7I. DAPLE suppresses proliferation and tumorigenesis via its GBA motif. (A) DAPLE's GBA motif is required for inhibition of cell transformation induced by oncogenic KRas. NIH3T3 cells stably expressing HA-KRas G12V alone, or coexpressing HA-KRas G12V with myc-DAPLE-WT or various mutants were analyzed for their ability to form colonies in soft agar prior to staining with MTT. The top panel displays representative images of colony-containing plates. Bar graphs in the lower panel shows % inhibition of colony formation (Y axis) by each DAPLE construct compared to NIH3T3 cells transformed with KRas G12V alone. Lysates of NIH3T3 cells were analyzed for DAPLE and Ras constructs by immunoblotting (IB; see FIG. 16B). (B) DAPLE is required for inhibition of anchorage-dependent tumor growth by Wnt5a. Control (shLuc) and DAPLE-depleted (sh DAPLE 1) HeLa cells were analyzed for their ability to form colonies on plastic plates in the presence (+) or absence (−) of Wnt5a during a 2 week period prior to fixation and staining with crystal violet. Left panel shows the photograph of the crystal violet-stained wells of a 6-well plate. The number of colonies was counted by ImageJ (Colony counter). Right panel shows bar graphs that display the % inhibition of colony formation (Y axis) seen in each condition normalized to control (shLuc) HeLa cells. (C) DAPLE's GBA motif is required for inhibition of anchorage-dependent tumor growth by Wnt5a. DAPLE-depleted (sh DAPLE 1) HeLa cells stably expressing either DAPLE WT or FA were analyzed for their ability to form colonies on plastic plates in the presence (+) or absence (−) of Wnt5a prior to fixation and staining with crystal violet, photographed and analyzed as in B. Left panel shows the photograph of the crystal violet-stained wells of a 6-well plate. Right panel shows bar graphs that display the % inhibition of colony formation (Y axis) seen in each condition normalized to control (shLuc) HeLa cells. (D-F) DAPLE's GBA motif is required for inhibition of anchorage-independent tumor growth. DLD1 cells expressing either control vector or various myc-DAPLE constructs were analyzed for their ability to form colonies in soft agar for 2-3 weeks. In panel D representative fields photographed at 20× magnification are shown. The number of colonies was counted by light microscopy throughout the depth of the matrix in 15 randomly chosen fields. In panel E bar graphs display the number of colonies (Y axis) seen in each cell line in D. In panel F lysates of DLD1 cells used in D were analyzed for DAPLE constructs by immunoblotting (IB). (G,H) DAPLE's GBA motif is required for inhibition of anchorage-dependent tumor growth. DLD1 cells used in D were analyzed for their ability to form adherent colonies on plastic plates during 2-3 weeks prior to fixation and staining with crystal violet. In panel G photograph of the crystal violet-stained E-well plate is displayed. The number of colonies was counted by ImageJ (Colony counter). In panel H bar graphs display the % inhibition of colony formation (Y axis) seen in each cell line in G normalized to control DLD1 cells. (I) Schematic summary. Modulation of G protein activity by DAPLE's GBA motif is a key determinant of cellular phenotype(s) triggered by Wnt5a. In cells expressing DAPLE-WT, a functionally intact GBA motif (+) can activate Gαi, enhance PM-based motogenic signals (PI3K-Akt and Rac1 activation), trigger EMT and cell migration/invasion. In cells expression DAPLE-FA, without the functional GBA motif (−) G protein remains inactive, non-canonical Wnt signaling is suppressed, which increases stability of β-catenin and upregulation of Wnt target genes, resulting in increased transformation, proliferation and tumor cell growth.

FIGS. 8A-8L. Expression of DAPLE mRNA is suppressed during oncogenesis by copy number loss, but expressed later during metastasis. (A) DAPLE mRNA is downregulated in colorectal cancers. A meta-analysis was performed using all the available high-throughput microarray data from Genomic Spatial Event (GSE) database (see Table 1) to compare the levels of expression of DAPLE mRNA in colorectal cancer vs matched normal controls. Bar graphs display the results of such meta-analysis as fold change in DAPLE mRNA (Y axis) in colorectal carcinomas normalized to matched normal controls. (B) DAPLE mRNA is downregulated during the adenoma-to-carcinoma step of oncogenesis in the colon. DAPLE mRNA was analyzed by qPCR in normal colon, advanced adenomas and colorectal carcinomas. Bar graphs display the relative levels of DAPLE mRNA normalized to GAPDH, as determined by the calculation 2-ΔCT with reference to an absolute baseline CT of 40 cycles. Error bars represent mean±S.D. (C) DAPLE mRNA is downregulated in microsatellite stable (MSS), but not microsatellite unstable (MSI) colorectal cancers. A meta-analysis was performed using all the available high-throughput microarray data from Genomic Spatial Event (GSE) database (see Table 2) to compare the levels of expression of DAPLE mRNA in MSI vs MSS colorectal cancers vs their respective matched normal controls. Bar graphs display the results of such meta-analysis as fold change in DAPLE mRNA (Y axis) in colorectal carcinomas normalized to normal controls. (D) Downregulation in DAPLE mRNA in microsatellite stable (MSS) colorectal cancers directly correlates with the degree of chromosomal instability (CIN) in the tumor. High-throughput microarray data from Genomic Spatial Event (GSE) database (PMID: 22547595, GSE: 30540) was analyzed for the levels of expression of DAPLE mRNA in MSS colorectal cancers (stages II and III) with varying degrees of chromosomal instability [CIN-low (LOH ratio <33%) and CIN-high (LOH ratio ≥33%)] and compared to MSI tumors. Bar graphs display the results of such analysis as fold change in DAPLE mRNA (Y axis) in CIN-low or CIN-high colorectal carcinomas compared to MSI tumors. (E) Downregulation of DAPLE mRNA in the primary tumor early during cancer progression prognosticates tumor recurrence/metastasis. High-throughput microarray data from Genomic Spatial Event (GSE) database (PMID: 22917480, GSE: 37892) was analyzed for the levels of expression of DAPLE mRNA in 130 stage II microsatellite stable (MSS) tumors without (No Mets) or with (Mets) tumor recurrence/metastatic progression. (F) Loss of copy number for CCDC88C (DAPLE gene) occurs at the late stages of adenoma-to-carcinoma progression. Array CGH (comparative genomic hybridization) data from Genomic Spatial Event (GSE) database was analyzed for ccdc88c copy number variations (CNVs) in 41 progressed adenomas (i.e., adenomas that present a focus of cancer). Progressed adenomas were analyzed for CNVs relative to ploidy level in the DNA in laser-microdissected adenoma and carcinoma fractions and compared to adjacent normal epithelial fractions as matched controls. (G) Cell-free mRNA transcripts of DAPLE is detected in patients with colorectal cancer, but not in normal control subjects. Microarray data from Genomic Spatial Event (GSE) database (PMID: 18843029, GSE: 10715) was analyzed for DAPLE mRNA expression in peripheral blood samples of healthy subjects (n=11) and of 121 patients with early (Dukes A, B) or late (Duke's C, D) stages of colorectal cancer. (H) Levels of DAPLE mRNA are frequently elevated in EpCAM (epithelial cell adhesion molecule) immunoisolated circulating tumor cells (CTCs) from patients with metastatic colorectal cancer, compared to normal subjects. Immunoisolated CTC fractions from the peripheral blood of 51 patients with metastatic (stage IV) colorectal cancer or from healthy subjects were analyzed for DAPLE mRNA by Taqman qPCR and adjusted for leukocyte contaminants by normalizing to CD45. Scatter-plots display the level of DAPLE expression in each patient within each group. A normality test confirmed that datasets in both groups were distributed normally. No significant differences were observed in the CD45 levels between two groups (not shown). (I, J) High levels of DAPLE mRNA expression in CTCs is associated with poorer progression-free (PFS; I) and overall (OS; J) survival in patients with metastatic colorectal carcinoma. Optimal cut-off values for DAPLE mRNA expression were statistically derived (see detailed "Materials and Methods") to generate subgroups of patients with high or low expression levels. Time-dependent survival probabilities were estimated with the Kaplan-Meier method, and the log-rank test was used to compare the subgroups. (K) Schematic summarizing profile of DAPLE expression during oncogenic progression in the colon. Degree of up- (green) or downregulation (red) in DAPLE mRNA is indicated by increasing shades of each color during the normal-to-adenoma-to-carcinoma progression in the colon is shown. (L) Proposed model for how a bimodal dysregulation of tumor suppressor DAPLE, and resultant deregulation of non-canonical Wnt signaling may propel oncogenic progression in the colon. DAPLE's ability to modulate G proteins via its GBA motif exerts a potent tumor suppressive effect in the normal mucosa. Early during oncogenesis (top, from left to right), downregulation of DAPLE (marked by 'X') occurs at the step of adenoma to cancer conversion, in part by DNA copy loss (bottom) due to focal deletion affecting the long arm of Chr 14. Consequently, low expression of DAPLE mRNA and protein triggers transformation and tumor growth/progression. Later during cancer invasion, expression of DAPLE is triggered via unknown mechanisms, which favors (arrow) tumor recurrence and prognosticates poor survival.

FIGS. 10A-10E. Binding of DAPLE to Gαi triggers activation of Gi at the PM after Wnt5a stimulation. (A, B) DAPLE competes for binding to Gαi3 with peptides/proteins that dock onto the switchII/α3 cleft of the G protein. (A) Purified, recombinant GST-Gαi3 preloaded with GDP and immobilized on glutathione-agarose beads (~0.3 mM) was incubated with a fixed concentration (~0.2 mM) of purified His-DAPLE-CT (aa 1650-2028) in the presence of the indicated concentrations of KB-752 or a control peptide. Resin-bound proteins were eluted, separated by SDS-PAGE and analyzed by Ponceau S-staining and immunoblotting (IB) with anti-His antibodies. No binding to GST alone was detected. One experiment representative of 3 is shown. (B) Analogous experiments to those described in A were carried out using His-GIV-CT WT and His-GIV-CT F1685A (as negative control) instead of peptides. (C-E) DAPLE is essential for activation of trimeric Gi at the plasma membrane after Wnt5a stimulation. (C, D) Two independent shRNA sequences targeting the 3' UTR of the gene efficiently (<90%) depletes DAPLE mRNA (A) and protein (B) from HeLa cells. The knock-down efficiency was assessed by comparing DAPLE mRNA by qPCR (C) or protein by immunoblotting (IB) (D) on HeLa cells stably expressing two DAPLE-targeting (shDAPLE 1 and shDAPLE 2) or control (shLuc) shRNA sequences. (E) Control (Luc shRNA) or DAPLE-depleted (DAPLE shRNA1) HeLa cells co-transfected with Gαi1-YFP, Gβ1-CFP and Gγ2 were starved overnight in media containing 0.2% FBS prior to stimulation with Wnt5a and analyzed for FRET using confocal microscope. Representative freeze-frame images from live-cell movies are shown, which display acceptor (Gαi1-YFP), donor (Gβ1-CFP) and intensities of acceptor emission due to FRET in each pixel (from left to right). Activation of Gi, as determined by the loss of interaction (i.e., FRET efficiency) between Gαi1-YFP and Gβ1-CFP is observed at the PM exclusively after ligand stimulation (compare t0 and t5) in Luc shRNA treated control cells, but not in DAPLE-depleted cells. Red circle=Region of interest (ROI) at the PM.

FIG. 20A-O. DAPLE-V2 is a potent suppressor of the β-Catenin/TCF/LEF pathway and tumor growth, but has no effect on EMT or cell invasion. (A-B) Monolayers of DLD1 7TGP cell lines stably expressing vector control, DAPLE-fl-WT or DAPLE-V2 WT or FA were starved and stimulated with Wnt5a. Images display representative fields analyzed by fluorescence microscopy. The intensity of eGFP signals denote Wnt transcriptional activity. In A, compared to DLD1 cells expressing vector control, both DAPLE-fl-WT and DAPLE-V2-WT showed inhibition of eGFP; inhibition with DAPLE-V2 was more robust. In B, DAPLE-V2-WT, but not DAPLE-V2-FA inhibited eGFP. Immunoblots (IB) of equal aliquots of whole cell lysates of DLD1-7TGP cells expressing control vector, DAPLE-V2-WT or DAPLE-V2-FA are displayed in FIG. 2-figure supplement 1A. (E-H) DLD1 cells stably expressing vector control, or DAPLE-fl-WT, or DAPLE-V2 WT or FA mutant were analyzed for their ability to form adherent colonies on plastic plates during 2-3 weeks prior to fixation and staining with crystal violet. In panels E and G photographs of a representative well of the crystal violet-stained 6-well plates are displayed. The number of colonies was counted by ImageJ (Colony counter). In panels F and H bar graphs display the # of colonies per well (Y axis) seen in each cell line in E and G, respectively. Panels E-F show that both DAPLE-fl and V2 can inhibit tumor growth; the latter is more efficient that the former. Panels G-H show that the GBA motif of DAPLE-V2 is required for inhibition of anchorage-dependent tumor growth observed in E-F. (C-D) HeLa cells transfected with myc-DAPLE constructs as indicated were analyzed for AXIN-2 and SFRP-1 mRNA by qPCR. Results were normalized internally to mRNA levels of the housekeeping gene, GAPDH. Bar graphs display the fold change in each RNA (Y axis) normalized to the expression in cells expressing control vector. Error bars represent mean±S.D of 3 independent experiments. As shown in the case of DAPLE-fl previously (Aznar et al., eLife 2015), DAPLE-V2's GBA motif is required for suppression of Wnt target genes. (I-J) mRNA expression of the EMT markers LOX-L3 and Vimentin were analyzed by qPCR. Results were normalized internally to mRNA levels of the housekeeping gene, GAPDH. Bar graphs display the fold change in each RNA (Y axis) normalized to the expression in cells expressing vector control. Error bars represent mean±S.E.M of 3 independent experiments. DAPLE-fl, but not DAPLE-V2 enhances the expression of genes that trigger EMT, and such enhancement requires an intact GBA motif (K-L) Spheroids (S) of NIH3T3 cells expressing WT or FA mutant of myc-DAPLE-fl or V2 isoform were analyzed for their ability to invade matrigel in response to Wnt5a using a Cultrex-3D Spheroid Invasion Kit (Trevigen). Representative images of spheroid edges are displayed (K). An increase of invasion tracks (arrowheads) were noted only from the edge of tumor spheroids formed by cells expressing myc-DAPLE-fl-WT, but not FA. Neither the WT nor the FA mutant of DAPLE-V2 could trigger invasion. Area of invasion was quantified using ImageJ and displayed as bar graphs (L). Error bars representing mean±S.D of 3 independent experiments. (M-N) Paired samples from non-invasive center and the invasive edges of colorectal cancers were analyzed for DAPLE-fl (M) and DAPLE-V2(N) expression by qPCR. Bar graph displays the relative abundance of DAPLE expression (Y axis). DAPLE-fl, but not DAPLE-V2 is increased in the invading margins of tumors compared to the non-invasive tumor cores. Error bars represent mean±S.D. n=13. (O) Schematic summarizing the effect of the newly discovered GBA motif in DAPLE-fl and DAPLE-V2 on tumor growth and tumor invasion. The GBA motif of DAPLE-fl inhibits tumor growth and enhances tumor invasion, whereas the GBA motif of DAPLE-V2 exclusively inhibits tumor growth. Red lines=Inhibition. Green lines=Enhancement. The thickness of the lines depicts the relative strength of phenotypes.

FIG. 23A-N. The full length (DAPLE-fl) and short (DAPLE-V2) isoforms of DAPLE cooperatively suppress cell proliferation and their low expression in stage II colorectal cancers carries a worse prognosis. (A-C) HeLa cells depleted of DAPLE (sh1DAPLE) stably expressing either DAPLE-fl alone, or DAPLE-V2 alone or both were analyzed for DAPLE expression by immunoblotting (A) and rate of cell proliferation assays (B, C). Graphs display the rates of proliferation of various HeLa-GIV cell lines, as determined by cell counting (B) and cell viability assays (C). Results are presented as mean±S.E.M; n=3. p<0.01; *p<0.001. (D) Paired colorectal tumors and their adjacent normal tissue were analyzed for relative expression of DAPLE isoforms by qPCR. Bar graph displays the relative abundance of DAPLE expression (Y axis). Error bars represent mean±S.D. (E) 173 stage II colorectal cancers with known K-Ras mutant status were analyzed for levels of expression of DAPLE-fl and V2 mRNA by by Taqman qPCR and normalized to GAPDH. Optimal cut-off values for DAPLE mRNA expression were statistically derived (see detailed "Materials and Methods") to generate subgroups of patients with high or low expression levels. The number of tumors with or without mutant K-Ras that had either low or high expression of DAPLE isoforms are tabulated in FIG. 3-source data 1. Bar graphs display the incidence (expressed as %) of K-Ras mutation (Y axis) when either DAPLE isoforms are either high or low. Red and blue colors indicate whether the tumors harbored oncogenic mutant or WT copy of K-Ras, respectively. The incidence of mutation is displayed on the top of each bar. Tumors with low DAPLE-V2 had a significant chance that they also harbor mutant K-Ras. No such relationship was seen between levels of expression of DAPLE-fl and mutant K-Ras. (F-H) Bar graphs display the incidence of distant metastasis (as %; Y axis) in stage II colorectal cancers with either low or high levels of expression of DAPLE-fl alone (F), or DAPLE-V2 alone (G), or both DAPLE isoforms were (H). (I-N) Kaplan-Meier plot of recurrence-free (RFS) and disease-specific (DSS) survival curves of patients with stage II colorectal cancer are stratified by their levels of expression of DAPLE-fl alone (I-J), or DAPLE-V2 alone (K-L), or both DAPLE isoforms (M-N). In the RFS curves, cancers with low DAPLE-V2 alone exhibited decreased recurrence-free survival (K; significant by Log-Rank test). Although a similar trend was seen also in the case of DAPLE-fl (I), significance was not reached. Cancers with low levels of both isoforms exhibited decreased recurrence (M) with higher significance than each isoform alone. In the DSS curves, cancers with low DAPLE-fl alone or DAPLE-V2 alone exhibited decreased disease specific survival (J, L; significant by Log-Rank test). Cancers with low levels of both isoforms exhibited decreased survival (N) with higher significance than each isoform alone.

FIG. 23A-B. Tumors with high proliferative index, as determined by Ki67 staining, were more likely than not to also have low levels of DAPLE-V2. 173 stage II colorectal cancers with known Ki67 index were analyzed for levels of expression of DAPLE-fl mRNA (A) and DAPLE-V2 (B) mRNA by qPCR. The number of tumors with low or high Ki67 index that had either low or high expression of DAPLE isoforms are tabulated in Table 4. Bar graphs display the incidence (expressed as %) of high Ki67 index (Y axis) when either DAPLE isoforms are either high or low. Red and blue indicated whether the tumors had high or low Ki67 index, respectively. The incidence of high Ki67 index is displayed on the top of each bar. Tumors with low DAPLE-V2 had a significant chance that they had a higher Ki67 index. No such relationship was seen between levels of expression of DAPLE-fl and Ki67 index.

FIG. 24A-I. DAPLE-fl, but not DAPLE-V2, is elevated in circulating tumor cells (CTCs) and its high expression carries a worse prognosis. (A-B) EpCAM (epithelial cell adhesion molecule)-immunoisolated CTC fractions from the peripheral blood of patients with metastatic colorectal cancer (stage IV CRC) or from healthy subjects were analyzed for DAPLE-fl (A) or DAPLE-V2 (B) mRNA by Taqman qPCR and adjusted for leukocyte contaminants by normalizing to CD45. Bar graph displays the level of DAPLE expression in each cohort. A normality test confirmed that datasets in both groups were distributed normally. No significant differences were observed in the CD45 levels between two groups (not shown). Compared to normal subjects, levels of DAPLE-fl (A), but not DAPLE-V2 (B) mRNA is frequently elevated in CTCs from patients with metastatic colorectal cancer. (C-H) Optimal cut-off values for DAPLE mRNA expression were statistically derived (see detailed "Materials and Methods") to generate subgroups of patients with high or low expression levels. Time-dependent progression-free (PFS) and overall (OS) survival probabilities were estimated with the Kaplan-Meier method, and the log-rank test was used to compare the subgroups. High levels of DAPLE-fl mRNA expression in CTCs was associated with poorer progression-free (PFS; C), disease specific (DSS; D) and overall (OS; E) survival in patients with metastatic colorectal carcinoma. High levels of DAPLE-V2 expression in CTCs was associated with poorer PFS (F), but had no effect on DSS (G) or OS (H). (I) Schematic summarizing profile of expression of DAPLE-fl and V2 isoforms during cancer initiation and metastatic progression in the colon. Upper: Various steps and histopathological stages of colorectal cancer progression is shown. Major genetic mutations/deletions of key genes that herald the step-wise progression is indicated. Lower: Changes in the profile of expression of both DAPLE isoforms (DAPLE V2=green; DAPLE-fl=purple) and their relationship to the previously identified patterns of non-canonical Wnt signaling (gray) is shown. The known profiles of other major parameters commonly used in the determination of histologic grade of tumors is also shown.

DETAILED DESCRIPTION OF THE INVENTION

Figure 2L:
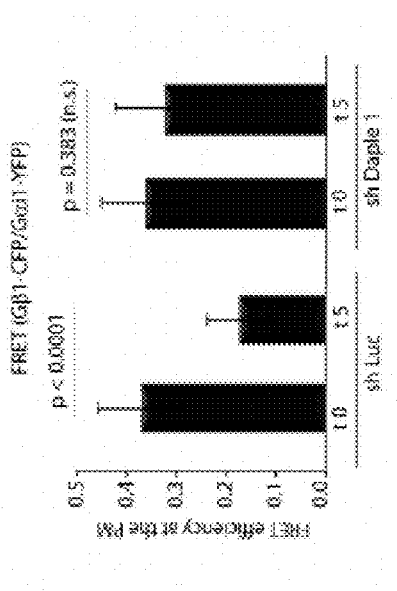
Figure 2K:
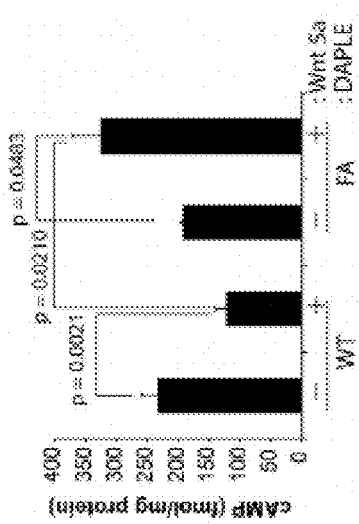
Figure 2K:
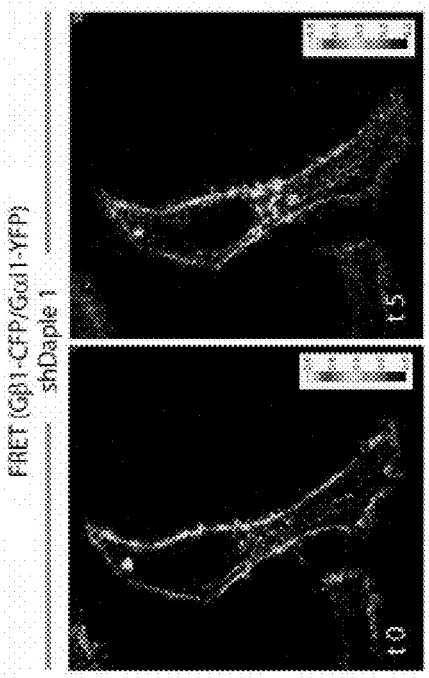

Wnt signaling is essential for tissue homeostasis and its dysregulation causes cancer. Wnt ligands trigger signaling by activating Frizzled receptors (FZDRs), which belong to the G-protein coupled receptor superfamily. However, the mechanisms of G protein activation in Wnt signaling remain controversial. The invention provides that FZDRs activate G proteins and trigger non-canonical Wnt signaling via the Dishevelled binding protein, DAPLE. DAPLE contains a Gα-Binding and Activating (GBA) motif which activates Gαi proteins and an adjacent domain that directly binds FZDRs, thereby linking Wnt stimulation to G protein activation. This triggers non-canonical Wnt responses, i.e., suppresses the β-catenin/TCF/LEF pathway and tumorigenesis, but enhances PI3K-Akt and Rac1 signals and tumor cell invasiveness. In colorectal cancers, DAPLE is suppressed during adenoma-to-carcinoma transformation, and expressed later in metastasized tumor cells. Thus, DAPLE activates Gαi and enhances non-canonical Wnt signaling by FZDRs, and its dysregulation can impact both tumor initiation and progression to metastasis.

Definitions

As used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

Throughout this description, various components may be identified having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

As used herein, the term "combination" of a DAPLE inhibitor or activator and at least a second pharmaceutically active ingredient means at least two, but any desired combination of compounds can be delivered simultaneously or sequentially (e.g., within a 24 hour period). It is contemplated that when used to treat various diseases, the compositions and methods of the present invention can be utilized with other therapeutic methods/agents suitable for the same or similar diseases. Such other therapeutic methods/agents can be co-administered (simultaneously or sequentially) to generate additive or synergistic effects. Suitable therapeutically effective dosages for each agent may be lowered due to the additive action or synergy.

Figure 19:
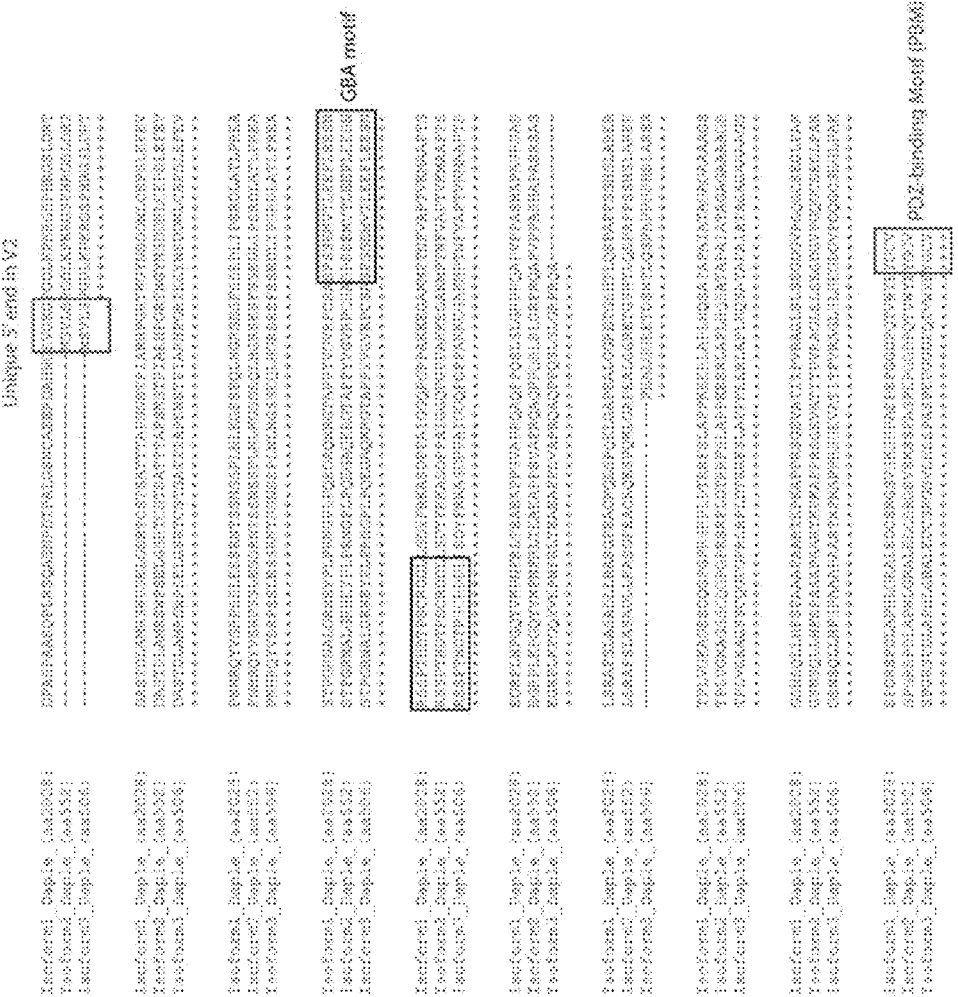
FIG. 19. Sequence alignment of the three isoforms, DAPLE-fl (SEQ ID NO: 2), DAPLE-V2 (SEQ ID NO: 23) and DAPLE-V2'(SEQ ID NO: 24), is displayed. Red Box=Unique residues at the 5' end of DAPLE-V2. Blue Box=GBA motif identified previously (Aznar et al., eLife 2015). Green Box=PDZ-binding motif (PBM) that was reported earlier (Oshita A et al., Genes Cells, 2003).

As used herewith, the term "DAPLE" refers to the Dishevelled binding protein DAPLE. The C-terminal region of DAPLE contains a Gα-Binding and Activating (GBA) motif which activates Gαi proteins, an adjacent domain that directly binds FZDRs, and a motif involved in binding of the PDZ domain of Dishevelled. The N-terminal region contains a coiled-coil domain, also referred to as a HOOK domain, which mediates DNA binding. There are three isoforms of human DAPLE as shown in FIG. 19, which differ in the length of the N-terminal region; only the first two isoforms (2028 and 552 amino acids in length) have been confirmed scheme from DAPLE-fl) in the C-terminus of both DAPLE-fl and DAPLE-V2 and is set forth in SEQ ID NO: 28. The sequence of the minimal PDZ-binding domain (PBM) of human DAPLE is YGCV, located at amino acids 2025 to 2028 (using the numbering scheme from DAPLE-fl) in the C-terminus of both DAPLE-fl and DAPLE-V2 and is set forth in SEQ ID NO: 29. The N-terminus of DAPLE-fl contains the HOOK and coiled-coil domains. The HOOK domain DNA and protein sequence corresponds to amino acids 1-246 of human DAPLE-fl (accession # UniProtKB/Swiss-Prot: Q9P219.3). The coiled-coil domain DNA and protein sequence corresponds to amino acids 247-1393 of human DAPLE-fl (accession # UniProtKB/Swiss-Prot: Q9P219.3).

Further details on the three isoforms of hDAPLE are as follows:

| Name | Transcript ID | Size (bp) | Protein | Biotype | CCDS | UniProt | RefSeq |
|---|---|---|---|---|---|---|---|
| CCDC88C-001 DAPLE-fl | ENST00000389857 | 7474 | 2028aa (~230-250 kDa) | Protein coding | CCDS45151 | Q9P219 | NM_001080414 NP_001073883 |
| CCDC88C-201 DAPLE-V2 | — | 3242 | 552aa (~60 kDa) 1-1476: missing from RefSeq. 1477-1481: SVGKG (SEQ ID NO: 2) -> MSVLS (SEQ ID NO: 23) | Protein coding | — | Q9P219-2 | — |
| CCDC88C-202 DAPLE-V2' | ENST00000331194 | 3104 | 506aa (~55 kDa) 1-1476 and 1786-1831: missing from RefSeq. 1477-1481: SVGKG (SEQ ID NO: 2) -> MSVLS (SEQ ID NO: 24) | Protein coding | — | A0A0A0MR69 | — | to exist in humans, while the third (506 amino acids in length, "DAPLE-V2'") is a hypothetical isoform. The sequence of the full length human isoform ("DAPLE-fl" or "full length isoform") is set forth in SEQ ID NOs: 1 and 2. The sequence of the confirmed human short isoform DAPLE-V2 is set forth in SEQ ID NO: 23. The sequence of the hypothetical human DAPLE-V2' is set forth in SEQ ID NO: 24. The third isoform predicted to exist differs only by a few more amino acid stretches missing from the DAPLE-V2 sequence. Both short isoforms, DAPLE-V2 and DAPLE-V2', have a unique 5' end (see FIG. 19). This sequence allows the short form, DAPLE-V2, to be targeted and distinguished from the long full length isoform of DAPLE (DAPLE-fl).

Figure 18A:
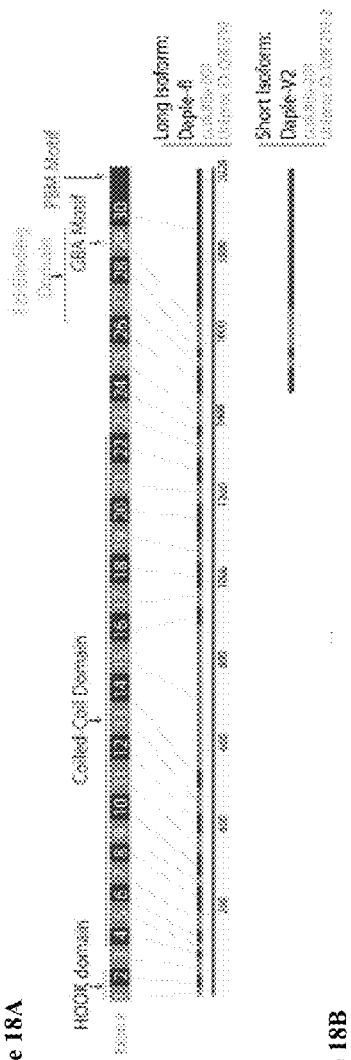
FIG. 18A-H. Identification and characterization of a short isoform of CCDC88C (DAPLE) that contains minimal C-terminal modules to bind trimeric Gαi, Dv1 and Frizzled receptor. (A) Schematic showing the distribution of exons in the long ("DAPLE-fl") and short isoforms of DAPLE (the more prevalent short isoform is referred to as "DAPLE-V2"). The various modules of DAPLE-fl reported thus far and the corresponding exons are indicated on the top. Names of the RNA transcript and encoded protein are indicated on the right. (B) Schematic comparing the domain distribution of DAPLE-fl and the shorter isoform DAPLE-V2. (C) RNA isolated from 14 normal colon samples were analyzed for copy numbers of full length (fl) or short (V2) isoform of DAPLE. Relative expression (Y axis) of both isoforms are displayed as bar graphs. (D) Whole cell lysates of colonic epithelial from normal subjects were analyzed for DAPLE, Gαi3 and tubulin by immunoblotting (IB). Both full length (fl) and short isoform (V2) were detected. (E) Purified, recombinant GST-Gαi3 preloaded with GDP and immobilized on glutathione-agarose beads was incubated with cell lysates of Cos7 cells (input) expressing myc-DAPLE-V2 WT or F194A (FA) as indicated. Bound proteins were analyzed for DAPLE-V2 (myc) and Gβ by immunoblotting (IB). Equal loading of GST-tagged proteins were confirmed by Ponceau S staining. F194A mutation disrupts binding of DAPLE-V2 to Gαi3. (F) Purified, recombinant GST-tagged PDZ domain of Dv1 immobilized on glutathione-agarose beads was incubated with cell lysates of Cos7 cells (input) expressing myc-DAPLE-V2 WT or delta PBM (ΔPBM) as indicated. Bound proteins were analyzed for DAPLE-V2 (myc) by immunoblotting (IB). Equal loading of GST-tagged proteins were confirmed by Ponceau S staining. Deletion of the C-terminal PDZ-binding motif disrupts binding of DAPLE-V2 to PDZ domain of Dv1. (G) Purified, recombinant GST-tagged carboxy terminus of FZD7R (Fzl7-CT) immobilized on glutathione-agarose beads was incubated with cell lysates of Cos7 cells (input) expressing myc-DAPLE-V2 WT, FA or delta PBM (ΔPBM) as indicated. Bound proteins were analyzed for DAPLE-V2 (myc) by immunoblotting (IB). Equal loading of GST-tagged proteins were confirmed by Ponceau S staining. WT and mutants of DAPLE-V2 bound similarly to FZD7R. (H) Schematic of C-terminus of DAPLE-fl interacting with Gαi via the GBA motif.
Figure 18B:
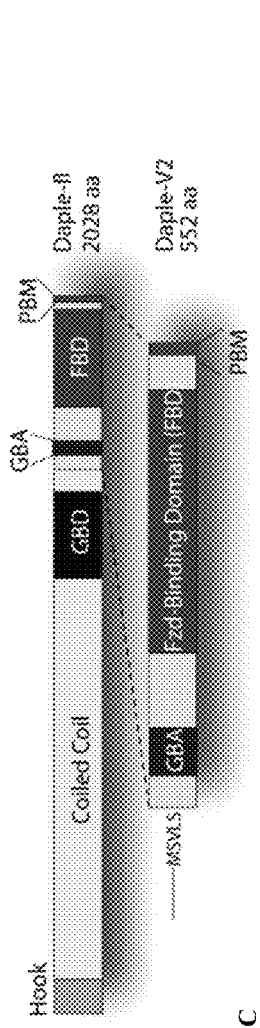
Figure 18D:
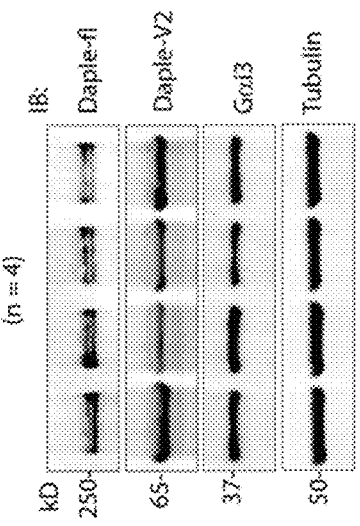
Figure 18C:
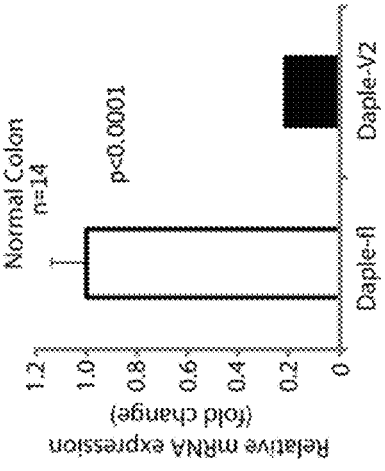
Figure 18E:
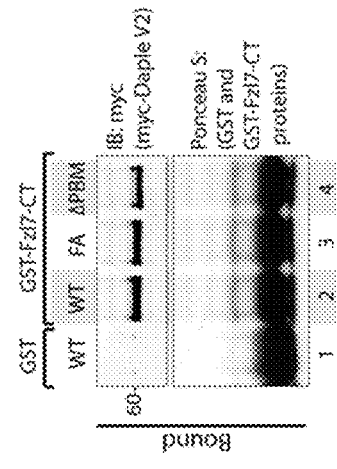
Figure 18F:
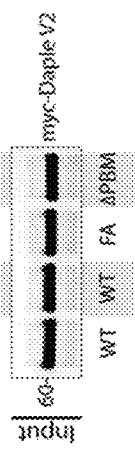
Figure 18G:
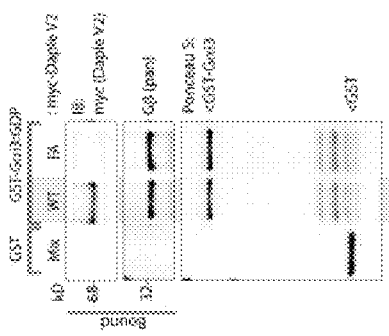
Figure 18H:
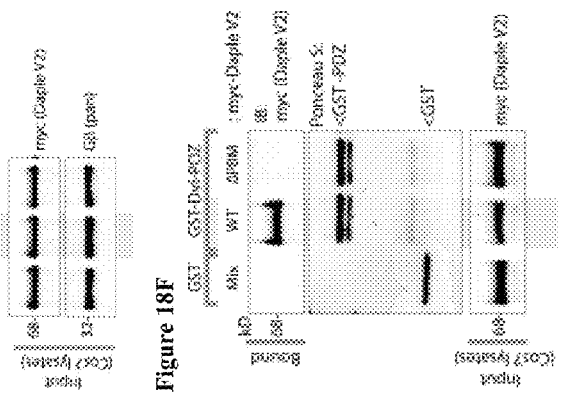

The sequence of the minimal GBA motif of the human DAPLE is SPSSEMVTLEEFLEESNRSSPTHDTP-SCRDDL, located at amino acids 1664 to 1685 (using the numbering scheme from DAPLE-fl) in the C-terminus of both DAPLE-fl and DAPLE-V2 and is set forth in SEQ ID NO: 27. The sequence of the minimal FZDR-binding domain of the human DAPLE is LDTRRFSLAPPKEER-LAPLHQSATAPAIATAGAGAAAAGSGSNSQLLH FSPAAAPAARTKPKAPPRSGEVATIT-PVRAGLSLSEGDGVPGQGCSEGLPAKSPGRSPDL APHLGRALEDCSRGSVSKSSPASPEPGGDPQTVWYE, located at amino acids 1881 to 2024 (using the numbering As shown in FIGS. 18A-B and FIG. 19, the N-terminal region (aa 1-1476) is unique to human Daple-fl. Further, the short stretch of 5 aa (MSVLS) (SEQ ID NO: 23) is unique to DAPLE-V2 (and DAPLE-V2'). This information is critical for designing si/shRNA/CRISPR selectively targeting one, but not the other isoform. Specifically, shRNA targeting human DAPLE-fl but not DAPLE-V2 or DAPLE-V2' includes shDaple1: CAGTAGAACACTCATTTGCAA (SEQ ID NO: 25) and shDaple2: AGGCACCTGCCTTC-CTAGATT (SEQ ID NO: 26).

Further, the timing of loss of DAPLE expression (as measured by mRNA analyses) is different between the two isoforms of DAPLE. A significant correlation between low Daple-V2 expression and mutant K-RAS status has been found. However, no such correlation was seen in the case of Daple-fl. Daple-fl is lost at the stage of adenoma to carcinoma progression, which coincides with the loss of p53. Daple-fl is subsequently overexpressed in circulating tumor cells, which correlates with increased propensity for tumor metastasis and cancer progression.

The terms "cell growth" and "growth of a cell" refer to the ability of a cell (e.g., a cancer cell) to (i) grow (i.e., to increase in cytoplasmic and organelle volume (G1 phase) and/or to increase in genetic material (G2 phase) following the replication during S phase) and (ii) divide to produce two "daughter cells" (M phase).

The term "self-renewal" refers to the ability of a cell (e.g., a cancer cell) to go through cycles of cell division while maintaining the undifferentiated state.

The term "tumorigenicity" refers to the ability of a cancer cell to produce tumors (e.g., as determined by using inoculation of NOD. SCID mice, or athymic (nude) mice/rats, or newborn mice/rats treated with either irradiation or anti-thymocyte globulin).

As used herein, the term "antibody" encompasses immunoglobulins of different classes (i.e., IgA, IgG, IgM, IgD, and IgE) and subclasses (such as IgG1, IgG2 etc.) and includes, without limitation, chimeric antibodies, single-domain antibodies (sdAb, Nanobody), single chain antibodies, humanized antibodies, antibody fragments (e.g., Fab, F(ab')$_2$, Fv, scFv fragments), single domain antibodies, single variable domain antibodies, immunoglobulin single variable domain (e.g., comprising merely one variable domain $V_H$ or $V_L$ or larger polypeptides that comprise one or more monomers of an antibody single variable domain polypeptide sequence), monoclonal antibodies, polyclonal antibodies, multispecific antibodies (e.g., bispecific antibodies). As used herein, the term "bispecific antibody" denotes a single polypeptide chain comprising two binding domains.

In the context of the present invention insofar as it relates to any of the disease conditions recited herein, the terms "treat", "treatment", and the like mean to relieve or alleviate at least one symptom associated with such condition, or to slow or reverse the progression of such condition, or to arrest, delay the onset (i.e., the period prior to clinical manifestation of a disease) and/or reduce the risk of developing or worsening a disease (e.g., a cancer characterized by Wnt signaling disturbances, such as for example and not limitation, ovarian cancer, leukemias, lymphomas, melanomas, blood cancers, and gut cancers, e.g., gastric, small bowel, colon and colorectal).

As used herein the term "therapeutically effective" applied to dose or amount refers to that quantity of a compound or pharmaceutical composition that is sufficient to result in a desired activity upon administration to a subject in need thereof. Note that when a combination of active ingredients is administered (e.g., a combination of two or more inhibitors of DAPLE-fl) the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M J. Gait ed. 1984); *Nucleic Acid Hybridization* (B. D. Hames & S. J. Higgins eds. 1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

Methods of the Invention

In one aspect, the invention provides a method for inhibiting growth, self-renewal, and/or metastatic behavior of a cancer cell (e.g., a cancer cell characterized by Wnt signaling disturbances, such as for example and not limitation, an ovarian cancer cell, a leukemia cell (e.g., myeloid/lymphoid neoplasms), a lymphoma cell, a melanoma cell, blood cancer cells, and gastrointestinal cancer cells, e.g., gastric, small bowel, colon, and colorectal cancer cells) comprising selectively inhibiting expression or function of the full length isoform of DAPLE (DAPLE-fl) in said cancer cell. In one embodiment, such cancer cell is a circulating tumor cell (CTC). In one specific embodiment, such cancer cell is a cancer initiating stem cell (CISC). In one embodiment, such cancer cell is a metastatic cancer cell. In one embodiment, selective inhibition of expression or function of DAPLE-fl is achieved by exposing said cancer cell to an effective amount of a DAPLE-fl inhibitor. In one specific embodiment, the DAPLE-fl inhibitor interacts with a region within the unique N-terminal region of DAPLE-fl (or a corresponding nucleotide sequence) which is not present in the short isoform of DAPLE (DAPLE-V2).

In another aspect, the invention provides a method for treating a cancer (e.g., a cancer characterized by Wnt signaling disturbances, such as for example and not limitation, ovarian cancer, leukemias (e.g., myeloid/lymphoid neoplasms), lymphomas, melanomas, blood cancers, and gastrointestinal cancers, e.g., gastric, small bowel, colon, and colorectal cancers) in a subject in need thereof, said method comprising selectively inhibiting expression or function of the full length isoform of DAPLE (DAPLE-fl) in cancer cells of said subject. In one embodiment, such cancer is a metastatic cancer. In a related aspect, the invention provides a method for inhibiting and/or preventing cancer metastasis and/or recurrence (e.g., a cancer characterized by Wnt signaling disturbances, such as for example and not limitation, ovarian cancer, leukemias (e.g., myeloid/lymphoid neoplasms), lymphomas, melanomas, blood cancers, and gastrointestinal cancers, e.g., gastric, small bowel, colon, and colorectal cancers) in a subject in need thereof, comprising selectively inhibiting expression or function of the full length isoform of DAPLE (DAPLE-fl) in cancer cells of said subject. In one embodiment, expression or function of DAPLE-fl is inhibited in circulating tumor cells (CTCs). In one specific embodiment, expression or function of DAPLE-fl is inhibited in cancer initiating stem cell (CISC). In one embodiment, selective inhibition of expression or function of DAPLE-fl is achieved by exposing said cancer cells to an effective amount of a DAPLE-fl inhibitor. In one specific embodiment, the DAPLE-fl inhibitor interacts with a region within the unique N-terminal region of DAPLE-fl (or a corresponding nucleotide sequence) which is not present in the short isoform of DAPLE (DAPLE-V2).

In another aspect, the invention provides a method for inhibiting growth, self-renewal, or tumorigenicity of a cancer cell (e.g., a cancer cell characterized by Wnt signaling disturbances, such as for example and not limitation, an ovarian cancer cell, a leukemia cell (e.g., myeloid/lymphoid neoplasms), a lymphoma cell, a melanoma cell, blood cancer cells, and gastrointestinal cancer cells, e.g., gastric, small bowel, colon, and colorectal cancer cells) comprising selectively increasing expression or function of the short isoform of DAPLE (DAPLE-V2) in said cancer cell. In a related aspect, the invention provides a method for inhibiting progression of an adenoma cell to a cancer cell comprising selectively increasing expression or function of the short isoform of DAPLE (DAPLE-V2) in said adenoma cell. In one embodiment, selective increase in expression or function of DAPLE-V2 is achieved by overexpression of DAPLE-V2 in said cell. Such overexpression may be achieved, for example and not limitation, by using any conventional expression vector that is used for gene therapy (e.g., a lentiviral vector, an adenoviral vector, etc.). In another embodiment, selective increase in expression or function of DAPLE-V2 is achieved by exposing said cell to an effective amount of a DAPLE activator that selectively increases expression or function of DAPLE-V2 in said cell.

In another aspect, the invention provides a method for treating a cancer (e.g., a cancer characterized by Wnt signaling disturbances, such as for example and not limitation, ovarian cancer, leukemias (e.g., myeloid/lymphoid neoplasms), lymphomas, melanomas, blood cancers, and gut cancers, e.g., gastric, small bowel, colon and colorectal cancers) in a subject in need thereof, comprising selectively increasing expression or function of the short isoform of DAPLE (DAPLE-V2) in cancer cells of said subject. In a related aspect, the invention provides a method for inhibiting progression of an adenoma to a cancer in a subject in need thereof comprising selectively increasing expression or function of the short isoform of DAPLE (DAPLE-V2) in adenoma cells of said subject. In one embodiment, selective increase in expression or function of DAPLE-V2 is achieved by overexpression of DAPLE-V2 in said adenoma and/or cancer cells. Such overexpression may be achieved, for example and not limitation, by using any conventional expression vector that is used for gene therapy (e.g., a lentiviral vector, an adenoviral vector, etc.). In another embodiment, selective increase in expression or function of DAPLE-V2 is achieved by exposing said adenoma and/or cancer cells to an effective amount of a DAPLE activator that selectively increases expression or function of DAPLE-V2 in said cell.

In any of the above embodiments, the DAPLE-fl inhibitor and/or DAPLE-V2 activator may be administered in a pharmaceutical composition, alone or in combination with one or more other active ingredient(s) and further with one or more pharmaceutically acceptable carriers and/or excipients.

In certain embodiments of any of the methods of the invention, the full length isoform of DAPLE [NBCI Reference Sequence NM_001080414.3 (mRNA) (SEQ ID NO: 1) and NP_001073883.2 (protein); SEQ ID NO: 2)] is selectively inhibited. In certain embodiments of any of the methods of the invention, the inhibitor of the full length isoform of DAPLE is an interfering RNA (RNAi) molecule (e.g., a shRNA molecule), a small molecule inhibitor, or an antibody specific for the full length isoform of DAPLE as described in more detail herein. In certain embodiments of any of the methods of the invention, the cancer cells are cancer cells characterized by Wnt signaling disturbances, including ovarian cancer cells, leukemia cancer cells (e.g., myeloid/lymphoid neoplasms), lymphoma cancer cells, melanoma cells, blood cancers, and gut cancer cells, e.g., gastric, small bowel, colon and colorectal cancer cells. In certain embodiments of any of the methods of the invention, the subject is human, and/or an experimental animal model.

In certain embodiments, the RNAi molecules are delivered by a suitable viral vector, such as for example and not limitation, by lentiviral or adenoviral vectors (e.g., pSico Puro vector and the pLKO system).

In any of the above embodiments, the DAPLE-fl inhibitor and/or DAPLE-V2 activator may be administered in a pharmaceutical composition, alone or in combination with one another, and further with one or more pharmaceutically acceptable ingredients (such as for example and not limitation, a carrier, another cancer therapeutic).

DAPLE-fl inhibitors useful in the methods of the invention include, without limitation, small molecules and biologics (e.g., antibodies, peptides, nucleic acid-based inhibitors) which are described in more detail below. Such inhibitors can be delivered to tumors via any delivery method known in the art, including, without limitation, systemic delivery (e.g., intravenous, intramuscular, oral, intranasal, by inhalation, sublingual, mucosal, etc.), direct injection within tumors (e.g., via intraoperative injection within the tumor or in the walls of the resection cavity by the surgeon; or stereotactic implantation of catheters within the tumor, followed by convection-enhanced delivery (CED) of a DAPLE inhibitor), superselective intra-arterial infusion of a DAPLE inhibitor within the vascular territory of the tumor (e.g., through an endovascular catheter), and viral vector delivery for nucleic acid-based inhibitors (e.g., using lentiviral vectors, which by virtue of a modified envelope, selectively infect or transduce CD133+ cancer cells, see Bayin et al., 2014, PlosOne, DOI:10,1371/Journal.pone.0116114; or retroviral replicating vectors, see Huang et al., 2013, Cancer Gene Ther. 20:544-551).

DAPLE-fl inhibitors may also include Dishevelled regulators, now known or later discovered, as it has been shown herein that DAPLE acts via interaction with Dishevelled. DAPLE-fl inhibitors may also include other regulators of the Wnt signaling pathway, such as for example and not limitation, nuclear beta Catenin, K-Ras, BRAF, and p53, now known or later discovered.

It is also contemplated herein that more than one inhibitor of DAPLE-fl can be used, and/or such one or more inhibitor(s) can be further combined with other therapeutic agents and/or therapies suitable for treatment of cancers, including, for example, cancers characterized by Wnt signaling disturbances, including ovarian cancer, leukemias (e.g., myeloid/lymphoid neoplasms), lymphomas, melanomas, blood cancers, and gut cancers, e.g., gastric, small bowel, colon and colorectal cancers. Two or more active agents may be co-administered to generate additive or synergistic effects. Suitable therapeutically effective dosages for each agent may be lowered due to the additive action or synergy. In certain embodiments, the use of DAPLE-fl inhibitors can be combined with, e.g., radiation therapy, surgery, chemotherapy (e.g., temozolamide, VEGF inhibitors [such as, e.g., bevacizumab/Avastin], Cilengitide, rindopepimut and other EGFR modulators, nitrosoureas [such as, e.g., lomustine, carmustine/BCNU, CCNU], tyrosine kinase inhibitors), immune cell therapy (e.g., autologous, genetically engineered T-cells and/or dendritic cells [DCs]), cancer vaccines (e.g., cellular- or peptide-based), oncolytic viruses (e.g., Ad-RTS-IL-12), Stupp protocol (radiation+temozolamide), alternating electric field therapy (e.g., NovoTTF), etc.

Another method of inhibiting DAPLE-fl expression comprises reducing the copy number of DAPLE-fl in genomic DNA of target cells. For example and not limitation, the copy number may be reduced by gene depletion of DAPLE-fl by methods commonly known in the art, such as for example and not limitation, by CRISPR/Cas-9 systems.

It is also contemplated herein that more than one activator of DAPLE-V2 can be used, and/or such one or more activator(s) can be further combined with other therapeutic agents and/or therapies suitable for treatment of cancers, including, for example, cancers characterized by Wnt signaling disturbances, including ovarian cancer, leukemias (e.g., myeloid/lymphoid neoplasms), lymphomas, melanomas, blood cancers, blood cancers, and gut cancers, e.g., gastric, small bowel, colon and colorectal cancers. Two or more active agents may be co-administered to generate additive or synergistic effects. Suitable therapeutically effective dosages for each agent may be lowered due to the additive action or synergy. In certain embodiments, the use of DAPLE-V2 activators can be combined with, e.g., radiation therapy, surgery, chemotherapy (e.g., temozolamide, VEGF inhibitors [such as, e.g., bevacizumab/Avastin], Cilengitide, rindopepimut and other EGFR modulators, nitrosoureas [such as, e.g., lomustine, carmustine/BCNU, CCNU], tyrosine kinase inhibitors), immune cell therapy (e.g., autologous, genetically engineered T-cells and/or dendritic cells [DCs]), cancer vaccines (e.g., cellular- or peptide-based), oncolytic viruses (e.g., Ad-RTS-IL-12), Stupp protocol (radiation+temozolamide), alternating electric field therapy (e.g., NovoTTF), etc.

Another method of activating DAPLE-fl expression comprises increasing the copy number of DAPLE-V2 in genomic DNA of target cells. For example and not limitation, the copy number may be increased by gene duplication of DAPLE-V2 by methods commonly known in the art, such as for example and not limitation, by CRISPR/Cas-9 systems.

Inhibitors of DAPLE-fl

In conjunction with the above methods, the present invention provides inhibitors of DAPLE-fl expression or function, which include, but are not limited to, biologics (e.g., nucleic acid-based inhibitors, peptides, antibodies) and small molecules.

Inhibitors of DAPLE-fl Expression

Non-limiting examples of inhibitors of DAPLE-fl expression include interfering RNA molecules (e.g., shRNA or siRNA), dsRNA, RNA polymerase III transcribed DNAs, antisense nucleic acids, and genome editing methods such as, e.g., methods which involve the use of Clustered Regularly Interspaced Short Palindromic Repeats (CRISPR)/Cas9 gene systems, methods which involve the use of zinc finger nucleases (ZFNs), methods which involve the use of transcription activator-like effector nucleases (TALENs), as well as methods which involve the use of any other nucleases that can cause DNA breaks or bind to DNA.

RNA interference (RNAi) is a process of sequence-specific post-transcriptional gene silencing by which double stranded RNA (dsRNA) homologous to a target locus can specifically inactivate gene function (Hammond et al., Nature Genet. 2001; 2:110-119; Sharp, Genes Dev. 1999; 13:139-141). This dsRNA-induced gene silencing is mediated by short double-stranded small interfering RNAs (siRNAs) generated from longer dsRNAs by ribonuclease III cleavage (Bernstein et al., Nature 2001; 409:363-366 and Elbashir et al., Genes Dev. 2001; 15:188-200). RNAi-mediated gene silencing is thought to occur via sequence-specific RNA degradation, where sequence specificity is determined by the interaction of an siRNA with its complementary sequence within a target RNA (see, e.g., Tuschl, Chem. Biochem. 2001; 2:239-245). RNAi can be activated by introduction of siRNAs (Elbashir, et al., Nature 2001; 411: 494-498) or short hairpin RNAs (shRNAs) bearing a fold back stem-loop structure (Paddison et al., Genes Dev. 2002; 16: 948-958; Sui et al., Proc. Natl. Acad. Sci. USA 2002; 99:5515-5520; Brummelkamp et al., Science 2002; 296:550-553; Paul et al., Nature Biotechnol. 2002; 20:505-508).

shRNA/siRNA comprises a double stranded structure typically containing 15 to 50 base pairs and preferably 21 to 25 base pairs and having a nucleotide sequence identical or nearly identical to an expressed target gene or RNA within the cell. The siRNA/shRNA inhibitors of the present invention are preferably short double stranded nucleic acid duplexes (or stem-loop structures in case of shRNA) comprising annealed complementary single stranded nucleic acid molecules. However, the invention also encompasses embodiments in which the siRNAs comprise an annealed RNA:DNA duplex, wherein the sense strand of the duplex is a DNA molecule and the antisense strand of the duplex is a RNA molecule. In some embodiments, duplexed siRNAs have a 2 or 3 nucleotide 3' overhang on each strand of the duplex. In some embodiments, siRNAs/shRNAs have 5'-phosphate and 3'-hydroxyl groups.

According to the present invention, siRNAs may be introduced to a target cell as an annealed duplex siRNA, or as single stranded sense and antisense nucleic acid sequences that, once within the target cell, anneal to form the siRNA duplex. Alternatively, the sense and antisense strands of the siRNA may be encoded on an expression construct that is introduced to the target cell. Upon expression within the target cell, the transcribed sense and antisense strands may anneal to reconstitute the siRNA. 100% sequence complementarity between the siRNA and the target nucleic acid is not required to practice the invention. Expression of shRNA in cells can be obtained by delivery of plasmids or through viral or bacterial vectors. A variety of viral vectors can be used to obtain shRNA expression in cells including adeno-associated viruses (AAVs), adenoviruses, retroviruses, and lentiviruses.

Two main isoforms of human DAPLE exist: long (DAPLE-fl) and short (DAPLE-V2). The long or full length isoform contains a coiled-coil binding domain in the N-terminal region. The short isoform DAPLE-V2 does not contain the coiled-coil binding domain (a putative third short isoform, DAPLE-V2', also does not contain the coiled-coil binding domain). As discussed herein, there is an amino acid difference between the two isoforms (see also FIG. 19). Therefore, the two isoforms can be distinguished by inhibitors specific for the two different N-terminal (or 5') ends of the isoforms, on both the nucleic acid and protein levels.

The two main human DAPLE isoforms are DAPLE-fl and DAPLE-V2:

SEQ ID NO: 2 (NCBI Reference Sequence NP_001073883.2)—DAPLE Full length isoform

MDVTVSELLELFLQSPLVTWVKTFGPFGSGSQDNLTMYMDLVDGIFLNQI

MLQIDPRPTNQRINKHVNNDVNLRIQNLTILVRNIKTYYQEVLQQLIVMN

LPNVLMIGRDPLSGKSMEEIKKVLLLVLGCAVQCERKEEFIERIKQLDIE

TQAGIVAHIQEVTHNQENVFDLQWLELPDVAPEELEALSRSMVLHLRRLI

DQRDECTELIVDLTQERDYLQAQHPPSPIKSSSADSTPSPTSSLSSEDKQ

HLAVELADTKARLRRVRQELEDKTEQLVDTRHEVDQLVLELQKVKQENIQ

-continued

LAADARSARAYRDELDSLREKANRVERLELELTRCKEKLHDVDFYKARME

ELREDNIILIETKAMLEEQLTAARARGDKVHELEKENLQLKSKLHDLELD

RDTDKKRIEELLEENMVLEIAQKQSMNESAHLGWELEQLSKNADLSDASR

KSFVFELNECASSRILKLEKENQSLQSTIQGLRDASLVLEESGLKCGELE

KENHQLSKKIEKLQTQLEREKQSNQDLETLSEELIREKEQLQSDMETLKA

DKARQIKDLEQEKDHLNRAMWSLRERSQVSSEARMKDVEKENKALHQTVT

EANGKLSQLEFEKRQLHRDLEQAKEKGERAEKLERELQRLQEENGRLARK

VTSLETATEKVEALEHESQGLQLENRTLRKSLDTLQNVSLQLEGLERDNK

QLDAENLELRRLVETMRFTSTKLAQMERENQQLEREKEELRKNVDLLKAL

GKKSERLELSYQSVSAENLRLQQSLESSSHKTQTLESELGELEAERQALR

RDLEALRLANAQLEGAEKDRKALEQEVAQLEKDKKLLEKEAKRLWQQVEL

KDAVLDDSTAKLSAVEKESRALDKELARCRDAAGKLKELEKDNRDLTKQV

TVHARTLTTLREDLVLEKLKSQQLSSELDKLSQELEKVGLNRELLLQEDD

SGSDTKYKILEGRNESALKTTLAMKEEKIVLLEAQMEEKASLNRQLESEL

QMLKKECETLRQNQGEGQHLQNSFKHPAGKTAASHQGKEAWGPGHKEATM

ELLRVKDRAIELERNNAALQAEKQLLKEQLQHLETQNVTFSSQILTLQKQ

SAFLQEHNTTLQTQTAKLQVENSTLSSQSAALTAQYTLLQNHHTAKETEN

ESLQRQQEQLTAAYEALLQDHEHLGTLHERQSAEYEALIRQHSCLKTLHR

NLELEHKELGERHGDMLKRKAELEEREKVLTTEREALQQEQRTNALAMGE

NQRLRGELDRVNFLHHQLKGEYEELHAHTKELKTSLNNAQLELNRWQARF

DELKEQHQTMDISLTKLDNHCELLSRLKGNLEEENHHLLSQIQLLSQQNQ

MLLEQNMENKEQYHEEQKQYIDKLNALRRHKEKLEEKIMDQYKFYDPPPK

KKNHWIGAKALVKLIKPKKEGSRERLKSTVDSPPWQLESSDPASPAASQP

LRSQAENPDTPALGSNCAEERDAHNGSVGKGPGDLKPKRGSPHRGSLDRT

DASTDLAMRSWPSELGSRTCSTSATTTAPSNSTPIARHPGRTKGYNSDDN

LCEPSLEFEVPNHRQYVSRPSSLESSRNTSSNSSPLNLKGSSEQLHGRSE

SFSSEDLIPSRDLATLPREASTPGRNALGRHEYPLPRNGPLPQEGAQKRG

TAPPYVGVRPCSASPSSEMVTLEEFLEESNRSSPTHDTPSCRDDLLSDYF

RKASDPPAIGGQPGPPAKKEGAKMPTNFVAPTVKMAAPTSEGRPLKPGQY

VKPNFRLTEAEAPPSVAPRQAQPPQSLSLGRPRQAPVPPASHAPASRSAS

LSRAFSLASADLLRASGPEACKQESPQKLGAPEALGGRETGSHTLQSPAP

PSSHSLARERTPLVGKAGSSCQGPGPRSRPLDTRRFSLAPPKEERLAPLH

QSATAPAIATAGAGAAAAGSGSNSQLLHFSPAAAPAARTKPKAPPRSGEV

ATITPVRAGLSLSEGDGVPGQGCSEGLPAKSPGRSPDLAPHLGRALEDCS

RGSVSKSSPASPEPGGDPQTVWYEYGCV

SEQ ID NO: 23—DAPLE short isoform DAPLE-V2:

MSVLSPGDLKPKRGSPHRGSLDRTDASTDLAMRSWPSELGSRTCSTSATT

TAPSNSTPIARHPGRTKGYNSDDNLCEPSLEFEVPNHRQYVSRPSSLESS

RNTSSNSSPLNLKGSSEQLHGRSESFSSEDLIPSRDLATLPREASTPGRN

-continued

ALGRHEYPLPRNGPLPQEGAQKRGTAPPYVGVRPCSASPSSEMVTLEEFL

EESNRSSPTHDTPSCRDDLLSDYFRKASDPPAIGGQPGPPAKKEGAKMPT

NFVAPTVKMAAPTSEGRPLKPGQYVKPNFRLTEAEAPPSVAPRQAQPPQS

LSLGRPRQAPVPPASHAPASRSASLSRAFSLASADLLRASGPEACKQESP

QKLGAPEALGGRETGSHTLQSPAPPSSHSLARERTPLVGKAGSSCQGPGP

RSRPLDTRRFSLAPPKEERLAPLHQSATAPAIATAGAGAAAAGSGSNSQL

LHFSPAAAPAARTKPKAPPRSGEVATITPVRAGLSLSEGDGVPGQGCSEG

LPAKSPGRSPDLAPHLGRALEDCSRGSVSKSSPASPEPGGDPQTVWYEYG

CV

The sequence of the full length isoform differs from the short isoform as discussed herein.

In one specific embodiment, four shRNA DAPLE inhibitors are provided, which are capable of binding to both DAPLE-fl and DAPLE-V2: hDAPLEsh1 forward: 5' TGTAGAACACTCATTTGCAATTCAAGAGATTGCAAATGAGTGTTCTACTTTTTTC (SEQ ID NO: 5); hDAPLEsh1 reverse: 5' TCGAGAAAAAAGTAGAACACTCATTTGCAATCTCTTGAATTGCAAATGAGTGTTCTACA (SEQ ID NO: 6); hDAPLEsh2 forward: 5' TGCACCTGCCTTCCTAGATTTTCAAGAGAAATCTAGGAAGGCAGGTGCT TTTTTC (SEQ ID NO: 7); and hDAPLEsh2 reverse: 5' TCGAGAAAAAAGCACCTGCCTTCCTAGATTTCTCTTGAAAATCTAGGAAGGCAGGTG CA (SEQ ID NO: 8).

The DAPLE-fl isoform can be selectively inhibited by the following shRNA inhibitors: shDaple1: CAGTAGAACACTCATTTGCAA (SEQ ID NO: 25) and shDaple2: AGGCACCTGCCTTCCTAGATT (SEQ ID NO: 26). In certain embodiments, shDAPLE1 and shDAPLE2 can selectively inhibit DAPLE-fl in cancer initiating stem cells (CISCs).

Due to the differences described herein regarding the 5' region of DAPLE-fl versus DAPLE-V2, shRNAs that specifically target the 5' region (including the 5'untranslated (UTR) region) of the DAPLE isoforms should be able to distinguish between the two isoforms.

In certain embodiments, the full length isoform of DAPLE, DAPLE-fl, is selectively inhibited (SEQ ID NO: 2; NCBI Reference Sequence NP_001073883.2). The full length isoform is known to be expressed in the normal epithelium, downregulated during normal to cancer progression, and then subsequently upregulated in few cancer cells (especially those disseminated in the circulation) during metastatic progression. The upregulation of the full length form observed later during cancer progression identified herein as being associated with cancer progression and lower survival rates. In other embodiments, the short isoform of DAPLE, DAPLE-V2, is selectively enhanced (SEQ ID NO: 23). The short isoform is identified herein as being associated with normal epithelial cells and tumor suppression, as well as improved survival rates.

In certain embodiments, the invention provides the use of genome editing methods for inhibiting expression of DAPLE-fl gene. Non-limiting examples of useful genome editing methods include, e.g., methods which involve the use of Clustered Regularly Interspaced Short Palindromic Repeats (CRISPR)/Cas9 gene systems, methods which involve the use of zinc finger nucleases (ZFNs), methods which involve the use of transcription activator-like effector nucleases (TALENs), as well as methods which involve the use of any other nucleases that can cause DNA breaks or bind to DNA. Genome editing tools such as TALENs, ZFNs, and CRISPR/Cas9 system are examples of targeted nuclease systems: these systems have a DNA-binding member that localizes the nuclease to a target site. The site is then cut by the nuclease. TALENs and ZFNs have the nuclease fused to the DNA-binding member. CRISPR/Cas9 are cognates that find each other on the target DNA. The DNA-binding member is typically designed in light of the intended cognate sequence so as to obtain a nucleolytic action at or near an intended site. For more information on these genome editing methods see, e.g., WO 2013163628, US 20140273235, EP 2336362, WO 2014093479, WO 2014089290, U.S. Pat. No. 8,795,965, US 20140357530, WO 2011091324, U.S. Pat. No. 8,106,255, US 20120192298, US 20110023159, and US20110281306.

In certain embodiments, the invention provides the use of CRISPR/Cas9 system for inhibiting expression of DAPLE-fl gene and/or for increasing expression of DAPLE-V2 gene. The CRISPR/Cas9 has been used to create a simple, RNA-programmable method to mediate genome editing in mammalian cells, and to generate gene knockouts (via insertion/deletion) or knockins (via homology directed repair (HDR)). To create DAPLE gene disruptions, a single guide RNA (sgRNA) can be generated to direct the Cas9 nuclease to a specific genomic location. Cas9-induced double strand breaks are repaired via the non-homologous end joining DNA repair (NHEJ) or the homology directed repair (HDR) DNA repair pathway. The repair is error prone, and thus insertions and deletions (INDELs) may be introduced that can disrupt gene function. See e.g., Sander & Joung, Nature Biotechnology, 32:347-355, 2014; Takara Clotech: The CRISPR/Cas9 system for targeted genome editing; and New England BioLabs: CRISPR/Cas9 and Targeted Genome Editing: A New Era in Molecular Biology).

Antisense oligonucleotides, including antisense DNA, RNA, and DNA/RNA molecules, act to directly block the translation of mRNA by binding to targeted mRNA and preventing protein translation. Preferably, antisense oligonucleotides are of at least about 15 bases and are complementary to unique regions of the target DNA sequence. Such antisense oligonucleotides can be synthesized, e.g., by conventional techniques (see, e.g., Dallas et al., (2006) Med. Sci. Monit. 12(4):RA67-74; Kalota et al., (2006) Handb. Exp. Pharmacol. 173:173-96; Lutzelburger et al., (2006) Handb. Exp. Pharmacol. 173:243-59).

RNA polymerase III-transcribed DNAs contain promoters, such as the U6 promoter. These DNAs can be transcribed to produce small hairpin RNAs in the cell that can function as siRNA or linear RNAs that can function as antisense RNA. The inhibitor may be polymerized in vitro, recombinant RNA, contain chimeric sequences, or derivatives of these groups. The inhibitor may contain ribonucleotides, deoxyribonucleotides, synthetic nucleotides, or any suitable combination such that the target RNA and/or gene is inhibited. In addition, these forms of nucleic acid may be single, double, triple, or quadruple stranded (see for example Bass (2001) Nature, 411, 428 429; Elbashir et al., (2001) Nature, 411, 494 498; and PCT Publication Nos. WO 00/44895, WO 01/36646, WO 99/32619, WO 00/01846, WO 01/29058, WO 99/07409, WO 00/44914).

Aptamer nucleic acid sequences are readily made that bind to a wide variety of target molecules. The aptamer nucleic acid sequences useful in the methods of the invention can be comprised entirely of RNA or partially of RNA, or entirely or partially of DNA and/or other nucleotide analogs. Aptamers are typically developed to bind particular ligands by employing known in vivo or in vitro (most typically, in vitro) selection techniques known as SELEX (Systematic Evolution of Ligands by Exponential Enrichment). Methods of making aptamers are described in, for example, Ellington and Szostak (1990) Nature 346:818, Tuerk and Gold (1990) Science 249:505, U.S. Pat. No. 5,582,981; PCT Publication No. WO 00/20040; U.S. Pat. No. 5,270,163; Lorsch and Szostak (1994) Biochem. 33:973; Mannironi et al., (1997) Biochem. 36:9726; Blind (1999) Proc. Nat'l. Acad. Sci. USA 96:3606-3610; Huizenga and Szostak (1995) Biochem. 34:656-665; PCT Publication Nos. WO 99/54506, WO 99/27133, and WO 97/42317; and U.S. Pat. No. 5,756,291.

Nucleic acid-based inhibitors of the invention may include one or more modifications, e.g., to increase intracellular stability and efficacy (e.g., modifications to the base moiety, sugar moiety, phosphate moiety, phosphate-sugar backbone, or a combination thereof). For example, the phosphodiester linkages may be modified to include at least one heteroatom other than oxygen, such as nitrogen or sulfur. In this case, for example, the phosphodiester linkage may be replaced by a phosphothioester linkage. Similarly, bases may be modified to block the activity of adenosine deaminase. Other examples of useful modifications are morpholino modifications and locked nucleic acids (LNA). Where the nucleic acid-based inhibitor molecule is produced synthetically, or by in vitro transcription, a modified nucleoside may be introduced during synthesis or transcription.

Non-limiting examples of modified base moieties include inosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyl adenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2, 6-diaminopurine.

Non-limiting examples of modified sugar moieties include arabinose, 2-fluoroarabinose, xylulose, and hexose. Modified siRNAs may contain substituted sugar moieties comprising one of the following at the 2' position: OH, SH, SCH$_3$, F, OCN, O(CH$_2$)$_n$NH$_2$ or O(CH$_2$)$_n$CH$_3$ where n is from 1 to about 10; C$_1$ to C$_{10}$ lower alkyl, substituted lower alkyl, alkaryl or aralkyl; Cl; Br; CN; CF$_3$; OCF$_3$; O-; S-, or N-alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted sialyl; a fluorescein moiety; a reporter group; a group for improving the pharmacokinetic properties; or a group for improving the pharmacodynamic properties, and other substituents having similar properties. Modified nucleic acid-based inhibitors may also have sugar mimetics such as cyclobutyls or other carbocyclics in place of the pentofuranosyl group.

Non-limiting examples of modifications of phosphate backbone include a phosphorothioate, a phosphorodithioate, a phosphoramidothioate, a phosphoramidate, a phosphordiamidate, a methylphosphonate, a phosphotriester, an alkyl phosphotriester, and a formacetal or analog thereof, as well as chimeras between methylphosphonate and phosphodiester, short chain alkyl, or cycloalkyl intersugar linkages or short chain heteroatomic or heterocyclic intersugar linkages. Specific non-limiting examples include those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds.

Also envisioned are modified nucleic acid-based inhibitors having morpholino backbone structures in which the bases are linked to 6-membered morpholine rings, which are connected to other morpholine-linked bases via non-ionic phosphorodiamidate intersubunit linkages. Morpholino derivatives are highly resistant to nucleases and have good targeting predictability (U.S. Pat. No. 5,034,506; Summerton, Biochim. Biophys. Acta 1999; 1489:141-158; Summerton and Weller, Antisense Nucleic Acid Drug Dev. 1997; 7:187-195; Arora et al., J. Pharmacol. Exp. Ther. 2000; 292:921-928; Qin et al., Antisense Nucleic Acid Drug Dev. 2000; 10:11-16; Heasman et al., Dev. Biol. 2000; 222:124-134; Nasevicius and Ekker, Nat. Genet. 2000; 26:216-220).

Another type of a useful modification is the peptide-nucleic acid (PNA) backbone: the phosphodiester backbone of the oligonucleotide may be replaced with a polyamide backbone, the bases being bound directly or indirectly to the aza nitrogen atoms of the polyamide backbone (Nielsen et al., Science 1991; 254:1497).

In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) with a 2'-O, 4'-C methylene bridge. This bridge restricts the flexibility of the ribofuranose ring and locks the structure into a rigid C3-endo conformation, conferring enhanced hybridization performance and exceptional biostability.

Modified nucleic acid-based inhibitors can include appending groups such as, e.g., peptides, or agents facilitating transport across the cell membrane (see, e.g., Letsinger et al., Proc. Natl. Acad. Sci. USA 1989; 86:6553-6556; Lemaitre et al., Proc. Natl. Acad. Sci. USA 1987; 84:648-652; PCT Publication No. WO 88/09810), or blood-brain barrier (see, e.g., PCT Publication No. WO 89/10134), etc.

Nucleic acid-based inhibitors of the invention can be synthesized by standard methods known in the art, e.g., by use of an automated synthesizer. In one embodiment, RNA molecules can be chemically synthesized using appropriately protected ribonucleoside phosphoramidites and a conventional DNA/RNA synthesizer. In case of siRNA molecules, following chemical synthesis, single stranded RNA molecules are deprotected, annealed to form siRNAs, and purified (e.g., by gel electrophoresis or HPLC). Commercial suppliers of synthetic RNA molecules or synthesis reagents include, e.g., Proligo (Hamburg, Germany), Dharmacon Research (Lafayette, Colo.), Pierce Chemical (part of Perbio Science, Rockford, Ill.), Glen Research (Sterling, Va.), ChemGenes (Ashland, Mass.) and Cruachem (Glasgow, UK).

Alternatively, standard procedures may be used for in vitro transcription of RNA from DNA templates carrying RNA polymerase promoter sequences (e.g., T7 or SP6 RNA polymerase promoter sequences) (Donzé and Picard, Nucleic Acids Res. 2002; 30:e46; Yu et al., Proc. Natl. Acad. Sci. USA 2002; 99:6047-6052; Weintraub, H. et al., Trends in Genetics, Vol. 1 (1) 1986). In the case of siRNA molecules, the sense and antisense transcripts may be synthesized in two independent reactions and annealed later, or may be synthesized simultaneously in a single reaction. siRNA molecules may be formed within a cell by transcription of RNA from an expression construct introduced into the cell. For example, both a protocol and an expression construct for in vivo expression of siRNAs are described in Yu et al., supra.

The expression constructs for in vivo production of nucleic acid-based inhibitors of the invention comprise encoding sequences operably linked to elements necessary for the proper transcription, including promoter elements and transcription termination signals. Non-limiting examples of promoters for use in such expression constructs include the polymerase-III H1-RNA promoter (see, e.g., Brummelkamp et al., supra) and the U6 polymerase-III promoter (see, e.g., Sui et al., supra; Paul, et al. supra; and Yu et al., supra). The expression constructs can further comprise vector sequences that facilitate the cloning of the expression constructs. Standard vectors that may be used in practicing the current invention are known in the art (e.g., pSilencer 2.0-U6 vector, Ambion Inc., Austin, Tex.).

Antibody Inhibitors

The invention provides that the DAPLE inhibitors can also be antibodies, including, without limitation, monoclonal antibodies, polyclonal antibodies, recombinant antibodies, chimeric antibodies, naturally occurring antibodies, or specific antigen binding and/or functional domains, motifs, or fragments thereof. The antibodies of the invention include human antibodies, non-human animal antibodies from any animal species (e.g., mouse, rat, rabbit, chicken, dog, goat, camelids [dromedaries, camels, llamas and alpacas], and monkey), and/or humanized antibodies. The invention provides in the broadest scope anti-DAPLE antibodies, now known and/or commercially available, or later developed.

Antibodies can be used for research, diagnostics, and therapeutics.

Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

In certain embodiments, the antibodies of the invention are directed to one or more epitopes within the unique N-terminal region of DAPLE-fl which is not present in DAPLE-V2 (i.e., aa 1-1476 of human DAPLE-fl). In other embodiments, the antibodies are directed to one or more epitopes within the unique N-terminal region of DAPLE-V2 not present in DAPLE-fl (i.e., the short stretch of 5 N-terminal aa (MSVLS) in human DAPLE-V2). See FIG. 19. In one embodiment, the anti-DAPLE antibody is directed to the coiled coil domain and/or the HOOK domain of the N-terminal region.

In another embodiment, the anti-DAPLE antibody is directed to a sequence within the C-terminal domain of DAPLE. Such anti-DAPLE antibody may recognize the sequences contained within any or all of the GBA motif, the FZDR binding motif, and/or the PDZ binding motif (SEQ ID NOs: 27-29). Non-limiting specific examples of such anti-DAPLE antibodies include, but are not limited to, anti-DAPLE antibodies produced by Millipore. Such anti-DAPLE antibody is specific to His-Daple-CT, and specifically amino acids 1650-2028 of DAPLE-fl. This His- Daple-CT detects both short (DAPLE-V2) and long (DAPLE-fl) forms of DAPLE, without distinguishing one from another.

The antibodies of the invention can also be either full length antibodies or single-domain antibodies.

The invention also encompasses bispecific antibodies, which bind to two different antigens (e.g., one arm binds to a specific epitope on DAPLE protein, and the other arm binds to a molecule specific to the cancer characterized by Wnt signaling disturbances, e.g., a marker specific to ovarian cancer, leukemias (e.g., myeloid/lymphoid neoplasms), lymphomas, melanomas, blood cancers, and/or gut cancers, e.g., gastric, small bowel, colon and colorectal cancers). In certain embodiments, the recombinant bispecific antibodies are diabodies, which are a class of small bivalent and bispecific antibody fragments that can be expressed in bacteria (e.g. *E. coli*), yeast (e.g. *Pichia pastoris*), and cells from higher eukaryotic organisms in functional form and with high yields (up to 1 g/L). Diabodies comprise a heavy (VH) chain variable domain connected to a light chain variable domain (VL) on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites.

To construct bispecific diabodies, the variable domains derived from antibody A and antibody B can be fused to create the two chains VHA-VLB, VHB-VLA. Each chain is inactive in binding to antigen, but recreates the functional antigen binding sites of antibodies A and B on pairing with the other chain.

Antibodies useful in the methods of the invention can be generated using any antibody producing methods, now known or later developed in the art. For example, phage display methods can be used. In phage display methods, functional antibody domains are displayed on the surface of phage particles which carry the nucleic acid sequences encoding them. In a particular embodiment, such phage can be utilized to display antigen binding domains expressed from a repertoire or combinatorial antibody library (e.g., human or murine). In particular, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector. The vector is electroporated in *E. coli* and the *E. coli* is infected with helper phage. Phage used in these methods are typically filamentous phage including fd and M13 binding domains expressed from phage with Fab, Fv or disulfide stabilized Fv antibody domains recombinantly fused to either the phage gene III or gene VIII protein. Phage expressing an antigen binding domain that binds to or-portions thereof can be selected or identified with antigen e.g., using labeled antigen or antigen bound or captured to a solid surface or bead. Alternatively it is also possible to produce the recombinant bispecific antibody constructs of the present invention by hybridoma fusion.

Depending on the mode of application, bispecific antibodies can be administered to a patient. One of the problems which may occur is that bispecific antibodies are very quickly excreted from the body of the patient and accumulate in excreting organs like the kidney. One option to overcome this problem is to isolate ex vivo T cells from the blood of the patients for example by leukapheresis and to incubate T cells with the diabody. Such incubated mixtures can thereafter be re-administered to the patient.

In case of ovarian cancer, leukemias (e.g., myeloid/lymphoid neoplasms), lymphomas, melanomas, blood cancers, and gut cancers, e.g., gastric, small bowel, colon and colorectal cancer treatments relying on systemic delivery, anti-DAPLE antibodies may have to cross into or be transported (e.g., actively or passively) into such cancers. This may be possible using small antibodies or antibody fragments. Alternatively, enhanced and/or targeted delivery of anti-DAPLE antibodies can be achieved by using bispecific antibodies with the second antigen being specific to said cancer type. Alternatively, antibodies can be administered directly into the tumor, e.g., by injection or using continuous peristaltic pumps.

In some embodiments, the anti-DAPLE antibodies will need to be able to function within the target cell. Specifically, the antibodies must be able to enter the target cell cytoplasm and/or organelles and must also be soluble and capable of specifically binding to DAPLE within an intracellular environment. These intracellular antibodies can be introduced into cells by a variety of methods, including for example and not limitation, various cell penetrating compositions (see, e.g., WO 2013/138795, WO 2015/031837, U.S. Pat. No. 7,157,087), and vesicles comprising liposomes and/or block copolymers (see, e.g., WO 2009/138473). Stability of intracellular antibodies can be improved by, for example and not limitation, the methods and compositions taught in U.S. Pat. No. 7,608,453, WO 2004046186, U.S. Pat. Nos. 8,853,362, and 7,258,986.

Small Molecule Inhibitors

The present invention also encompasses various small molecule inhibitors of DAPLE-fl gene expression and/or protein function. Small molecules are a diverse group of synthetic and natural substances generally having low molecular weights (preferably less than about 2000 Daltons, less than about 1000 Daltons, or less than about 500 Daltons). Small molecules, without limitation, may be, for example, nucleic acids, peptides, polypeptides, peptide nucleic acids, peptidomimetics, carbohydrates, lipids, or other organic (carbon containing) or inorganic molecules and may be synthetic or naturally occurring or optionally derivatized. Such small molecules may be a therapeutically deliverable substance or may be further derivatized to facilitate delivery or targeting.

The above compounds may be obtained by methods known to skilled practitioners. Synthesis, characterization, and biological activity data for some of these compounds are disclosed in, e.g., Scifinder, Chem. Pharm. Bull. 49(8) 988-998 (2001); J Pharmacol Sci 96, 42-52 (2004).

Small molecule inhibitors of DAPLE-fl can be isolated from natural sources (for example, plants, fungi, microbes and the like) or isolated from random or combinatorial chemical libraries of synthetic or natural compounds, or synthesized. See Werner et al., (2006) Brief Funct. Genomic Proteomic 5(1):32-6. Many random or combinatorial libraries are known in the art that can be used. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) Tib Tech 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Examples of chemically synthesized libraries are described in Fodor et al., (1991) Science 251:767-773; Houghten et al., (1991) Nature 354:84-86; Lam et al., (1991) Nature 354:82-84; Medynski, (1994) BioTechnology 12:709-710; Gallop et al., (1994) J. Medicinal Chemistry 37(9):1233-1251; Ohlmeyer et al., (1993) Proc. Natl. Acad. Sci. USA 90:10922-10926; Erb et al., (1994) Proc. Natl. Acad. Sci. USA 91:11422-11426; Houghten et al., (1992) Biotechniques 13:412; Jayawickreme et al., (1994) Proc. Natl. Acad. Sci. USA 91:1614-1618; Salmon et al., (1993) Proc. Natl. Acad. Sci. USA 90:11708-11712; PCT Publication No. WO 93/20242, dated Oct. 14, 1993; and Brenner et al., (1992) Proc. Natl. Acad. Sci. USA 89:5381-5383.

Examples of phage display libraries are described in Scott et al., (1990) Science 249:386-390; Devlin et al., (1990) Science, 249:404-406; Christian, et al., (1992) J. Mol. Biol. 227:711-718; Lenstra, (1992) J. Immunol. Meth. 152:149-157; Kay et al., (1993) Gene 128:59-65; and PCT Publication No. WO 94/18318.

Screening the libraries can be accomplished by any variety of commonly known methods. See, for example, the following references, which disclose screening of peptide libraries: Parmley and Smith, (1989) Adv. Exp. Med. Biol. 251:215-218; Scott and Smith, (1990) Science 249:386-390; Fowlkes et al., (1992) BioTechniques 13:422-427; Oldenburg et al., (1992) Proc. Natl. Acad. Sci. USA 89:5393-5397; Yu et al., (1994) Cell 76:933-945; Staudt et al., (1988) Science 241:577-580; Bock et al., (1992) Nature 355:564-566; Tuerk et al., (1992) Proc. Natl. Acad. Sci. USA 89:6988-6992; Ellington et al., (1992) Nature 355:850-852; U.S. Pat. Nos. 5,096,815; 5,223,409; and 5,198,346, all to Ladner et al.; Rebar et al., (1993) Science 263:671-673; and PCT Pub. WO 94/18318.

Identification and screening of inhibitors of DAPLE-fl can be further facilitated by X-ray crystallography, neutron diffraction, nuclear magnetic resonance spectrometry, and other techniques for structure determination. These techniques provide for the rational design or identification of inhibitors. Methods for screening and identifying DAPLE inhibitors are known in the art, and the invention contemplates any inhibitor screening and identification approaches, now known or later developed, in the art.

Compositions and Methods of Administration

The invention further provides that the DAPLE-fl inhibitors of the present invention can be used as pharmaceutical compositions and can be optionally combined with other DAPLE-fl inhibitors of the invention or other therapeutic molecules and/or treatments for cancers. Further, activators of DAPLE-V2, including gene therapy vectors for overexpression of DAPLE-V2, can be used as pharmaceutical compositions and can be optionally combined with other DAPLE-V2 activators of the invention, DAPLE-fl inhibitors of the invention, or other therapeutic molecules and/or treatments for cancers. In certain embodiments, a DAPLE-fl inhibitor and/or DAPLE-V2 activator is used before, during, and/or after such other therapeutic molecules and/or treatments. Non-limiting examples of additional therapeutic molecules and treatments for cancers which can be combined with the use of DAPLE-fl inhibitors and/or DAPLE-V2 activators include, e.g., radiation therapy, surgery, chemotherapy (e.g., temozolamide, VEGF inhibitors [such as, e.g., bevacizumab/Avastin], Cilengitide, rindopepimut and other EGFR modulators, nitrosoureas [such as, e.g., lomustine, carmustine/BCNU, CCNU], tyrosine kinase inhibitors), immune cell therapy (e.g., autologous, genetically engineered T-cells and/or dendritic cells [DCs]), cancer vaccines (e.g., cellular- or peptide-based), oncolytic viruses (e.g., Ad-RTS-IL-12), Stupp protocol (radiation+temozolamide), alternating electric field therapy (e.g., NovoTTF), etc.

In some embodiments of the invention, at least one inhibitor of DAPLE-fl and/or DAPLE-V2 activator is formulated into a suitable pharmaceutical preparation such as, e.g., solution, suspension, tablet, dispersible tablet, pill, capsule, powder, sustained release formulation or elixir, for oral administration; sterile solution or suspension for parenteral administration; powdered or liquid spray, nose drops, a gel or ointment for intranasal administration; powdered or liquid spray for administration by inhalation; films for sublingual administration; patch for transdermal administration, etc. An inhibitor of DAPLE can be formulated into pharmaceutical compositions using any of the techniques and procedures known in the art (see, e.g., Ansel Introduction to Pharmaceutical Dosage Forms, Fourth Edition 1985, 126). In some embodiments, at least one activator of DAPLE-V2 is a gene therapy vector for overexpression of DAPLE-V2, such as a lentiviral or adenoviral vector.

In the compositions, effective concentrations of one or more inhibitors of DAPLE-fl and/or activators of DAPLE-V2, or pharmaceutically acceptable derivatives thereof, is (are) mixed with a suitable pharmaceutical carrier or vehicle.

Pharmaceutically acceptable derivatives include acids, bases, enol ethers and esters, salts, esters, hydrates, solvates and prodrug forms. A suitable derivative is selected such that its pharmacokinetic properties are superior with respect to at least one characteristic to the corresponding parent agent. The inhibitor of DAPLE-fl and/or activator of DAPLE-V2 may be derivatized prior to formulation.

The amount of the inhibitor of DAPLE-fl and/or activator of DAPLE-V2 administered and the regimen of administration depends on absorption, inactivation and excretion rates of the active agent, the physicochemical characteristics of the agent, the severity of the condition to be alleviated, the age, condition, body weight, sex and diet of the patient, the disease state, other medications administered, and other factors known to those of skill in the art. An effective amount to treat the disease would broadly range (e.g., between about 0.001 mg and about 2000 mg per kg body weight of the recipient per day), and may be administered as a single dose or divided doses.

It is to be further understood that for any particular subject, specific dosage regimens should be adjusted over time according to the individual need and the professional judgment of the person administering or supervising the administration of the compositions.

The compositions are intended to be administered by a suitable route, including by way of example and without limitation, systemically (e.g., intravenously, intramuscularly, orally, intranasally, by inhalation, sublingually, mucosally, etc.), by direct injection within tumors (e.g., via intraoperative injection within the tumor or in the walls of the resection cavity by the surgeon; or stereotactic implantation of catheters within the tumor, followed by convection-enhanced delivery (CED) of a DAPLE-fl inhibitor and/or activator of DAPLE-V2), by superselective intra-arterial infusion of a DAPLE inhibitor within the vascular territory of the tumor (e.g., through an endovascular catheter), and by viral vector delivery for nucleic acid-based inhibitors (e.g., using lentiviral vectors, which by virtue of a modified envelope, selectively infect or transduce CD133+ cancer cells, or retroviral replicating vectors). The compositions are in liquid, semi-liquid or solid form and are formulated in a manner suitable for each route of administration.

Solutions or suspensions can include any of the following components, in any combination: a sterile diluent, including by way of example without limitation, water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity, such as sodium chloride or dextrose.

In instances in which the agents exhibit insufficient solubility, methods for solubilizing agents may be used. Such methods are known to those of skill in this art, and include, but are not limited to, using co-solvents, such as, e.g., dimethylsulfoxide (DMSO), using surfactants, such as TWEEN®80, or dissolution in aqueous sodium bicarbonate. Pharmaceutically acceptable derivatives of the agents may also be used in formulating effective pharmaceutical compositions.

The composition can contain along with the active agent, for example and without limitation: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active agent as defined above and optional pharmaceutical adjuvants in a carrier, such as, by way of example and without limitation, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, such as, by way of example and without limitation, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art (e.g., Remington's Pharmaceutical Sciences, Mack Publishing Company, Easton, Pa., 15th Edition, 1975). The composition or formulation to be administered will, in any event, contain a quantity of the active agent in an amount sufficient to alleviate the symptoms of the treated subject.

The active agents or pharmaceutically acceptable derivatives may be prepared with carriers that protect the agent against rapid elimination from the body, such as time release formulations or coatings. The compositions may include other active agents to obtain desired combinations of properties.

Oral pharmaceutical dosage forms include, by way of example and without limitation, solid, gel and liquid. Solid dosage forms include tablets, capsules, granules, and bulk powders. Oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or agents of a similar nature: a binder; a diluent; a disintegrating agent; a lubricant; a glidant; a sweetening agent; and a flavoring agent.

Examples of binders include, by way of example and without limitation, microcrystalline cellulose, gum tragacanth, glucose solution, acacia mucilage, gelatin solution, sucrose, and starch paste. Lubricants include, by way of example and without limitation, talc, starch, magnesium or calcium stearate, lycopodium and stearic acid. Diluents include, by way of example and without limitation, lactose, sucrose, starch, kaolin, salt, mannitol, and dicalcium phosphate. Glidants include, by way of example and without limitation, colloidal silicon dioxide. Disintegrating agents include, by way of example and without limitation, crosscarmellose sodium, sodium starch glycolate, alginic acid, corn starch, potato starch, bentonite, methylcellulose, agar and carboxymethylcellulose. Coloring agents include, by way of example and without limitation, any of the approved certified water soluble FD and C dyes, mixtures thereof; and water insoluble FD and C dyes suspended on alumina hydrate. Sweetening agents include, by way of example and without limitation, sucrose, lactose, mannitol and artificial sweetening agents such as saccharin, and any number of spray dried flavors. Flavoring agents include, by way of example and without limitation, natural flavors extracted from plants such as fruits and synthetic blends of agents which produce a pleasant sensation, such as, but not limited to peppermint and methyl salicylate. Wetting agents include, by way of example and without limitation, propylene glycol monostearate, sorbitan monooleate, diethylene glycol monolaurate, and polyoxyethylene laural ether. Emetic-coatings include, by way of example and without limitation, fatty acids, fats, waxes, shellac, ammoniated shellac and cellulose acetate phthalates. Film coatings include, by way of example and without limitation, hydroxyethylcellulose, sodium carboxymethylcellulose, polyethylene glycol 4000 and cellulose acetate phthalate.

If oral administration is desired, the agent could be provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

When the dosage unit form is a capsule, it can contain, in addition to material of the above type, a liquid carrier such as fatty oil. In addition, dosage unit forms can contain various other materials which modify the physical form of the dosage unit, for example, coatings of sugar and other enteric agents. The agents can also be administered as a component of an elixir, suspension, syrup, wafer, sprinkle, chewing gum or the like. A syrup may contain, in addition to the active agents, sucrose as a sweetening agent and certain preservatives, dyes and colorings and flavors. The active materials can also be mixed with other active materials which do not impair the desired action, or with materials that supplement the desired action, such as antacids, H2 blockers, and diuretics.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents may be used in any of the above dosage forms.

Solvents include, by way of example and without limitation, glycerin, sorbitol, ethyl alcohol and syrup. Examples of preservatives include, without limitation, glycerin, methyl and propylparaben, benzoic acid, sodium benzoate and alcohol. Non-aqueous liquids utilized in emulsions include, by way of example and without limitation, mineral oil and cottonseed oil. Emulsifying agents include, by way of example and without limitation, gelatin, acacia, tragacanth, bentonite, and surfactants such as polyoxyethylene sorbitan monooleate. Suspending agents include, by way of example and without limitation, sodium carboxymethylcellulose, pectin, tragacanth, Veegum and acacia. Diluents include, by way of example and without limitation, lactose and sucrose. Sweetening agents include, by way of example and without limitation, sucrose, syrups, glycerin and artificial sweetening agents such as saccharin. Wetting agents include, by way of example and without limitation, propylene glycol monostearate, sorbitan monooleate, diethylene glycol monolaurate, and polyoxyethylene lauryl ether. Organic acids include, by way of example and without limitation, citric and tartaric acid. Sources of carbon dioxide include, by way of example and without limitation, sodium bicarbonate and sodium carbonate. Coloring agents include, by way of example and without limitation, any of the approved certified water soluble FD and C dyes, and mixtures thereof. Flavoring agents include, by way of example and without limitation, natural flavors extracted from plants, such as fruits, and synthetic blends of agents which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245, 4,409,239, and 4,410,545. For a liquid dosage form, the solution (e.g., in a polyethylene glycol) may be diluted with a sufficient quantity of a pharmaceutically acceptable liquid carrier (e.g., water) to be easily measured for administration.

Alternatively, liquid or semi-solid oral formulations may be prepared by dissolving or dispersing the active agent or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. No. RE28,819 and U.S. Pat. No. 4,358,603. Briefly, such formulations include, but are not limited to, those containing an agent provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes, such as acetaldehyde diethyl acetal.

Tablets and capsules formulations may be coated as known by those of skill in the art in order to modify or sustain dissolution of the active ingredient. Thus, for example and without limitation, they may be coated with a conventional enterically digestible coating, such as phenylsalicylate, waxes and cellulose acetate phthalate.

Parenteral administration, generally characterized by injection, either subcutaneously, intramuscularly or intravenously, is also contemplated herein. Injectables can be prepared in conventional forms, either as liquid solutions or suspensions, solid forms suitable for solution or suspension in liquid prior to injection, or as emulsions. Suitable excipients include, by way of example and without limitation, water, saline, dextrose, glycerol or ethanol. In addition, if desired, the pharmaceutical compositions to be administered may also contain minor amounts of non-toxic auxiliary substances, such as wetting or emulsifying agents, pH buffering agents, stabilizers, solubility enhancers, and other such agents, such as, for example, sodium acetate, sorbitan monolaurate, triethanolamine oleate and cyclodextrins.

Implantation of a slow-release or sustained-release system, such that a constant level of dosage is maintained (e.g., U.S. Pat. No. 3,710,795) is also contemplated herein. Briefly, an inhibitor of NtSe or MR is dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate) that is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer) that is insoluble in body fluids. The agent diffuses through the outer polymeric membrane in a release rate controlling step. The percentage of active agent contained in such parenteral compositions is highly dependent on the specific nature thereof, as well as the activity of the agent and the needs of the subject.

Lyophilized powders can be reconstituted for administration as solutions, emulsions, and other mixtures or formulated as solids or gels. The sterile, lyophilized powder is prepared by dissolving an agent provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain, by way of example and without limitation, a single dosage (10-1000 mg, such as 100-500 mg) or multiple dosages of the agent. The lyophilized powder can be stored under appropriate conditions, such as at about 4° C. to room temperature. Reconstitution of this lyophilized powder with water for injection provides a formulation for use in parenteral administration. For reconstitution, about 1-50 mg, such as about 5-35 mg, for example, about 9-30 mg of lyophilized powder, is added per mL of sterile water or other suitable carrier. The precise amount depends upon the selected agent. Such amount can be empirically determined.

The inhibitors of DAPLE-fl and/or activators of DAPLE-V2 or pharmaceutically acceptable derivatives thereof may be formulated as aerosols for application e.g., by inhalation or intranasally (e.g., as described in U.S. Pat. Nos. 4,044,126, 4,414,209, and 4,364,923). These formulations can be in the form of an aerosol or solution for a nebulizer, or as a microtine powder for insufflation, alone or in combination with an inert carrier such as lactose. In such a case, the particles of the formulation will, by way of example and without limitation, have diameters of less than about 50 microns, such as less than about 10 microns.

The agents may be also formulated for local or topical application, such as for application to the skin and mucous membranes (e.g., intranasally), in the form of nasal solutions, gels, creams, and lotions.

Other routes of administration, such as transdermal patches are also contemplated herein. Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

In one embodiment, in order to enhance tissue delivery of the inhibitor of DAPLE-fl and/or activator of DAPLE-V2, the patient is treated in a manner so as to increase the selective permeability of the tissue, e.g., the blood-brain barrier (BBB). Treatments to selectively increase the permeability of the BBB in a patient include, but are not limited to, the administration of about 1 to about 1000 µg/kg body weight, preferably about 10 to about 100 µg/kg bodyweight, of IGF-I (e.g., as a bolus injection to a patient about 0.5 to 10 hours, preferably about 1 hour, before the inhibitor administration).

Inhibitors of DAPLE-fl and/or activators of DAPLE-V2 for use in the present invention may be packaged as articles of manufacture containing packaging material and a label that indicates that the inhibitor is used for inhibiting the expression and/or function of DAPLE-fl and/or activating the expression and/or function of DAPLE-V2 for treatment of a cancer.

Diagnostic and Screening Methods of the Invention

In one embodiment, the invention provides a method for determining whether a subject diagnosed with an adenoma is at an increased risk for progression of said adenoma to a cancer, said method comprising:
(a) determining the expression level of DAPLE-V2 isoform in adenoma cells of the subject,
(b) comparing the expression level determined in step (a) to a control level, and
(c) determining that the subject is at an increased risk for progression of said adenoma to a cancer if the expression level of DAPLE-V2 isoform is decreased in adenoma cells of the subject as compared to the control level.

In another embodiment, the invention provides a method for determining whether a subject diagnosed with an adenoma is at an increased risk for progression of said adenoma to a cancer, said method comprising:
(a) determining the expression levels of DAPLE-fl and DAPLE-V2 isoforms in adenoma cells of the subject,
(b) comparing the expression levels determined in step (a) to corresponding control levels, and (c) determining that the subject is at an increased risk for progression of said adenoma to a cancer if the expression levels of both DAPLE-fl and DAPLE-V2 isoforms are decreased in adenoma cells of the subject as compared to the corresponding control levels.

In one embodiment of the above methods, the control is a predetermined standard. In another embodiment, the control is the expression level of the DAPLE-fl or DAPLE-V2 in corresponding normal cells of the same tissue origin from the same subject.

In one specific embodiment, optimal cut-off values of DAPLE isoform expression levels for determining the subject's increased risk are selected by using maximally selected log-rank statistics performed by R Software version 2.13.0 (R Foundation for Statistical Computing, Vienna, Austria) on expression levels in tumor/cancer cells compared to corresponding normal cells of the same tissue origin from the same subject.

In any of the above embodiments, the risk stratification of patients who were found to have adenomas during screening methods, such as for example and not limitation, colonoscopy, may be further enhanced by the use of additional biomarker screens/panels. For example, such additional biomarker screens/panels may include the biology of cancer/tumor formation (including, e.g., polyp formation) and progression of cancer from normal tissue to cancerous (e.g., from normal to adenoma to carcinoma). Some studies have indeed tried to come up with marker panels (see Gupta S. et al., Cancer Prev Res (Phila). 2014 October; 7(10):1023-34. doi: 10.1158/1940-6207.CAPR-14-0140), but none have been commercialized or approved for patient care. The results included herein suggest that one of the last steps in adenoma to carcinoma progression, that may be assessed in conjunction with other sequential molecular mishap to fully evaluate the risk of cancer progression in any given adenoma. The following are the events/biomarkers that may enhance the ability of DAPLE to serve as a risk-determination factor in cancer/tumor (e.g., polyp) analysis: 1) Nuclear beta Catenin (by IHC); 2) KRAS mutation (by genotyping); 3) BRAF mutation (by immunohistochemistry [IHC] for V600E or genotyping); 3) Daple copy loss in regions of adenoma (using FISH approach, or IHC to monitor protein reduction compared to adjacent normal epithelium or the adenoma); 4) Existence of concurrent p53 loss/mutation (by IHC or genotyping).

In another embodiment, the invention provides a method for determining whether a subject diagnosed with a cancer is at an increased risk for metastasis and/or recurrence of said cancer, the method comprising:

(a) determining an expression level of the DAPLE-fl isoform in cancer cells of the subject, (b) comparing the expression level of the DAPLE-fl isoform determined in step (a) to a control level, and (c) determining that the subject is at an increased risk for metastasis and/or recurrence of said cancer if the expression level of DAPLE-fl isoform in cancer cells of the subject is increased as compared to the control level.

In one embodiment of the above methods, the control is a predetermined standard. In another embodiment, the control is the expression level of DAPLE-fl in the primary tumor.

In one specific embodiment, the optimal cut-off values of full length DAPLE isoform expression levels for determining the subject's increased risk are selected by using IBM® SPSS® Statistics Version 19 (SPSS Inc., IBM Corporation, Somers, N.Y., USA) and/or maximally selected log-rank statistics performed by R Software version 2.13.0 (R Foundation for Statistical Computing, Vienna, Austria) on expression levels in circulating tumor/cancer cells compared to corresponding normal cells of the same tissue origin from the same subject.

In one embodiment of the above method, the DAPLE-fl expression is determined in circulating tumor cells (CTCs) of the subject. CTCs may include a mixed population of tumor cells, such as for example and not limitation, those that have stem-like properties and can initiate new tumors elsewhere, called cancer initiating stem cells (CISCs). In one specific embodiment, the DAPLE-fl expression is determined in cancer-initiating stem cells (CISCs) of the subject.

In any of the above embodiments, the adenoma cells, cancer cells, CTCs and/or CISCs may be isolated using known methods from any solid or liquid adenoma or cancer, such as for example and not limitation, cancers characterized by Wnt signaling disturbances, including ovarian cancer, leukemias (e.g., myeloid/lymphoid neoplasms), lymphomas, melanomas, blood cancers, blood cancers, and gut cancers, e.g., gastric, small bowel, colon and colorectal cancers.

In any of the above embodiments, the risk stratification of patients who were found to have adenomas during screening methods, such as for example and not limitation, colonoscopy, may be further enhanced by the use of additional biomarker screens/panels. For example, such additional biomarker screens/panels may include the biology of cancer/tumor formation (including, e.g., polyp formation) and progression of cancer from normal tissue to cancerous (e.g., from normal to adenoma to carcinoma). Some studies have indeed tried to come up with marker panels (see Gupta S. et al., Cancer Prev Res (Phila). 2014 October; 7(10):1023-34. doi: 10.1158/1940-6207.CAPR-14-0140), but none have been commercialized or approved for patient care. The results included herein suggest that one of the last steps in adenoma to carcinoma progression, that may be assessed in conjunction with other sequential molecular mishap to fully evaluate the risk of cancer progression in any given adenoma. The following are the events/biomarkers that may enhance the ability of DAPLE to serve as a risk-determination factor in cancer/tumor (e.g., polyp) analysis: 1) Nuclear beta Catenin (by IHC); 2) KRAS mutation (by genotyping); 3) BRAF mutation (by IHC for V600E or genotyping); 3) Daple copy loss in regions of adenoma (using FISH approach, or IHC to monitor protein reduction compared to adjacent normal epithelium or the adenoma); 4) Existence of concurrent p53 loss/mutation (by IHC or genotyping).

In any of the above embodiments, the expression of DAPLE-fl and/or DAPLE-V2 isoforms may be measured by mRNA levels and/or protein levels. The mRNA levels of the DAPLE isoforms may be measured using methods commonly known in the field, such as for example and not limitation, PCR-based methods such as quantitative reverse transcription polymerase chain reaction and quantitative real-time PCR, as well as RNAse protection assays, Northern blot analysis, DNA array/microarray analysis, gel electrophoresis, sequencing and sequence analysis, in situ hybridization assays such as fluorescent in situ hybridization (FISH) assays, or similar RNA or cDNA quantitation methods (see, e.g., Parker & Barnes, Methods in Molecular Biology 106:247 283 (1999), Hod, Biotechniques 13:852 854 (1992), Weis et al., Trends in Genetics 8:263 264 (1992)) with primers specific for either both DAPLE isoforms or a single DAPLE isoform, as well as other genes for use as controls. Primers for selectively detecting a single DAPLE isoform (e.g., DAPLE-fl or DAPLE-V2) can be directed to sequences within the nucleic acid sequence encoding the unique N-terminal region of DAPLE-fl which is not present in DAPLE-V2 [i.e., aa 1-1476 of human DAPLE-fl] or sequences within the nucleic acid sequence encoding the unique N-terminal region of DAPLE-V2 not present in DAPLE-fl [i.e., the short stretch of 5 N-terminal aa (MSVLS) in human DAPLE-V2]). Exemplary primers specific for both DAPLE-fl and DAPLE-V2 include 5'-TGACATGGAGACCCTGAAGGCTGA-3' (SEQ ID NO: 9) and 5'-TTTCATGCGGGCCTCACTGCTGA-3' (SEQ ID NO: 10). Exemplary primers specific for control genes include 5'-TCAGTTGTAGGCAAGCTGCGACGT-3' (SEQ ID NO: 11) and 5'-AAGCCAGAGGCTGGTACCTA-GAAC-3 (SEQ ID NO: 12) for GAPDH; 5'-ATGGGTGC-TATCCACCTGAG-3' (SEQ ID NO: 13) and 5'-GAGTCG-GATCCTGGTCTCT-3' (SEQ ID NO: 14) for LOXL3; 5'-AAGAGAACTTTGCCGTTGAA-3' (SEQ ID NO: 15) and 5'-GTGATGCTGAGAAGTTTCGT-3' (SEQ ID NO: 16) for Vim; 5'-GAGTTTGCACTGAGGATGAAAA-3' (SEQ ID NO: 17) and 5'-GCTTCTTCTTCTTGGGGACA-3' (SEQ ID NO: 18) for SFPR-1; 5'-GAGTGGACTTGT-GCCGACTTCA-3' (SEQ ID NO: 19) and 5'-GGTGGCTG-GTGCAAAGACATAG-3' (SEQ ID NO: 20) for AXIN-2; and 5'-TTGCAGCCTTCTCAGCCAA-3' (SEQ ID NO: 21) and 5'-GGAGGCAAAAGCAAATCACTG-3' (SEQ ID NO: 22) for OPN. Primers specific for DAPLE-fl isoform include, e.g., shDaple1: CAGTAGAACACTCATTTGCAA (SEQ ID NO: 25) and shDaple2: AGGCACCTGCCTTC-CTAGATT (SEQ ID NO: 26).

The protein levels of the DAPLE isoforms may be measured using methods commonly known in the field, such as for example and not limitation, antibody-based methods [e.g., Western blotting, enzyme-linked immunosorbent assays (ELISA), immunoprecipitation, immunodetection, radioimmunoassays (RIA), enzyme immunoassays (EIA), immunohistochemistry (IHC), antibody arrays and/or protein chips (e.g., U.S. Patent Application Nos. 2003/0013208; 2002/0155493, 2003/0017515 and U.S. Pat. Nos. 6,329,209 and 6,365,418) and other in situ hybridization assays], gel electrophoresis (e.g., 1-D or 2-D gel-based analysis systems), sequencing and sequence analysis, and chromatographic/spectrometric detection including but not limited to mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See, e.g., U.S. Patent Application Nos. 2003/0199001, 2003/0134304, 2003/0077616. Additional methods for determining nucleic acid and/or protein expression in samples are described, for example, in U.S. Pat. Nos. 6,271,002; 6,218,122; 6,218,114; and 6,004,755; and in Wang et al, J. Clin. Oncol., 22(9): 1564-1671 (2004); and Schena et al, Science, 270:467-470 (1995). Specific examples of anti-DAPLE antibodies suitable for use herein are described above, including antibodies for distinguishing DAPLE-fl and DAPLE-V2 isoforms (e.g., antibodies directed to one or more epitopes within the unique N-terminal region of DAPLE-fl which is not present in DAPLE-V2 [i.e., aa 1-1476 of human DAPLE-fl] or antibodies directed to one or more epitopes within the unique N-terminal region of DAPLE-V2 not present in DAPLE-fl [i.e., the short stretch of 5 N-terminal aa (MSVLS) in human DAPLE-V2]).

In any of the above embodiments, circulating tumor/cancer cells (CTCs) may be prepared by the methods described in Bednarz-Knoll et al., Breast Can Res, 2011 13:228. Exemplary methods include EPCAM-based assays, e.g., CellSearch system, CTC-chip, MagSweeper, laser scanning cytometry, Ikoniscope imaging system, Ariol system, and AdnaTest, and functional assays, e.g., EPISPOT assay, Vita-Assay or cell adhesion matrix (CAM) assay, as well as ISET, FAST, and DEP-FF methods.

Any of the above diagnostic methods can further comprise a step of isolating cells from the subject prior to determination of the level of DAPLE isoforms.

Any of the above diagnostic methods can be followed by administering a relevant cancer treatment to the subject.

Any of the above diagnostic methods can comprise the use of a computer for calculating and comparing DAPLE levels.

In a further aspect, the invention provides a method of identifying a DAPLE-fl inhibitor for treatment of a cancer, comprising contacting a candidate agent with a DAPLE-fl-expressing cancer cell and determining expression level or a function of DAPLE-fl in said cancer cell, wherein a decrease of expression level or function of DAPLE-fl, as compared with said level or function prior to the agent exposure, indicates that said agent is a DAPLE-fl inhibitor. In one embodiment, the method can further comprise determining expression level or a function of DAPLE-V2 in said cancer cell to ensure that the candidate agent selectively inhibits DAPLE-fl while it does not affect the expression or function of DAPLE-V2.

In a further aspect, the invention provides a method of identifying a DAPLE-V2 activator for treatment of a cancer, comprising contacting a candidate agent with a DAPLE-V2-expressing adenoma cell and determining expression level or a function of DAPLE-V2 in said cell, wherein an increase of expression level or function of DAPLE-V2, as compared with said level or function prior to the agent exposure, indicates that said agent is a DAPLE-V2 activator. In one embodiment, the method can further comprise determining expression level or a function of DAPLE-fl in said adenoma cell to ensure that the candidate agent selectively activates DAPLE-V2 while it does not affect the expression or function of DAPLE-fl.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

The following examples demonstrate that a novel G protein regulatory motif enables DAPLE to couple G protein activation to FZDRs, which in turn initiates non-canonical Wnt signaling pathways. The examples further demonstrate how bimodal dysregulation in DAPLE expression modulates non-canonical Wnt signaling during cancer progression.

Example 1

Materials & Methods
Reagents and Antibodies

Unless otherwise indicated, all reagents were of analytical grade and obtained from Sigma-Aldrich. Cell culture media were purchased from Invitrogen. All restriction endonucleases and *Escherichia coli* strain DH5a were purchased from New England Biolabs. *E. coli* strain BL21 (DE3), phalloidin-Texas Red were purchased from Invitrogen. Genejuice transfection reagent was from Novagen. PfuUltra DNA polymerase was purchased from Stratagene. Recombinant Wnt3a and Wnt5a were purified as previously described (Willert, 2008). Briefly, conditioned media (CM) were collected the day after confluence was reached. WNT proteins were purified from 6 liters of CHO CM. CM was complemented with 1% Triton X-100 (v/v), 20 mM Tris-Cl pH 7.5 and 0.01% $NaN_3$. Goat anti-rabbit and goat anti-mouse Alexa Fluor 680 or IRDye 800 F(ab')2 used for immunoblotting were from Li-Cor Biosciences. Mouse anti-His, anti-FLAG (M2), anti-α tubulin and anti-actin were obtained from Sigma; anti-Myc and anti-HA were obtained from Cell Signaling and Covance, respectively. Rabbit anti-pan-Gβ (M-14), anti-Gαi3, anti-DVL, and anti-βcatenin were obtained from Santa Cruz Biotechnology; anti-Akt and phospho-Akt (S473) were obtained from Cell Signaling; anti-Rac1 was obtained from BD Transduction Laboratories. Anti-DAPLE antibodies were generated in collaboration with Millipore using the C-terminus of DAPLE (aa 1660-2028) as an immunogen.

Plasmid Constructs and Mutagenesis

Cloning of N-terminally tagged myc-DAPLE was carried out in two steps by piece-meal assembly. A fragment of hDAPLE obtained from Kazusa [KIAA1509; clone fh14721, inserted into pBluescript II SK (+)] was used as a source of 3' nucleotide by 2131-6087. The N-terminus of hDAPLE was artificially synthesized (Genscript, San Diego) and used as a source for the 5' nucleotide by 1-2130. The full length hDAPLE gene [corresponding to the NCBI Ref Seq NM_001080414.3 (mRNA) (SEQ ID NO: 1) and NP_001073883.2 (protein) (SEQ ID NO: 2)] was assembled by inserting 5' and 3' fragments into pcDNA3.1 between NotI/EcoRI and EcoRI/BamHI, respectively. The EcoRI cloning site in the middle of the DAPLE sequence was eliminated by mutagenesis. The entire gene length was sequenced prior to cloning it into myc-pcDNA 3.1 (+) between KpnI/EcoRI to generate myc-DAPLE. All subsequent site-directed mutagenesis and truncated constructs (myc-DAPLE full length F1675A (FA), myc-DAPLE deleted from aa 2025-2028 (ΔPBM), myc-DAPLEFA+ΔPBM (2M) and myc-DAPLECT 1650-2028 aa) were carried out on this template using Quick Change as per manufacturer's protocol. The GST-DAPLE-CT WT, His-DAPLE-CT WT and FA constructs (1650-1880 aa and 1650-2028 aa) used for in vitro protein-protein interaction assays were cloned from myc-DAPLEpcDNA3.1 and inserted within the pGEX-4T or pET28b vectors, respectively, between NdeI/EcoRI restriction sites.

The HA-tagged FZD7R construct was generated by cloning the human receptor (ATCC #10658884; Gen Bank BC015915.1; RefSeq: NM_003507.1) in pcDNA 3.1 between HindIII/EcoRI and by subsequently inserting a HA tag at the C-terminus by mutagenesis. FZD7R-CFP construct was a generous gift from Carl-Philip Heisenberg (Institute of Science and Technology, Austria) (Witzel et al, 2006). Gαi3-YFP and Gαi1-YFP (internally tagged Gαi subunits: the coding sequence for YFP was inserted in the αb-αc loop after Ala-121 of Giα1 and Ala-114 of Giα3 which does not affect their biochemical properties), CFP-Gβ1 and untagged Gγ are a generous gift from Moritz Bunemann (Philipps-Universität Marburg, Germany) (Bunemann et al, 2003; Gibson & Gilman, 2006). Mouse Dvl1 and HA-Ras G12V were generous gifts from Mikhail V. Semenov (Harvard Medical School) and Robert Hayward (London, UK), respectively.

Cloning of rat Gα-proteins into pGEX-4T-1 (GST-Gαi3, GST-Gαi1, GST-Gαi2 and GST-Gαo), GST-Gαi3 K248M and W258F; His-Gαi3; Gαi3-FLAG; Gαi3-HA; and GST-GIV CT 1671-1755 aa have been described previously (Garcia-Marcos et al, 2010; Garcia-Marcos et al, 2009; Ghosh et al, 2010; Ghosh et al, 2008) (Garcia-Marcos et al, 2010; Garcia-Marcos et al, 2009; Garcia-Marcos et al, 2011b). GST-tagged C-termini of FZDRs 3-8 (Yao et al, 2004) were generous gifts from Ryoji Yao (JFCR Research Institute, Japan). The C-terminal cytoplasmic tails of human FZD1 (aa 614-647) and mouse FZD2 (aa 537-570) were cloned into the BamHI/EcoRI sites of pGEX-4T-1 to generate the plasmids for bacterial expression of GST-FZD1-CT and GST-FZD2-CT, respectively. GST-PBD was a generous gift from Gary Bokoch (The Scripps Research Institute, La Jolla).

DAPLE shRNA constructs were created using the following approach. Promising targets at the 3' UTR region of human DAPLE (NM_001080414) were identified using the pSicoOligomaker software. The two most promising hits were chosen based on favorable score (>7). Duplexed oligos were designed against those targets and cloned in pSico Puro vector between HpaI and XhoI. Details of targets for hDAPLE sequence and oligos used are provided below:

Targets for hDAPLE 3' UTR (Coding DNA Sequence is from by 155-6241)

```
                                       SEQ ID NO: 3
    6570      GTAGAACACTCATTTGCAA (shRNA 1)

SEQ ID NO: 4
    6929      GCACCTGCCTTCCTAGATT (shRNA 2)
``` hDAPLEsh1 forward:

```
                                                     SEQ ID NO: 5
5'TGTAGAACACTCATTTGCAATTCAAGAGATTGCAAATGAGTGTTCTA

CTTTTTTC
``` hDAPLEsh1 reverse:

```
                                                     SEQ ID NO: 6
5'TCGAGAAAAAAGTAGAACACTCATTTGCAATCTCTTGAATTGCAAA

TGAGTGTTCTACA
``` hDAPLEsh2 forward:

```
                                                     SEQ ID NO: 7
5'TGCACCTGCCTTCCTAGATTTTCAAGAGAAATCTAGGAAGGCAGGTG

CTTTTTTC
``` hDAPLEsh2 reverse:

```
                                                     SEQ ID NO: 8
5'TCGAGAAAAAAGCACCTGCCTTCCTAGATTTCTCTTGAAAATCTAGG

AAGGCAGGTGCA
```

Demonstration that the primers specific for the 3' untranslated region (UTR) detect both DAPLE-fl and DAPLE-V2 isoforms by qPCR:

|  | Control | shRNA1 | shRNA2 |
|---|---|---|---|
| Daple-fl | | | |
| Fold Change | 1.0 | 0.11 | 0.14 |
| Daple-V2 | | | |
| Fold Change | 1.0 | 0.19 | 0.29 |

Figure 21A:
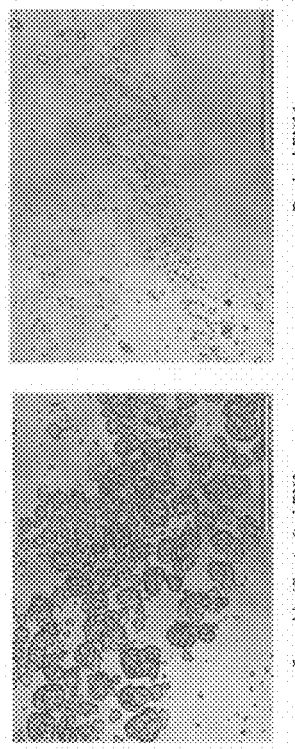
FIG. 21A-B. Selective depletion of DAPLE-fl in cancer initiating stem cells (CISCs) severely reduces the ability of CISCs to grow in tumor sphere cultures. Studies were done using the pLKO vector system (for shRNA delivery) in s707 cells that are cancer initiating stem cells (CISCs), from a 57 year old male with stage 1 colon cancer. This cell line was developed by Steven Lipkin's group (Sikandar et al., Cancer Res, 2010). In that manuscript, s707 is derived from patient #4. Thus, s707 is a cancer initiating stem cell slone derived from a moderately differentiated, stage 1, right colon, p53 negative, Kras negative tumor from a 57 year old male. No other information is readily available on other existing mutations. It was found that DAPLE-fl alone, not DAPLE-V2, was depleted in these cells using the shRNA approach using shRNA primers specific to DAPLE-fl as described herein. Depletion of DAPLE-fl alone severely reduced the ability of s707 cells to grow in tumor sphere cultures. (A) Images from a tumor sphere growth assay. Control or DAPLE-fl depleted s707 cells were allowed to grow in agar coated plates as tumor spheres (a measure of stemness). A week later, control cells continued to grow in spheres, whereas the DAPLE-depleted cells did not survive. (B) Bar graph showing the quantification of spheres (colony count, Y axis) in each condition.
Figure 21B:
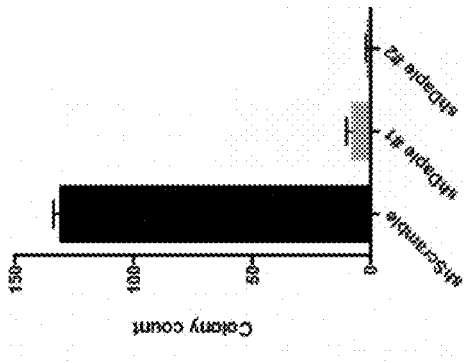
Figure 22B:
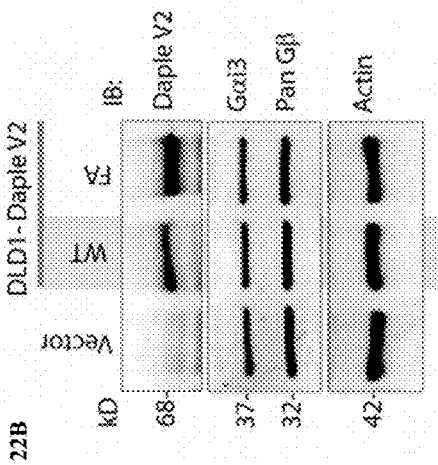
FIG. 22A-B. Expression of DAPLE-V2. (A) Whole cell lysates of DLD1 cells stably co-expressing the 7TGP reporter and either vector control or DAPLE-V2 were analyzed for DAPLE-V2, GFP and actin by immunoblotting (IB). The intensity of GFP indicates the extent of β-Catenin/TCF/LEF signals. (B) Whole cell lysates of DLD1 cells stably expressing vector control, DAPLE-V2 WT or FA were analyzed for DAPLE-V2, Gαi3, pan Gβ and actin by immunoblotting (IB).
Figure 22A:
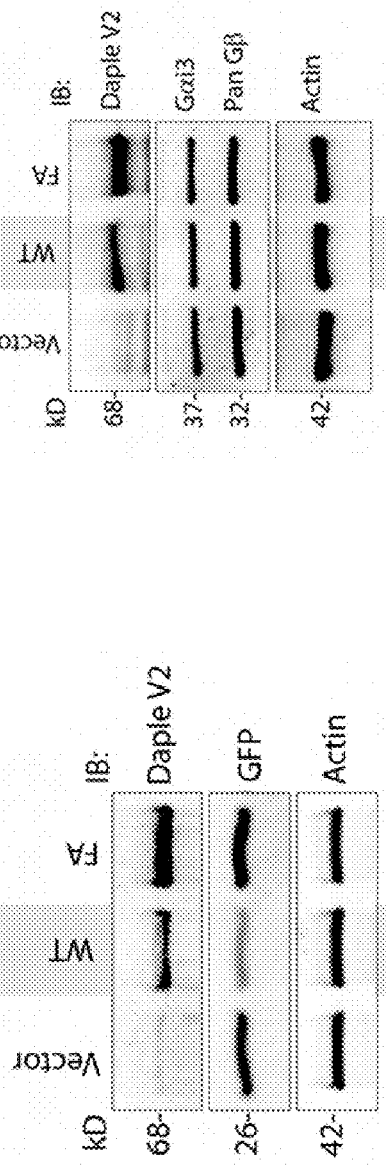

Primers specific for DAPLE-fl are shDaple1: CAGTAGAACACTCATTTGCAA (SEQ ID NO: 25) and shDaple2: AGGCACCTGCCTTCCTAGATT (SEQ ID NO: 26). These primers are particularly useful in targeting preferentially DAPLE-fl alone in cancer initiating stem cells (CISCs) as shown in FIG. 21.

Protein Expression and Purification

GST and His-tagged recombinant proteins were expressed in *E. coli* strain BL21 (DE3) (Invitrogen) and purified as described previously (Garcia-Marcos et al, 2011a; Ghosh et al, 2010; Ghosh et al, 2008). Briefly, bacterial cultures were induced overnight at 25° C. with 1 mM isopropylβ-D-1-thio-galactopyranoside (IPTG). Pelleted bacteria from 1 L of culture were resuspended in 20 mL GST-lysis buffer [25 mM Tris.HCl, pH7.5, 20 mM NaCl, 1 mM EDTA, 20% (vol/vol) glycerol, 1% (vol/vol) Triton X-100, 2×protease inhibitor mixture (Complete EDTA-free; Roche Diagnostics)] or in 20 mL His-lysis buffer [50 mM NaH2PO4 (pH 7.4), 300 mM NaCl, 10 mM imidazole, 1% (vol/vol) Triton X-100, 2×protease inhibitor mixture (Complete EDTA-free; Roche Diagnostics)] for GST or His-fused proteins, respectively. After sonication (three cycles, with pulses lasting 30 s/cycle, and with 2 min interval between cycles to prevent heating), lysates were centrifuged at 12,000×g at 4° C. for 20 min. Except for GST-FZD and GST-PBD constructs (see in vitro GST pulldown assay section), solubilized proteins were affinity purified on glutathione-Sepharose 4B beads (GE Healthcare) or HisPur Cobalt Resin (Pierce), dialyzed overnight against PBS, and stored at −80° C.

Cell Culture and the Rationale for Choice of Cells in Various Assays

Tissue culture was carried out essentially as described before (Garcia-Marcos et al, 2011a; Ghosh et al, 2010; Ghosh et al, 2008). A total of 5 different cell lines were used in this work, each chosen carefully based on its level of endogenous DAPLE expression and the type of assay. All these cell lines were cultured according to ATCC guidelines.

Cos7 cells were primarily used for transient overexpression of tagged DAPLE or Dv1 proteins and lysates of these cells were used as source of proteins in various protein-protein interaction (immunoprecipitation and pulldown) assays. These assays were carried out in Cos7 cells because they are easily and efficiently transfected (>90% efficiency) with most constructs. The added advantage is that they have no detectable endogenous DAPLE (by immunoblotting and qPCR) and provide a system to selectively analyze the properties of WT vs mutant DAPLE constructs without interference from endogenous DAPLE.

HeLa cells were primarily used to study the in-cellulo dynamics of interaction between DAPLE and FZD7R during non-canonical Wnt signaling because those cells have been extensively used to study Wnt5a-stimulated non-canonical signaling by various groups (Sato et al, 2010; Yamamoto et al, 2007). It was noted that HeLa cells have low amounts of endogenous DAPLE, and that it was an adequate system to study the role of DAPLE in cells because Wnt5a stimulation could trigger the previously described downstream signaling responses (Sato et al, 2010; Yamamoto et al, 2007). Noteworthy, the efficiency of transient transfection of various DAPLE constructs in these cells were >90%, as determined by immunofluorescence staining.

HEK293T cells were used exclusively for FRET and coimmunoprecipitation studies involving FZD7R/G proteins because these cells are widely used and preferred for such studies involving GPCR/G protein signaling due to several reasons. HEK293 cells are the single most widely used cell line for heterologous expression (both transient and stable expression) of GPCRs (Thomas & Smart, 2005) because they allow a robust expression of functional receptors compared to most cells (Massotte, 2003; Thomas & Smart, 2005). Microarray analyses have confirmed that they have an adequate transcriptome that supports various elements of GPCR/G protein signaling pathways, e.g., GPCR ligands, trimeric G proteins, scaffolding components that mediate receptor endocytosis, kinases and phosphatases that phosphoregulate GPCR functions, etc. (Atwood et al, 2011). It has been confirmed that they express endogenous DAPLE as a full length protein, at physiologic levels, and the localization of DAPLE (as determined by immunofluorescence) is primarily at the PM (data not shown), where FZDRs are activated.

Low passage NIH3T3 fibroblasts were used exclusively in 3-D Matrigel invasion assays and in neoplastic transformation assays to study the role of DAPLE in suppressing growth in soft agar upon Ras-mediated transformation. The rationale for their use in invasion assay lies in the fact that non-transformed NIH3T3 fibroblasts are poorly invasive in vitro and non-tumorigenic and non-metastatic in animal studies (Bondy et al, 1985; Chambers et al, 1990; Hill et al, 1988; Tuck et al, 1991). It is because of this reason, NIH3T3 cells are widely used to study proteins that can trigger a gain in invasive properties (Leitner et al, 2011). For the neoplastic transformation assays, Ras-transformed NIH3T3 cells were used because this is the gold standard assay used to study the role of a gene/protein in tumor transformation (Egan et al, 1987). The rationale for using NIH3T3 in both the above assays is further strengthened by the fact that they are highly transfectable (~80% transfection efficiency with myc-DAPLE) and express DAPLE at very low endogenous levels (as determined by immunoblotting and qPCR) compared to normal colonic epithelium. Such expression pattern allows us to study the effect of various mutant DAPLE constructs without significant interference due to the endogenous protein.

DLD1 were primarily used to study the effect of DAPLE on cancer cell growth properties (anchorage-dependent and independent) and to assess the effect of DAPLE on the classical Wnt signaling pathway (β Catenin/TCF/LEF). There are several reasons why this cell line was chosen: 1) colorectal cancer was the focus of this study and DLD1 cells were appropriate to translate the present findings because they are human colorectal cancer cells; 2) it was determined that levels of DAPLE are significantly lower (~10 fold) in these cells compared to normal colon (data not shown), thereby allowing us to study the effect of various mutant DAPLE constructs without significant interference due to the endogenous protein; 3) These cells have been extensively characterized with respect to most oncogenes (ATCC database), and are highly tumorigenic in 2-D and 3-D cultures due to a mutation in KRAS (G13D) (Ahmed et al, 2013; Shirasawa et al, 1993); 4) They are a sensitive model to study how various manipulations of the non-canonical Wnt signaling pathway oppose the canonical Wnt pathway during tumor growth because they constitutively secrete Wnt ligands to maintain high levels of the canonical signaling (Voloshanenko et al, 2013) within the growth matrix. Production and secretion of endogenous ligands bypasses the need to add exogenous ligands repeatedly during prolonged assays that last ~2 weeks.

Transfection; Generation of Stable Cell Lines and Cell Lysis

Transfection was carried out using Genejuice (Novagen) for DNA plasmids following the manufacturers' protocols. HeLa and DLD1 cell lines stably expressing DAPLE constructs were selected after transfection in the presence of 800 µg/ml G418 for 6 weeks. The resultant multiclonal pool was subsequently maintained in the presence of 500 µg/ml G418. DAPLE expression was verified independently using anti-Myc and anti-DAPLEantibodies by immunoblotting, and estimated to be ~5× the endogenous level. Unless otherwise indicated, for assays involving serum starvation, serum concentration was reduced to 0.2% FBS overnight for HeLa cells and 0% FBS for Cos7, HEK293T and DLD1 cells.

Whole-cell lysates were prepared after washing cells with cold PBS prior to resuspending and boiling them in sample buffer. Lysates used as a source of proteins in immunoprecipitation or pull-down assays were prepared by resuspending cells in Tx-100 lysis buffer [20 mM HEPES, pH 7.2, 5 mM Mg-acetate, 125 mM K-acetate, 0.4% Triton X-100, 1 mM DTT, supplemented with sodium orthovanadate (500 µM), phosphatase (Sigma) and protease (Roche) inhibitor cocktails], after which they were passed through a 28G needle at 4° C., and cleared (10,000×g for 10 min) before use in subsequent experiments.

Quantitative Immunoblotting

For immunoblotting, protein samples were separated by SDS-PAGE and transferred to PVDF membranes (Millipore). Membranes were blocked with PBS supplemented with 5% nonfat milk (or with 5% BSA when probing for phosphorylated proteins) before incubation with primary antibodies. Infrared imaging with two-color detection and band densitometry quantifications were performed using a Li-Cor Odyssey imaging system exactly as done previously (Garcia-Marcos et al, 2011a; Garcia-Marcos et al, 2010; Garcia-Marcos et al, 2012; Garcia-Marcos et al, 2011b; Ghosh et al, 2010). All Odyssey images were processed using Image J software (NIH) and assembled into figure panels using Photoshop and Illustrator software (Adobe).

In Vitro GST Pulldown and Immunoprecipitation Assays

Purified GST-Gαi3 or GST alone (5 µg) were immobilized on glutathione-Sepharose beads and incubated with binding buffer [50 mM Tris-HCl (pH 7.4), 100 mM NaCl, 0.4% (v:v) Nonidet P-40, 10 mM MgCl$_2$, 5 mM EDTA, 30 µM GDP, 2 mM DTT, protease inhibitor mixture] for 90 min at room temperature as described before (Garcia-Marcos et al, 2011a; Ghosh et al, 2010; Ghosh et al, 2008; Lin et al, 2011). Lysates (~250 µg) of Cos7 cells expressing appropriate myc-DAPLE constructs or purified His-DAPLE-CT (aa 1650-2028) protein (3 µg) were added to each tube, and binding reactions were carried out for 4 h at 4° C. with constant tumbling in binding buffer [50 mM Tris-HCl (pH 7.4), 100 mM NaCl, 0.4% (v:v) Nonidet P-40, 10 mM MgCl$_2$, 5 mM EDTA, 30 µM GDP, 2 mM DTT]. Beads were washed (4×) with 1 mL of wash buffer [4.3 mM Na$_2$HPO$_4$, 1.4 mM KH$_2$PO$_4$ (pH 7.4), 137 mM NaCl, 2.7 mM KCl, 0.1% (v:v) Tween 20, 10 mM MgCl$_2$, 5 mM EDTA, 30 µM GDP, 2 mM DTT] and boiled in Laemmli's sample buffer. In some experiments the 'active' conformation of the G protein was stabilized by replacing GDP in the binding and wash buffers with 30 µM GTPγS or a mixture of 30 µM GDP/30 µM AlCl$_3$/10 mM NaF. Immunoblot quantification was performed by infrared imaging following the manufacturer's protocols using an Odyssey imaging system (Li-Cor Biosciences).

GST-FZD7-CT and GST-PBD constructs were immobilized on glutathione-Sepharose beads directly from bacterial lysates by overnight incubation at 4° C. with constant tumbling. Next morning, GST-FZD7-CT immobilized on glutathione beads were washed and subsequently incubated with His-tagged DAPLE-CT or Gαi3 proteins at 4° C. with constant tumbling. Washes and immunoblotting were performed as previously.

For immunoprecipitation, cell lysates (~1-2 mg of protein) were incubated for 4 h at 4° C. with 2 µg of appropriate antibody, anti-HA mAb (Covance) for HA-Gαi3 or HA-FZD7, anti-FLAG (M2 from Sigma) mAb for FLAG-Gαi3, or their respective pre-immune control IgGs. Protein G (for all mAbs) Sepharose beads (GE Healthcare) were added and incubated at 4° C. for an additional 60 min. Beads were washed in PBS-T buffer [4.3 mM Na$_2$HPO$_4$, 1.4 mM KH$_2$PO$_4$, pH 7.4, 137 mM NaCl, 2.7 mM KCl, 0.1% (v:v) Tween 20, 10 mM MgCl$_2$, 5 mM EDTA, 2 mM DTT, 0.5 mM sodium orthovanadate] and bound proteins were eluted by boiling in Laemmli's sample buffer.

Homology Modeling

The structure of the synthetic peptide KB-752 bound to Gαi1 [PDB:1Y3A] was used as the template to generate the modeling project in Deep View/Swiss-PdbViewer v3.7 for DAPLE (aa 1668-1679) in complex with Gαi3. The modeling project was submitted to the Swiss-Model Server (http://swissmodel.expasy.org//SWISS-MODEL.html) (Schwede et al, 2003), and model images were generated by MolsoftICM (San Diego, Calif.).

Steady-State GTPase Assays

Under the experimental conditions of steady-state GTPase assays, GTP hydrolysis occurs as a two-step reaction, i.e., 1) GDP is released from the G protein and exchanged for GTP, and 2) the GTP loaded is hydrolyzed. Nucleotide exchange is the rate limiting step in this process because it is ~50-100 times slower than GTP hydrolysis by Gαi subunits (Mukhopadhyay & Ross, 2002). Thus, the steady-state GTPase activity reflects the rate of nucleotide exchange, and was performed as described previously (Garcia-Marcos et al, 2010; Garcia-Marcos et al, 2012; Garcia-Marcos et al, 2011b). Briefly, His-Gαi3 (100 nM) was preincubated with different concentrations of His-DAPLE-CT (aa 1650-2028) for 15 min at 30° C. in assay buffer [20 mM Na-HEPES, pH 8, 100 mM NaCl, 1 mM EDTA, 2 mM MgCl$_2$, 1 mM DTT, 0.05% (w:v) C12E10]. GTPase reactions were initiated at 30° C. by adding an equal volume of assay buffer containing 1 µM [γ-$^{32}$P]GTP (~50 c.p.m/fmol). For the time course experiments, duplicate aliquots (50 µl) were removed at different time points and reactions stopped with 950 µl ice-cold 5% (w/v) activated charcoal in 20 mM H$_3$PO$_4$, pH 3. For the dose-dependence curve experiments, reactions were stopped at 15 min. Samples were then centrifuged for 10 min at 10,000×g, and 500 µl of the resultant supernatant were scintillation counted to quantify released [$^{32}$P]Pi. For the time course experiments, data was expressed as raw c.p.m. For the dose-dependence curve experiments, the background [$^{32}$P]P$_i$ detected at 15 min in the absence of G protein was subtracted from each reaction and data expressed as percentage of the P$_i$ produced by His-Gαi3 in the absence of His-DAPLE-CT.

GTPγS Binding Assays

GTPγS binding was measured using a filter binding method as described previously (Garcia-Marcos et al, 2010; Garcia-Marcos et al, 2011b). His-Gαi3 (100 nM) was pre-incubated with different concentrations of His-DAPLE-CT (aa 1650-2028) for 15 min at 30° C. in assay buffer [20 mM Na-HEPES, pH 8, 100 mM NaCl, 1 mM EDTA, 25 mM $MgCl_2$, 1 mM DTT, 0.05% (w:v) C12E10]. Reactions were initiated at 30° C. by adding an equal volume of assay buffer containing 1 μM [$^{35}$S] GTPγS (~50 c.p.m/fmol). Duplicate aliquots (25 μl) were removed at different time points, and binding of radioactive nucleotide was stopped by addition of 3 ml, ice-cold wash buffer (20 mM Tris-HCl, pH 8.0, 100 mM NaCl, 25 mM $MgCl_2$). The quenched reactions were rapidly passed through BA-85 nitrocellulose filters (GE Healthcare) and washed with 4 ml wash buffer. Filters were dried and subjected to liquid scintillation counting. To determine the specific nucleotide binding, the background [$^{35}$S]GTPγS detected in the absence of G protein was subtracted from each reaction and data expressed as percentage of the [$^{35}$S] GTPγS bound by His-Gαi3 in the absence of His-DAPLE-CT.

FRET Studies

Figure 10E:
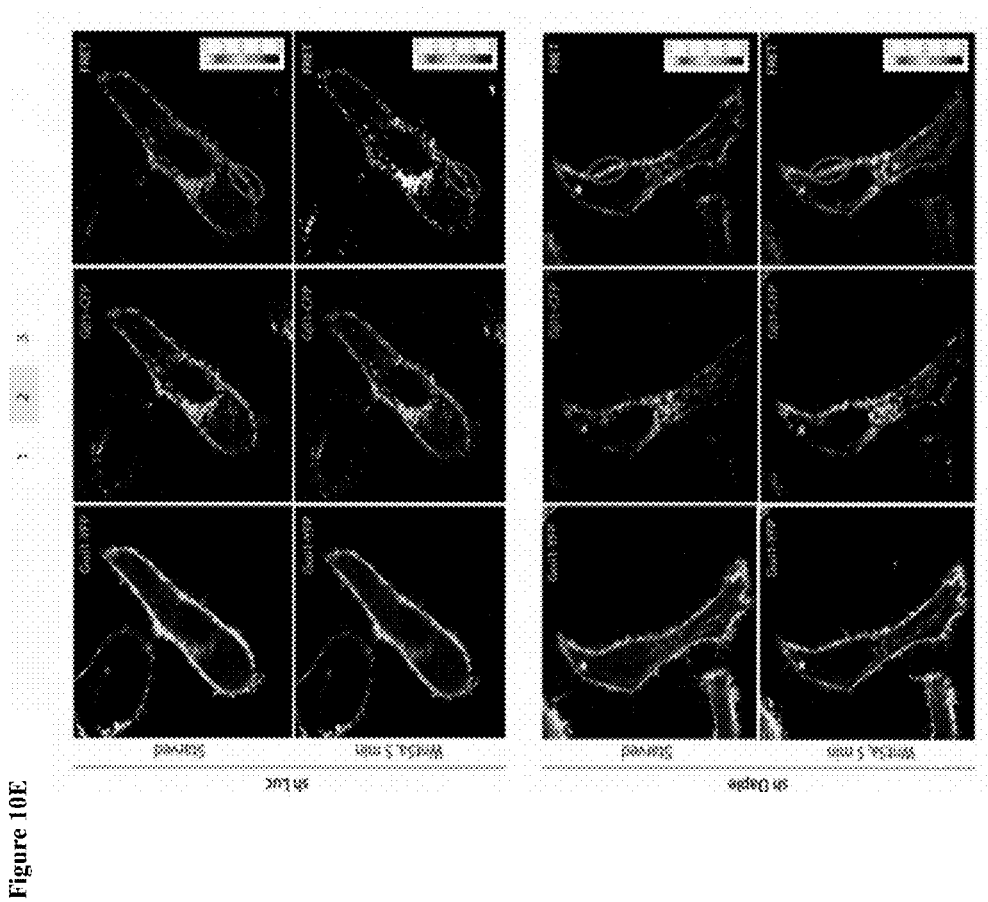

Förster Resonance Energy Transfer (FRET) experiments were performed using the classical ECFP- and EYFP-tagged proteins as donor and acceptor FRET-probe pairs, respectively. Previously validated and published FZD7-CFP construct was a generous gift from Carl-Philip Heisenberg (Witzel et al, 2006). Previously validated Gαi3-YFP and Gαi1-YFP (internally tagged Gαi subunits) and CFP-Gβ$_1$ were generous gifts from Moritz Bunemann (Bunemann et al, 2003; Gibson & Gilman, 2006). Interaction of FZD7-CFP and Gαi3-YFP proteins was studied in HEK293T cells using a Leica inverted laser scanning confocal microscope. Axial scans of 0.5μ thickness that resolved most of the P.M from a single cell was chosen for imaging and the signal in the donor and acceptor channels was ensured to be in mesoscopic regime to avoid inhomogeneity's between samples (Midde et al, 2014). Loss of FRET upon Gi activation and heterotrimer dissociation was measured between Gαi1-YFP and CFP-Gβ$_1$ proteins co-expressed in living HeLa cells using Olympus FV1000 inverted confocal laser scanning microscope equipped with a 60× 1.49 N.A oil immersed objective designed to minimize chromatic aberration and enhance resolution for 405-605 nm imaging as described previously (Midde et al, 2015). Images were sequentially acquired through Donor, FRET and Acceptor channels using 405 and 488 laser lines to excite CFP and YFP, respectively. FRET efficiency was calculated on a pixel by pixel basis from ratiometric images obtained in individual channels (donor, acceptor and FRET) through a RiFRET plugin in Image J software (Roszik et al, 2009). All images are corrected for the spectral cross-talk obtained from cells transfected with either donor or acceptor probes alone. Regions of interest (ROI) were randomly drawn at the plasma membrane (an example is shown in FIG. 10E) to compute FRET efficiency.

Gαi Activity as determined by Anti-Gαi: GTP mAb

For immunoprecipitation of active Gαi3, freshly prepared cell lysates (2-4 mg) were incubated for 30 min at 4° C. with the conformational Gαi:GTP mouse antibody (1 μg) (Lane et al, 2008b) or with control mouse IgG. Protein G Sepharose beads (GE Healthcare) were added and incubated at 4° C. for additional 30 min (total duration of assay is 1 h). Beads were immediately washed 3 times using 1 ml of lysis buffer (composition exactly as above; no nucleotides added) and immune complexes were eluted by boiling in SDS as previously described (Lopez-Sanchez et al, 2014).

Measurement of cAMP

HeLa cells were transfected with DAPLE-WT or DAPLE-FA, serum starved (0.2% FBS, 16 h) and incubated with isobutylmethylxanthine (IBMX, 200 μM, 20 min) followed by Wnt5a stimulation (100 ng/ml, 20 min) and Forskolin (10 uM, 10 min). To stop the reaction, cell medium was replaced with 150 μl of ice-cold TCA 7.5% (w/v). cAMP content in TCA extracts was determined by radioimmunoassay (MA) and normalized. To the amount of protein [(determined using a dyebinding protein assay (Bio-Rad)] per sample as previously described (Ostrom et al, 2001).

Gβγ Displacement Assays

This assay was performed as described previously (Garcia-Marcos et al, 2009). Briefly, GST alone or GST-Gαi3 proteins immobilized on glutathione-agarose beads were incubated overnight at 4° C. with HEK293T cell lysates in binding buffer [50 mM Tris-HCl, pH 7.4, 100 mM NaCl, 0.4% (v:v) NP-40, 10 mM $MgCl_2$, 5 mM EDTA, 2 mM DTT, protease inhibitor cocktail supplemented with 30 μM GDP]. Unbound Gβγ-subunits were washed twice with the same buffer and proteins bound to the glutathione-agarose beads divided into equal aliquots containing ~5 μg (~0.4 μM) GST-fusion proteins. Aliquots were incubated with increasing concentrations (0.05-1 μM) of purified His-DAPLE-CT (1650-2028) wild-type or 1 μM His-DAPLE-CT F1675A in binding buffer supplemented with GDP (~200 μl) for 5 h at 4° C. Glutathione-agarose beads were washed and bound proteins eluted by boiling in Laemmli sample buffer and separated by SDS-PAGE.

Rac1 Activity Assays

Rac1 activity in HeLa cells lines was monitored using GST-tagged PAK1-binding domain (PBD; pGEX-PBD) as described previously (Benard & Bokoch, 2002). Briefly, Escherichia coli strain BL21 bacteria transformed with pGEX-PBD were grown at 37° C. and GST-PBD expression was induced at OD600 with 1 mM IPTG for 3 h at 37° C. with shaking. Bacterial lysates were prepared as described above in protein purification section, cleared of debris by centrifugation and subsequently aliquots of lysates were stored at −80° C. until use. Aliquots of bacterial lysates were thawed, cleared of precipitated proteins by centrifugation at 14,000×g for 20 min, and the cleared supernatant was subsequently incubated with glutathione beads overnight at 4° C. with constant tumbling to prepare purified bead-bound GST-PBD freshly for each assay.

To analyze the role of DAPLE in regulation of Rac1 activity HeLa cells were used. For assays done on cells at steady-state, cells were maintained overnight in a media containing 2% or 0.2% FBS prior to lysis. Lysis was carried out first in RIPA buffer [20 mM HEPES pH 7.4, 180 mM NaCl, 1 mM EDTA, 1% Triton X-100, 0.5% sodium deoxycholate, 0.1% SDS, supplemented with 1 mMDTT, sodium orthovanadate (500 μM), phosphatase (Sigma), and protease (Roche) inhibitor mixtures] for 15 min on ice, and then for an additional 15 min after addition of an equal volume of Triton X-100 lysis buffer [20 mM Hepes (pH 7.2), 5 mM Mg-acetate, 125 mM K-acetate, 0.4% Triton X-100, 1 mM DTT, supplemented with sodium orthovanadate (500 μM), phosphatase (Sigma), and protease (Roche) inhibitor mixtures]. During the second 15 min of incubation, cells were broken by passing through a 28-gauge needle at 4° C. and lysates were subsequently cleared (10,000×g for 10 min) before use. For assays done with/without ligand stimulation, HeLa cells serum-starved (0.2% FBS) overnight and subsequently treated or not with 100 ng/ml Wnt5a for 5 min at prior lysis as above. Equal aliquots of lysates were incubated with bead-bound GST-PBD for 1 h at 4° C. with constant tumbling. Beads were washed in PBS-T buffer [4.3 mM $Na_2HPO_4$, 1.4 mM $KH_2PO_4$, pH 7.4, 137 mM NaCl, 2.7 mM KCl, 0.1% (v:v) Tween 20, 10 mM $MgCl_2$, 5 mM EDTA, 2 mM DTT, 0.5 mM sodium orthovanadate] and bound proteins were eluted by boiling in Laemmli's sample buffer.

Immunofluorescence

HeLa cell lines were fixed at room temperature with 3% paraformaldehyde for 20-25 min, permeabilized (0.2% Triton X-100) for 45 min and incubated for 1 h each with primary and then secondary antibodies as described previously (Ghosh, Garcia-Marcos et al. 2008). Dilutions of antibodies and reagents were as follows: Myc (1:500); Phalloidin (1:1000); DAPI (1:2000); goat anti-mouse (488 and 594) Alexa-conjugated antibodies (1:500); anti-phospho-Histone H3 (Ser28) (1:150). Cells were imaged on a Leica SPE confocal microscope using a 63x oil objective and 488, 561 and 405 laser lines for excitation (Lopez-Sanchez et al, 2014). All individual images were processed using Image J software and assembled for presentation using Photoshop and Illustrator software (Adobe).

β-Catenin Reporter Assays

These assays were carried out using the well-established reporter 7xTcf-eGFP (7TGP) (Fuerer & Nusse, 2010). Stable cells lines expressing this reporter were generated by lentiviral transduction and subsequent selection using standard procedures. Lentiviral infection and selection were performed according to standard procedures. Briefly, 10 cm plates DLD1 cells at 70% confluency were incubated with media containing 8 μg/mL polybrene and 10 μl of lentivirus for 6 h. After 24 hours post infection, selection of puromycin-resistant clones was initiated by adding the antibiotic at 2 μg/ml final concentration. The resultant DLD1-7TGP stable cells were subsequently transfected with various myc-DAPLE constructs and selected for G418 resistance as described earlier in methods. The DLD1-7TGP cells stably expressing myc-DAPLE were incubated overnight at 0.2% FBS, analyzed by fluorescence microscopy, and photographed prior to lysis. Whole cell lysates samples were then boiled in Laemmli's sample buffer and GFP protein expression was monitored by immunoblotting.

Scratch-Wounding, Trans-Well Chemotaxis and 3D-Matrigel Invasion Assays

Scratch-wound assays were done as described previously (Ghosh et al, 2008). Briefly, monolayer cultures (100% confluent) of HeLa cells expressing DAPLE-WT or DAPLE-FA were scratch-wounded using a 20 μl pipette tip and incubated in 2% FBS media. The cells were subsequently monitored by phase-contrast microscopy over the next 24 h. To quantify cell migration (expressed as percent of wound closure) images were analyzed using Image J software to calculate the difference between the wound area at 0 h and that at 12 h divided by the area at 0 hx100.

Chemotactic cell migration assays were performed using Corning® Transwell plates according to the manufacturer's protocol. HeLa cells were trypsinized, counted and placed in a Transwell with media containing 0.2% FBS (5000 cells/well). Media in the bottom chamber of each well was supplemented with 0.2% FBS and 100 ng/ml Wnt5a to trigger chemotactic migration. Cells were allowed to migrate for 24 h and fixed prior staining. Cells that had successfully migrated to the side of the permeable membrane facing the bottom chamber were visualized by staining the membrane with Giemsa. Cell migration (expressed as number of cells/high power field) was quantified by analyzing 15-20 random fields per membrane insert per condition for the number of Giemsa stained cells.

NIH3T3 cell invasion assay in 3D culture was performed according to the manufacturer's protocol (Trevigen, Cultrex 3D Spheroid BME Cell Invasion Assay, catalog #3500-096-K). Briefly, non-invasive NIH3T3 cells (~3000 cells) transfected with empty vector (control) or myc-DAPLEconstructs were incubated first in the Spheroid Formation extracellular matrix (ECM) containing 0.2% FBS for 3 days. Invasion matrix was then added and layered on top with media containing FBS. Serum-triggered cell invasion was photographed under light microscope everyday for 10 days and fresh media (FBS concentration is increased each time in order to maintain a gradient) was replenished every 48 h. Photographs were analyzed and pseudocolored by Image J to reflect cell density.

Analysis of Mitotic Index

The mitosis rate of HeLa cells stably expressing DAPLE-WT and DAPLE-FA was measured by phospho-Histone H3 (Ser28) (mitotic index) exactly as done previously (Ghosh et al, 2010). Mitotic index was determined by dividing the number of positively stained cells/the total number of DAPI-stained nucleix100.

Transformation Assay

Neoplastic transformationin Ras-transformed NIH3T3 fibroblasts was analyzed using standard assays of colony formation in soft agar as described previously (Clark et al, 1995). Low passage NIH3T3 cells (~5000) stably co-transfected with appropriate myc-DAPLE construct (2 μg cDNA) and HA-Ras G12V (1 μg cDNA) were analyzed for their ability to form tumor foci in soft agar plates. Plates were incubated in 5% CO2 at 37° C. for ~2 weeks in growth media supplemented with 2% FBS. They were finally incubated with 0.1% (wt/vol)dimethylthiazol-2-yl)2 2,5-diphenyl tetrazolium bromide (MTT; Sigma) in PBS for 1 h to visualize colonies. The remaining NIH3T3 cells not used for this assay were lysed and analyzed for myc-DAPLE and Ha-Ras G12V expression by immunoblotting.

Anchorage-Independent Tumor Growth Assay

Anchorage-independent growth of DLD1 cells was analyzed in agar as described previously (Wallert M A, 2007). Briefly, petri plates (60 mm) were pre-layered with 3 ml 1% Bacto agar (Life Technologies) in DMEM containing 10% FBS. Approximately ~5000 DLD1 cells stably expressing various DAPLE constructs were then plated on top in 3 ml of 0.3% agar-DMEM with 10% FBS. All assays were carried out using three replicate plates at a seeding density of ~5000 cells/plate. Following overnight incubation in 5% $CO_2$ incubator, 1 ml DMEM supplemented with 2% FBS was added to maintain hydration. After 2 wks of growth, colonies were stained with 0.005% crystal violet/methanol for 1 h, and subsequently photographed by light microscopy. The number of colonies in ~15-20 randomly-selected fields were counted under 10x magnification. The remaining DLD1 cells were lysed and analyzed by immunoblotting to confirm DAPLE construct expression. Each experiment was analyzed in triplicate.

Anchorage-Dependent Tumor Growth Assay

Anchorage-dependent growth was monitored on solid (plastic) surface as described previously (Franken et al, 2006). Briefly, anchorage-dependent growth was monitored on solid (plastic) surface. Approximately ~1000 DLD1 cells stably expressing various DAPLE constructs were plated in 6-well plates and incubated in 5% $CO_2$ at 37° C. for ~2 weeks in 0.2% FBS growth media. Colonies were then stained with 0.005% crystal violet for 1 h. The remaining DLD1 cells were lysed and analyzed by immunoblotting to confirm DAPLE construct expression. Each experiment was analyzed in triplicate.

Ccdc88c (DAPLE) mRNA Analysis in Circulating Tumor Cells (CTCs) from Patients with Metastatic Colorectal Carcinoma (mCRC)

Fifty-one patients with metastatic colorectal cancer from the Complexo Hospitalario Universitario de Santiago de Compostela, Spain were enrolled (Barbazan et al, 2012). All participants signed an informed consent specifically approved for this study by the Ethical Committee of the Complexo Hospitalario Universitario of Santiago de Compostela (code of approval: 2009/289). Inclusion criteria were the presence of measurable metastatic colorectal cancer (stage IV) and an Eastern Cooperative Oncology Group (ECOG) performance status not greater than 2. Disease progression, evaluated by computerized tomography, was defined following RECIST 1.1 guidelines (1) as an increase in the number of metastatic lesions, growth of existing lesions in more than 20% or both during treatment. Furthermore, 24 healthy individuals with similar age ranges to those of patients were included as negative controls CTCs were isolated using an EpCAM-based immunoisolation (dynabeads) using the CELLection Epithelial Enrich kit (Life Technologies) and CTC RNA was purified with the Qiamp Viral kit (Qiagen) as previously described (Barbazan et al, 2012). Briefly, Superscript III based cDNA synthesis (Life Technologies) was carried out to preamplify a region within the coiled-coil domain of DAPLE to maximize posterior detection rates (TaqMan Preamp kit, Applied Biosystems). Preamplified samples were subsequently subjected to TaqMan real-time PCR amplification (Applied Biosystems) (probe numbers Hs00380245_m1 and Hs00325884_m1). Nonspecific blood cells in the CTC-enriched isolates were accounted for by analyzing the expression of CD45 as a lymphoid cell marker (not present in cancer cells). All the results for DAPLE are normalized with the expression of CD45 (in all sample types). Briefly, the Ct value (coming from qPCRs) for DAPLE and CD45 are subtracted to 40 (maximum number of cycles in qPCR) to get an intuitive value (more value, more expression). DAPLE40-ct values are normalized with those from CD45, afterwards.

RNA Isolation and Quantitative PCR (qPCR)

Total RNA was isolated using an RNeasy kit (QIAGEN) as per the manufacturers' protocol. First-strand cDNA was synthesized using Superscript II reverse transcriptase (Invitrogen), followed by ribonuclease H treatment (Invitrogen) prior to performing quantitative real-time PCR. Reactions omitting reverse transcriptase were performed in each experiment as negative controls. Reactions were then run on a real-time PCR system (ABI StepOnePlus; Applied Biosystems). Gene expression was detected with SYBR green (Invitrogen), and relative gene expression was determined by normalizing to GAPDH using the $\Delta C_T$ method.

Primer Sequences are Listed as Follows:

| Gene | Forward | Reverse |
| --- | --- | --- |
| DAPLE-CC | 5'-TGA CAT GGA GAC CCT GAA GGC TGA-3' SEQ ID NO: 9 | 5'-TTTCATGCGGGCCTCACTGCTGA-3' SEQ ID NO: 10 |
| GAPDH | 5'-TCA GTT GTA GGC AAG CTG CGA CGT-3' SEQ ID NO: 11 | 5'-AAGCCAGAGGCTGGTACCTAGAAC-3 SEQ ID NO: 12 |
| LOXL3 | 5'-ATGGGTGCTATCCACCTGAG-3' SEQ ID NO: 13 | 5'-GAGTCGGATCCTGGTCTCTG-3' SEQ ID NO: 14 |
| Vim | 5'-AAGAGAACTTTGCCGTTGAA-3' SEQ ID NO: 15 | 5'-GTGATGCTGAGAAGTTTCGT-3' SEQ ID NO: 16 |
| SFPR-1 | 5'-GAGTTTGCACTGAGGATGAAAA-3' SEQ ID NO: 17 | 5'-GCTTCTTCTTCTTGGGGACA-3' SEQ ID NO: 18 |
| AXIN-2 | 5'-GAGTGGACTTGTGCCGACTTCA-3' SEQ ID NO: 19 | 5'-GGTGGCTGGTGCAAAGACATAG-3' SEQ ID NO: 20 |
| OPN | 5'-TTGCAGCCTTCTCAGCCAA-3' SEQ ID NO: 21 | 5'-GGAGGCAAAAGCAAATCACTG-3' SEQ ID NO: 22 |

Analysis of DAPLE mRNA Expression in Advanced Adenomas and Cancers

Advanced adenomas were collected and analyzed as described previously (Toiyama et al, 2013). All patients provided written informed consent and the study was approved by institutional review boards of Baylor University Medical Center, Dallas, USA and the Okayama University Hospital, Okayama, Japan. Colorectal carcinomas used in this work were derived from a previously well-characterized, chemo-naive, stage II colorectal cancer cohort from Munich (Nitsche et al, 2012). The ethics committee of the Klinikum rechts der Isar, Munich, Germany, approved collection of the patient samples (#1926/07, and #5428/12). All samples were obtained after prior informed written consent. For each sample, 20 to 30 mg of frozen tumor tissue was removed for further analysis using a cryostat microtome (CM3050 S, Leica Microsystems, Wetzlar, Germany). Histology-guided sample selection (Maak et al, 2013) was performed by a pathologist to ensure a sufficient amount of tumor cells (good cellularity and >30% tumor cells). RNA was obtained using the Qiagen® AllPrep DNA/RNA Mini Kit (Qiagen GmbH, Hilden, Germany) according to the manufacturer's protocol. Subsequently qPCR was performed as described above.

Data Analysis and Statistics

All experiments were repeated at least three times, and results were presented either as one representative experiment or as average±SD or SEM. Statistical significance was assessed with two-tailed Student's t test.

Statistical evaluation for CTC studies were performed using IBM® SPSS® Statistics Version 19 (SPSS Inc., IBM Corporation, Somers, N.Y., USA). In order to derive optimal cut-off values of DAPLE expression levels, maximally selected log-rank statistics performed by R Software version 2.13.0 (R Foundation for Statistical Computing, Vienna, Austria) were used. To consider multiple test issue within these analyses, the R-function maxstat.test was employed (Hothorn & Zeileis, 2008). Time-dependent survival probabilities were estimated with the Kaplan-Meier method, and the log-rank test was used to compare independent subgroups. All statistical tests were performed two-sided, and p-values less than 0.05 were considered to be statistically significant.

Example 2: DAPLE Possesses a Gα-Binding and Activating (GBA) Motif and Binds to Gαi Subunits It was recently discovered the first GEF motif for trimeric G proteins, i.e., the GBA motif, in the C-terminal region of the non-receptor protein GIV (Garcia-Marcos et al, 2009). It was shown that GIV binds and activates Ga subunits of the Gi subfamily via its GBA motif and regulates signal transduction. GIV is one of the 3 members of the CCDC88 family, which have in common an N-terminal HOOK domain followed by a long coiled-coil region but are highly divergent in their C-terminal region (Enomoto et al, 2006; Le-Niculescu et al, 2005): CCDC88b (aka GIPIE) completely lacks this C-terminal region whereas the C-terminal region of CCDC88c (aka DAPLE) shows significant divergence (15% identity, 26% similarity) compared to CCDC88a's (i.e., GIV) (FIG. 1A). The divergence in the C-terminal sequence allows CCDC88 proteins to associate with different proteins and regulate diverse biological processes (Enomoto et al, 2006; Le-Niculescu et al, 2005), e.g., a PDZ-binding motif (PBM) is found exclusively in DAPLE, at its extreme C-terminus, which binds the PDZ domain of Dishevelled (Dv1) and regulates Wnt signaling (Kobayashi et al, 2005; Oshita et al, 2003). Despite these apparent sequence differences among CCDC88 family members, a more detailed analysis of the C-terminal sequences of GIV and DAPLE from different vertebrate species revealed a cryptic GBA motif in DAPLE localized within the otherwise highly divergent C-terminal region (FIG. 1A). This putative GBA motif (aa 1668-1683) in DAPLE shares a high degree of similarity to previously reported GBA motifs found in proteins (Garcia-Marcos et al, 2009; Garcia-Marcos et al, 2011b) and synthetic peptides (Austin et al, 2008; Johnston et al, 2005) with GEF activity towards Gαi proteins (FIG. 1B). As a first step to investigate the functionality of this GBA motif co-immunoprecipitation (IP) experiments were carried out, which revealed that full-length endogenous DAPLE in HEK293 cells interacts with the trimeric G protein Gαi3 (FIG. 1C). It was next investigated if the interaction between DAPLE and G proteins presents the biochemical properties previously reported for other GBA motif sequences, i.e., they bind directly to the G protein with submicromolar to low micromolar affinity when it is in the inactive but not active conformation (Ghosh et al, 2008; Tall et al, 2003). Recombinant purified GST-Gαi3 bound robustly to purified His-DAPLE CT (aa 1650-2028, containing the GBA motif) when loaded with GDP (inactive) but not when loaded with GDP/AlF$_4^-$ or GTPγS (both mimic the GTP-bound active G protein) (FIG. 1D). Equivalent results were obtained when lysates of mammalian cells expressing full-length DAPLE were used in the pulldown assays (FIG. 1E). Binding of His-Gαi3-GDP to GST-DAPLE CT was saturable and fitting of the data to a one-site binding curve revealed a submicromolar equilibrium dissociation constant (Kd=0.11±0.03 µM, n=4), indicating a slightly higher affinity of the G protein for DAPLE than for GIV (Kd=0.24±0.03 µM, n=4) (FIG. 1F).

Figure 9:
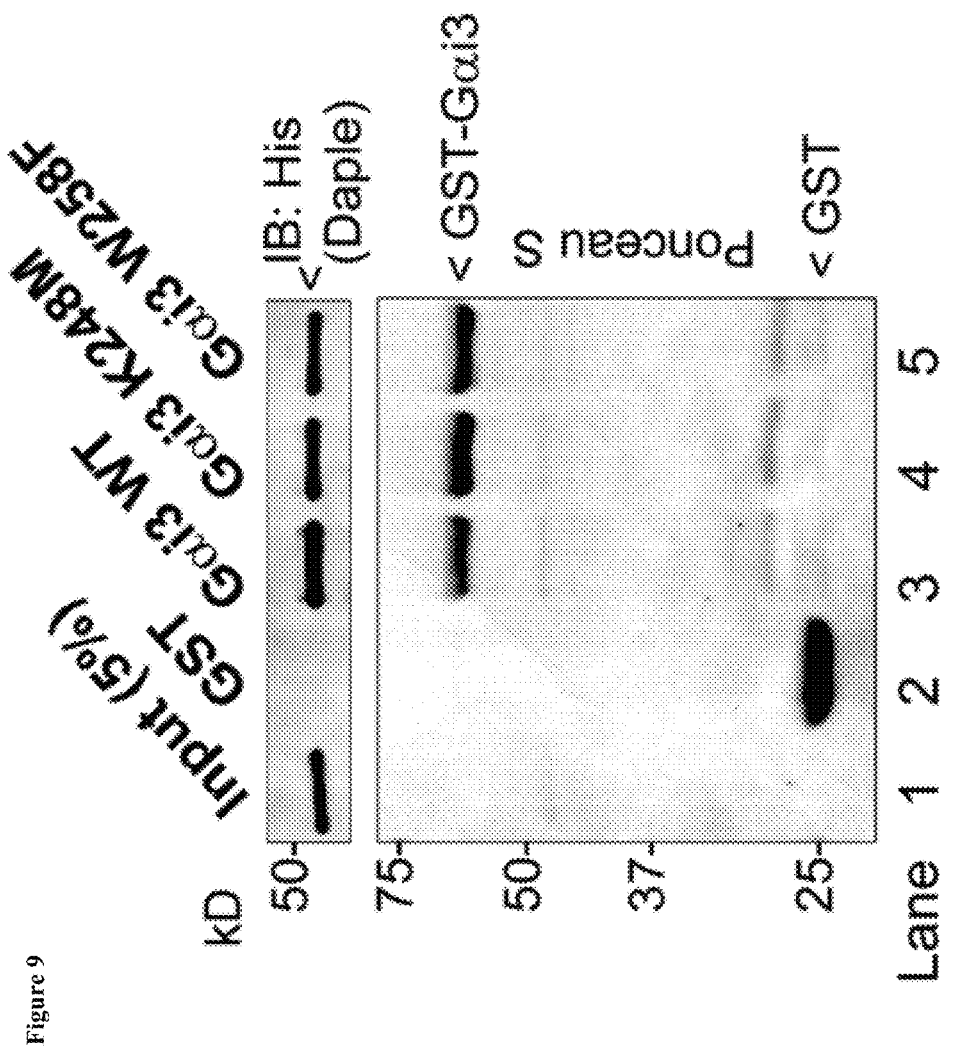
FIG. 9. DAPLE binds mutants of Gαi3 that do not bind GIV (W258F) or Calnuc (K248M). Purified, recombinant GST-Gαi3 (WT and mutants) preloaded with GDP and immobilized on glutathione-agarose beads was incubated with purified His-DAPLE-CT (aa 1650-2028) as indicated. Resin-bound proteins were eluted, separated by SDS-PAGE and analyzed by Ponceau S-staining and immunoblotting (IB) with anti-His antibodies. No binding to GST alone was detected.

Another common feature among previously reported GBA motifs is their high G protein specificity, i.e., they not only bind preferentially to Gi subfamily members but can discriminate within this subfamily by binding to Gαi subunits but not to the close homologue Gαo (~75% overall similarity to Gαi1/2/3 subunits) (Slep et al, 2008). It was found that this is also the case for DAPLE because it interacts with Gαi1, Gαi2 and Gαi3 (although binding to Gαi2 is partially reduced compared to Gαi1 and Gαi3) (FIG. 1G) but not with Gαo (FIG. 1H). Despite these biochemical properties shared with related GBA motifs, it was found that binding of DAPLE to Gαi has unique structural determinants that differentiate it from other proteins with a GBA motif, i.e., GIV and Calnuc. It was found that mutants of Gαi3 that were previously shown (Garcia-Marcos et al, 2010; Garcia-Marcos et al, 2011b) to be incapable of binding to GIV or Calnuc (i.e., W258F or K248M, respectively) retain their ability to bind DAPLE (FIG. 1I, FIG. 9). This result indicates that the DAPLE-Gαi3 interface has unique molecular features that provide specificity by making it different from other GBA motif-G protein interactions.

Taken together, these results demonstrate that DAPLE possesses a GBA motif, and that its interaction with G proteins presents all the biochemical features, i.e., G protein activation status dependence, affinity and specificity, characteristic of a GBA motif-containinG protein.

Example 3: Identification of Critical Structural Determinants for the Interaction Between Gαi and DAPLE's GBA Motif To gain insights into the interface between DAPLE and Gαi proteins, the previously published atomic structure of KB-752, a synthetic GEF peptide similar to the GBA motif (FIG. 1A), in complex with Gαi1 (Johnston et al, 2005) was studied. This structure was used as a template to build a homology model of the complex between the GBA motif of DAPLE and Gαi3 (FIG. 2A). The first prediction based on this model was that DAPLE would bind to a hydrophobic cleft on the G protein located between the switch II (SwII) region and the α3 helix. This seemed to be the case because two molecules known to bind onto the SwII/α3 cleft, i.e., the synthetic GEF peptide KB-752 (FIG. 10A) and His-GIV-CT (aa 1660-1870, containing its GEF motif) (FIG. 10B), competed with His-DAPLE-CT for binding to GST-Gαi3. The identity of the binding pocket was further substantiated using site-directed mutagenesis. Analysis of the homology model suggested that a major molecular contact is established by the hydrophobic interaction between the aromatic residues W211 and F215 located in the SwII region of Gαi3 and DAPLE's F1675 (FIG. 2A). Binding of His-DAPLE-CT to GST-Gαi3 was dramatically impaired upon mutation of W211 or F215 to Alanine (Ala; A) (FIG. 2B), indicating that these hydrophobic residues of the SwII/α3 cleft serve as a docking site for DAPLE. Importantly, W211A and F215A mutations have been previously shown not to disturb the native biochemical properties of Gαi proteins (Thomas et al, 2004), and therefore their inability to bind DAPLE is not a consequence of an overall defect in G protein folding or function. Furthermore, mutation of DAPLE's F1675, the residue in its GBA motif predicted to interact with W211 and F215 of the G protein (FIG. 2A) to Ala abolished GST-Gαi3 binding to either recombinant His-DAPLE-CT (FIG. 2C) or full-length myc-DAPLE expressed in mammalian cells (FIG. 2D). Equivalent results were obtained in co-IP experiments in that binding of full-length myc-DAPLE and Gαi3 co-expressed in mammalian cells was dramatically impaired upon mutation of F1675 to A (FIG. 2E; henceforth referred to as FA). Taken together, these results demonstrate that DAPLE utilizes its GBA motif to bind onto the SwII/α3 hydrophobic cleft of Gαi3.

Example 4: DAPLE is a Bona Fide Guanine Nucleotide Exchange Factor (GEF) for Gαi In Vitro GEFs are defined by their ability to accelerate the rate of nucleotide exchange. To determine if binding of DAPLE to Gαi3 accelerates the rate of nucleotide exchange on the G protein, two well-established enzymatic assays were carried out—the steady-state GTPase assay which indirectly reflects the rate of nucleotide exchange (Mukhopadhyay & Ross, 2002), and the GTPγS-binding assay which directly measures the rate of nucleotide exchange. It was found that incubation of His-Gαi3 with His-DAPLE-CT accelerated the rate of steady-state GTP hydrolysis ~3-fold over the basal activity (FIG. 2F). This acceleration of Gαi3 steady-state GTPase activity by DAPLE was dose-dependent, with an $EC_{50}$ of 0.25±0.06 µM (similar to the estimated Kd for the DAPLE-Gαi3 interaction, FIG. 1F), and was greatly diminished (>90%) in parallel reactions in which His-DAPLE-CT WT was replaced by the Gαi3 binding-deficient mutant F1675A (FIG. 2G). It was further validated that DAPLE is a bona fide GEF for Gαi using GTPγS binding assays which showed that the initial rate of nucleotide binding by His-Gαi3 was increased by His-DAPLE-CT in a dose-dependent manner, but it was not significantly affected by His-DAPLE-CT FA (FIG. 2H). Thus, DAPLE activates Gαi proteins in vitro by virtue of a GEF activity associated to its GBA motif.

Example 5: DAPLE Activates Gαi in Cells Responding to Wnt5a

Next it was determined whether DAPLE activates G proteins in mammalian cells responding to Wnt5a. To this end, HeLa cells stably expressing DAPLE-targeting shRNA sequences under the control Cre recombinase activity were generated (see Supplemental Materials for the rationale behind the choice of this cell type and others in subsequent sections). Upon Cre treatment, two independent shRNA sequences reduced DAPLE mRNA levels by >80% (FIG. 10C) and the DAPLE protein to virtually undetectable levels (FIG. 10D) compared to cells expressing a control shRNA targeting luciferase (shLuc). These cells were used in a previously validated assay in which activation of Gi is monitored by dissociation of fluorescently tagged Gαi and Gβγ subunits with a resultant loss of Förster resonance energy transfer (FRET) (Bunemann et al, 2003; Gibson & Gilman, 2006; Janetopoulos et al, 2001) (FIG. 2I-L). When control HeLa cells co-expressing Gαi1-YFP (internal tag), CFP-G$β_1$ (N-terminal tag) and G$γ_2$ (untagged) were stimulated with Wnt5a a significant loss of FRET was observed, i.e., Gi heterotrimer dissociated into Gαi-YFP and CFP-Gβγ subunits at the plasma membrane (PM) within 5 min as determined by a significant drop in FRET efficiency from 0.36±0.08 to 0.17±0.06 (FIG. 2J, L, FIG. 10E), indicating that Gi is activated in response to Wnt5a. No significant drop in FRET was observed in DAPLE-depleted cells (FIG. 2K, L; FIG. 10E), indicating that donor-CFP-Gβγ and acceptor-Gαi-YFP subunits continued to interact (i.e., Gi heterotrimers remained intact) at the PM regardless of Wnt5a stimulation, and that Gαi remained inactive. These results demonstrate that DAPLE is essential for activation of Gi upon Wnt5a stimulation.

Figure 2N:
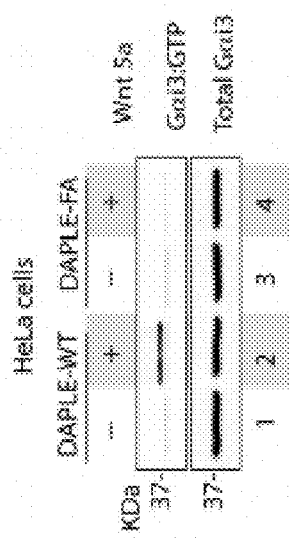
Figure 2M:
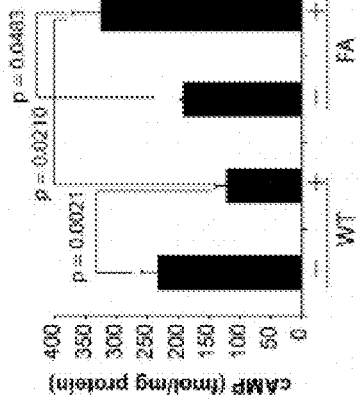

Next it was determined if the GBA motif in DAPLE is essential for activation of Gαi in cells responding to Wnt5a. To this end, activation of Gαi was analyzed in HeLa cells expressing DAPLE-WT or FA using an anti-Gαi:GTP mAb that specifically recognizes Gαi in a GTP-bound active conformation (Lane et al, 2008a). Previous work by others (Lane et al, 2008a) and by the present inventore=s (Lopez-Sanchez et al, 2014) has demonstrated that this antibody can specifically recognize active Gαi in cells. When Gαi from HeLa cells was immunoprecipitated, active Gαi3 was immunoprecipitated exclusively after Wnt5a stimulation in cells expressing DAPLE-WT (FIG. 2M), but not in those expressing DAPLE-FA. These results indicate that an intact GBA motif is essential for DAPLE to activate Gαi3 after Wnt5a stimulation. To further substantiate this, the intracellular levels of cAMP were determined as a measure of the activity of adenylyl cyclase, which is directly inhibited by active Gαi subunits. It was found that Wnt5a stimulation suppressed cAMP levels by ~50% in HeLa cells expressing DAPLE-WT, but no such suppression occurred in cells expressing DAPLE-FA (FIG. 2N). Taken together, these results demonstrate that DAPLE is a bona fide GEF that activates Gαi proteins in vitro and in cells responding to Wnt5a via its GBA motif.

Example 6: DAPLE Activates Rac1 and PI3K-Akt Signaling Via Release of Free Gβγ Subunits In addition to modulation of cellular cAMP, another major consequence of activating Gαi subunits is the release of free Gβγ subunits, which in turn modulates a wide array of signaling pathways (Smrcka, 2008; Smrcka, 2013). Comparative analysis of the crystal structure of the Gαi1·βγ trimer and the homology model of DAPLE's GBA motif bound to Gαi3 revealed that Gβγ and DAPLE have overlapping binding sites on Gαi subunits (FIG. 3A). Based on this, it was hypothesized that binding of DAPLE to Gαi will displace Gβγ from trimeric Gαi·βγ complexes. It was found that is indeed the case because His-DAPLE-CT WT but not the FA mutant (which cannot bind Gαi) displaced Gβγ from a pre-assembled complex with GST-Gαi3 (FIG. 3B). The $IC_{50}$ for this displacement was 0.16±0.01 µM (FIG. 3C), which is consistent with the estimated affinity of DAPLE for Gαi3 (FIG. 1F).

To determine if the 'free' Gβγ released by DAPLE's GBA motif modulated cellular signaling, two signaling pathways, Rac1 and PI3K-Akt, were analyzed because previous studies have demonstrated a direct and critical role of 'free' Gβγ subunits in enhancement of these signals (Leopoldt et al, 1998; Niu et al, 2003; Ueda et al, 2008; Welch et al, 2002; Xu et al, 2012), and because they represent major signals downstream of the non-canonical Wnt pathway (Anastas et al, 2014; Kawasaki et al, 2007; Nishita et al, 2010). Rac1 activity, as determined in pulldown assays using the p21 binding domain (PBD) of PAK1 (Knaus et al, 2007), was suppressed in DAPLE-depleted HeLa cells both at steady-state in the presence of low serum (FIG. 3D) as well as after Wnt5a stimulation (FIG. 3E). Furthermore, Wnt5a triggered activation of Rac1 in cells expressing DAPLE-WT, but not the FA mutant (FIG. 3F). These findings indicate that DAPLE, and its GBA motif are required for the efficient activation of Rac1 activity. Similarly, it was found that activation of Akt, as determined by phosphorylation of the kinase at Ser473 was enhanced in cells expressing DAPLE WT, but not the FA mutant, both at steady-state in the presence of low serum (FIG. 3G), as well as after Wnt5a stimulation (FIG. 3H), indicating that DAPLE's GBA motif is essential for enhancement of PI3K/Akt signaling.

To pinpoint whether the enhanced Rac1 and Akt signals are triggered directly by 'free' Gβγ subunits that are released by DAPLE, a Gβγ inhibitor, i.e., Gallein, was used that selectively blocks the interaction between Gβγ with key downstream effectors (Bonacci et al, 2006; Lehmann et al, 2008; Seneviratne et al, 2011; Smrcka et al, 2008; Urano et al, 2008). It was found that incubation of HeLa cells expressing DAPLE WT with Gallein effectively inhibited both Rac1 (FIG. 3I) and Akt (FIG. 3J) activities to levels observed in cells expressing DAPLE FA, whereas the inactive analogue, Fluorescein had no such effect. These results indicate that DAPLE enhances Rac1 and Akt signaling at least in part by facilitating the release of 'free' Gβγ subunits, which subsequently trigger signaling via downstream intermediates.

In summary, these results indicate that the dissociation of Gαi·βγ heterotrimers triggered upon Wnt5a stimulation by DAPLE's GBA motif sets off at least two major immediate events within the G protein signaling cascade—1) GTP-loading of Gαi subunits which subsequently inhibits the adenylyl cyclase/cAMP pathway, and 2) release of Gβγ subunits that trigger the activation of non-canonical Wnt signaling pathways including Rac1 and PI3K-Akt.

Figure 4A:
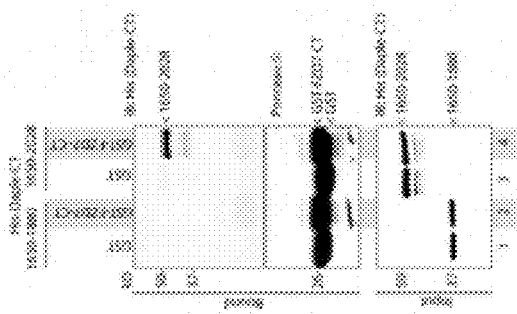
Figure 4B:
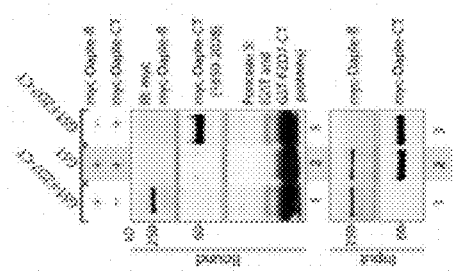
Figure 11B:
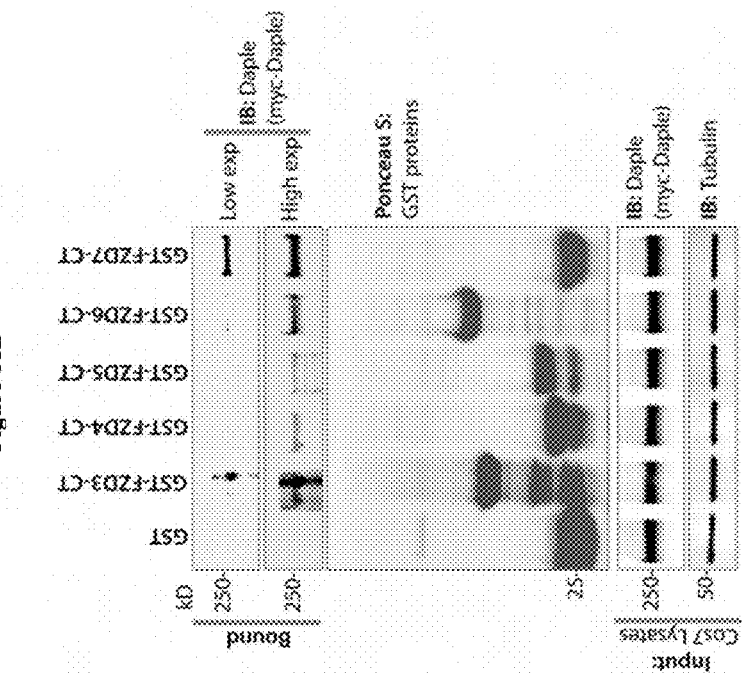
FIG. 11A-11C. DAPLE preferentially binds the cytoplasmic tail of the FZD7R. (A) A sequence homology-based cluster tree of vertebrate Frizzled receptors is shown. The Frizzled (FZD; IUPHAR nomenclature) family roughly clusters into four distinct families based on sequence identity (modified from (Verkaar & Zaman, 2010): (I) FZD 1, 2 and 7, (II) Frizzled-5 and -8, (III) Frizzled-3 and -6, (IV) Frizzled-4, -9 and -10. The Smoothened (SMO) receptor is a distant relative of FZD receptors that functions in Hedgehog signal transduction. (B, C) Lysates of cells expressing myc-DAPLE full length was used as source of DAPLE in pulldown assays with immobilized recombinant GST-tagged C-termini of various FZDRs. Bound proteins were analyzed for DAPLE by immunobloting (IB). Full length DAPLE binds preferentially to the cytoplasmic tail of FZD7R, to an intermediate extent to the cytoplasmic tail FZD6R and only weakly the cytoplasmic tails of other FZDRs.
Figure 11A:
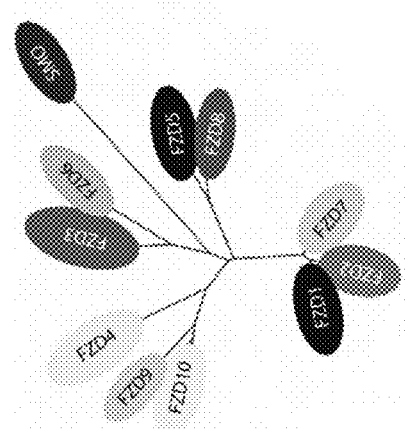
Figure 11C:
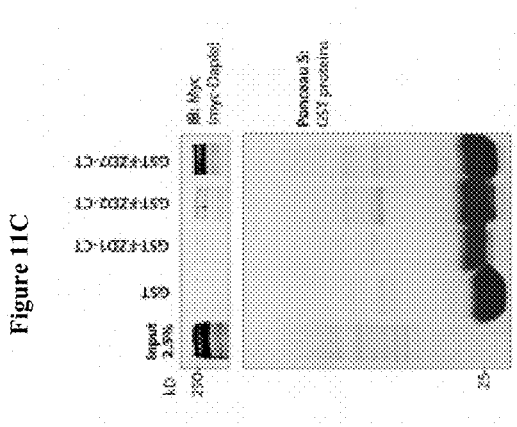
Figure 12A:
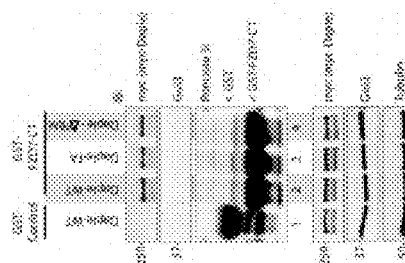
FIGS. 12A-12C. DAPLE binds to the C-terminus of FZD7R and links Gαi to ligand-activated receptors. (A) HEK cells expressing HA-tagged FZD7R were starved for 24 h (0% FBS) and stimulated with Wnt5a for 5 min as indicated prior to lysis. Immunoprecipitation was carried out on lysates with Anti-HA or control mouse IgGs and protein G beads. Equal aliquots of lysates (bottom) and immune complexes (top) were analyzed for DAPLE, Gαi3, FZD7R (HA) and tubulin by immunoblotting (IB). Endogenous DAPLE and Gαi3 are recruited to FZD7R exclusively after Wnt5a stimulation. (B) Lysates of Cos7 cells expressing myc-tagged DAPLE-WT or GBA-deficient (FA) and PBM-deficient (ΔPBM) mutants were used as source of DAPLE in pulldown assays with GST-FZD7-CT immobilized on glutathione beads. Bound proteins were analyzed for DAPLE by immunoblotting (IB). Mutant DAPLE proteins bound FZD7 as efficiently as DAPLE-WT. (C) HEK cells co-transfected with FZD7-CFP, Gαi3-YFP and DAPLE-WT or FA were starved and subsequently stimulated with Wnt5a and analyzed for FRET using confocal microscope. Representative freeze-frame images from live-cell movies are shown, which display (from left to right) donor (FZD7-CFP), acceptor (Gαi3-YFP), DAPLE (far-red; 632 nm) and intensities of acceptor emission due to FRET in each pixel. Interaction (i.e., FRET) is observed exclusively after Wnt5a stimulation in cells expressing DAPLE-WT, but not DAPLE-FA.

Example 7: DAPLE Links G Proteins to Ligand-Activated Frizzled Receptors Via its GBA Motif Because DAPLE enhances non-canonical Wnt signaling that is initiated by FZDRs, it needed to be determined how DAPLE may modulate signals downstream of these receptors, and if they interact. Several purified GST-tagged FZDR cytoplasmic tail proteins were tested for their ability to bind DAPLE from Cos? lysates (FIGS. 11A-C). More specifically, FZDRs 1-8 were tested, which belong to 3 evolutionary distinct subfamilies within the FZDR superfamily (FIG. 11A) containing divergent sequences in their C-terminus that determine which regulatory proteins are assembled (Dijksterhuis et al, 2014; Schulte, 2010). DAPLE bound robustly to FZD7R, and only weakly to others, indicating that DAPLE may engage preferentially with FZD7R (FIGS. 11B & 11C). Based on this result FZD7R was used in all subsequent assays to further analyze the interaction between DAPLE and FZDR. It was found that both endogenous and exogenously expressed DAPLE and Gαi3 co-immunoprecipitated with FZD7R exclusively after Wnt5a stimulation (FIG. 4A, FIG. 12A), indicating that DAPLE and Gαi3 form complexes with ligand-activated FZD7R. Immunofluorescence studies revealed that in starved HEK293 cells DAPLE is cytosolic in distribution, but in cells responding to Wnt5a DAPLE is localized at the plasma membrane (PM), where it colocalized with FZD7R (FIG. 4B). These findings suggest that the ligand-dependent interaction between FZD7R and DAPLE seen in 4A occurs at the PM.

Figure 4C:
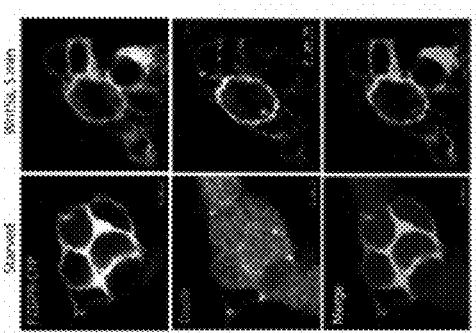
Figure 4D:
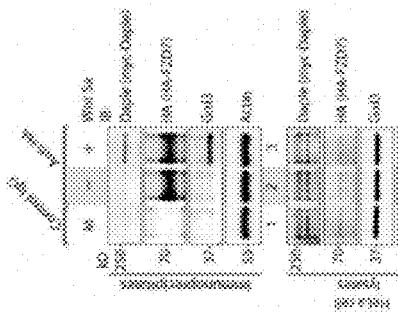
Figure 12B:
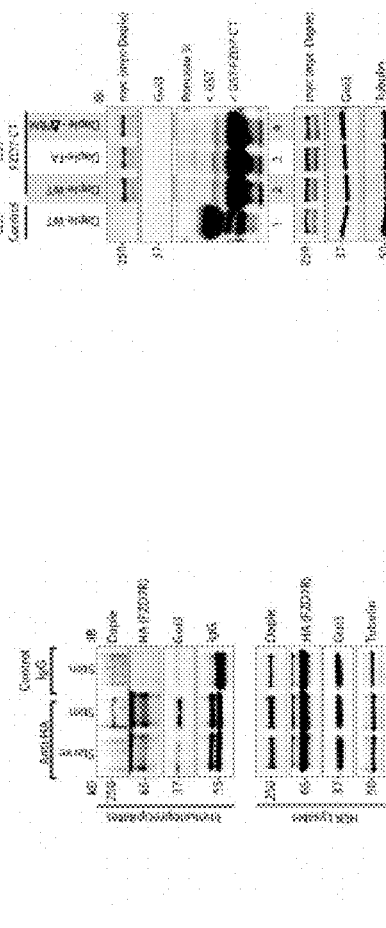

Next it was asked which region of DAPLE interacts with FZD7R and whether the binding is direct. It was found that the C-terminal ~380 aa of DAPLE (aa 1650-2028) was sufficient to interact with GST-FZD7R-CT as efficiently as the full length DAPLE (FIG. 4C). Pulldown assays with the purified, recombinant His-tagged identical segment (aa 1650-2028) of DAPLE revealed that the binding is direct (FIG. 4D). A shorter C-terminal fragment of DAPLE (aa 1650-1880) which lacks the ~150 aa at the extreme C-terminus does not (FIG. 4D). Furthermore, the GEF-deficient (FA) and the PDZ-binding motif-deficient (ΔPBM) mutants bound GST-FZD7R-CT as efficiently as DAPLE WT (FIG. 12B). These findings demonstrate that—1) the FZD7R-DAPLE interaction is direct; 2) that the aa 1650-2028 in the C-terminus of DAPLE is sufficient to mediate the interaction; 3) that the extreme C-terminal ~150 aa within the C-terminus (1881-2029) is essential for the interaction, whereas both the GBA and PBM motifs are dispensable.

Figure 4E:
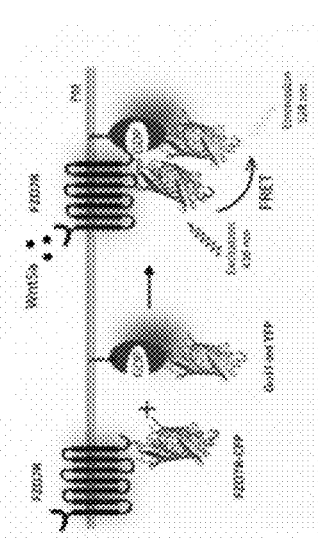
Figure 4F:
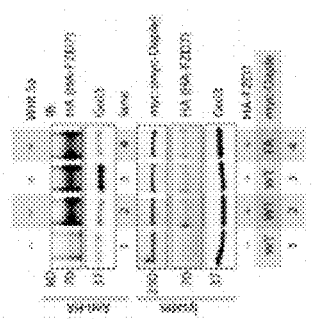
Figure 4G:
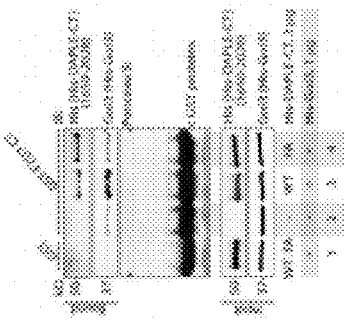
Figure 12C:
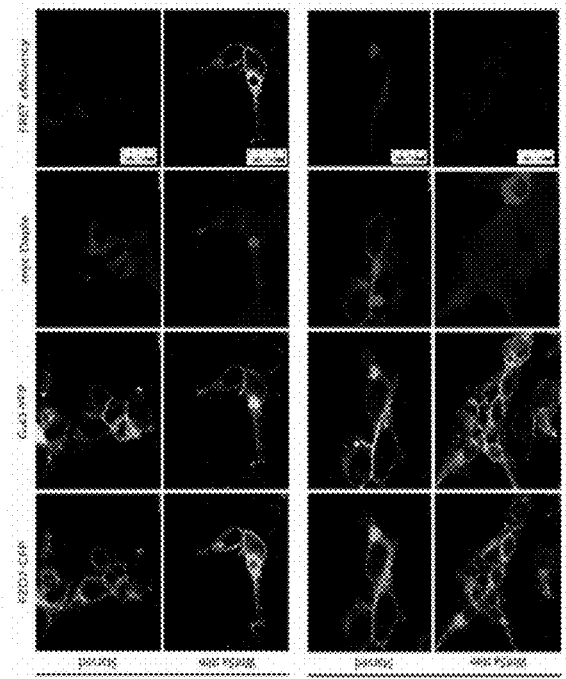

Because Gαi3 coimmunoprecipitated with ligand-activated FZD7R-DAPLE complexes (FIG. 4A), it was next asked if the interaction observed is direct, or mediated by DAPLE. GST pulldown assays were first carried out with recombinant His-Gαi3 and the GST-tagged cytoplasmic tail of FZD7R. It was found that Gαi3 bound weakly to GST-FZD7R-CT (FIG. 4E; lane 2); however, binding was increased ~5 fold in the presence of recombinant DAPLE-CT WT, but not the FA mutant. This raised the possibility that the ligand-dependent interaction between Gαi and FZD7 that was seen in cells (FIG. 4A) is indirect and mediated by the GBA motif in DAPLE. Indeed ligand-dependent recruitment of Gαi3 to FZD7R occurred exclusively in cells expressing full length DAPLE-WT (where GBA motif is intact), but not the FA mutant (FIG. 4F). Next, the spatiotemporal dynamics of ligand-dependent complex formation between FZD7R and Gαi3 was analyzed in HEK293 cells by FRET imaging (FIG. 4G). It was found that the probe-pair FZD7R-CFP and Gαi3-YFP interact at the PM within 5 min after ligand stimulation (FRET efficiency=0.25±0.06) (FIGS. 4H, I). No such interaction was observed in starved cells (FRET efficiency=0.04±0.01), demonstrating that Wnt5a triggers the assembly of complexes between ligand-activated FZD7R and Gαi3 at the PM. Furthermore, ligand-dependent assembly of such complexes occurred in cells expressing DAPLE-WT, but not the FA mutant (FIGS. 4J & 4K; FIG. 12C), further confirming that DAPLE serves as in intermediate protein that couples FZD7R to Gαi3. Although the interaction between ligand-activated FZD7R and DAPLE does not require the GBA motif (FIG. 12B), the recruitment of Gαi into the complex requires a functionally intact GBA to trigger the formation of FZD7R(active)-DAPLE-Gαi complexes. Thus, two non-overlapping modules in-tandem within DAPLE's C-terminus cooperate to facilitate the assembly of FZD7R(active)-DAPLE-Gαi ternary complexes (FIG. 4L)—1) a GBA motif that binds Gαi, and 2) a stretch of C-terminus (aa 1681-2024) is essential for binding to FZD7R.

Figure 13B:
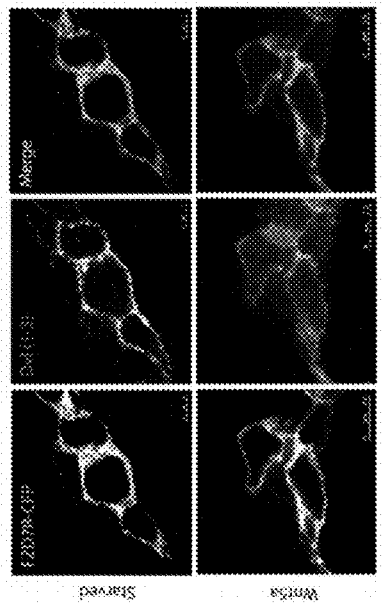
FIGS. 13A-13D. DAPLE competes with Dv1 for binding to FZD7R and inhibits the canonical β-caenin/TCF/LEF signaling pathway. (A) Equal aliquots of lysates from Cos7 cells expressing Dvl1 alone (lane 2), myc-DAPLE alone (lane 3) or coexpressing both (lanes 1, 4) were used as source of DAPLE and Dv1 in GST pulldown assays with recombinant, immobilized GST or GST-FZD7-CT. Bound proteins were analyzed for Dvl1 and DAPLE by immunoblotting (IB). Binding of each protein was higher when expressed alone (lanes 2, 3) than when co-expressed (lane 4). (B) Dvl loses colocalization with FZD7R at the plasma membrane after Wnt5a stimulation. HEK293 cells expressing FZD7-CFP were grown on coverslips coated with Poly-D-Lysine, starved overnight and treated with 0.1 mg/ml Wnt5a as in 4B. Cells were fixed and stained for endogenous Dvl (red) and analyzed by confocal microscopy. (C, D) Generation and characterization of DLD1 7TGP cell lines stably expressing DAPLE. (C) DLD1 7TGP cell lines stably expressing DAPLE-WT or FA were starved and stimulated analyzed for DAPLE expression and phosphorylation of Akt by immunoblotting (IB). (D) Images display representative fields from monolayers of DLD1 cells grown in 0.2% FBS by fluorescence microscopy. The intensity of eGFP signals denote Wnt transcriptional activity. Inset shows immunoblots (IB) of equal aliquots of whole cell lysates of DLD1-7TGP cells expressing control vector, DAPLE-WT or DAPLE-FA. Compared to DLD1 cells expressing DAPLE-WT, those expressing DAPLE-FA also express higher levels of GFP protein, indicative of higher Wnt transcriptional activity.
Figure 13A:
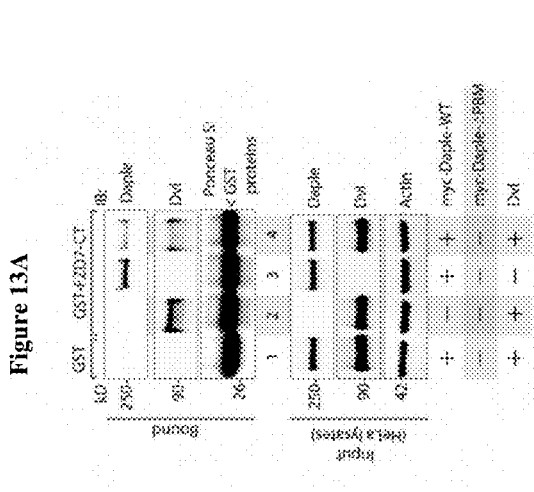

Example 8: DAPLE Competes with Disheveled (Dv1) for Binding to FZDRs and Antagonizes Wnt Signaling Via the β-Catenin/TCF/LEF Pathway Previous studies have demonstrated that Dv1, a key scaffold protein in the Wnt signaling pathway interacts with both FZDRs (Schulte & Bryja, 2007) and DAPLE (Oshita et al, 2003) and shapes both canonical and non-canonical Wnt signals. Furthermore, Dv1 interferes with the engagement of Gi proteins with ligand-activated FZDRs (Kilander et al, 2014), suggesting a possible interplay between Dv1 and the FZDR-DAPLE-Gi signaling axis defined here. First, it was investigated how the ligand-dependent DAPLE-FZD7R interaction affects Dv1's ability to bind DAPLE. It was found that DAPLE co-immunoprecipitated with Dv1 exclusively in starved cells and that such complexes were undetectable after stimulation with Wnt5a (FIG. 5A), indicating that the dissociation of DAPLE-Dv1 complexes coincides with the assembly of DAPLE-FZD7R complexes were observed in FIG. 4A. Next it was investigated how DAPLE affects the interaction between Dv1 and FZDR. It was found that expression of DAPLE in HEK293 cells reduces Dv1 association with FZD7R in pulldown (FIG. 13A) and co-immunoprecipitation experiments (FIG. 5B), suggesting that DAPLE and Dv1 may compete with each other for binding to FZD7R. Furthermore, immunofluorescence studies confirmed that localization of Dv1 at the PM in cells expressing FZD7R was reduced within 5 min after Wnt5a stimulation (FIG. 13B), which coincides with the ligand-dependent recruitment of DAPLE (FIG. 4B). It was found that DAPLE and Dv1 actually compete for binfing to FZD7R because increasing amounts of purified His-DAPLE-CT (1650-2028), but not a shorter fragment (His-DAPLE 1650-1880, which lacks the FZD7R-binding region) increased the formation of DAPLE-FZDR complexes and reduced Dv1 binding to the GST-fused C-terminal tail of FZD7R (FIG. 5C). Furthermore, immunofluorescence studies revealed, that in cells without DAPLE, stimulation with Wnt5a does not trigger the loss of Dv1 from the PM observed in control cells (FIG. 5D), suggesting that the competition observed in vitro (FIG. 5C) may occur also in cells. Taken together these results indicate that DAPLE determines the relocalization of Dv1 upon Wnt5a stimulation by displacing the latter from FZDRs.

Because the interplay between of DAPLE and Dv1 is modulated by Wnt5a and the GBA motif of DAPLE regulates Wnt5a signaling responses, next it was examined if/how the DAPLE-Gαi interaction affects the interaction between Dv1 and DAPLE. In in vitro competition assays with recombinant proteins it was found that binding between DAPLE and Dv1 was reduced with increasing amounts of His-Gαi3 (FIG. 5E). No such reduction was noted when the DAPLE-CT-WT was replaced by the GBA-deficient FA mutant (that cannot bind G proteins) in the above assays. These findings indicate that Gαi3 competes with Dv1 for binding to DAPLE-CT, and that an intact GBA motif is essential for such competition. Together, these results suggest that the Gαi-DAPLE and DAPLE-FZD7R interactions described herein have at least two major effects on the interplay between DAPLE, Dv1 and FZD7R: 1) DAPLE and Dv1 compete for binding to the C-terminus of FZD7R, and 2) Gαi and Dv1 compete for binding to the C-terminus of DAPLE. Consequently, stimulation with Wnt5a triggers the dissociation of DAPLE-Dv1 and FZD7R-Dv1 complexes, and favors the assembly of FZD7R-DAPLE-Gαi signaling complexes at the PM in detriment of FZD7R-Dv1 complexes.

Figure 5L:
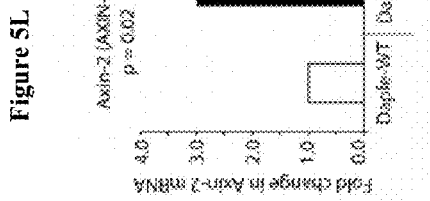
Figures 5J, 5K:
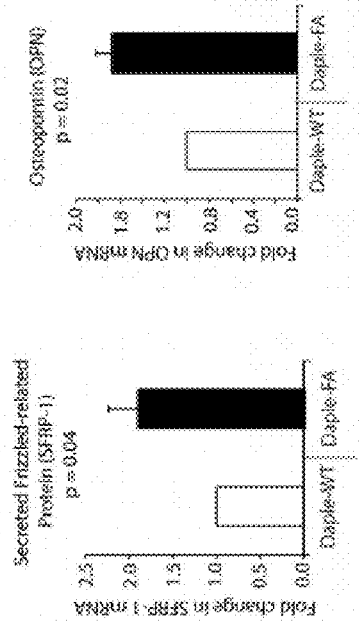
Figure 13D:
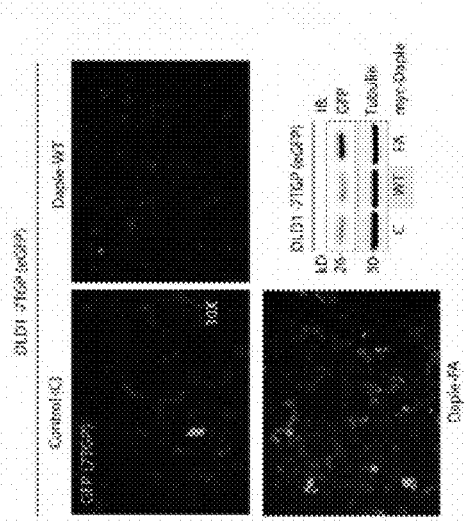
Figure 13C:
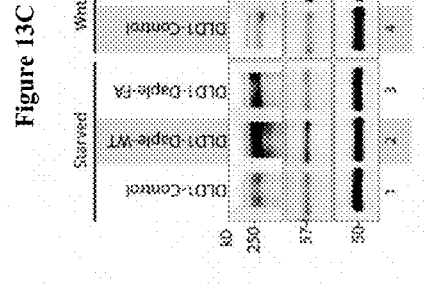
Figure 14B:
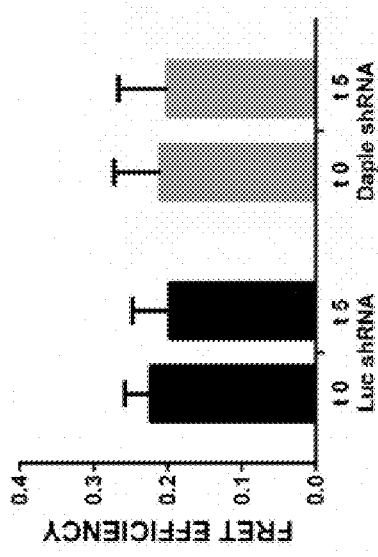
FIGS. 14A-14G. DAPLE and its GBA motif do not affect canonical Wnt signaling. (A-D) DAPLE does not activate Gi after Wnt3 stimulation. (A, B) Control (Luc shRNA) or DAPLE-depleted (DAPLE shRNA) HeLa cells were cotransfected with $G\alpha i1$-YFP, $G\beta$-CFP and untagged $G\gamma$, serum starved overnight (0.2% FBS) and subsequently stimulated with either Wnt3 and analyzed for FRET by confocal microscopy. Representative freeze-frame images from live-cell movies are shown (A), which display intensities of acceptor emission due to FRET in each pixel. Activation of Gi was insignificant, as determined by continued interaction (i.e., continued FRET) between $G\alpha i1$ and $G\beta 1\gamma 2$ both before and after Wnt3 stimulation (compare t0 and t5) both in control (Luc shRNA) and in DAPLE-depleted HeLa cells. Bar graphs (B) display FRET intensities observed in control (Luc shRNA) vs DAPLE-depleted HeLa cells. Error bars representing mean+/−S.D. of 5 randomly chosen ROIs at the PM per cell, from 2-3 cells per experiment, from 3 independent experiments. These results are in striking contrast to the findings after Wnt5a stimulation (see FIG. 2I-L). (C, D) Control (Luc shRNA) or DAPLE-depleted (DAPLE shRNA) HeLa cells were serum-starved (0.2% FBS) and treated (+) or not (−) with Wnt3 (C) or Wnt5a (D) for 15 min prior to lysis. Equal aliquots of lysates were subjected to immunoprecipitation with antibodies that selectively recognize active $G\alpha i$ subunits in their GTP-bound state. Immune complexes (top) and lysates (bottom) were analyzed for active $G\alpha i3$:GTP and total $G\alpha i3$ by immunoblotting (IB). Wnt5a robustly activates $G\alpha i3$, and this activation is abolished upon DAPLE depletion, whereas Wnt3 marginally activates $G\alpha i3$ and this activation is not diminished upon DAPLE depletion. (E) Myc-DAPLE is translocated to the PM after Wnt5a, but not after Wnt3 stimulation. HeLa cells were transfected with myc-tagged DAPLE-WT, serum starved overnight (0.2% FBS) and subsequently stimulated with either Wnt5a or Wnt3 as indicated. Cells were fixed at 5 min after ligand stimulation and analyzed for localization of myc-DAPLE by immunofluorescence. Myc-DAPLE was found in cytosolic distribution prior to ligand stimulation in starved cells. Upon stimulation with Wnt5a DAPLE was found to localize sharply at the PM. Upon stimulation with Wnt3 myc-DAPLE remained in cytosolic location. (F) Endogenous DAPLE is translocated to the PM after Wnt5a, but not after Wnt3 stimulation. HEK cells transfected with CFP-tagged FZD7R were serum starved for 24 h (0% FBS) and subsequently stimulated with either Wnt5a or Wnt3 as indicated. Cells were fixed at 5 min after ligand stimulation and analyzed for localization of endogenous DAPLE by immunofluorescence. DAPLE was found in cytosolic distribution prior to ligand stimulation in starved cells (see FIG. 4B). Upon stimulation with Wnt3 DAPLE remained in cytosolic location, however, upon stimulation with Wnt5a DAPLE was found to localize at the PM, where it colocalized with FZD7R (see FIG. 4B). (G) DAPLE's GBA motif does not affect Wnt3-dependent stabilization of $\beta$ Catenin. HEK 293 cells were transfected with DAPLE-WT or FA mutant, serum starved (0% FBS) for 24 h, and subsequently stimulated with Wnt3 for 4 h (lanes 1-6), 8 h (lanes 7-12) or 20 h (lanes 13-18) prior to lysis. Equal aliquots of cytoplasmic extracts were analyzed for $\beta$ Catenin, DAPLE and tubulin by immunoblotting. $\beta$ Catenin was stabilized (increased, compare even lanes with odd lanes) in each condition tested, without significant differences between DAPLE-WT vs DAPLE-FA at any time points observed. A representative experiment from a total of 4 independent experiments is shown.
Figure 14A:
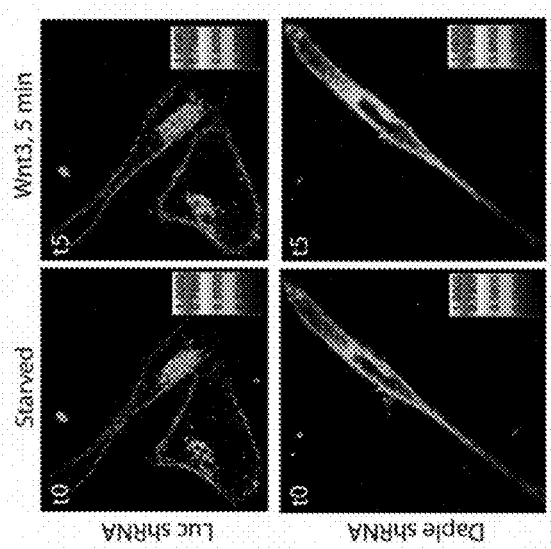
Figure 14D:
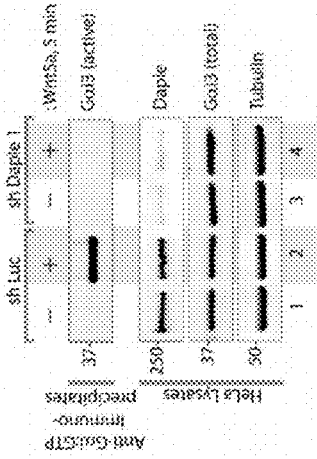
Figure 14C:
Figure 14F:
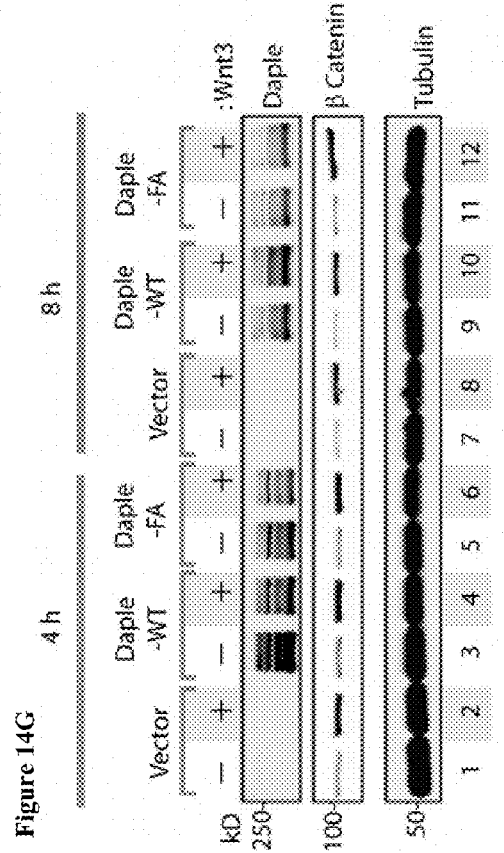
Figure 14G:
Figure 14E:
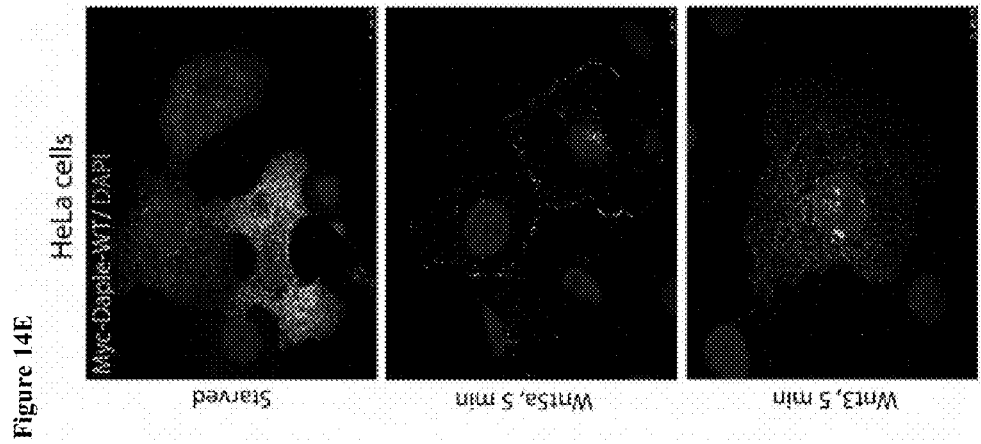

Next it was asked what might be the consequences of replacing Dv1 with DAPLE and activation of G proteins in the vicinity of ligand-activated FZD7R on β-Catenin/TCF/LEF signaling. Prior studies have demonstrated that activation of G proteins downstream of FZDRs is sufficient for antagonistic suppression of β-Catenin dependent signaling (Slusarski et al, 1997a; Slusarski et al, 1997b). Others have implicated binding of Dv1 to FZDRs is required for the enhancement of the β-Catenin/TCF/LEF pathway of signaling (Gαo & Chen, 2010). It was asked if activation of G proteins via DAPLE's GBA motif may antagonize β-Catenin stability/signaling. It was found that HeLa cells without DAPLE (FIGS. 5F & 5G) or those expressing the GEF-deficient DAPLE FA mutant (FIGS. 5H & 5I) had increased levels of β-catenin protein compared to respective controls, indicating that DAPLE and its GBA motif are required for maintenance of low levels of β-catenin, and that in their absence β-catenin is stabilized. Consistently, increased stability of β-catenin was also associated with enhanced transcription of downstream target genes SFRP-1, Osteopontin and Axin-2 (FIG. 5J-L). Similar results were obtained when the β-catenin/TCF/LEF pathway was analyzed in DLD1 colon cancer cells stably expressing DAPLE-WT or FA mutant (FIG. 13C) using 7-TGP, a eGFP expressing WNT activity reporter construct (Fuerer & Nusse, 2010). WNT activity was enhanced in cells expressing DAPLE-FA, but not DAPLE-WT (FIG. 13D), consistent with the prior findings in HeLa cells. Finally, it was found that DAPLE specifically functions within the non-canonical Wnt signaling cascade and not within the canonical Wnt pathway, e.g., stimulation of the canonical Wnt pathway with WNT3a did not require DAPLE to activate Gi (FIGS. 14A-D), did not trigger the recruitment of DAPLE to the PM (FIGS. 14E & 14F) and did not affect the stabilization of β-Catenin (FIG. 14G). These results suggest that the repressive effects of DAPLE observed on the β-catenin/TCF/LEF pathway (FIG. 5J-L) are likely due to enhancement of the antagonistic non-canonical Wnt signaling pathway.

Figure 5M:
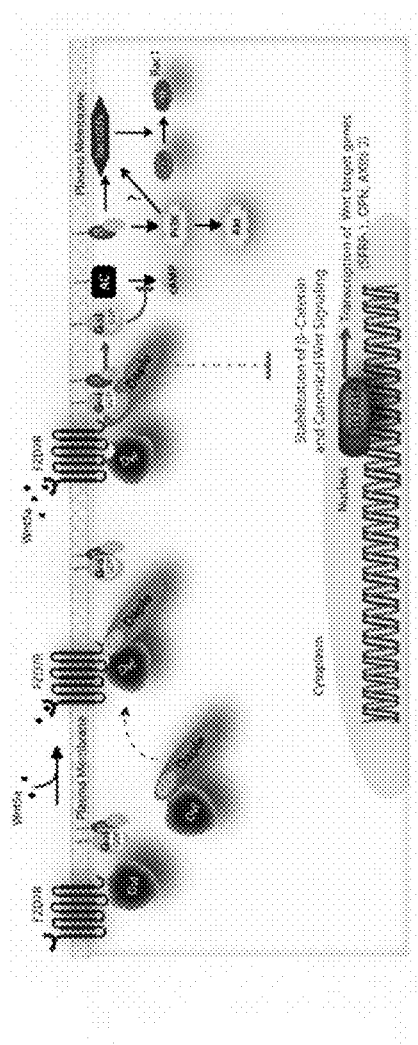

Taken together these results support an overall model (FIG. 5M) in which DAPLE orchestrates non-canonical Wnt signaling by favoring the recruitment and activation of G proteins and displacement of Dv1 from activated FZDRs upon WntSa stimulation. This leads to enhancement of Akt and Rac1 signaling (via 'free' Gβγ) and suppression of cellular cAMP (via Gαi:GTP), which is accompanied by diminished activity of the β-Catenin/TCF/LEF pathway.

Figure 15B:
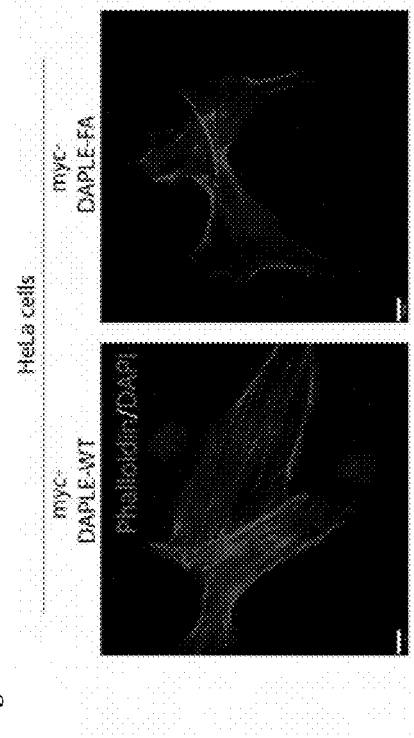
FIGS. 15A-15D. DAPLE enhances cell migration, promotes formation of actin stress-fibers, and triggers invasion, all via its GBA motif. (A) DAPLE-FA, but not DAPLE-WT inhibits 2-D cell migration. Confluent monolayers of HeLa cells transiently transfected with myc-DAPLE WT or FA (~90% efficacy of transfection confirmed by immunofluorescence) or control vector were scratch-wounded and incubated for 24 h in a 0.2% serum media. Wound closure was monitored and quantified as detailed in Experimental Procedures. % wound closure (Y axis) in various cell lines are displayed as bar graphs. For each cell line ~3-5 scratch-wounds were analyzed in each assay. Expression of DAPLE-FA significantly delays wound closure. Error bars represent mean±S.E.M of 3 independent experiments. (B) DAPLE-WT, but not DAPLE-FA triggers formation of actin stress fibers. DAPLE-depleted HeLa cells transiently transfected with myc-DAPLE WT or FA were grown on cover slips in the presence of 0.2% FBS, fixed, and subsequently analyzed for actin cytoskeleton patterns by staining with Phalloidin. Abundance of stress fibers running across the cell bodies was seen in cells expressing DAPLE-WT. DAPI/nucleus is shown. Bars=10 μm. (C) Whole cell lysates of HeLa cell lines used in transwell chemotaxis assays in FIG. 15A were analyzed for DAPLE expression by immunoblotting (IB). (D) DAPLE WT, but not FA triggers cell invasion. Spheroids of NIH3T3 cells expressing myc-DAPLE WT and FA were analyzed for their ability to invade matrigel in response to serum stimulation using a Cultrex-3D Spheroid Invasion Kit (Trevigen; see Experimental Procedures). Tracks created by invading cells were noted only in cells expressing myc-DAPLE WT. Area of invasion was quantified using ImageJ (as shown with interrupted blue line). Bar graphs showing the quantification of the area of invasion are shown in FIG. 15C.
Figure 15D:
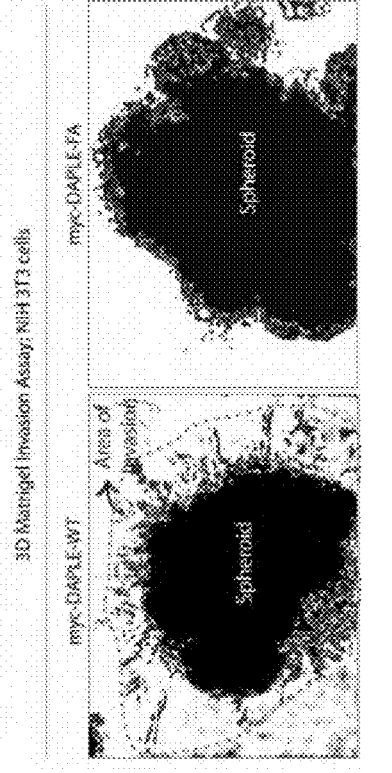
Figure 15A:
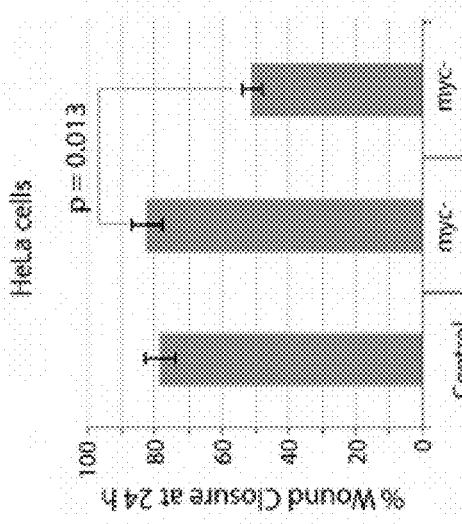
Figure 15C:
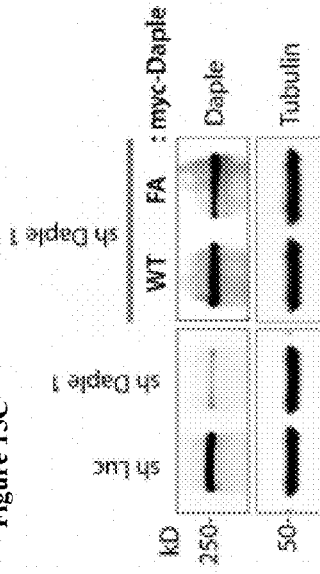

Example 9: The GBA Motif in DAPLE Triggers Tumor Cell Migration but Suppresses Growth and Proliferation Next it was investigated how non-canonical Wnt signaling via the Wnt5a/FZDR-DAPLE-Gαi axis impacts cancer cell behavior. The cellular phenotypes that are modulated by WntSa and non-canonical Wnt signaling during different stages of cancer progression were first analyzed (McDonald & Silver, 2009). In the normal mucosa this pathway serves as a tumor-suppressor, by antagonizing the canonical WNT-β-catenin signaling pathway (Chien et al, 2009; MacLeod et al, 2007; Torres et al, 1996; Ying et al, 2007; Ying et al, 2008), whereas in advanced tumors it triggers cell migration/invasion by enhancing PI3K-Akt and Rac1 pathways and the formation of actin stress fibers (Liu et al, 2013; Nishita et al, 2010; Zhang et al, 2014). Consistent with the role of DAPLE's GBA motif in enhancement of Akt and Rac1 activities (FIG. 3), it was found that monolayers of DAPLE-depleted HeLa cells stably expressing DAPLE-WT, but not DAPLE FA, efficiently closed wounds and generated actin stress-fibers (FIGS. 15A-C) and migrated fficiently along a gradient of Wnt5a in chemotaxis assays (FIG. 6A). To determine if DAPLE can trigger cell invasion through basement membrane proteins 3-D matrigel invasion assays were carried out. Non-invasive NIH3T3 cells (Albini et al, 1987) stably expressing DAPLE-WT, DAPLE-FA or vector control were grown into tumor spheroids, and subsequently analyzed for cell invasion through matrix (FIGS. 6B & 6C). Enhanced invasion (as determined by the area of invasion; FIG. 15B) was detected exclusively in the presence of DAPLE-WT, but not in cells expressing control vector or DAPLE-FA, indicating that DAPLE is sufficient to trigger cell invasion, and that a functionally intact GBA motif is essential. Compared to cells expressing DAPLE-FA, those expressing DAPLE-WT had significantly higher expression of Lox-L3 and Vimentin, two genes commonly associated with epithelial-mesenchymal transition (EMT) (FIGS. 6D & 6E), indicating that higher invasiveness was accompanied by an EMT gene signature.

Figure 7D:
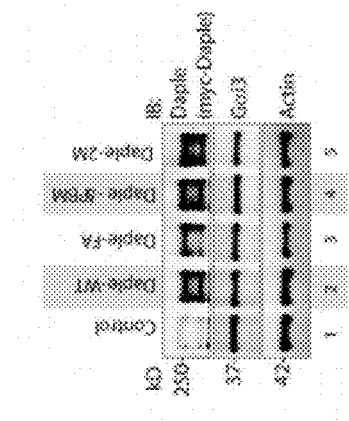
Figure 7E:
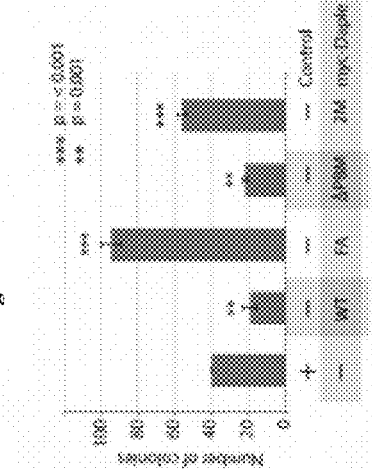
Figure 7G:
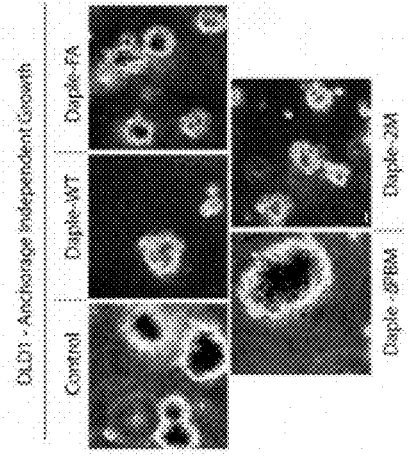
Figure 7F:
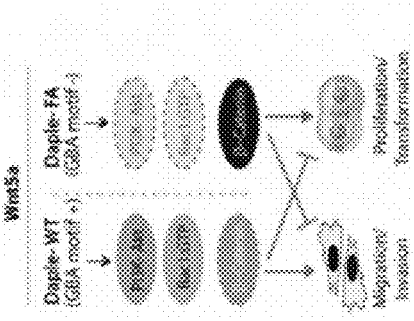
Figure 7H:
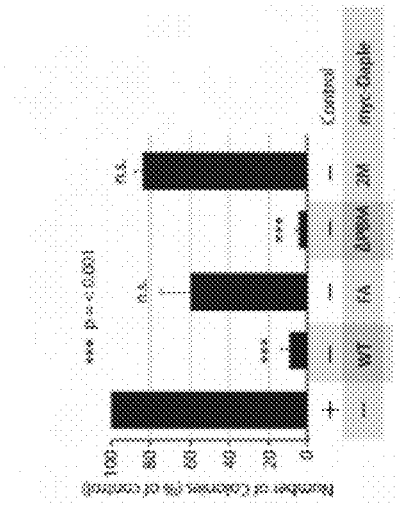
Figure 7I:
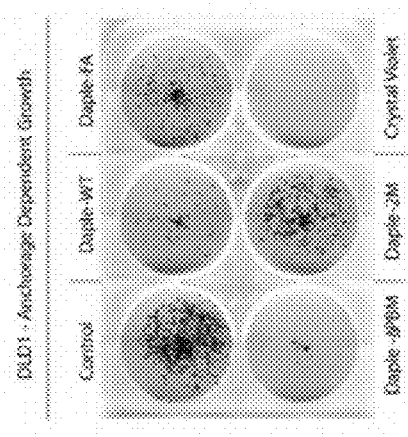
Figure 16B:
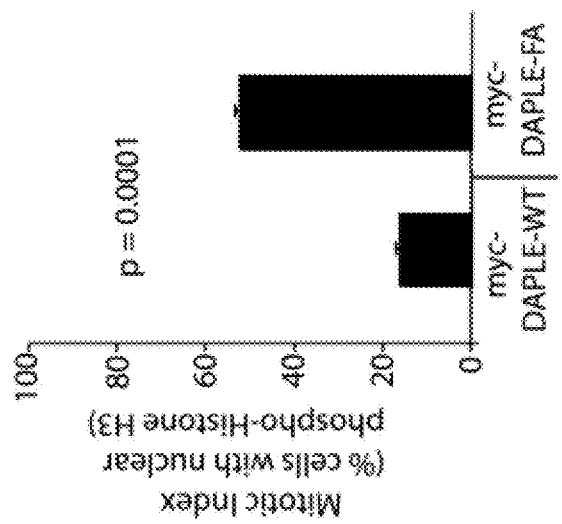
FIGS. 16A-16B. DAPLE suppresses cell proliferation via its GBA motif. (A) Compared to cells expressing DAPLE-WT those expressing DAPLE-FA have higher mitotic index, as determined by nuclear localization of phosphorylated histone H3. HeLa cells expressing myc-DAPLE WT or FA were grown on cover slips in the presence of 0.2% FBS, fixed and stained for phospho-histone H3 and DAPI. Bar graphs display % cells with nuclear phospho-histone H3 (y axis). Error bars representing mean±S.D. of 3 independent experiments. (B) Lysates of NIH3T3 cells NIH3T3 cells used in Ras-induced transformation assays (see FIG. 16A) were analyzed for DAPLE and Ras constructs by immunoblotting (IB).
Figure 16A:
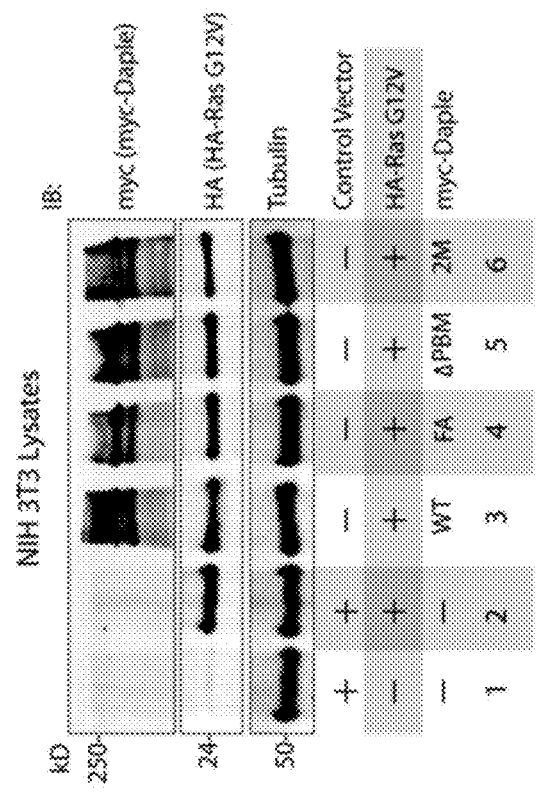

Next the role of DAPLE and its GBA motif was investigated in the modulation of other key cellular phenotypes regulated by non-canonical Wnt signaling during tumorigenesis, i.e., cell proliferation, transformation and growth (Jamieson et al, 2014; Niehrs & Acebron, 2012). For this three cell lines were used: HeLa cell lines, the constitutively active Ras-transformed NIH3T3 cells, and the DLD1 colorectal cancer cells in which transformation is driven by hyperactive β-catenin signaling in addition to active Ras mutations. DLD1 colorectal cancer cells were chosen to study because DAPLE is virtually undetectable in these cells compared to normal colon, thereby allowing reconstitution of expression exogenously and analysis of the effect of WT and mutant DAPLE constructs without significant interference due to the endogenous protein. Expression of DAPLE-WT reduced the number of colonies formed by Ras-transformed NIH3T3 in soft-agar by ~65% (FIG. 7A; FIG. 16A), indicating that DAPLE's GBA motif is required for suppressing neoplastic transformation. The mitotic index, as determined by the presence of phosphorylated Histone H3 in the nucleus (Hans & Dimitrov, 2001) was higher in HeLa cells expressing DAPLE-FA compared to those expressing DAPLE-WT (FIG. 16B), indicating that DAPLE's GBA motif suppresses mitosis. When the tumor-suppressive effect of Wnt5a on HeLa cells in anchorage-dependent tumor growth assays was assessed, it was found that tumor growth was suppressed in the control cells, but such suppression was lost in cells depleted of endogenous DAPLE (FIG. 7B). This loss of tumor-suppressive effect of Wnt5a was restored by expressing DAPLE-WT but not by expressing the DAPLE-FA mutant (FIG. 7C), indicating that a functionally intact GBA motif in DAPLE is essential for Wnt5a to exert its tumor suppressive effects. DAPLE-WT also inhibited anchorage-independent tumor growth of DLD1 cells by ~50% (FIGS. 7D-F), and inhibited anchorage-dependent tumor growth of DLD1 cells by ~90% (FIGS. 7G & 7H), demonstrating that DAPLE suppresses cellular transformation and growth across all assays. This tumor suppressive effect was mediated via the GBA motif because, compared to DAPLE-WT, expression of DAPLE-FA not only failed to inhibit cell transformation (FIG. 7A) and growth (FIGS. 7C & 7H), but also enhanced oncogenicity (FIG. 7E). Noteworthy, expression of a DAPLE mutant that cannot bind Dvl (DAPLE-ΔPBM) but has an intact GBA motif retained the tumor suppressive properties of DAPLE-WT across all assays, whereas a mutant that lacks both the GBA and the Dvl-binding PBM motifs (DAPLE-2M) mirrored the phenotype of the FA mutant, indicating that the G protein regulatory GBA motif, and not the Dvl-binding PBM motif is essential for the tumor suppressive function of DAPLE. Taken together, these findings demonstrate that DAPLE inhibits cell transformation and proliferation during tumor growth, but enhances cell motility and cytoskeletal remodeling during invasion; both require the GBA motif which regulates G protein activity (FIG. 7I).

Example 10: Expression of DAPLE is Dysregulated During Cancer Progression

Figure 8I:
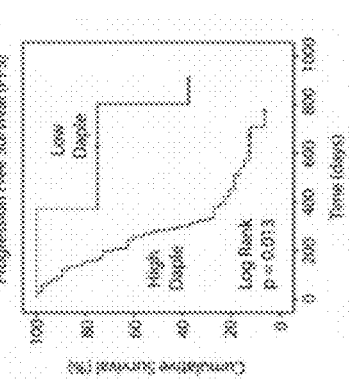
Figure 17C:
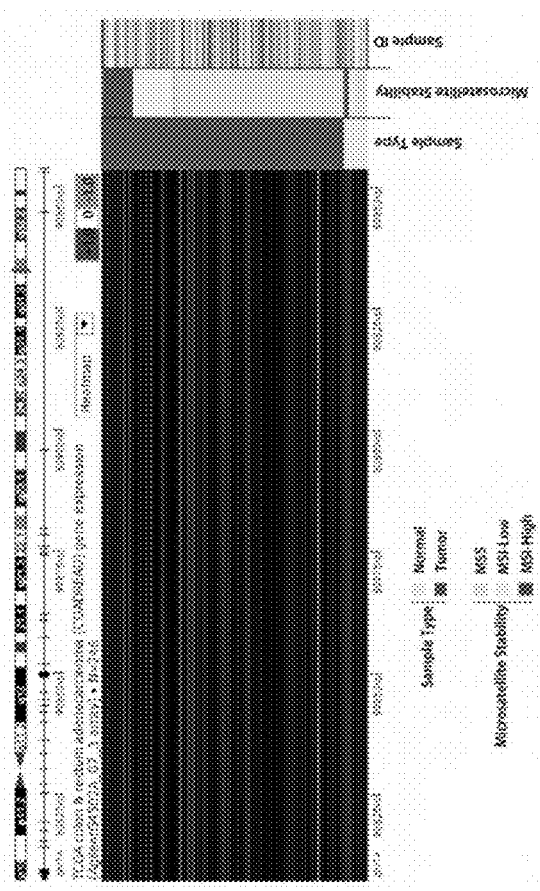
FIG. 17A-17G. Expression of DAPLE mRNA is suppressed in colorectal cancers, in part by copy number loss. (A, B) Publicly available Kaiser Colon database was analyzed for DAPLE mRNA expression in adenocarcinomas of the colon (A) and rectum (B) and their respective normal controls. DAPLE mRNA expression levels are displayed using log 2 median centered ratio boxplots for normal vs cancer that were generated using the UCSC Cancer Genome Browser. Numbers in parenthesis represent total number of samples analyzed. (C) The TCGA colon cancer database was analyzed for DAPLE mRNA expression in 246 colorectal adenocarcinomas. DAPLE mRNA expression levels are displayed as heat maps generated using the UCSC Cancer Genome Browser. Red=High DAPLE; Green=Low DAPLE. Samples are arranged by sample type (normal vs cancer) and microsatellite status (MSI low or high vs MSS) as indicated on the right margin of the heat map. (D) Schematic of chromosome 14 is shown. Ccdc88c gene which encodes DAPLE (red arrow) is located within a frequently deleted region of Chr 14 (blue box). (E, F) Publicly available TCGA database was analyzed for number of copies of DAPLE gene in adenocarcinomas of the colon (E) and rectum (F) compared to matched normal mucosa and in blood cells. Copy number units of ccdc88c (DAPLE) in various matched samples are displayed using log 2 median centered ratio boxplots for that were generated using the UCSC Cancer Genome Browser. Numbers in parenthesis represent total number of samples analyzed. Compared to matched normal mucosa or peripheral blood, lower copy numbers of DAPLE gene was observed in adenocarcinomas of colon and rectum. (G) The TCGA colon cancer database was analyzed for the relationship between DAPLE copy number loss and microsatellite status in 461 tumor samples. DAPLE copy number in each tumor is displayed as heat map generated using the UCSC Cancer Genome Browser. Samples are arranged by microsatellite status (MSI low or high vs MSS) as indicated on the right margin of the heat map. A large majority of tumors had copy number loss, but not gain. Tumors that had a loss of copy for the DAPLE gene are invariably MSS tumors, or MSI-low tumors. Copy number loss is virtually absent among MSI-high tumors.

Because Wnt5a and the non-canonical Wnt pathway is known to be dysregulated during cancer progression (i.e., suppressed early during neoplastic transformation and upregulated later during metastasis) (McDonald & Silver, 2009), next it was asked whether the expression of DAPLE is similarly altered during oncogenesis in the colon. Analysis of several publicly available microarray databases revealed expression of DAPLE mRNA was reduced by ~2-fold in adenocarcinomas of the colon or rectum compared to matched normals (FIG. 8A; FIGS. 17A & 17B; Table 1).

TABLE 1

Meta-Analysis of DAPLE mRNA Expression in Colorectal Cancer vs Matched Normal Colon.

| GSE Series ID | Reference | Total Samples Analyzed (Cancer/Normal) | Fold Change (mRNA) | p-Value |
|---|---|---|---|---|
| GSE21815- Gene expression profiles in laser microdissected colorectal cancer tissues | PMID: 21862635 | 132/8 | ↓2.01 | 0.0108 |
| GSE21510- Clinical Significance of Osteoprotegrin Expression in Human Colorectal Cancer | PMID: 21270110 | 148 | ↓1.9 | 8.8E-5 |
| GSE22598- Clinical Significance of UNC5B Expression in Colorectal Cancer | PMID: 21922135 | 17 (paired cancer and normal) | ↓1.69 | 0.0027 |
| GSE18105 - Colorectal cancer gene expression profile | PMID: 20162577 | 77 (paired cancer and normal) | ↓1.68 | 0.0031 |
| GSE41328 - Colon adenocacinoma and matched normal tissue - Lab 2 | PMID: 17160039 | 5 (paired cancer and normal) | ↓1.63 | 0.0139 |
| GSE41328 - Colon adenocacinoma and matched normal tissue - Lab 2 (different primer pair) | PMID: 17160039 | 5 (paired cancer and normal) | ↓1.58 | 0.0087 |
| GSE5350_ GPL570 - Microarray Quality Control (MAQC) Project | PMID: 16964229 | 10 (paired cancer and normal) | ↓1.52 | 0.0001 |

When DAPLE mRNA was analyzed in another cohort of patients by qPCR, it was confirmed that DAPLE is indeed downregulated in cancers (FIG. 8B), but not in the precancerous advanced polyps (defined as any adenoma with >25% villous features, or ≥1.0 cm in size, or high-grade dysplasia); the latter showed a modest upregulation in DAPLE mRNA (FIG. 8B). This suggests that the suppression of DAPLE is fairly late during oncogenesis coinciding with late adenoma-to-cancer progression. Meta-analysis of various microarray databases at The Cancer Genome Atlas (TCGA) further revealed that expression of DAPLE mRNA is significantly suppressed in microsatellite stable (MSS) colorectal tumors, which account for ~85% of all colorectal cancers and are characterized by the presence of chromosomal instability (FIG. 8C, FIG. 17C; Table 2), whereas tumors with high degree of microsatellite instability (MSI-high) express at levels similar to normal colon (FIG. 8C; FIG. 17C). Among MSS tumors, the degree of suppression of DAPLE correlated with the degree of chromosomal instability (CIN) (FIG. 8D).

TABLE 2

Meta-Analysis of DAPLE mRNA Expression in Microsatellite Unstable (MSI) vs Stable (MSS) Colorectal Cancers.

| GSE Series ID | Reference | Total Samples Analyzed (Cancer/ Normal) | Fold Change (mRNA) | p-Value |
|---|---|---|---|---|
| GSE13294- Expression data from primary colorectal cancers | PMID: 19088021 | 155 | ↓1.49 | 2.9E−8 |
| GSE4554- Gene expression signature of colorectal cancer with microsatellite instability | PMID: 17047040 | 84 | ↓2.11 | 6.5E−5 |
| GSE2138- Colon cancer profiling | PMID: 16247484 | 20 | ↓1.78 | 0.0181 |
| GSE13067 - Expression data from primary colorectal cancers | PMID: 19088021 | 74 | ↓1.31 | 0.0415 |

Furthermore, as shown previously in the case of other tumor suppressors (Pino & Chung, 2010), it was found that suppression of DAPLE mRNA in the primary tumors at the time of diagnosis was associated with disease progression, as determined by formation of distant metastasis in a cohort of patients with stage II colorectal cancers (FIG. 8E). Taken together, these results indicate that expression of DAPLE is frequently reduced during oncogenesis that such reduction is more common in the setting of chromosomal instability, and that reduced expression of DAPLE in primary tumors may predict disease progression.

Figure 17D:
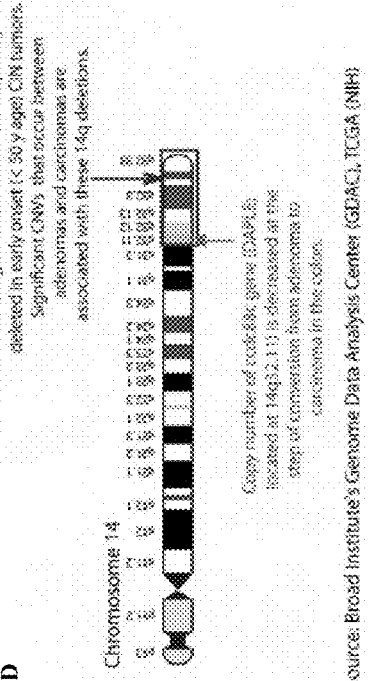
Figure 17A:
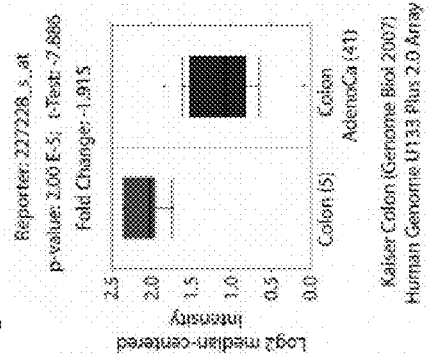
Figure 17B:
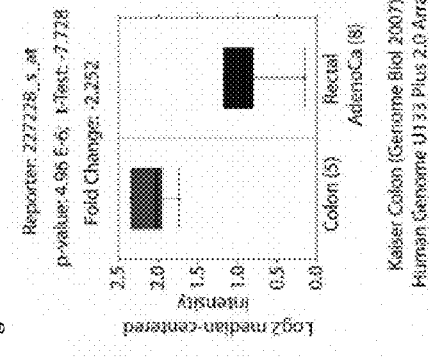
Figure 17G:
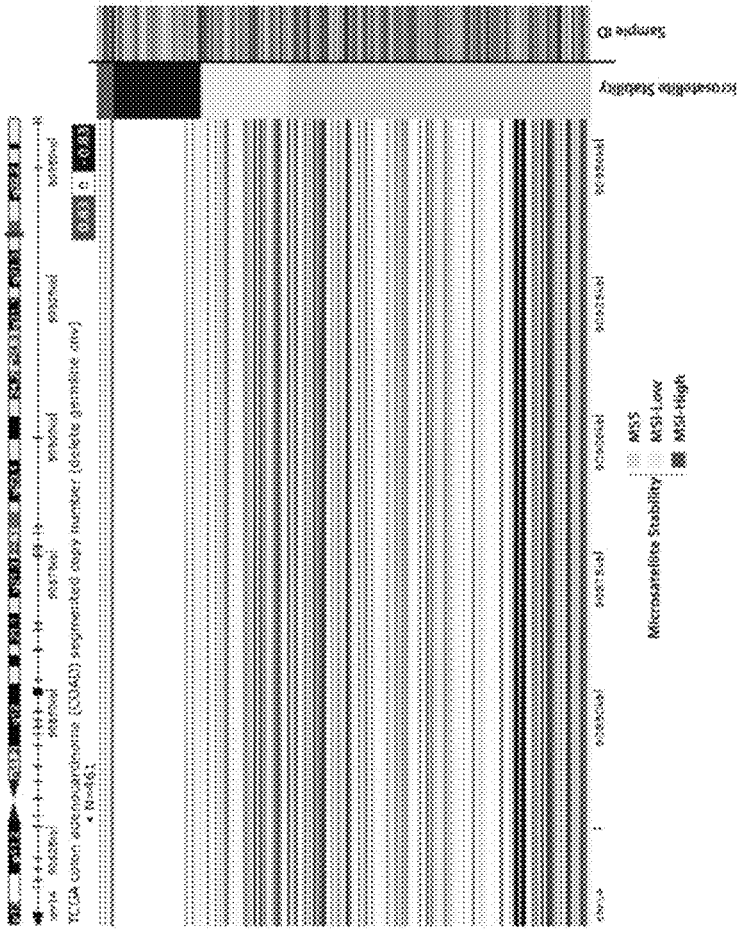
Figure 17E:
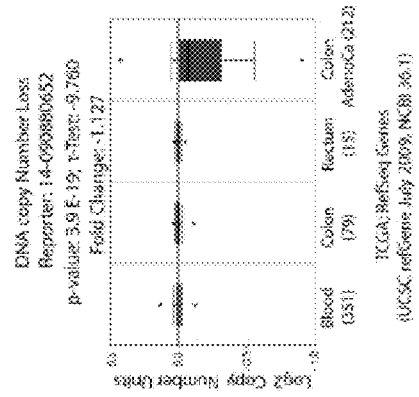
Figure 17F:
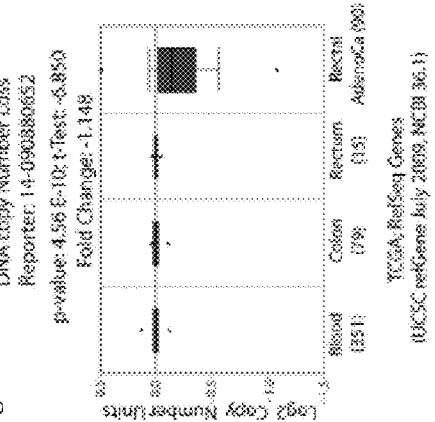

While seeking clues into how DAPLE might be downregulated in some tumors, but not all, it was noted that ccdc88c, the gene that encodes DAPLE is located in a region of Chr 14 (14q32.11) that is most frequently deleted in early onset (<50 y) colorectal tumors (FIG. 17D). In fact, 14q deletions are most often associated with significant copy number variations (CNVs) that occur during adenoma-to-carcinoma conversion (Tsafrir et al, 2006). An analysis of microarray-based comparative genomic hybridization (CGH) obtained from polyps that had progressed to cancer revealed that significant loss of DAPLE copy number was observed in the carcinoma portion, but not in the adenoma portion of these advanced polyps compared to matched normal tissue (FIG. 8F). Loss of DAPLE copy number was noted in adenocarcinomas of both the colon and the rectum (FIGS. 17E & 17F), and this phenomenon was invariably associated with chromosomal instability in MSS tumors (FIG. 17G). These findings indicate that focal deletions of Chr 14 with resultant loss of copy number may in part contribute to downregulation of DAPLE observed in colorectal cancers.

Figure 8K:
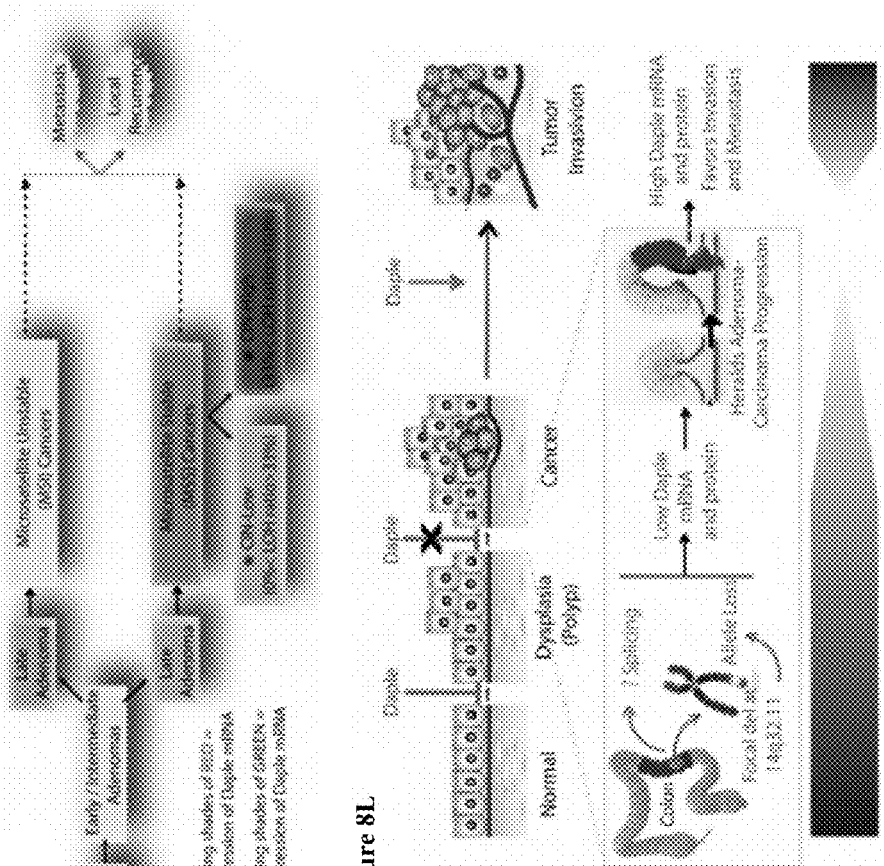
Figure 8J:
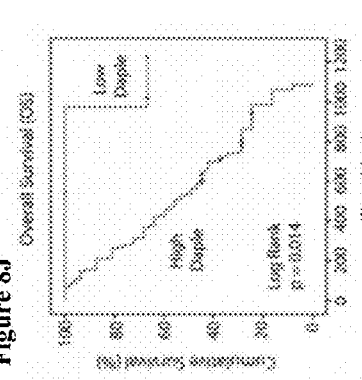

Next it was asked how DAPLE expression changes in disseminated tumor cells and serum. Compared to normal subjects, DAPLE mRNA was elevated in both cell-free RNA samples (FIG. 8G) and in tumor cells (FIG. 8H) isolated from peripheral circulation of patients with colorectal cancer. It was found that expression of DAPLE in circulating tumor cells (CTCs) of patients with metastatic colorectal cancer was associated with progression of disease/recurrence (FIG. 8I) and poor survival (FIG. 8J). Furthermore, higher DAPLE expression in CTCs correlated positively with increased expression of genes that are known to trigger EMT (Table 3). These results indicate that DAPLE is expressed in disseminated tumor cells and that higher expression is associated with EMT and poorer clinical outcomes.

TABLE 3

DAPLE expression in CTCs positively correlates with markers of EMT

| | | CCDC88c (DAPLE) | ZEB2 | LOXL3 |
|---|---|---|---|---|
| CCDC88c (DAPLE) | Pearson Correlation | 1 | 0.894 | 0.776 |
| | P value (2-tailed) | | 0.000 | 0.000 |
| | N (# patients) | 50 | 50 | 50 |
| ZEB2 | Pearson Correlation | 0.894 | 1 | 0.797 |
| | P value (2-tailed) | 0.000 | | 0.000 |
| | N (# patients) | 50 | 50 | 50 |
| LOXL3 | Pearson Correlation | 0.776 | 0.797 | 1 |
| | P value (2-tailed) | 0.000 | 0.000 | |
| | N (# patients) | 50 | 50 | 50 |

Taken together, these results define the profile of dysregulated DAPLE expression during oncogenic progression in the colon (FIG. 8K): DAPLE is first suppressed during adenoma-to-carcinoma progression, and expressed later in disseminated tumor cells.

Example 11: DAPLE Isoforms

As discussed at length herein, two main isoforms of DAPLE are found in humans: DAPLE-fl (SEQ ID NO: 2) and DAPLE-V2 (SEQ ID NO: 23). It has been demonstrated herein that it is possible to design primers specific for both isoforms and to selectively target one isoform over another using primers for the 3' UTR of hDAPLE (SEQ ID NOs: 3 and 4). In contrast, primers shDaple1: CAGTAGAACACT-CATTTGCAA (SEQ ID NO:25) and shDaple2: AGGCAC-CTGCCTTCCTAGATT (SEQ ID NO:26) are specific for the DAPLE-fl isoform.

Studies were done using the pLKO vector system (for shRNA delivery) in s707 cells that are Cancer initiating stem cells (CISCs), from a 57 year old male (patient #4) with stage 1 colon cancer. This cell line was developed by Steven Lipkin's group (Sikandar et al., Cancer Res, 2010). Thus, s707 is a cancer initiating stem cell clone derived from a moderately differentiated, stage 1, right colon, p53 neg, Kras neg tumor from a 57 year old male. FIGS. 21A and B show the results of depleting Daple from cancer initiating stem cells, s707. It was found that Daple-fl alone, not Daple-V2, was depleted in these cells using the shRNA approach. Depletion of Daple-fl alone severely reduced the ability of s707 cells to grow in tumor sphere cultures.

Figure 24I:
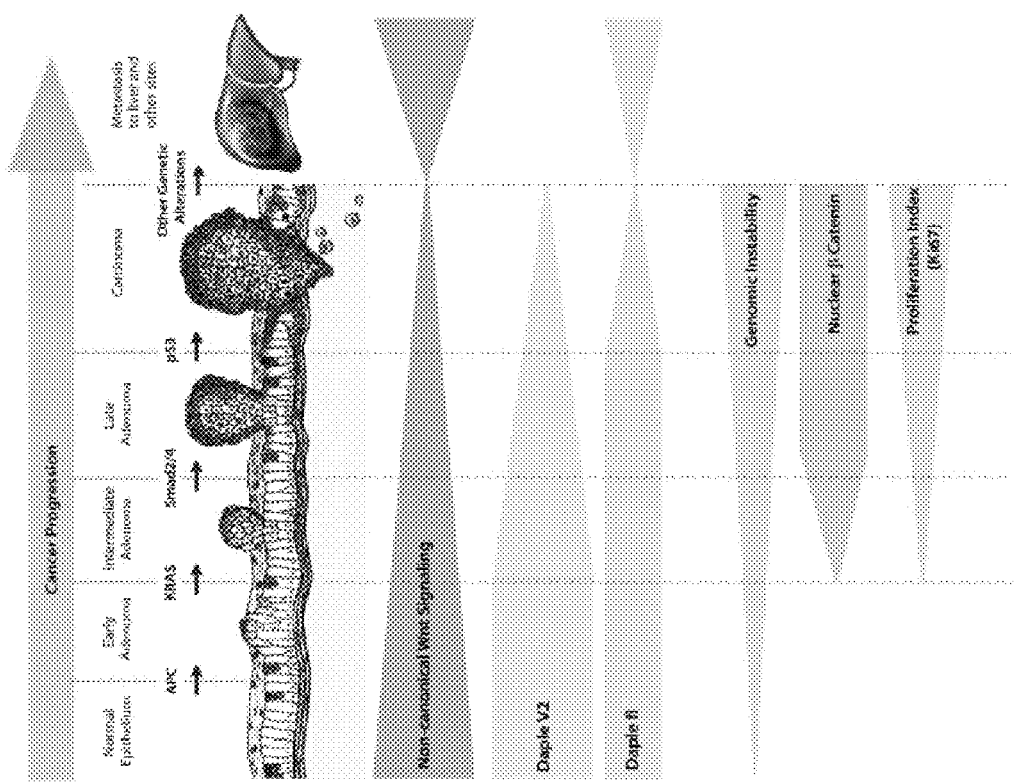

It was further found that the full length (Daple-fl) and short (Daple-V2) isoforms of Daple cooperatively suppress cell proliferation and their low expression in stage II colorectal cancers carries a worse prognosis. Specific data demonstrating the results depicted in FIGS. 23 and 24 is as follows:

| | Low Daple-fl | High Daple-fl |
|---|---|---|
| Oncogenic K-Ras Mutation | 37 | 15 |
| Wild-Type K-Ras | 72 | 38 |

| | Low Daple-V2 | High Daple-V2 |
|---|---|---|
| Oncogenic K-Ras Mutation | 22 | 30 |
| Wild-Type K-Ras | 33 | 93 |

|  | Ki67 Index | Osteo-pontin | SASH1 | MACC1 | Age | CEA | Tumor length (cm) | Tumor differen-tiation | Grading |
|---|---|---|---|---|---|---|---|---|---|
| | | | | Daple-V2 | | | | | |
| r-value | −0.1794 | −0.01889 | 0.2041 | −0.1462 | 0.05122 | 0.3203 | 0.01046 | −0.04673 | 0.02109 |
| P value (two-tailed) | 0.0245 | 0.8063 | 0.0074 | 0.0564 | 0.5059 | 0.0019 | 0.892 | 0.5439 | 0.7842 |
| | | | | Daple-FL | | | | | |
| r-value | 0.04645 | −0.03408 | 0.1224 | −0.1131 | 0.02617 | 0.03007 | 0.007986 | −0.06434 | −0.00821 |
| P value (two-tailed) | 0.561 | 0.6553 | 0.1077 | 0.1373 | 0.7325 | 0.7736 | 0.917 | 0.4004 | 0.9147 |

Example 12: Discussion

Frizzled receptors activate Gi proteins via DAPLE. The major finding in this work is the discovery of a G protein regulatory function in DAPLE which activates trimeric G proteins downstream of FZDRs. Herein is provided biochemical and in-cellulo evidence for the presence of a GBA motif that activates Gαi and an independent domain within the C-terminal region of DAPLE which directly binds the cytoplasmic tail of FZDRs. Such a coexistence allows DAPLE to link G protein activation to ligand-activated FZDRs within ternary FZDR-DAPLE-Gαi complexes at the PM. It was also demonstrated that FZDRs and Gαi come within close proximity of each other (~10 nm based on FRET imaging studies) within these complexes, suggesting a direct interaction between them on the DAPLE platform. In cells without DAPLE, or in cells expressing a mutant in which the GBA motif is selectively disrupted, FZDRs and G proteins do not approach each other and G protein is not activated, demonstrating an obligatory role for DAPLE's GBA motif in the assembly of FZDR-Gαi complexes. These findings provide a new perspective on the role of G proteins in Wnt signaling because previous work has widely debated the fundamental question whether the 7-TM FZDRs can directly bind and activate G proteins. Arguments that have favored the classification of FZDRs as GPCRs are supported by experimental evidence that FZDRs indeed signal via G proteins, e.g., structure-based bioinformatic prediction, pertussis toxin sensitive signaling pathways, genetic linkage with G proteins, and ability to bind β-arrestin for subsequent internalization (Ahumada et al, 2002; Gαo & Wang, 2006; Katanaev et al, 2005; Liu et al, 2001; Liu et al, 2005; Ma & Wang, 2006; Slusarski et al, 1997a). Arguments that refute such classification highlight the lack of direct experimental proof of G-protein interaction with FZDRs, and that most studies use experimental models (overexpressed receptors or gain-of-function) which do not necessarily implicate necessity (Schulte & Bryja, 2007). The present work breaks the impasse in the field by the discovery of an alternative mechanism of G protein activation by FZDRs: it is proposed that the C-terminus of DAPLE is the long sought molecular linker that couples FZDRs to efficient G protein activation by virtue of its ability to simultaneously bind receptors and activate G proteins. However, that some FZDRs may directly couple with other G proteins under certain circumstances cannot be ruled out (see below).

DAPLE is a new member in the family of non-receptor GEFs that function via GBA-motif. Herein it is demonstrated that DAPLE is a new member of a family of non-receptor activators of G protein, thereby adding to the growing evidence that trimeric G proteins can be activated by mechanisms differing from classical GPCR-mediated activation. It is further demonstrated that DAPLE activates Gi via a signature sequence, i.e., the GBA motif that allows proteins and synthetic peptides to exert GEF activity on G proteins and provides a structural basis for non-receptor mediated activation of G proteins (Austin et al, 2008; Garcia-Marcos et al, 2009; Garcia-Marcos et al, 2011b; Johnston et al, 2005). DAPLE shares overall homology with GIV, the prototype GBA motif-containinG protein, and both of them are classified as members of the CCDC88 family. Interestingly, the C-terminal domains of these two proteins, in which their conserved GBA motifs are located, share very little overall similarity. These observations suggest that DAPLE and GIV arose from a common ancestor protein and that the GBA function was selectively preserved while the rest of the C-terminal domain diverged in evolution.

DAPLE has the biochemical features of a GEF: it binds preferentially to inactive, GDP-bound Gαi subunits and accelerates the rate of nucleotide exchange. The GEF activity of DAPLE, i.e., its ability to accelerate the exchange of nucleotide, is more robust than that previously reported for FZDRs in similar in vitro assays (~2.5-3-fold activation compared to ~1.5-fold) (Koval & Katanaev, 2011). Inefficient activation of G proteins by FZDRs (~5-20% efficacy compared to that observed for a 'classical' GPCR, i.e., Adenosine 2B receptor) has also been documented in yeast (Nichols et al, 2013) which lack homologues of DAPLE. The present studies measuring G protein activation in DAPLE-depleted cells or in cells without a functional GBA motif in DAPLE helped establish an obligatory role of DAPLE as a bona fide G protein activator which enables FZDRs to indirectly activate Gi to robust levels. These findings cannot rule out other possibilities, e.g., that FZDRs may directly activate Gi to a lesser extent under certain circumstances, or that DAPLE and FZDRs may activate different subsets of G proteins. The latter possibility is exemplified by Gαo which has been most widely reported as a target for FZDRs (Bikkavilli et al, 2008; Egger-Adam & Katanaev, 2010; Katanaev & Buestorf, 2009; Katanaev et al, 2005; Liu et al, 2001; Liu et al, 1999) but not for DAPLE (this work). The marked preference of DAPLE for a-subunits of the Gi family is a common feature shared with previously described GBA proteins; DAPLE, GIV, Calnuc, NUCB2 (Garcia-Marcos et al, 2009; Garcia-Marcos et al, 2011b) or the synthetic peptides KB-752 and GSP (Austin et al, 2008; Johnston et al, 2005) can exquisitely distinguish between Gαi and Gαo proteins, despite their being closely related and sharing 75% sequence homology.

Although the biochemical properties of DAPLE as a G protein regulator are similar to those of other proteins with a GBA motif, herein is provided evidence that the coupling between DAPLE and Gαi-subunits has unique structural determinants. DAPLE can bind to two Gαi3 mutants, W258F and K248M, that abolish binding to GIV and Calnuc, respectively. Moreover, it has been previously shown (Garcia-Marcos et al, 2010; Garcia-Marcos et al, 2011b) that these mutants are able to discriminate between GIV and Calnuc (K248M binds GIV, but not Calnuc, and W258F binds Calnuc, but not GIV), which further suggest that different GBA-Gαi interactions have unique properties that impart a high degree of specificity. The validated homology models of these GBA-Gαi interactions (Garcia-Marcos et al, 2009; Garcia-Marcos et al, 2011b) offer some clues into the origin of such specificity: Despite docking onto the SwII/α3 hydrophobic cleft of Gαi, all GBA-motif containinG proteins make additional and unique contacts with Gαi which generate specificity for each GBA motif. It is suggested that the DAPLE:Gαi interface has unique features that distinguish it from GIV:Gαi or Calnuc:Gαi interfaces, and exploiting such structural specificity may help devise strategies to selectively target the DAPLE:Gαi interface, and thereby, modulate WNT signaling.

G protein regulatory function of DAPLE is essential for enhancement of non-canonical Wnt signaling. Herein it is demonstrated that recruitment of DAPLE-Gαi complexes to the cytoplasmic tail of ligand activated FZDRs dictates several closely intertwined spatial and temporal aspects of post-receptor signaling events within the non-canonical Wnt pathway. At the immediate post-receptor level, DAPLE competes with Dvl, the major signaling scaffold for Wnt signaling (Gαo & Chen, 2010), for binding to FZDR, and recruits and activates Gαi in close proximity to activated receptors at the PM. That Dvl and DAPLE/Gαi complexes may compete for binding to FZDR is in keeping with others' findings that overexpression of Dvl interferes with the engagement of Gi proteins with ligand-activated FZDRs (Kilander et al, 2014), and that Dvl is unlikely to directly link G proteins to FZDRs, as proposed by some (Schulte & Bryja, 2007). Once recruited, DAPLE's GEF activity triggers Gi activation which leads to inhibition of cellular cAMP via Gαi:GTP and activation of non-canonical Wnt signaling pathways involved in cell motility (e.g., PI3K and Rac1) via 'free' Gβγ. The consequences of these signaling mechanism are enhanced formation of actin stress fibers, 2D-cell migration after wounding, 3D-invasion through basement membrane proteins, and upregulation of genes that trigger EMT; all phenotypes that have been previously attributed to enhancement of non-canonical Wnt signaling (Minami et al, 2010). It is also shown herein that the FZD7R-DAPLE-Gi axis suppresses responses associated with tumorigenesis, e.g., β-catenin/TCF/LEF signaling, oncogenic transformation, anchorage independent growth and anchorage-dependent colony formation; all attributable to its ability to activate G proteins via its GBA motif. Because the FZDR-DAPLE-Gi axis specifically modulates non-canonical Wnt signals, but has no effect on canonical Wnt responses, it is hypothesized that DAPLE suppresses the canonical β-catenin/TCF/LEF pathway primarily by enhancing the antagonistic non-canonical Wnt pathway (Chien et al, 2009; MacLeod et al, 2007; Torres et al, 1996; Ying et al, 2007; Ying et al, 2008). Although the mechanism(s) by which the non-canonical Wnt pathway inhibits the canonical β-catenin/TCF/LEF pathway remains unclear, and some have proposed that such decisions are made at the level of the receptors (Logan & Nusse, 2004), how DAPLE-dependent G protein signaling in the vicinity of the receptors may affect this process remains unclear. The present finding herein that DAPLE binds preferentially to some FZDRs, and not others, could influence the decision of canonical vs non-canonical Wnt signaling, or alternatively, activation of Gαi and inhibition of cellular cAMP by DAPLE could directly antagonize a previously described role of the adenylate cyclase/cAMP/PKA pathway in phosphorylating and stabilizing β-catenin (Hino et al, 2005). Regardless of the mechanism(s) involved, activation of Gi and enhancement of non-canonical Wnt signaling is accompanied by the suppression of the canonical β-catenin pathway in cells expressing DAPLE-WT, which correlates with all the key anti-growth and anti-transformation phenotypes that define a tumor suppressor/anti-oncogene (Cooper, 2000). Although it is possible that some of the effects of the FZDR-DAPLE-Gi axis in tumor suppression are mediated by the destabilization of β-catenin, further investigations are required to clarify this point. It is hypothesized that the G protein regulatory function of DAPLE is essential for enhancing at least two major cellular phenotypes previously attributed to non-canonical Wnt signaling (McDonald & Silver, 2009), suppression of cell transformation and growth, and enhancement of cell invasion. As for potential implications in other key cellular processes that are deregulated during cancer progression, it is noteworthy that non-canonical Wnt signaling has also been demonstrated to play a crucial role in planar cell polarity and asymmetric cell division in stem cells (Bentzinger et al, 2014; Bentzinger et al, 2013). Several studies have shown that the Wnt7A/FZD7 pathway establishes front-rear cell polarity and directional migration of human myogenic progenitors and facilitate the extension of satellite stem cells, all by activating PI3K/Akt pathway and Rac1 (Bentzinger et al, 2014; Bentzinger et al, 2013). Because one of the major roles of the FZDR-DAPLE-Gi axis is enhancement of PI3K and Rac1 activities, it is possible that this axis also aids in the establishment of cell polarity and/or the maintenance of stem-ness via enhancement of the non-canonical Wnt pathway. Further studies are required to determine if such is the case.

DAPLE expression and non-canonical Wnt signaling are similarly dysregulated during oncogenesis. It is shown herein that DAPLE is downregulated during oncogenesis at the step of conversion from adenoma to carcinoma, and that lower expression of DAPLE in the primary tumor is associated with higher frequency of cancer recurrence. It is also shown herein that expression of DAPLE in circulating tumor cells correlated with an increased EMT signature, disease progression (growth of current metastasis or formation of new metastasis) and poorer survival. This bimodal dysregulation (suppressed first, expressed later) and bi-faceted role (tumor suppressor in the normal epithelium, but enhancer of tumor invasion in cancer cells) during cancer progression mirrors what was previously unequivocally documented for the non-canonical Wnt5a signaling (McDonald & Silver, 2009)—Wnt5a signaling is suppressed earlier to allow cellular transformation and tumor growth, and enhanced later during tumor invasion. However, molecular mechanisms for such bimodal deregulation of the bi-faceted non-canonical Wnt pathway remain poorly understood. Such phenomenon is not restricted to DAPLE or the Wnt pathway, because major signaling programs like the TGFβ-SMAD pathway has also been shown to display similar bimodal deregulation and a bi-faceted role (Akhurst & Derynck, 2001), and a similar phenomenon is observed in the case of DAPLE's closely related orthologue, GIV (Ghosh et al, 2010): Downregulation of GIV by alternative splicing triggered proliferation early during tumor growth, whereas an increase in GIV by transcriptional upregulation enhanced cell invasion later during oncogenesis. Because DAPLE serves as a bona fide enhancer of the non-canonical Wnt pathway, it is hypothesized that up- or downregulation in DAPLE expression contributes, at least in part, to the bimodal deregulation of the Wnt5a signaling pathway observed in cancers.

It is also demonstrated herein that the mechanism for downregulation of DAPLE in cancers follows typical tumor suppressor genetics during neoplastic transformation (Payne & Kemp, 2005). Downregulation of DAPLE mRNA coincided with adenoma-to-carcinoma transition, and the frequency of such downregulation in the primary tumor directly correlated with the degree of CIN. A loss of copy number of DAPLE DNA, and consequent downregulation of gene expression and function was noted in the primary tumors, predominantly among the tumors with CIN. This pattern is in keeping with the well-documented role of CIN in generating loss of heterozygosity (LOH) and haploinsufficiency of other tumor suppressors (Sotillo et al, 2009). In the case of DAPLE, such insufficiency is likely to increase the fitness of cells that have undergone such a LOH because depletion of DAPLE suppresses non-canonical Wnt signaling and allows unrestricted propagation of canonical Wnt pathways. Consequently, proliferation/growth is triggered, which enables these cells to rapidly outcompete the remaining population. Based on the location of ccdc88c (DAPLE gene) at a site on the long arm of Chr 14 which is known to be frequently deleted in a variety of cancers (Hu et al, 2002; Rouault et al, 2012; Suzuki et al, 1989), it is hypothesized that tumors harboring a focal deletion at that site are in part driven by insufficient expression of the tumor suppressor DAPLE. Additional mechanisms, e.g., alternative splicing, may further contribute to oncogenesis via dysregulation of DAPLE expression, as described in a rare and fatal human developmental anomaly (Ekici et al, 2010). This anomaly was attributed to deregulation of Wnt signaling due to a loss of DAPLE's 29th exon which contains the G protein regulatory GBA motif. Although many other mechanisms may be involved, loss of DAPLE expression, or a selective loss of its G protein regulatory function has emerged as a final common pathway which disrupts DAPLE-Gαi axis of Wnt signaling and derails tissue homeostasis.

Figure 8L:
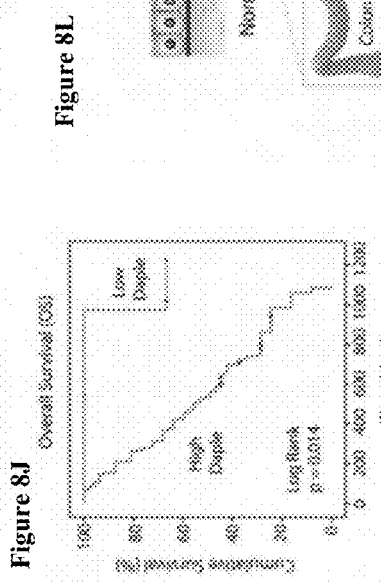

The precise molecular mechanism(s) that enhances DAPLE expression or function, and consequently triggers an EMT signature and cell invasion during cancer progression remains unclear. Transcriptional compensation for loss of an allele (Guidi et al, 2004) or gain-of-function mutations (van Oijen & Slootweg, 2000) are possible mechanisms, as shown previously in the case of other tumors suppressors. In this regard, it is noteworthy that although DAPLE bound the cytoplasmic tails of several FZDRs to varying extent, the preference for FZD7R was striking and may provide some clues as to why/how DAPLE may enhance tumor progression. Although all FZDRs promiscuously interact with more than one of the many Wnt isoforms to activate canonical and/or non-canonical Wnt signaling (King et al, 2012), FZD7 stands out as a receptor that functions at the crossroads of canonical and non-canonical Wnt signaling pathways in a unique way. FZD7R is a downstream target of β-catenin in cancer cells (Barker & Clevers, 2006), and consequently, enhanced canonical Wnt signaling upregulates FZD7R expression during cancer progression. It has been proposed that such increased FZD7R expression due to aberrant canonical Wnt signals may serve as a positive forward-feedback mechanism to perpetuate Wnt/β-catenin signaling, thus facilitating colorectal cancer progression and metastasis. Because DAPLE appears to be upregulated during cancer invasion and in circulating cancer cells (and such upregulation is associated with worse prognosis) and enhances non-canonical Wnt signaling downstream of FZD7R, it is possible that DAPLE's functional interaction with this receptor further enhances prometastatic signaling via amplification of the non-canonical Wnt pathway, which synergizes with the previously proposed forward-feedback canonical Wnt signaling loop during cancer progression. It is hypothesized that such preferential signaling downstream of FZD7R and the temporal profile of expression of DAPLE are well-poised to suppress or enhance non-canonical Wnt signaling and aid in different steps of tumor progression (see descriptions of FIG. 8L).

In conclusion, the data presented herein describe DAPLE as a novel regulator of G protein activity which directly binds FZDRs and enables these 7-TM receptors to recruit and activate Gi, and trigger non-canonical Wnt signaling to suppress tumorigenesis and enhance tumor invasion. These findings set a new paradigm for the long-debated mechanisms by which FZDRs are coupled to G protein activation. As a potent tumor suppressor with multiple intriguing domains e.g., the newly identified GBA and the Frizzled-binding domain, DAPLE presents many signaling interfaces that could be developed as targets for modulating Wnt signaling. Because its levels of expression in primary tumors, circulating cell-free transcripts and in circulating tumor cells may indicate tumor characteristics, DAPLE presents many avenues for further development as clinically useful diagnostic and prognostic biomarkers.

REFERENCES

Ahmed D, Eide P W, Eilertsen I A, Danielsen S A, Eknaes M, Hektoen M, Lind G E, Lothe R A (2013) Epigenetic and genetic features of 24 colon cancer cell lines. *Oncogenesis* 2: e71

Ahumada A, Slusarski D C, Liu X, Moon R T, Malbon C C, Wang H Y (2002) Signaling of rat Frizzled-2 through phosphodiesterase and cyclic GMP. *Science* (New York, N.Y) 298: 2006-2010

Akhurst R J, Derynck R (2001) TGF-beta signaling in cancer—a double-edged sword. *Trends in cell biology* 11: S44-51

Albini A, Iwamoto Y, Kleinman H K, Martin G R, Aaronson S A, Kozlowski J M, McEwan R N (1987) A rapid in vitro assay for quantitating the invasive potential of tumor cells. *Cancer research* 47: 3239-3245

Anastas J N, Kulikauskas R M, Tamir T, Rizos H, Long G V, von Euw E M, Yang P T, Chen H W, Haydu L, Toroni R A, Lucero O M, Chien A J, Moon R T (2014) WNT5A enhances resistance of melanoma cells to targeted BRAF inhibitors. *The Journal of clinical investigation*

Atwood B K, Lopez J, Wager-Miller J, Mackie K, Straiker A (2011) Expression of G protein-coupled receptors and related proteins in HEK293, AtT20, BV2, and N18 cell lines as revealed by microarray analysis. *BMC genomics* 12: 14

Austin R J, Ja W W, Roberts R W (2008) Evolution of class-specific peptides targeting a hot spot of the Galphas subunit. *Journal of molecular biology* 377: 1406-1418

Barbazan J, Alonso-Alconada L, Muinelo-Romay L, Vieito M, Abalo A, Alonso-Nocelo M, Candamio S, Gallardo E, Fernandez B, Abdulkader I, de Los Angeles Casares M, Gomez-Tato A, Lopez-Lopez R, Abal M (2012) Molecular characterization of circulating tumor cells in human metastatic colorectal cancer. *PloS one* 7: e40476

Barker N, Clevers H (2006) Mining the Wnt pathway for cancer therapeutics. *Nature reviews Drug discovery* 5: 997-1014

Benard V, Bokoch G M (2002) Assay of Cdc42, Rac, and Rho GTPase activation by affinity methods. *Methods in enzymology* 345: 349-359

Bentzinger C F, von Maltzahn J, Dumont N A, Stark D A, Wang Y X, Nhan K, Frenette J, Cornelison D D, Rudnicki M A (2014) WNT7a stimulates myogenic stem cell motility and engraftment resulting in improved muscle strength. *The Journal of cell biology* 205: 97-111

Bentzinger C F, Wang Y X, von Maltzahn J, Soleimani V D, Yin H, Rudnicki M A (2013) Fibronectin regulates WNT7a signaling and satellite cell expansion. *Cell stem cell* 12: 75-87

Bikkavilli R K, Feigin M E, Malbon C C (2008) G alpha o mediates WNT-JNK signaling through dishevelled 1 and 3, RhoA family members, and MEKK 1 and 4 in mammalian cells. *Journal of cell science* 121: 234-245

Blumer J B, Lanier S M (2014) Activators of G protein signaling exhibit broad functionality and define a distinct core signaling triad. *Molecular pharmacology* 85: 388-396

Bonacci T M, Mathews J L, Yuan C, Lehmann D M, Malik S, Wu D, Font J L, Bidlack J M, Smrcka A V (2006) Differential targeting of Gbetagamma-subunit signaling with small molecules. *Science* (New York, N.Y.) 312: 443-446

Bondy G P, Wilson S, Chambers A F (1985) Experimental metastatic ability of H-ras-transformed NIH3T3 cells. *Cancer research* 45: 6005-6009

Bunemann M, Frank M, Lohse M J (2003) Gi protein activation in intact cells involves subunit rearrangement rather than dissociation. *Proceedings of the National Academy of Sciences of the United States of America* 100: 16077-16082

Chambers A F, Denhardt G H, Wilson S M (1990) ras-transformed NIH 3T3 cell lines, selected for metastatic ability in chick embryos, have increased proportions of p21-expressing cells and are metastatic in nude mice. *Invasion & metastasis* 10: 225-240

Chien A J, Moore E C, Lonsdorf A S, Kulikauskas R M, Rothberg B G, Berger A J, Major M B, Hwang S T, Rimm D L, Moon R T (2009) Activated WNT/beta-catenin signaling in melanoma is associated with decreased proliferation in patient tumors and a murine melanoma model. *Proceedings of the National Academy of Sciences of the United States of America* 106: 1193-1198

Clark G J, Cox A D, Graham S M, Der C J (1995) Biological assays for Ras transformation. *Methods in enzymology* 255: 395-412

Cooper G M (2000) The Cell: A Molecular Approach. 2nd edition Sunderland (MA): *Sinauer Associates*; Tumor Suppressor Genes. Available from: http://www.ncbi.nlm.nih.gov/books/NBK9894/

Dijksterhuis J P, Petersen J, Schulte G (2014) WNT/Frizzled signalling: receptor-ligand selectivity with focus on FZD-G protein signalling and its physiological relevance: IUPHAR Review 3. *British journal of pharmacology* 171: 1195-1209

Dissanayake S K, Wade M, Johnson C E, O'Connell M P, Leotlela P D, French A D, Shah K V, Hewitt K J, Rosenthal D T, Indig F E, Jiang Y, Nickoloff B J, Taub D D, Trent J M, Moon R T, Bittner M, Weeraratna A T (2007) The WNT5A/protein kinase C pathway mediates motility in melanoma cells via the inhibition of metastasis suppressors and initiation of an epithelial to mesenchymal transition. *The Journal of biological chemistry* 282: 17259-17271

Egan S E, Wright J A, Jarolim L, Yanagihara K, Bassin R H, Greenberg A H (1987) Transformation by oncogenes encodinG protein kinases induces the metastatic phenotype. *Science* (New York, N.Y.) 238: 202-205

Egger-Adam D, Katanaev V L (2010) The trimeric G protein Go inflicts a double impact on axin in the WNT/frizzled signaling pathway. *Developmental dynamics: an official publication of the American Association of Anatomists* 239: 168-183

Ekici A B, Hilfinger D, Jatzwauk M, Thiel C T, Wenzel D, Lorenz I, Boltshauser E, Goecke T W, Staatz G, Morris-Rosendahl D J, Sticht H, Hehr U, Reis A, Rauch A (2010) Disturbed WNT Signalling due to a Mutation in CCDC88C Causes an Autosomal Recessive Non-Syndromic Hydrocephalus with Medial Diverticulum. *Molecular syndromology* 1: 99-112

Enomoto A, Ping J, Takahashi M (2006) Girdin, a novel actin-bindinG protein, and its family of proteins possess versatile functions in the Akt and Wnt signaling pathways. *Annals of the New York Academy of Sciences* 1086: 169-184

Franken N A, Rodermond H M, Stap J, Haveman J, van Bree C (2006) Clonogenic assay of cells in vitro. *Nature protocols* 1: 2315-2319

Fuerer C, Nusse R (2010) Lentiviral vectors to probe and manipulate the Wnt signaling pathway. *PloS one* 5: e9370

Gαo C, Chen Y G (2010) Dishevelled: The hub of WNT signaling. *Cellular signalling* 22: 717-727

Gαo Y, Wang H Y (2006) Casein kinase 2 Is activated and essential for WNT/beta-catenin signaling. *The Journal of biological chemistry* 281: 18394-18400

Garcia-Marcos M, Ear J, Farquhar M G, Ghosh P (2011a) A GDI (AGS3) and a GEF (GIV) regulate autophagy by balancing G protein activity and growth factor signals. *Molecular biology of the cell* 22: 673-686

Garcia-Marcos M, Ghosh P, Ear J, Farquhar M G (2010) A structural determinant that renders G alpha(i) sensitive to activation by GIV/girdin is required to promote cell migration. *The Journal of biological chemistry* 285: 12765-12777

Garcia-Marcos M, Ghosh P, Farquhar M G (2009) GIV is a nonreceptor GEF for G alpha i with a unique motif that regulates Akt signaling. *Proceedings of the National Academy of Sciences of the United States of America* 106: 3178-3183

Garcia-Marcos M, Kietrsunthorn P S, Pavlova Y, Adia M A, Ghosh P, Farquhar M G (2012) Functional characterization of the guanine nucleotide exchange factor (GEF) motif of GIV protein reveals a threshold effect in signaling. *Proceedings of the National Academy of Sciences of the United States of America* 109: 1961-1966

Garcia-Marcos M, Kietrsunthorn P S, Wang H, Ghosh P, Farquhar M G (2011b) G protein binding sites on Calnuc (nucleobindin 1) and NUCB2 (nucleobindin 2) define a new class of G(alpha)i-regulatory motifs. *The Journal of biological chemistry* 286: 28138-28149

Ghosh P, Beas A O, Bornheimer S J, Garcia-Marcos M, Forry E P, Johannson C, Ear J, Jung B H, Cabrera B, Carethers J M, Farquhar M G (2010) A G{alpha}i-GIV molecular complex binds epidermal growth factor receptor and determines whether cells migrate or proliferate. *Molecular biology of the cell* 21: 2338-2354

Ghosh P, Garcia-Marcos M, Bornheimer S J, Farquhar M G (2008) Activation of Galphai3 triggers cell migration via regulation of GIV. *The Journal of cell biology* 182: 381-393

Gibson S K, Gilman A G (2006) Gialpha and Gbeta subunits both define selectivity of G protein activation by alpha2-adrenergic receptors. *Proceedings of the National Academy of Sciences of the United States of America* 103: 212-217

Grumolato L, Liu G, Mong P, Mudbhary R, Biswas R, Arroyave R, Vijayakumar S, Economides A N, Aaronson S A (2010) Canonical and noncanonical WNTs use a common mechanism to activate completely unrelated coreceptors. *Genes & development* 24: 2517-2530

Guidi C J, Veal T M, Jones S N, Imbalzano A N (2004) Transcriptional compensation for loss of an allele of the Ini1 tumor suppressor. *The Journal of biological chemistry* 279: 4180-4185

Hans F, Dimitrov S (2001) Histone H3 phosphorylation and cell division. *Oncogene* 20: 3021-3027

Hill S A, Wilson S, Chambers A F (1988) Clonal heterogeneity, experimental metastatic ability, and p21 expression in H-ras-transformed NIH 3T3 cells. *Journal of the National Cancer Institute* 80: 484-490

Hino S, Tanji C, Nakayama K I, Kikuchi A (2005) Phosphorylation of beta-catenin by cyclic AMP-dependent protein kinase stabilizes beta-catenin through inhibition of its ubiquitination. *Molecular and cellular biology* 25: 9063-9072

Hothorn T, Zeileis A (2008) Generalized maximally selected statistics. *Biometrics* 64: 1263-1269

Hu J, Pang J C, Tong C Y, Lau B, Yin X L, Poon W S, Jiang C C, Zhou L F, Ng H K (2002) High-resolution genome-wide allelotype analysis identifies loss of chromosome 14q as a recurrent genetic alteration in astrocytic tumours. *British journal of cancer* 87: 218-224

Ishitani T, Kishida S, Hyodo-Miura J, Ueno N, Yasuda J, Waterman M, Shibuya H, Moon R T, Ninomiya-Tsuji J, Matsumoto K (2003) The TAK1-NLK mitogen-activated protein kinase cascade functions in the WNT-5a/Ca(2+) pathway to antagonize WNT/beta-catenin signaling. *Molecular and cellular biology* 23: 131-139

Jamieson C, Sharma M, Henderson B R (2014) Targeting the beta-catenin nuclear transport pathway in cancer. *Seminars in cancer biology*

Janetopoulos C, Jin T, Devreotes P (2001) Receptor-mediated activation of heterotrimeric G-proteins in living cells. *Science* (New York, N.Y.) 291: 2408-2411

Johnston C A, Willard F S, Jezyk M R, Fredericks Z, Bodor E T, Jones M B, Blaesius R, Watts V J, Harden T K, Sondek J, Ramer J K, Siderovski D P (2005) Structure of Galpha(i1) bound to a GDP-selective peptide provides insight into guanine nucleotide exchange. *Structure* (London, England: 1993) 13: 1069-1080

Katanaev V L, Buestorf S (2009) Frizzled Proteins are bona fide G protein-Coupled Receptors. *Nature precedings* http://hdl.handle.net/10101/npre.2009.2765.1

Katanaev V L, Ponzielli R, Semeriva M, Tomlinson A (2005) Trimeric G protein-dependent frizzled signaling in *Drosophila*. *Cell* 120: 111-122

Kawasaki A, Torii K, Yamashita Y, Nishizawa K, Kanekura K, Katada M, Ito M, Nishimoto I, Terashita K, Aiso S, Matsuoka M (2007) Wnt5a promotes adhesion of human dermal fibroblasts by triggering a phosphatidylinositol-3 kinase/Akt signal. *Cellular signalling* 19: 2498-2506

Kilander M B, Petersen J, Andressen K W, Ganji R S, Levy F O, Schuster J, Dahl N, Bryja V, Schulte G (2014) Disheveled regulates precoupling of heterotrimeric G proteins to Frizzled 6. *FASEB journal: official publication of the Federation of American Societies for Experimental Biology* 28: 2293-2305

King T D, Zhang W, Suto M J, Li Y (2012) Frizzled7 as an emerging target for cancer therapy. *Cellular signalling* 24: 846-851

Klaus A, Birchmeier W (2008) WNT signalling and its impact on development and cancer. *Nature reviews Cancer* 8: 387-398

Knaus U G, Bamberg A, Bokoch G M (2007) Rac and Rap GTPase activation assays. *Methods in molecular biology* (Clifton, N.J.) 412: 59-67

Kobayashi H, Michiue T, Yukita A, Danno H, Sakurai K, Fukui A, Kikuchi A, Asashima M (2005) Novel DAPLE-like protein positively regulates both the WNT/beta-catenin pathway and the WNT/JNK pathway in *Xenopus*. *Mechanisms of development* 122: 1138-1153

Koval A, Katanaev V L (2011) WNT3a stimulation elicits G-protein-coupled receptor properties of mammalian Frizzled proteins. *The Biochemical journal* 433: 435-440

Koval A, Purvanov V, Egger-Adam D, Katanaev V L (2011) Yellow submarine of the WNT/Frizzled signaling: submerging from the G protein harbor to the targets. *Biochemical pharmacology* 82: 1311-1319

Kuhl M, Sheldahl L C, Park M, Miller J R, Moon R T (2000) The WNT/Ca2+ pathway: a new vertebrate Wnt signaling pathway takes shape. *Trends in genetics: TIG* 16: 279-283

Lane J R, Henderson D, Powney B, Wise A, Rees S, Daniels D, Plumpton C, Kinghorn I, Milligan G (2008a) Antibodies that identify only the active conformation of G(i) family G protein alpha subunits. *FASEB Journal: official publication of the Federation of American Societies for Experimental Biology* 22: 1924-1932

Lane J R, Powney B, Wise A, Rees S, Milligan G (2008b) G protein coupling and ligand selectivity of the D2L and D3 dopamine receptors. *The Journal of pharmacology and experimental therapeutics* 325: 319-330

Lanier S M (2004) AGS proteins, GPR motifs and the signals processed by heterotrimeric G proteins. *Biology of the cell/under the auspices of the European Cell Biology Organization* 96: 369-372

Le-Niculescu H, Niesman I, Fischer T, DeVries L, Farquhar M G (2005) Identification and characterization of GIV, a novel Galpha i/s-interactinG protein found on COPI, endoplasmic reticulum-Golgi transport vesicles. *The Journal of biological chemistry* 280: 22012-22020

Lee M J, Dohlman H G (2008) Coactivation of G protein signaling by cell-surface receptors and an intracellular exchange factor. *Current biology: CB* 18: 211-215

Lehmann D M, Seneviratne A M, Smrcka A V (2008) Small molecule disruption of G protein beta gamma subunit signaling inhibits neutrophil chemotaxis and inflammation. *Molecular pharmacology* 73: 410-418

Leitner L, Shaposhnikov D, Mengel A, Descot A, Julien S, Hoffmann R, Posern G (2011) MAL/MRTF-A controls migration of non-invasive cells by upregulation of cytoskeleton-associated proteins. *Journal of cell science* 124: 4318-4331

Leopoldt D, Hanck T, Exner T, Maier U, Wetzker R, Nurnberg B (1998) Gbetagamma stimulates phosphoinositide 3-kinase-gamma by direct interaction with two domains of the catalytic p110 subunit. *The Journal of biological chemistry* 273: 7024-7029

Lin C, Ear J, Pavlova Y, Mittal Y, Kufareva I, Ghassemian M, Abagyan R, Garcia-Marcos M, Ghosh P (2011) Tyrosine phosphorylation of the Galpha-interactinG protein GIV promotes activation of phosphoinositide 3-kinase during cell migration. *Science signaling* 4: ra64

Liu J, Zhang Y, Xu R, Du J, Hu Z, Yang L, Chen Y, Zhu Y, Gu L (2013) PI3K/Akt-dependent phosphorylation of GSK3beta and activation of RhoA regulate Wnt5a-induced gastric cancer cell migration. *Cellular signalling* 25: 447-456

Liu T, DeCostanzo A J, Liu X, Wang H, Hallagan S, Moon R T, Malbon C C (2001) G protein signaling from activated rat frizzled-1 to the beta-catenin-Lef-Tcf pathway. *Science* (New York, N.Y.) 292: 1718-1722

Liu T, Liu X, Wang H, Moon R T, Malbon C C (1999) Activation of rat frizzled-1 promotes Wnt signaling and differentiation of mouse F9 teratocarcinoma cells via pathways that require Galpha(q) and Galpha(o) function. *The Journal of biological chemistry* 274: 33539-33544

Liu X, Rubin J S, Kimmel A R (2005) Rapid, WNT-induced changes in GSK3beta associations that regulate beta-catenin stabilization are mediated by Galpha proteins. *Current biology: CB* 15: 1989-1997

Logan C Y, Nusse R (2004) The Wnt signaling pathway in development and disease. *Annual review of cell and developmental biology* 20: 781-810

Lopez-Sanchez I, Dunkel Y, Roh, Y-S. M, Y., De Minicis S, Muranyi M, Singh S, Shanmugam K, Aroonsakool N, Murray F, Ho S B, Seki E, Brenner D A, Ghosh P (2014) GIV/Girdin is a central hub for pro-fibrogenic signalling networks during liver fibrosis. *Nature Comm* In Press Ma L, Wang H Y (2006) Suppression of cyclic GMP-dependent protein kinase is essential to the WNT/cGMP/Ca2+ pathway. *The Journal of biological chemistry* 281: 30990-31001

Maak M, Simon I, Nitsche U, Roepman P, Snel M, Glas A M, Schuster T, Keller G, Zeestraten E, Goossens I, Janssen K P, Friess H, Rosenberg R (2013) Independent validation of a prognostic genomic signature (ColoPrint) for patients with stage II colon cancer. *Annals of surgery* 257: 1053-1058

MacLeod R J, Hayes M, Pacheco I (2007) Wnt5a secretion stimulated by the extracellular calcium-sensing receptor inhibits defective Wnt signaling in colon cancer cells. *American journal of physiology Gastrointestinal and liver physiology* 293: G403-411

Malbon C C (2004) Frizzleds: new members of the superfamily of G-protein-coupled receptors. *Frontiers in bioscience: a journal and virtual library* 9: 1048-1058

Massotte D (2003) G protein-coupled receptor overexpression with the baculovirus-insect cell system: a tool for structural and functional studies. *Biochimica et biophysica acta* 1610: 77-89

Mayor R, Theveneau E (2014) The role of the non-canonical WNT-planar cell polarity pathway in neural crest migration. *The Biochemical journal* 457: 19-26

McDonald S L, Silver A (2009) The opposing roles of WNT-5a in cancer. *British journal of cancer* 101: 209-214

Medrek C, Landberg G, Andersson T, Leandersson K (2009) WNT-5a-CKI{alpha} signaling promotes {beta}-catenin/E-cadherin complex formation and intercellular adhesion in human breast epithelial cells. *The Journal of biological chemistry* 284: 10968-10979

Midde K, Aznar N, Laederich M B, Ma G S, Kunkel M, Newton A, Ghosh P (2015) Multi-modular Biosensors Reveal a Novel Platform for Activation of G proteins by Growth Factor Receptors. *Proceedings of the National Academy of Sciences of the United States of America*, in press Midde K, Rich R, Saxena A, Gryczynski I, Borejdo J, Das H K (2014) Membrane Topology of Human Presenilin-1 in SK-N-SH Cells Determined by Fluorescence Correlation Spectroscopy and Fluorescent Energy Transfer. *Cell biochemistry and biophysics*

Minami Y, Oishi I, Endo M, Nishita M (2010) Ror-family receptor tyrosine kinases in noncanonical Wnt signaling: their implications in developmental morphogenesis and human diseases. *Developmental dynamics: an official publication of the American Association of Anatomists* 239: 1-15

Mukhopadhyay S, Ross E M (2002) Quench-flow kinetic measurement of individual reactions of G-protein-catalyzed GTPase cycle. *Methods in enzymology* 344: 350-369

Natochin M, Campbell T N, Barren B, Miller L C, Hameed S, Artemyev N O, Braun J E (2005) Characterization of the G alpha(s) regulator cysteine strinG protein. *The Journal of biological chemistry* 280: 30236-30241

Nichols A S, Floyd D H, Bruinsma S P, Narzinski K, Baranski T J (2013) Frizzled receptors signal through G proteins. *Cellular signalling* 25: 1468-1475

Niehrs C (2001) Developmental biology. Solving a sticky problem. *Nature* 413: 787-788

Niehrs C, Acebron S P (2012) Mitotic and mitogenic WNT signalling. *The EMBO journal* 31: 2705-2713

Nishita M, Itsukushima S, Nomachi A, Endo M, Wang Z, Inaba D, Qiao S, Takada S, Kikuchi A, Minami Y (2010) Ror2/Frizzled complex mediates Wnt5a-induced AP-1 activation by regulating Dishevelled polymerization. *Molecular and cellular biology* 30: 3610-3619

Nitsche U, Rosenberg R, Balmert A, Schuster T, Slotta-Huspenina J, Herrmann P, Bader F G, Friess H, Schlag P M, Stein U, Janssen K P (2012) Integrative marker analysis allows risk assessment for metastasis in stage II colon cancer. *Annals of surgery* 256: 763-771; discussion 771

Niu J, Profirovic J, Pan H, Vaiskunaite R, Voyno-Yasenetskaya T (2003) G protein betagamma subunits stimulate p114RhoGEF, a guanine nucleotide exchange factor for RhoA and Rac1: regulation of cell shape and reactive oxygen species production. *Circulation research* 93: 848-856

Olson D J, Gibo D M (1998) Antisense WNT-5a mimics WNT-1-mediated C57MG mammary epithelial cell transformation. *Experimental cell research* 241: 134-141

Oner S S, Maher E M, Gabay M, Tall G G, Blumer J B, Lanier S M (2013) Regulation of the G-protein regulatory-Galphai signaling complex by nonreceptor guanine nucleotide exchange factors. *The Journal of biological chemistry* 288: 3003-3015

Oshita A, Kishida S, Kobayashi H, Michiue T, Asahara T, Asashima M, Kikuchi A (2003) Identification and characterization of a novel Dvl-bindinG protein that suppresses WNT signalling pathway. *Genes to cells: devoted to molecular & cellular mechanisms* 8: 1005-1017

Ostrom R S, Gregorian C, Drenan R M, Xiang Y, Regan J W, Insel P A (2001) Receptor number and caveolar co-localization determine receptor coupling efficiency to adenylyl cyclase. The *Journal of biological chemistry* 276: 42063-42069

Payne S R, Kemp C J (2005) Tumor suppressor genetics. *Carcinogenesis* 26: 2031-2045

Pino M S, Chung D C (2010) The chromosomal instability pathway in colon cancer. *Gastroenterology* 138: 2059-2072

Roszik J, Lisboa D, Szollosi J, Vereb G (2009) Evaluation of intensity-based ratiometric FRET in image cytometry—approaches and a software solution. *Cytometry Part A: the journal of the International Society for Analytical Cytology* 75: 761-767

Rouault A, Banneau G, Macgrogan G, Jones N, Elarouci N, Barouk-Simonet E, Venat L, Coupier I, Letouze E, de Reynies A, Bonnet F, Iggo R, Sevenet N, Longy M (2012) Deletion of chromosomes 13q and 14q is a common feature of tumors with BRCA2 mutations. *PloS one* 7: e52079

Sato A, Yamamoto H, Sakane H, Koyama H, Kikuchi A (2010) Wnt5a regulates distinct signalling pathways by binding to Frizzled2. *The EMBO journal* 29: 41-54

Sato M, Blumer J B, Simon V, Lanier S M (2006) Accessory proteins for G proteins: partners in signaling. *Annual review of pharmacology and toxicology* 46: 151-187

Schulte G (2010) International Union of Basic and Clinical Pharmacology. LXXX. The class Frizzled receptors. *Pharmacological reviews* 62: 632-667

Schulte G, Bryja V (2007) The Frizzled family of unconventional G-protein-coupled receptors. *Trends in pharmacological sciences* 28: 518-525

Schwede T, Kopp J, Guex N, Peitsch M C (2003) SWISS-MODEL: An automated protein homology-modeling server. *Nucleic acids research* 31: 3381-3385

Seneviratne A M, Burroughs M, Giralt E, Smrcka A V (2011) Direct-reversible binding of small molecules to G protein betagamma subunits. *Biochimica et biophysica acta* 1814: 1210-1218

Sheldahl L C, Park M, Malbon C C, Moon R T (1999) Protein kinase C is differentially stimulated by WNT and Frizzled homologs in a G-protein-dependent manner. *Current biology: CB* 9: 695-698

Shirasawa S, Furuse M, Yokoyama N, Sasazuki T (1993) Altered growth of human colon cancer cell lines disrupted at activated Ki-ras. *Science (New York, N.Y.)* 260: 85-88

Siderovski D P, Willard F S (2005) The GAPs, GEFs, and GDIs of heterotrimeric G-protein alpha subunits. *International journal of biological sciences* 1: 51-66

Slep K C, Kercher M A, Wieland T, Chen C K, Simon M I, Sigler P B (2008) Molecular architecture of Galphao and the structural basis for RGS16-mediated deactivation. *Proceedings of the National Academy of Sciences of the United States of America* 105: 6243-6248

Slusarski D C, Corces V G, Moon R T (1997a) Interaction of WNT and a Frizzled homologue triggers G-protein-linked phosphatidylinositol signalling. *Nature* 390: 410-413

Slusarski D C, Yang-Snyder J, Busa W B, Moon R T (1997b) Modulation of embryonic intracellular Ca2+ signaling by WNT-5A. *Developmental biology* 182: 114-120

Smrcka A V (2008) G protein betagamma subunits: central mediators of G protein-coupled receptor signaling. *Cellular and molecular life sciences: CMLS* 65: 2191-2214

Smrcka A V (2013) Molecular targeting of Galpha and Gbetagamma subunits: a potential approach for cancer therapeutics. *Trends in pharmacological sciences* 34: 290-298

Smrcka A V, Lehmann D M, Dessal A L (2008) G protein betagamma subunits as targets for small molecule therapeutic development. *Combinatorial Chemistry & High Throughput Screening* 11: 382-395

Sotillo R, Schvartzman J M, Benezra R (2009) Very CINful: whole chromosome instability promotes tumor suppressor loss of heterozygosity. *Cancer Cell* 16: 451-452

Suzuki T, Yokota J, Mugishima H, Okabe I, Ookuni M, Sugimura T, Terada M (1989) Frequent loss of heterozygosity on chromosome 14q in neuroblastoma. *Cancer Research* 49: 1095-1098

Tall G G, Krumins A M, Gilman A G (2003) Mammalian Ric-8A (synembryn) is a heterotrimeric Galpha protein guanine nucleotide exchange factor. *The Journal of Biological Chemistry* 278: 8356-8362

Thomas C J, Du X, Li P, Wang Y, Ross E M, Sprang S R (2004) Uncoupling conformational change from GTP hydrolysis in a heterotrimeric G protein alpha-subunit. *Proceedings of the National Academy of Sciences of the United States of America* 101: 7560-7565

Thomas P, Smart T G (2005) HEK293 cell line: a vehicle for the expression of recombinant proteins. *Journal of Pharmacological and Toxicological Methods* 51: 187-200

Toiyama Y, Takahashi M, Hur K, Nagasaka T, Tanaka K, Inoue Y, Kusunoki M, Boland C R, Goel A (2013) Serum miR-21 as a diagnostic and prognostic biomarker in colorectal cancer. *Journal of the National Cancer Institute* 105: 849-859

Torres M A, Yang-Snyder J A, Purcell S M, DeMarais A A, McGrew L L, Moon R T (1996) Activities of the WNT-1 class of secreted signaling factors are antagonized by the WNT-5A class and by a dominant negative cadherin in early *Xenopus* development. *The Journal of Cell Biology* 133: 1123-1137

Tsafrir D, Bacolod M, Selvanayagam Z, Tsafrir I, Shia J, Zeng Z, Liu H, Krier C, Stengel R F, Barany F, Gerald W L, Paty P B, Domany E, Notterman D A (2006) Relationship of gene expression and chromosomal abnormalities in colorectal cancer. *Cancer Research* 66: 2129-2137

Tuck A B, Wilson S M, Khokha R, Chambers A F (1991) Different patterns of gene expression in ras-resistant and ras-sensitive cells. *Journal of the National Cancer Institute* 83: 485-491

Ueda H, Nagae R, Kozawa M, Morishita R, Kimura S, Nagase T, Ohara O, Yoshida S, Asano T (2008) Heterotrimeric G protein betagamma subunits stimulate FLJ00018, a guanine nucleotide exchange factor for Rac1 and Cdc42. *The Journal of Biological Chemistry* 283: 1946-1953

Urano D, Nakata A, Mizuno N, Tago K, Itoh H (2008) Domain-domain interaction of P-Rex1 is essential for the activation and inhibition by G protein betagamma subunits and PKA. *Cellular Signalling* 20: 1545-1554 van Oijen M G, Slootweg P J (2000) Gain-of-function mutations in the tumor suppressor gene p53. *Clinical Cancer Research: An Official Journal of the American Association for Cancer Research* 6: 2138-2145

Verkaar F, Zaman G J (2010) A model for signaling specificity of WNT/Frizzled combinations through co-receptor recruitment. *FEBS Letters* 584: 3850-3854

Voloshanenko O, Erdmann G, Dubash T D, Augustin I, Metzig M, Moffa G, Hundsrucker C, Kerr G, Sandmann T, Anchang B, Demir K, Boehm C, Leible S, Ball C R, Glimm H, Spang R, Boutros M (2013) WNT secretion is required to maintain high levels of WNT activity in colon cancer cells. *Nature Communications* 4: 2610

Wallert M A P J. (2007) Soft Agar Assay for Colony Formation

Weeraratna A T, Jiang Y A, Hostetter G, Rosenblatt K, Duray P, Bittner M, Trent J M (2002) Wnt5a signaling directly affects cell motility and invasion of metastatic melanoma. *Cancer Cell* 1: 279-288

Welch H C, Coadwell W J, Ellson C D, Ferguson G J, Andrews S R, Erdjument-Bromage H, Tempst P, Hawkins P T, Stephens L R (2002) P-Rex1, a PtdIns(3,4,5)P3- and Gbetagamma-regulated guanine-nucleotide exchange factor for Rac. *Cell* 108: 809-821

Willert K H (2008) Isolation and application of bioactive WNT proteins. *Methods in Molecular Biology* (Clifton, N.J.) 468: 17-29

Winklbauer R, Medina A, Swain R K, Steinbeisser H (2001) Frizzled-7 signalling controls tissue separation during *Xenopus* gastrulation. *Nature* 413: 856-860

Witzel S, Zimyanin V, Carreira-Barbosa F, Tada M, Heisenberg C P (2006) WNT11 controls cell contact persistence by local accumulation of Frizzled 7 at the plasma membrane. *The Journal of Cell Biology* 175: 791-802

Xu H, Kardash E, Chen S, Raz E, Lin F (2012) Gbetagamma signaling controls the polarization of zebrafish primordial germ cells by regulating Rac activity. *Development* (Cambridge, England) 139: 57-62

Yamamoto H, Kitadai Y, Oue N, Ohdan H, Yasui W, Kikuchi A (2009) Laminin gamma2 mediates Wnt5a-induced invasion of gastric cancer cells. *Gastroenterology* 137: 242-252, 252 e241-246

Yamamoto H, Yoo S K, Nishita M, Kikuchi A, Minami Y (2007) Wnt5a modulates glycogen synthase kinase 3 to induce phosphorylation of receptor tyrosine kinase Ror2. *Genes to Cells: devoted to molecular & cellular mechanisms* 12: 1215-1223

Yao R, Natsume Y, Noda T (2004) MAGI-3 is involved in the regulation of the JNK signaling pathway as a scaffold protein for frizzled and Ltap. *Oncogene* 23: 6023-6030

Ying J, Li H, Chen Y W, Srivastava G, Gao Z, Tao Q (2007) WNT5A is epigenetically silenced in hematologic malignancies and inhibits leukemia cell growth as a tumor suppressor. *Blood* 110: 4130-4132

Ying J, Li H, Yu J, Ng K M, Poon F F, Wong S C, Chan A T, Sung J J, Tao Q (2008) WNT5A exhibits tumor-suppressive activity through antagonizing the WNT/beta-catenin signaling, and is frequently methylated in colorectal cancer. *Clinical Cancer Research: An Official Journal of the American Association for Cancer Research* 14: 55-61

Zhang A, He S, Sun X, Ding L, Bao X, Wang N (2014) Wnt5a promotes migration of human osteosarcoma cells by triggering a phosphatidylinositol-3 kinase/Akt signals. *Cancer Cell International* 14: 15

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

Sequences

Full length human DAPLE (DAPLE-fl) (NCBI Reference Sequence NM_001080414.3) (SEQ ID NO: 1):

```
GCGGAACGTGGGCTCGCGCGCCCCGCCTTTGTCTCCCGGGCGCGAGCCGC

CGCAGCCCCGCGCCCGCTGCTCGCTGCGGAGCCGTTTTGTGCCGCGGCGC

GGGGGAACGGGGACGCGGGGCGGGGGGCGCGGAGCCGGCGGGCGCAGCCT

CAGCATGGACGTGACAGTCTCGGAGCTCCTGGAGCTCTTCCTGCAGAGCC

CGCTGGTGACCTGGGTGAAAACTTTTGGCCCGTTTGGAAGCGGCAGCCAG

GACAACCTGACTATGTACATGGATTTAGTGGACGGCATCTTTTTGAACCA

AATTATGCTGCAAATAGATCCCAGGCCCACAAATCAACGCATCAATAAGC

ACGTCAACAATGATGTGAACCTTCGCATTCAGAATTTGACCATCTTGGTG

AGAAACATTAAGACCTACTACCAGGAAGTTCTCCAGCAGCTGATTGTAAT

GAATTTGCCCAATGTTTTGATGATTGGCAGAGACCCACTGTCTGGGAAGA

GCATGGAGGAAATCAAGAAGGTGCTGCTGCTGGTGCTGGGCTGTGCTGTC

CAGTGTGAGAGGAAAGAGGAGTTCATTGAAAGAATCAAACAGCTGGACAT

TGAGACCCAGGCTGGCATCGTGGCCCATATCCAGGAGGTGACTCACAACC

AAGAGAACGTGTTTGACCTGCAGTGGCTGGAGCTGCCCGACGTGGCTCCG

GAGGAGCTGGAGGCCCTGTCGAGGAGCATGGTGCTCCACCTGCGGAGGCT

CATCGACCAGCGGGACGAGTGCACCGAGCTGATCGTGGACCTCACTCAGG

AACGGGACTACCTGCAGGCACAGCATCCACCCAGCCCCATCAAGTCCTCC

AGCGCCGACTCCACTCCCAGCCCCACCAGCAGCCTCTCTAGCGAAGACAA

GCAGCACCTGGCCGTAGAGCTGGCCGACACCAAGGCCAGGCTGCGGCGCG

TCAGGCAGGAGCTGGAGGATAAGACAGAGCAGCTTGTGGACACCAGACAT

GAGGTGGACCAGCTGGTGCTGGAACTGCAGAAAGTTAAGCAGGAGAACAT

CCAGCTAGCGGCAGACGCCCGGTCTGCTCGTGCCTATCGAGACGAGCTGG

ATTCCCTGCGGGAGAAGGCGAACCGCGTGGAGAGGCTGGAGCTGGAGCTG

ACCCGCTGCAAGGAGAAGCTGCACGACGTGGACTTCTACAAGGCCCGCAT

GGAGGAGCTGAGAGAAGATAATATCATTTTAATTGAAACCAAGGCCATGC

TGGAGGAACAGCTGACTGCTGCTCGGGCCCGGGGCGATAAAGTCCATGAG

CTGGAAAAGGAGAACCTGCAGCTGAAATCCAAGCTTCACGACCTGGAATT

GGACCGGGACACAGATAAGAAACGAATTGAGGAGCTGCTGGAAGAAACA

TGGTCCTTGAGATTGCACAGAAGCAGAGCATGAACGAATCTGCCCACCTT

GGCTGGGAGCTGGAGCAGCTGTCCAAGAACGCAGACTTGTCAGACGCCTC

CAGGAAGTCGTTTGTGTTTGAGCTGAACGAATGTGCGTCCAGCCGCATCC

TGAAGCTGGAGAAGGAGAATCAGAGCCTCCAGAGCACCATCCAGGGGCTG

CGGGACGCGTCCCTGGTGTTGGAGGAGAGCGGCCTCAAGTGCGGGGAGCT

GGAGAAGGAGAACCACCAGCTCAGCAAGAAGATTGAAAAGTTACAAACCC

AGCTGGAGAGAGAAAAGCAGAGCAACCAAGATCTGGAGACCCTCAGTGAG

GAGCTGATCAGAGAGAAGGAGCAGCTGCAGAGTGACATGGAGACCCTGAA

GGCTGACAAAGCCAGGCAGATCAAGGACCTTGAGCAGGAAAAGGACCACC

TCAACCGAGCCATGTGGTCGCTGCGGGAGAGGTCGCAGGTCAGCAGTGAG

GCCCGCATGAAAGACGTGGAGAAGGAGAACAAAGCCCTCCACCAGACGGT

GACGGAGGCCAATGGCAAGCTCAGCCAGTTGGAGTTTGAGAAGCGGCAGC

TGCACAGGGACTTGGAGCAGGCCAAGGAGAAGGGGGAGCGGGCAGAGAAG

CTGGAGAGGGAGCTACAGCGACTCCAGGAGGAGAACGGGAGGCTGGCCAG

GAAGGTGACCTCCCTGGAGACAGCCACCGAGAAAGTCGAGGCCCTGGAGC

ATGAGAGCCAGGGCCTGCAGCTGGAGAACCGGACTCTGAGGAAGTCTCTG

GACACCTTGCAGAACGTGTCCCTGCAGCTTGAGGGCCTGGAGCGTGACAA
```

```
CAAGCAGCTGGACGCAGAGAACCTGGAGCTGCGCAGGCTGGTGGAGACCA
TGCGCTTCACCAGCACCAAGCTGGCACAGATGGAGAGGGAGAACCAGCAG
CTGGAGCGTGAGAAGGAGGAGCTGAGGAAGAACGTGGATCTGCTCAAGGC
GCTGGGCAAGAAGTCAGAGCGCCTGGAGCTCAGCTACCAGAGCGTGAGCG
CTGAGAACCTCCGGCTGCAGCAGAGCCTGGAGAGCAGCAGCCACAAGACG
CAGACCTTGGAGAGTGAGCTGGGCGAGCTGGAGGCTGAGCGCCAGGCGCT
GCGGCGGGACCTGGAGGCCCTCCGGCTGGCCAATGCACAGTTGGAGGGGG
CCGAGAAGGACAGGAAGGCCCTGGAGCAGGAGGTGGCCCAGCTCGAGAAG
GATAAGAAGCTGCTGGAGAAGGAGGCCAAGCGGCTGTGGCAGCAGGTGGA
GCTCAAGGATGCAGTCTTGGACGATAGCACTGCCAAACTGTCCGCCGTTG
AGAAGGAGAGCCGCGCGCTGGACAAGGAGCTGGCCCGCTGCAGGGACGCA
GCCGGCAAGCTGAAGGAGCTGGAGAAGGACAACCGGGACCTCACCAAGCA
AGTCACCGTGCATGCAAGGACACTGACAACTCTGAGGGAGGACCTGGTGC
TCGAGAAGCTGAAGAGCCAGCAGCTCAGCAGTGAGCTGGACAAGCTGAGC
CAGGAACTGGAGAAGGTCGGCCTCAACAGGGAGCTGCTGTTGCAGGAGGA
CGACAGCGGCAGTGACACAAAATACAAGATTTTGGAGGGCAGAAATGAAT
CAGCATTAAAAACAACACTAGCCATGAAAGAAGAAAAGATTGTGCTCTTA
GAAGCACAGATGGAAGAGAAAGCGAGCCTAAATCGCCAGTTAGAGAGTGA
GCTGCAGATGCTAAAGAAGGAGTGTGAGACCCTCAGGCAGAACCAGGGAG
AGGGGCAGCACTTGCAGAACTCTTTCAAGCACCCTGCGGGGAAGACAGCC
GCCAGTCACCAGGGGAAGGAGGCCTGGGGGCCCGGCCATAAGGAAGCCAC
CATGGAGCTTCTCCGAGTGAAGGACCGGGCCATCGAGCTGGAGCGGAATA
ATGCAGCTCTGCAGGCTGAGAAGCAGCTGCTAAAGGAACAGCTGCAGCAC
CTGGAGACCCAGAACGTGACCTTCAGCAGCCAGATCTTGACACTGCAGAA
ACAGAGCGCCTTCCTGCAGGAGCACAACACCACACTGCAGACCCAGACCG
CCAAGCTGCAGGTGGAGAACTCCACGCTGAGTTCCCAGAGCGCAGCGCTC
ACCGCGCAGTACACGCTGCTGCAGAACCACCACACGCCAAGGAGACGGA
GAACGAAAGCCTGCAGAGGCAGCAGGAGCAACTTACAGCGGCCTACGAGG
CCCTGCTGCAGGACCACGAGCACCTGGGCACGCTGCACGAGCGGCAATCG
GCCGAGTACGAGGCCCTCATCCGCCAGCACAGCTGCCTAAAGACACTGCA
TCGGAATCTGGAGCTGGAGCACAAGGAGCTCGGGGAGAGGCACGGTGACA
TGCTGAAGCGCAAGGCGGAGCTGGAGGAGCGGGAGAAGGTCTTGACCACT
GAGCGAGAGGCGCTGCAGCAGGAGCAGAGGACAAACGCCCTCGCCATGGG
CGAGAACCAGAGGCTGCGGGGCGAGCTGGACAGGGTCAATTTCCTGCACC
ACCAGCTGAAGGGGGAGTACGAGGAGCTGCACGCCCACACCAAGGAGCTG
AAAACCTCACTGAACAACGCGCAGCTGGAGCTCAACCGCTGGCAGGCCCG
CTTCGACGAGCTGAAGGAGCAGCACCAGACCATGGACATCTCGCTGACCA
AGCTGGACAACCACTGTGAGCTGCTCTCCCGTCTCAAGGGGAACTTGGAG
GAAGAAAATCATCACCTCCTGAGCCAGATCCAGCTGTTGAGCCAGCAGAA
CCAGATGCTTCTGGAGCAGAACATGGAGAACAAGGAGCAGTACCATGAGG
AGCAGAAGCAGTACATAGACAAATTAAATGCCTTACGAAGACATAAGGAA
AAGCTGGAAGAAAAAATCATGGATCAATACAAGTTCTATGATCCTCCTCC
AAAGAAGAAGAACCACTGGATTGGAGCCAAAGCCTTAGTCAAACTCATCA
AACCAAAGAAAGAGGGTTCGAGGGAACGCTTAAAATCCACCGTGGACAGC
CCTCCCTGGCAGCTGGAGTCCTCAGACCCCGCCTCGCCGGCGGCCTCTCA
GCCGCTCAGATCACAGGCCGGAGAACCCCGACACCCCCGCACTGGGCTCCA
ACTGTGCAGAAGAGCGCGACGCCCACAACGGGTCTGTGGGGAAAGGCCCT
GGGGATCTAAAACCAAAGCGAGGCTCCCCACACAGAGGCAGCCTTGACCG
CACAGATGCCTCCACCGATCTGGCCATGAGGTCCTGGCCCTCGGAGCTGG
GCTCCCGGACTTGCTCAACTTCAGCCACCACTACAGCCCCTTCCAACTCC
ACCCCCATCGCCCGGCACCCAGGCCGCACCAAAGGCTATAACTCAGATGA
CAACCTCTGTGAGCCATCCCTGGAGTTTGAGGTCCCCAACCACAGGCAGT
ACGTGTCGCGGCCAAGTAGCTTAGAGAGCAGTAGAAACACATCCAGCAAC
AGCTCACCTCTTAACCTAAAAGGCTCCTCCGAGCAGCTCCATGGCCGGTC
TGAGAGCTTCAGCAGCGAAGACCTGATCCCCAGCAGGGACCTGGCCACTT
TGCCCCGGGAAGCCAGCACACCGGGACGCAACGCCCTCGGCCGCCACGAG
TACCCCTTGCCTCGGAACGGGCCTCTCCCACAGGAGGGTGCCCAGAAGAG
GGGCACAGCCCCTCCCTACGTCGGAGTGCGGCCCTGCTCGGCCTCCCCCA
GCAGTGAGATGGTCACCTTGGAGGAGTTCCTGGAGGAGAGCAACCGCAGC
TCCCCCACCCATGACACTCCCAGTTGCCGGGATGACCTGCTGAGTGACTA
CTTCCGAAAGGCCAGCGATCCCCCAGCCATCGGAGGCCAACCAGGACCAC
CTGCCAAGAAAGAAGGGGCCAAGATGCCCACCAACTTTGTGGCCCCCACC
GTCAAAATGGCCGCCCCCACCTCGGAGGGGAGGCCGCTGAAGCCCGGGCA
GTACGTAAAGCCAAACTTCAGACTGACTGAGGCCGAGGCCCCACCCAGCG
TGGCCCCGAGACAGGCCCAGCCTCCCCAGAGCCTGTCTCTGGGCAGACCC
CGGCAGGCTCCGGTGCCCCCAGCTTCCCATGCACCTGCCAGCCGCAGTGC
CTCCTTGAGCCGGGCCTTCAGCCTGGCCTCAGCTGACCTTCTCCGGGCCA
GCGGGCCAGAGGCCTGCAAACAGGAGTCCCCTCAGAAGCTGGGGGCTCCT
GAGGCCTTAGGGGCAGAGAGACAGGCAGCCACACCCTGCAAAGCCCCGC
ACCCCCCAGCTCCCATAGCCTGGCCCGGGAGCGGACCCCACTTGTGGGAA
AGGCTGGCAGCTCCTGTCAGGGCCCAGGTCCCCGCAGCCGGCCGCTGGAC
ACGAGGCGCTTCTCCCTGGCTCCCCCAAAGGAGGAGAGGCTGGCCCCCCT
GCATCAGTCTGCCACAGCCCCGCCATTGCCACTGCAGGTGCTGGTGCTG
CTGCTGCTGGCAGTGGCAGCAACTCCCAGCTCCTGCACTTCTCACCTGCT
GCAGCCCCGGCTGCCAGGACCAAGCCCAAGGCGCCCCCACGCTCAGGGGA
GGTGGCCACCATCACCCCTGTCCGGGCAGGGCTCAGCCTCTCAGAGGGAG
ACGGGGTCCCGGGCAGGGCTGCAGTGAGGGGCTTCCGGCCAAGAGCCCA
GGTCGGTCTCCCGATTTGGCTCCCCACCTCGGCCGGGCCCTGGAGGACTG
CAGTCGAGGGAGCGTCTCAAAGAGCAGTCCGGCCTCCCCGGAGCCCGGCG
GGGATCCGCAGACCGTGTGGTATGAGTACGGCTGTGTGTGACTGTCTCGT
GGTTGAGCTCGCAAACCTGAAAACTACTGACGCGCCTTCCGACTCTCACG
```

```
GCCTTTTCTCTTGCTTGCCTGCGGTGCCAGGAGAGGGTTTGGAATGAGGA
AAGGGGTTCCCACGCATTTCTGCTGTTTGTTCTGTGAATGGAAACACTGT
GCCAAGCCCCAAGAGGATTACGCTTCCAGGTGTGTAACGTGTTTTCTGTG
TCTGCCGCTTCCAGCAGCTGATATCTTTGGAACAAATAATCCACGTCAGC
ATGGGGACCAATTAGGATGCAATGACAAACTGACTTCCCCCAAAGCAGAC
ACTACTCCAGTATGTCCCAGTAGAACACTCATTTGCAATGTGTTGAGCTC
CGTTAAGCACACACACACTCACACAACAGGCTTACGAGGCTCAGGCCTGG
CGGGTCAGAAAGCCCACTCCCTCTCCCAAGGCCACTGGATCCCAGGAGAA
GCCCAGACTGGCGATACTACAAAGGTCTCCAGGGCCTGGCAGACCCCAGA
GTCAGGCCTGCTGTTAAAAAGTGAGAGTGCTGCTGTTCCATTCCTGGGGT
CCCAAGCACTTCCCTTTACCCCAGGACCCAGGGCAGCCTGCAGGGCAGCT
GGCGGTGGCCTTGGCCATTTGCCCCCAGCCTCCAGCTGGCTCCTGAGCTC
TGCACCAGGGGTTTGGGGACCACACAGGCACCTGCCTTCCTAGATTTCC
CTGGCTCACTTTTCTGCAAACACTGGATCTGCCAGGCCTGGGGATTGGGG
GGCAGGAAAGAGGCCCCCATCCAGCCCCCTCCAGGCCAGTGTGCACAGTG
CACCGAGGGGTCATCCGCACAGAGCGAGGTGCAAGCTCGATGTGTAACCT
GGCTGCGGCACCCGACATCCCCGGTCTCGGGGTGTTGATTTATTTCTGAA
TAACTTTTTGGGTATAGAAACCAATTTTTTTTAATATATGACATGTATAT
GTACACACTCATGTGAAATATGTATACTTTGGGGGGATCTATTTATGTTC
CAGTGGGAGTCACTCTCTTCTGTCGGGAATCTTATCTGCTGCTTTGTGTC
TTTGGTCAGATTCCTGACAATTTAGTTTCCTGTTGTAAAGGTGCTTTTCC
TGGGGTGAACTAAACCTATTGATTTTTTTTTTTAAGATTTTTTTTTCCT
TTTGATTTAATATACTGAGAAAGAAATGGGAGACTTTTGAATGTTAACAA
GATCCATTTTAGGAGTGTTTGGGGTTGTGTATTAAATAGCCATTCATTCT
GGAACTCAAGGACAGGACTGTAATAAAATGGAATGGAACCGAAAAAAAAA
AAAAAAAAAAAAAAAAAAAAAA
```

Full length human DAPLE (DAPLE-fl) protein NP_001073883.2 (SEQ ID NO: 2):

```
MDVTVSELLELFLQSPLVTWVKTFGPFGSGSQDNLTMYMDLVDGIFLNQI
MLQIDPRPTNQRINKHVNNDVNLRIQNLTILVRNIKTYYQEVLQQLIVMN
LPNVLMIGRDPLSGKSMEEIKKVLLLVLGCAVQCERKEEFIERIKQLDIE
TQAGIVAHIQEVTHNQENVFDLQWLELPDVAPEELEALSRSMVLHLRRLI
DQRDECTELIVDLTQERDYLQAQHPPSPIKSSSADSTPSPTSSLSSEDKQ
HLAVELADTKARLRRVRQELEDKTEQLVDTRHEVDQLVLELQKVKQENIQ
LAADARSARAYRDELDSLREKANRVERLELELTRCKEKLHDVDFYKARME
ELREDNIILIETKAMLEEQLTAARARGDKVHELEKENLQLKSKLHDLELD
RDTDKKRIEELLEENMVLEIAQKQSMNESAHLGWELEQLSKNADLSDASR
KSFVFELNECASSRILKLEKENQSLQSTIQGLRDASLVLEESGLKCGELE
KENHQLSKKIEKLQTQLEREKQSNQDLETLSEELIREKEQLQSDMETLKA
DKARQIKDLEQEKDHLNRAMWSLRERSQVSSEARMKDVEKENKALHQTVT
EANGKLSQLEFEKRQLHRDLEQAKEKGERAEKLERELQRLQEENGRLARK
VTSLETATEKVEALEHESQGLQLENRTLRKSLDTLQNVSLQLEGLERDNK
QLDAENLELRRLVETMRFTSTKLAQMERENQQLEREKEELRKNVDLLKAL
GKKSERLELSYQSVSAENLRLQQSLESSSHKTQTLESELGELEAERQALR
RDLEALRLANAQLEGAEKDRKALEQEVAQLEKDKKLLEKEAKRLWQQVEL
KDAVLDDSTAKLSAVEKESRALDKELARCRDAAGKLKELEKDNRDLTKQV
TVHARTLTTLREDLVLEKLKSQQLSSELDKLSQELEKVGLNRELLLQEDD
SGSDTKYKILEGRNESALKTTLAMKEEKIVLLEAQMEEKASLNRQLESEL
QMLKKECETLRQNQGEGQHLQNSFKHPAGKTAASHQGKEAWGPGHKEATM
ELLRVKDRAIELERNNAALQAEKQLLKEQLQHLETQNVTFSSQILTLQKQ
SAFLQEHNTTLQTQTAKLQVENSTLSSQSAALTAQYTLLQNHHTAKETEN
ESLQRQQEQLTAAYEALLQDHEHLGTLHERQSAEYEALIRQHSCLKTLHR
NLELEHKELGERHGDMLKRKAELEEREKVLTTEREALQQEQRTNALAMGE
NQRLRGELDRVNFLHHQLKGEYEELHAHTKELKTSLNNAQLELNRWQARF
DELKEQHQTMDISLTKLDNHCELLSRLKGNLEEENHHLLSQIQLLSQQNQ
MLLEQNMENKEQYHEEQKQYIDKLNALRRHKEKLEEKIMDQYKFYDPPPK
KKNHWIGAKALVKLIKPKKEGSRERLKSTVDSPPWQLESSDPASPAASQP
LRSQAENPDTPALGSNCAEERDAHNGSVGKGPGDLKPKRGSPHRGSLDRT
DASTDLAMRSWPSELGSRTCSTSATTTAPSNSTPIARHPGRTKGYNSDDN
LCEPSLEFEVPNHRQYVSRPSSLESSRNTSSNSSPLNLKGSSEQLHGRSE
SFSSEDLIPSRDLATLPREASTPGRNALGRHEYPLPRNGPLPQEGAQKRG
TAPPYVGVRPCSASPSSEMVTLEEFLEESNRSSPTHDTPSCRDDLLSDYF
RKASDPPAIGGQPGPPAKKEGAKMPTNFVAPTVKMAAPTSEGRPLKPGQY
VKPNFRLTEAEAPPSVAPRQAQPPQSLSLGRPRQAPVPPASHAPASRSAS
LSRAFSLASADLLRASGPEACKQESPQKLGAPEALGGRETGSHTLQSPAP
PSSHSLARERTPLVGKAGSSCQGPGPRSRPLDTRRFSLAPPKEERLAPLH
QSATAPAIATAGAGAAAAGSGSNSQLLHFSPAAAPAARTKPKAPPRSGEV
ATITPVRAGLSLSEGDGVPGQGCSEGLPAKSPGRSPDLAPHLGRALEDCS
RGSVSKSSPASPEPGGDPQTVWYEYGCV
```

Short isoform V2 hDAPLE (SEQ ID NO: 23):

```
MSVLSPGDLKPKRGSPHRGSLDRTDASTDLAMRSWPSELGSRTCSTSATT
TAPSNSTPIARHPGRTKGYNSDDNLCEPSLEFEVPNHRQYVSRPSSLESS
RNTSSNSSPLNLKGSSEQLHGRSESFSSEDLIPSRDLATLPREASTPGRN
ALGRHEYPLPRNGPLPQEGAQKRGTAPPYVGVRPCSASPSSEMVTLEEFL
```

-continued

EESNRSSPTHDTPSCRDDLLSDYFRKASDPPAIGGQPGPPAKKEGAKMPT

NFVAPTVKMAAPTSEGRPLKPGQYVKPNFRLTEAEAPPSVAPRQAQPPQS

LSLGRPRQAPVPPASHAPASRSASLSRAFSLASADLLRASGPEACKQESP

QKLGAPEALGGRETGSHTLQSPAPPSSHSLARERTPLVGKAGSSCQGPGP

RSRPLDTRRFSLAPPKEERLAPLHQSATAPAIATAGAGAAAAGSGSNSQL

LHFSPAAAPAARTKPKAPPRSGEVATITPVRAGLSLSEGDGVPGQGCSEG

LPAKSPGRSPDLAPHLGRALEDCSRGSVSKSSPASPEPGGDPQTVWYEYG

CV

Short isoform V3 hDAPLE (DaPLE-V2' (SEQ ID NO: 24):

MSVLSPGDLKPKRGSPHRGSLDRTDASTDLAMRSWPSELGSRTCSTSATT

TAPSNSTPIARHPGRTKGYNSDDNLCEPSLEFEVPNHRQYVSRPSSLESS

RNTSSNSSPLNLKGSSEQLHGRSESFSSEDLIPSRDLATLPREASTPGRN

ALGRHEYPLPRNGPLPQEGAQKRGTAPPYVGVRPCSASPSSEMVTLEEFL

EESNRSSPTHDTPSCRDDLLSDYFRKASDPPAIGGQPGPPAKKEGAKMPT

NFVAPTVKMAAPTSEGRPLKPGQYVKPNFRLTEAEAPPSVAPRQAQPPQS

LSLGRPRQAPEALGGRETGSHTLQSPAPPSSHSLARERTPLVGKAGSSCQ

GPGPRSRPLDTRRFSLAPPKEERLAPLHQSATAPAIATAGAGAAAAGSGS

NSQLLHFSPAAAPAARTKPKAPPRSGEVATITPVRAGLSLSEGDGVPGQG

CSEGLPAKSPGRSPDLAPHLGRALEDCSRGSVSKSSPASPEPGGDPQTVW

YEYGCV

Targets for hDAPLE 3' UTR (Coding DNA Sequence is from by 155-6241):

SEQ ID NO: 3
6570    GTAGAACACTCATTTGCAA (shRNA 1)

SEQ ID NO: 4
6929    GCACCTGCCTTCCTAGATT (shRNA 2)

hDAPLEsh1 forward:

SEQ ID NO: 5
5'TGTAGAACACTCATTTGCAATTCAAGAGATTGCAAATGAGTGTTCTACTTTTTTC hDAPLEsh1 reverse:

SEQ ID NO: 6
5'TCGAGAAAAAAGTAGAACACTCATTTGCAATCTCTTGAATTGCAAATGAGTGTTCTACA hDAPLEsh2 forward:

SEQ ID NO: 7
5'TGCACCTGCCTTCCTAGATTTTCAAGAGAAATCTAGGAAGGCAGGTGCTTTTTTC hDAPLEsh2 reverse:

SEQ ID NO: 8
5'TCGAGAAAAAAGCACCTGCCTTCCTAGATTTCTCTTGAAAATCTAGGAAGGCAGGTGCA

Primer sequences for use in the invention are listed as follows:

| Gene | Forward | Reverse |
| --- | --- | --- |
| DAPLE-CC | 5'-TGA CAT GGA GAC CCT GAA GGC TGA-3' SEQ ID NO: 9 | 5'-TTTCATGCGGGCCTCACTGCTGA-3' SEQ ID NO: 10 |
| GAPDH | 5'-TCA GTT GTA GGC AAG CTG CGA CGT-3' SEQ ID NO: 11 | 5'-AAGCCAGAGGCTGGTACCTAGAAC-3 SEQ ID NO: 12 |
| LOXL3 | 5'-ATGGGTGCTATCCACCTGAG-3' SEQ ID NO: 13 | 5'-GAGTCGGATCCTGGTCTCTG-3' SEQ ID NO: 14 |
| Vim | 5'-AAGAGAACTTTGCCGTTGAA-3' SEQ ID NO: 15 | 5'-GTGATGCTGAGAAGTTTCGT-3' SEQ ID NO: 16 |
| SFPR-1 | 5'-GAGTTTGCACTGAGGATGAAAA-3' SEQ ID NO: 17 | 5'-GCTTCTTCTTCTTGGGGACA-3' SEQ ID NO: 18 |
| AXIN-2 | 5'-GAGTGGACTTGTGCCGACTTCA-3' SEQ ID NO: 19 | 5'-GGTGGCTGGTGCAAAGACATAG-3' SEQ ID NO: 20 |
| OPN | 5'-TTGCAGCCTTCTCAGCCAA-3' SEQ ID NO: 21 | 5'-GGAGGCAAAAGCAAATCACTG-3' SEQ ID NO: 22 | shDAPLE1 (preferentially targets DAPLE-fl) (SEQ ID NO: 25):

CAGTAGAACACTCATTTGCAA shDaple2 (preferentially targets DAPLE-fl) (SEQ ID NO: 26):

AGGCACCTGCCTTCCTAGATT

Minimal GBA motif. hDAPLE (aa 1664 to aa 1685 of hDAPLE) (SEQ ID NO: 27):

SPSSEMVTLEEFLEESNRSSPTHDTPSCRDDL

Minimal motif for Frizzled binding domain (aa 1881 to aa 2024 of hDAPLE) (SEQ ID NO: 28):

LDTRRFSLAPPKEERLAPLHQSATAPAIATAGAGAAAAGSGSNSQLLHFS
PAAAPAARTKPKAPPRSGEVATITPVRAGLSLSEGDGVPGQGCSEGLPAK
SPGRSPDLAPHLGRALEDCSRGSVSKSSPASPEPGGDPQTVWYE

Minimal PDZ-binding motif (PBM), hDAPLE (aa2025 to aa2028) (SEQ ID NO: 29): YGCV

LIST OF SEQUENCES

| SEQ ID NO | TYPE | SOURCE | SEQUENCE |
|---|---|---|---|
| 1 | DNA | Human | GCGGAACGTGGGCTCGCGCGCCCCGCCTTTGTCTC CCGGGCGCGAGCCGCCGCAGCCCCGCGCCCGCTGC TCGCTGCGGAGCCGTTTTGTGCCGCGGCGCGGGGG AACGGGGACGCGGGGCGGGGGGCGCGGAGCCGGC GGGCGCAGCCTCAGCATGGACGTGACAGTCTCGGA GCTCCTGGAGCTCTTCCTGCAGAGCCCGCTGGTGA CCTGGGTGAAAACTTTTGGCCCGTTTGGAAGCGGC AGCCAGGACAACCTGACTATGTACATGGATTTAGT GGACGGCATCTTTTTGAACCAAATTATGCTGCAAA TAGATCCCAGGCCCACAAATCAACGCATCAATAAG CACGTCAACAATGATGTGAACCTTCGCATTCAGAA TTTGACCATCTTGGTGAGAAACATTAAGACCTACT ACCAGGAAGTTCTCCAGCAGCTGATTGTAATGAAT TTGCCCAATGTTTTGATGATTGGCAGAGACCCACT GTCTGGGAAGAGCATGGAGGAAATCAAGAAGGTG CTGCTGCTGGTGCTGGGCTGTGCTGTCCAGTGTGA GAGGAAAGAGGAGTTCATTGAAAGAATCAAACAG CTGGACATTGAGACCCAGGCTGGCATCGTGGCCCA TATCCAGGAGGTGACTCACAACCAAGAGAACGTGT TTGACCTGCAGTGGCTGGAGCTGCCCGACGTGGCT CCGGAGGAGCTGGAGGCCCTGTCGAGGAGCATGGT GCTCCACCTGCGGAGGCTCATCGACCAGCGGGACG AGTGCACCGAGCTGATCGTGGACCTCACTCAGGAA CGGGACTACCTGCAGGCACAGCATCCACCCAGCCC CATCAAGTCCTCCAGCGCCGACTCCACTCCCAGCC CCACCAGCAGCCTCTCTAGCGAAGACAAGCAGCAC CTGGCCGTAGAGCTGGCCGACACCAAGGCCAGGCT GCGGCGCGTCAGGCAGGAGCTGGAGGATAAGACA GAGCAGCTTGTGGACACCAGACATGAGGTGGACCA GCTGGTGCTGGAACTGCAGAAAGTTAAGCAGGAG AACATCCAGCTAGCGGCAGACGCCCGGTCTGCTCG TGCCTATCGAGACGAGCTGGATTCCCTGCGGGAGA AGGCGAACCGCGTGGAGAGGCTGGAGCTGGAGCT GACCCGCTGCAAGGAGAAGCTGCACGACGTGGACT TCTACAAGGCCCGCATGGAGGAGCTGAGAGAAGA TAATATCATTTTAATTGAAACCAAGGCCATGCTGG AGGAACAGCTGACTGCTGCTCGGGCCCGGGGCGAT AAAGTCCATGAGCTGGAAAAGGAGAACCTGCAGC TGAAATCCAAGCTTCACGACCTGGAATTGGACCGG GACACAGATAAGAAACGAATTGAGGAGCTGCTGG AAGAAAACATGGTCCTTGAGATTGCACAGAAGCAG AGCATGAACGAATCTGCCCACCTTGGCTGGGAGCT GGAGCAGCTGTCCAAGAACGCAGACTTGTCAGACG CCTCCAGGAAGTCGTTTGTGTTTGAGCTGAACGAA TGTGCGTCCAGCCGCATCCTGAAGCTGGAGAAGGA GAATCAGAGCCTCCAGAGCACCATCCAGGGGCTGC GGGACGCGTCCCTGGTGTTGGAGGAGAGCGGCCTC AAGTGCGGGGAGCTGGAGAAGGAGAACCACCAGC TCAGCAAGAAGATTGAAAAGTTACAAACCCAGCTG GAGAGAGAAAAGCAGAGCAACCAAGATCTGGAGA CCCTCAGTGAGGAGCTGATCAGAGAGAAGGAGCA GCTGCAGAGTGACATGGAGACCCTGAAGGCTGACA AAGCCAGGCAGATCAAGGACCTTGAGCAGGAAAA GGACCACCTCAACCGAGCCATGTGGTCGCTGCGGG AGAGGTCGCAGGTCAGCAGTGAGGCCCGCATGAA AGACGTGGAGAAGGAGAACAAAGCCCTCCACCAG |

| SEQ ID NO | TYPE | SOURCE | SEQUENCE |
|---|---|---|---|
| | | | ACGGTGACGGAGGCCAATGGCAAGCTCAGCCAGTT |
| | | | GGAGTTTGAGAAGCGGCAGCTGCACAGGGACTTGG |
| | | | AGCAGGCCAAGGAGAAGGGGGAGCGGGCAGAGAA |
| | | | GCTGGAGAGGGAGCTACAGCGACTCCAGGAGGAG |
| | | | AACGGGAGGCTGGCCAGGAAGGTGACCTCCCTGG |
| | | | AGACAGCCACCGAGAAAGTCGAGGCCCTGGAGCA |
| | | | TGAGAGCCAGGGCCTGCAGCTGGAGAACCGGACTC |
| | | | TGAGGAAGTCTCTGGACACCTTGCAGAACGTGTCC |
| | | | CTGCAGCTTGAGGGCCTGGAGCGTGACAACAAGCA |
| | | | GCTGGACGCAGAGAACCTGGAGCTGCGCAGGCTG |
| | | | GTGGAGACCATGCGCTTCACCAGCACCAAGCTGGC |
| | | | ACAGATGGAGAGGGAGAACCAGCAGCTGGAGCGT |
| | | | GAGAAGGAGGAGCTGAGGAAGAACGTGGATCTGC |
| | | | TCAAGGCGCTGGGCAAGAAGTCAGAGCGCCTGGA |
| | | | GCTCAGCTACCAGAGCGTGAGCGCTGAGAACCTCC |
| | | | GGCTGCAGCAGAGCCTGGAGAGCAGCAGCCACAA |
| | | | GACGCAGACCTTGGAGAGTGAGCTGGGCGAGCTG |
| | | | GAGGCTGAGCGCCAGGCGCTGCGGCGGGACCTGG |
| | | | AGGCCCTCCGGCTGGCCAATGCACAGTTGGAGGGG |
| | | | GCCGAGAAGGACAGGAAGGCCCTGGAGCAGGAGG |
| | | | TGGCCCAGCTCGAGAAGGATAAGAAGCTGCTGGA |
| | | | GAAGGAGGCCAAGCGGCTGTGGCAGCAGGTGGAG |
| | | | CTCAAGGATGCAGTCTTGGACGATAGCACTGCCAA |
| | | | ACTGTCCGCCGTTGAGAAGGAGAGCCGCGCGCTGG |
| | | | ACAAGGAGCTGGCCCGCTGCAGGGACGCAGCCGG |
| | | | CAAGCTGAAGGAGCTGGAGAAGGACAACCGGGAC |
| | | | CTCACCAAGCAAGTCACCGTGCATGCAAGGACACT |
| | | | GACAACTCTGAGGGAGGACCTGGTGCTCGAGAAGC |
| | | | TGAAGAGCCAGCAGCTCAGCAGTGAGCTGGACAA |
| | | | GCTGAGCCAGGAACTGGAGAAGGTCGGCCTCAAC |
| | | | AGGGAGCTGCTGTTGCAGGAGGACGACAGCGGCA |
| | | | GTGACACAAAATACAAGATTTTGGAGGGCAGAAAT |
| | | | GAATCAGCATTAAAAACAACACTAGCCATGAAAG |
| | | | AAGAAAAGATTGTGCTCTTAGAAGCACAGATGGAA |
| | | | GAGAAAGCGAGCCTAAATCGCCAGTTAGAGAGTG |
| | | | AGCTGCAGATGCTAAAGAAGGAGTGTGAGACCCTC |
| | | | AGGCAGAACCAGGGAGAGGGGCAGCACTTGCAGA |
| | | | ACTCTTTCAAGCACCCTGCGGGGAAGACAGCCGCC |
| | | | AGTCACCAGGGGAAGGAGGCCTGGGGGCCCGGCC |
| | | | ATAAGGAAGCCACCATGGAGCTTCTCCGAGTGAAG |
| | | | GACCGGGCCATCGAGCTGGAGCGGAATAATGCAG |
| | | | CTCTGCAGGCTGAGAAGCAGCTGCTAAAGGAACAG |
| | | | CTGCAGCACCTGGAGACCCAGAACGTGACCTTCAG |
| | | | CAGCCAGATCTTGACACTGCAGAAACAGAGCGCCT |
| | | | TCCTGCAGGAGCACAACACCACACTGCAGACCCAG |
| | | | ACCGCCAAGCTGCAGGTGGAGAACTCCACGCTGAG |
| | | | TTCCCAGAGCGCAGCGCTCACCGCGCAGTACACGC |
| | | | TGCTGCAGAACCACCACACGGCCAAGGAGACGGA |
| | | | GAACGAAAGCCTGCAGAGGCAGCAGGAGCAACTT |
| | | | ACAGCGGCCTACGAGGCCCTGCTGCAGGACCACGA |
| | | | GCACCTGGGCACGCTGCACGAGCGGCAATCGGCCG |
| | | | AGTACGAGGCCCTCATCCGCCAGCACAGCTGCCTA |
| | | | AAGACACTGCATCGGAATCTGGAGCTGGAGCACAA |
| | | | GGAGCTCGGGGAGAGGCACGGTGACATGCTGAAG |
| | | | CGCAAGGCGGAGCTGGAGGAGCGGGAGAAGGTCT |
| | | | TGACCACTGAGCGAGAGGCGCTGCAGCAGGAGCA |
| | | | GAGGACAAACGCCCTCGCCATGGGCGAGAACCAG |
| | | | AGGCTGCGGGCGAGCTGGACAGGGTCAATTTCCT |
| | | | GCACCACCAGCTGAAGGGGGAGTACGAGGAGCTG |
| | | | CACGCCCACACCAAGGAGCTGAAAACCTCACTGAA |
| | | | CAACGCGCAGCTGGAGCTCAACCGCTGGCAGGCCC |
| | | | GCTTCGACGAGCTGAAGGAGCAGCACCAGACCATG |
| | | | GACATCTCGCTGACCAAGCTGGACAACCACTGTGA |
| | | | GCTGCTCTCCCGTCTCAAGGGGAACTTGGAGGAAG |
| | | | AAAATCATCACCTCCTGAGCCAGATCCAGCTGTTG |
| | | | AGCCAGCAGAACCAGATGCTTCTGGAGCAGAACAT |
| | | | GGAGAACAAGGAGCAGTACCATGAGGAGCAGAAG |
| | | | CAGTACATAGACAAATTAAATGCCTTACGAAGACA |
| | | | TAAGGAAAAGCTGGAAGAAAAAATCATGGATCAA |
| | | | TACAAGTTCTATGATCCTCCTCCAAAGAAGAAGAA |
| | | | CCACTGGATTGGAGCCAAAGCCTTAGTCAAACTCA |
| | | | TCAAACCAAAGAAAGAGGGTTCGAGGGAACGCTT |
| | | | AAAATCCACCGTGGACAGCCCTCCCTGGCAGCTGG |
| | | | AGTCCTCAGACCCCGCCTCGCCGGCGGCCTCTCAG |
| | | | CCGCTCAGATCACAGGCCGAGAACCCCGACACCCC |
| | | | CGCACTGGGCTCCAACTGTGCAGAAGAGCGCGACG |

| SEQ ID NO | TYPE | SOURCE | SEQUENCE |
|---|---|---|---|
| | | | CCCACAACGGGTCTGTGGGGAAAGGCCCTGGGGAT
CTAAAACCAAAGCGAGGCTCCCCACACAGAGGCA
GCCTTGACCGCACAGATGCCTCCACCGATCTGGCC
ATGAGGTCCTGGCCCTCGGAGCTGGGCTCCCGGAC
TTGCTCAACTTCAGCCACCACTACAGCCCCTTCCAA
CTCCACCCCCATCGCCCGGCACCCAGGCCGCACCA
AAGGCTATAACTCAGATGACAACCTCTGTGAGCCA
TCCCTGGAGTTTGAGGTCCCCAACCACAGGCAGTA
CGTGTCGCGGCCAAGTAGCTTAGAGAGCAGTAGAA
ACACATCCAGCAACAGCTCACCTCTTAACCTAAAA
GGCTCCTCCGAGCAGCTCCATGGCCGGTCTGAGAG
CTTCAGCAGCGAAGACCTGATCCCCAGCAGGGACC
TGGCCACTTTGCCCCGGGAAGCCAGCACACCGGGA
CGCAACGCCCTCGGCCGCCACGAGTACCCCTTGCC
TCGGAACGGGCCTCTCCCACAGGAGGGTGCCCAGA
AGAGGGGCACAGCCCTCCCTACGTCGGAGTGCGG
CCCTGCTCGGCCTCCCCCAGCAGTGAGATGGTCAC
CTTGGAGGAGTTCCTGGAGGAGAGCAACCGCAGCT
CCCCCACCCATGACACTCCCAGTTGCCGGGATGAC
CTGCTGAGTGACTACTTCCGAAAGGCCAGCGATCC
CCCAGCCATCGGAGGCCAACCAGGACCACCTGCCA
AGAAAGAAGGGGCCAAGATGCCCACCAACTTTGTG
GCCCCCACCGTCAAAATGGCCGCCCCCACCTCGGA
GGGGAGGCCGCTGAAGCCCGGGCAGTACGTAAAG
CCAAACTTCAGACTGACTGAGGCCGAGGCCCCACC
CAGCGTGGCCCCGAGACAGGCCCAGCCTCCCCAGA
GCCTGTCTCTGGGCAGACCCCGGCAGGCTCCGGTG
CCCCCAGCTTCCCATGCACCTGCCAGCCGCAGTGC
CTCCTTGAGCCGGGCCTTCAGCCTGGCCTCAGCTG
ACCTTCTCCGGGCCAGCGGGCCAGAGGCCTGCAAA
CAGGAGTCCCCTCAGAAGCTGGGGGCTCCTGAGGC
CTTAGGGGGCAGAGAGACAGGCAGCCACACCCTG
CAAAGCCCCGCACCCCCAGCTCCATAGCCTGGC
CCGGGAGCGGACCCCACTTGTGGGAAAGGCTGGCA
GCTCCTGTCAGGGCCCAGGTCCCCGCAGCCGGCCG
CTGGACACGAGGCGCTTCTCCCTGGCTCCCCCAAA
GGAGGAGAGGCTGGCCCCCCTGCATCAGTCTGCCA
CAGCCCCCGCCATTGCCACTGCAGGTGCTGGTGCT
GCTGCTGCTGGCAGTGGCAGCAACTCCCAGCTCCT
GCACTTCTCACCTGCTGCAGCCCCGGCTGCCAGGA
CCAAGCCCAAGGCGCCCCCACGCTCAGGGGAGGTG
GCCACCATCACCCCTGTCCGGGCAGGGCTCAGCCT
CTCAGAGGGAGACGGGGTCCCGGGGCAGGGCTGC
AGTGAGGGGCTTCCGGCCAAGAGCCCAGGTCGGTC
TCCCGATTTGGCTCCCCACCTCGGCCGGGCCCTGG
AGGACTGCAGTCGAGGGAGCGTCTCAAAGAGCAG
TCCGGCCTCCCCGGAGCCCGGCGGGATCCGCAGA
CCGTGTGGTATGAGTACGGCTGTGTGTGACTGTCTC
GTGGTTGAGCTCGCAAACCTGAAAACTACTGACGC
GCCTTCCGACTCTCACGGCCTTTTCTCTTGCTTGCC
TGCGGTGCCAGGAGAGGGTTTGGAATGAGGAAAG
GGGTTCCCACGCATTTCTGCTGTTTGTTCTGTGAAT
GGAAACACTGTGCCAAGCCCCAAGAGGATTACGCT
TCCAGGTGTGTAACGTGTTTTCTGTGTCTGCCGCTT
CCAGCAGCTGATATCTTTGGAACAAATAATCCACG
TCAGCATGGGGACCAATTAGGATGCAATGACAAAC
TGACTTCCCCCAAAGCAGACACTACTCCAGTATGT
CCCAGTAGAACACTCATTTGCAATGTGTTGAGCTC
CGTTAAGCACACACACACTCACACAACAGGCTTAC
GAGGCTCAGGCCTGGCGGGTCAGAAAGCCCACTCC
CTCTCCCAAGGCCACTGGATCCCAGGAGAAGCCCA
GACTGGCGATACTACAAAGGTCTCCAGGGCCTGGC
AGACCCCAGAGTCAGGCCTGCTGTTAAAAAGTGAG
AGTGCTGCTGTTCCATTCCTGGGGTCCCAAGCACTT
CCCTTTACCCCAGGACCCAGGGCAGCCTGCAGGGC
AGCTGGCGGTGGCCTTGGCCATTTGCCCCCAGCCT
CCAGCTGGCTCCTGAGCTCTGCACCAGGGGGTTTG
GGGACCACACAGGCACCTGCCTTCCTAGATTTCCC
TGGCTCACTTTTCTGCAAACACTGGATCTGCCAGGC
CTGGGGATTGGGGGCAGGAAAGAGGCCCCCATC
CAGCCCCCTCCAGGCCAGTGTGCACAGTGCACCGA
GGGGTCATCCGCACAGAGCGAGGTGCAAGCTCGAT
GTGTAACCTGGCTGCGGCACCCGACATCCCCGGTC
TCGGGGTGTTGATTTATTTCTGAATAACTTTTTGGG
TATAGAAACCAATTTTTTTTAATATATGACATGTAT
ATGTACACACTCATGTGAAATATGTATACTTTGGG |

| SEQ ID NO | TYPE | SOURCE | SEQUENCE |
|---|---|---|---|
| | | | GGGATCTATTTATGTTCCAGTGGGAGTCACTCTCTT<br>CTGTCGGGAATCTTATCTGCTGCTTTGTGTCTTTGG<br>TCAGATTCCTGACAATTTAGTTTCCTGTTGTAAAGG<br>TGCTTTTCCTGGGGTGAACTAAACCTATTGATTTTT<br>TTTTTTTAAGATTTTTTTTTCCTTTTGATTTAATATA<br>CTGAGAAAGAAATGGGAGACTTTTGAATGTTAACA<br>AGATCCATTTTAGGAGTGTTTGGGGTTGTGTATTAA<br>ATAGCCATTCATTCTGGAACTCAAGGACAGGACTG<br>TAATAAAATGGAATGGAACCGAAAAAAAAAAAAA<br>AAAAAAAAAAAAAAAAAA |
| 2 | Protein | Human | MDVTVSELLELFLQSPLVTWVKTFGPFGSGSQDNLT<br>MYMDLVDGIFLNQIMLQIDPRPTNQRINKHVNNDVN<br>LRIQNLTILVRNIKTYYQEVLQQLIVMNLPNVLMIGR<br>DPLSGKSMEEIKKVLLLVLGCAVQCERKEEFIERIKQL<br>DIETQAGIVAHIQEVTHNQENVFDLQWLELPDVAPEE<br>LEALSRSMVLHLRRLIDQRDECTELIVDLTQERDYLQ<br>AQHPPSPIKSSSADSTPSPTSSLSSEDKQHLAVELADT<br>KARLRRVRQELEDKTEQLVDTRHEVDQLVLELQKVK<br>QENIQLAADARSARAYRDELDSLREKANRVERLELE<br>LTRCKEKLHDVDFYKARMEELREDNIILIETKAMLEE<br>QLTAARARGDKVHELEKENLQLKSKLHDLELDRDTD<br>KKRIEELLEENMVLEIAQKQSMNESAHLGWELEQLS<br>KNADLSDASRKSFVFELNECASSRILKLEKENQSLQST<br>IQGLRDASLVLEESGLKCGELEKENHQLSKKIEKLQT<br>QLEREKQSNQDLETLSEELIREKEQLQSDMETLKADK<br>ARQIKDLEQEKDHLNRAMWSLRERSQVSSEARMKD<br>VEKENKALHQTVTEANGKLSQLEFEKRQLHRDLEQA<br>KEKGERAEKLERELQRLQEENGRLARKVTSLETATE<br>KVEALEHESQGLQLENRTLRKSLDTLQNVSLQLEGLE<br>RDNKQLDAENLELRRLVETMRFTSTKLAQMERENQQ<br>LEREKEELRKNVDLLKALGKKSERLELSYQSVSAENL<br>RLQQSLESSSHKTQTLESELGELEAERQALRRDLEAL<br>RLANAQLEGAEKDRKALEQEVAQLEKDKKLLEKEA<br>KRLWQQVELKDAVLDDSTAKLSAVEKESRALDKEL<br>ARCRDAAGKLKELEKDNRDLTKQVTVHARTLTTLRE<br>DLVLEKLKSQQLSSELDKLSQELEKVGLNRELLLQED<br>DSGSDTKYKILEGRNESALKTTLAMKEEKIVLLEAQM<br>EEKASLNRQLESELQMLKKECETLRQNQGEGQHLQN<br>SFKHPAGKTAASHQGKEAWGPGHKEATMELLRVKD<br>RAIELERNNAALQAEKQLLKEQLQHLETQNVTFSSQI<br>LTLQKQSAFLQEHNTTLQTQTAKLQVENSTLSSQSAA<br>LTAQYTLLQNHHTAKETENESLQRQQEQLTAAYEAL<br>LQDHEHLGTLHERQSAEYEALIRQHSCLKTLHRNLEL<br>EHKELGERHGDMLKRKAELEEREKVLTTEREALQQE<br>QRTNALAMGENQRLRGELDRVNFLHHQLKGEYEEL<br>HAHTKELKTSLNNAQLELNRWQARFDELKEQHQTM<br>DISLTKLDNHCELLSRLKGNLEEENHHLLSQIQLLSQQ<br>NQMLLEQNMENKEQYHEEQKQYIDKLNALRRHKEK<br>LEEKIMDQYKFYDPPPKKKNHWIGAKALVKLIKPKK<br>EGSRERLKSTVDSPPWQLESSDPASPAASQPLRSQAE<br>NPDTPALGSNCAEERDAHNGSVGKGPGDLKPKRGSP<br>HRGSLDRTDASTDLAMRSWPSELGSRTCSTSATTTAP<br>SNSTPIARHPGRTKGYNSDDNLCEPSLEFEVPNHRQY<br>VSRPSSLESSRNTSSNSSPLNLKGSSEQLHGRSESFSSE<br>DLIPSRDLATLPREASTPGRNALGRHEYPLPRNGPLPQ<br>EGAQKRGTAPPYVGVRPCSASPSSEMVTLEEFLEESN<br>RSSPTHDTPSCRDDLLSDYFRKASDPPAIGGQPGPPAK<br>KEGAKMPTNFVAPTVKMAAPTSEGRPLKPGQYVKPN<br>FRLTEAEAPPSVAPRQAQPPQSLSLGRPRQAPVPPASH<br>APASRSASLSRAFSLASADLLRASGPEACKQESPQKL<br>GAPEALGGRETGSHTLQSPAPPSSHSLARERTPLVGK<br>AGSSCQGPGPRSRPLDTRRFSLAPPKEERLAPLHQSAT<br>APAIATAGAGAAAAGSGSNSQLLHFSPAAAPAARTK<br>PKAPPRSGEVATITPVRAGLSLSEGDGVPGQGCSEGL<br>PAKSPGRSPDLAPHLGRALEDCSRGSVSKSSPASPEPG<br>GDPQTVWYEYGCV |
| 3 | DNA | Human | GTAGAACACTCATTTGCAA |
| 4 | DNA | Human | GCACCTGCCTTCCTAGATT |
| 5 | DNA | Synthetic | 5'TGTAGAACACTCATTTGCAATTCAAGAGATTGCA<br>AATGAGTGTTCTACTTTTTTC |

| SEQ ID NO | TYPE | SOURCE | SEQUENCE |
|---|---|---|---|
| 6 | DNA | Synthetic | 5'TCGAGAAAAAAGTAGAACACTCATTTGCAATCTC TTGAATTGCAAATGAGTGTTCTACA |
| 7 | DNA | Synthetic | 5'TGCACCTGCCTTCCTAGATTTTCAAGAGAAATCT AGGAAGGCAGGTGCTTTTTTC |
| 8 | DNA | Synthetic | 5'TCGAGAAAAAAGCACCTGCCTTCCTAGATTTCTC TTGAAAATCTAGGAAGGCAGGTGCA |
| 9 | DNA | Synthetic | 5'-TGACATGGAGACCCTGAAGGCTGA-3' |
| 10 | DNA | Synthetic | 5'-TTTCATGCGGGCCTCACTGCTGA-3' |
| 11 | DNA | Synthetic | 5'-TCAGTTGTAGGCAAGCTGCGACGT-3' |
| 12 | DNA | Synthetic | 5'-AAGCCAGAGGCTGGTACCTAGAAC-3 |
| 13 | DNA | Synthetic | 5'-ATGGGTGCTATCCACCTGAG-3' |
| 14 | DNA | Synthetic | 5'-GAGTCGGATCCTGGTCTCTG-3' |
| 15 | DNA | Synthetic | 5'-AAGAGAACTTTGCCGTTGAA-3' |
| 16 | DNA | Synthetic | 5'-GTGATGCTGAGAAGTTTCGT-3' |
| 17 | DNA | Synthetic | 5'-GAGTTTGCACTGAGGATGAAAA-3' |
| 18 | DNA | Synthetic | 5'-GCTTCTTCTTCTTGGGGACA-3' |
| 19 | DNA | Synthetic | 5'-GAGTGGACTTGTGCCGACTTCA-3' |
| 20 | DNA | Synthetic | 5'-GGTGGCTGGTGCAAAGACATAG-3' |
| 21 | DNA | Synthetic | 5'-TTGCAGCCTTCTCAGCCAA-3' |
| 22 | DNA | Synthetic | 5'-GGAGGCAAAAGCAAATCACTG-3' |
| 23 | Protein | Human | MSVLSPGDLKPKRGSPHRGSLDRTDASTDLAMRSWP SELGSRTCSTSATTTAPSNSTPIARHPGRTKGYNSDDN LCEPSLEFEVPNHRQYVSRPSSLESSRNTSSNSSPLNL KGSSEQLHGRSESFSSEDLIPSRDLATLPREASTPGRN ALGRHEYPLPRNGPLPQEGAQKRGTAPPYVGVRPCS ASPSSEMVTLEEFLEESNRSSPTHDTPSCRDDLLSDYF RKASDPPAIGGQPGPPAKKEGAKMPTNFVAPTVKMA APTSEGRPLKPGQYVKPNFRLTEAEAPPSVAPRQAQP PQSLSLGRPRQAPVPPASHAPASRSASLSRAFSLASAD LLRASGPEACKQESPQKLGAPEALGGRETGSHTLQSP APPSSHSLARERTPLVGKAGSSCQGPGPRSRPLDTRRF SLAPPKEERLAPLHQSATAPAIATAGAGAAAAGSGSN SQLLHFSPAAAPAARTKPKAPPRSGEVATITPVRAGLS LSEGDGVPGQGCSEGLPAKSPGRSPDLAPHLGRALED CSRGSVSKSSPASPEPGGDPQTVWYEYGCV |
| 24 | Protein | Human | MSVLSPGDLKPKRGSPHRGSLDRTDASTDLAMRSWP SELGSRTCSTSATTTAPSNSTPIARHPGRTKGYNSDDN LCEPSLEFEVPNHRQYVSRPSSLESSRNTSSNSSPLNL KGSSEQLHGRSESFSSEDLIPSRDLATLPREASTPGRN ALGRHEYPLPRNGPLPQEGAQKRGTAPPYVGVRPCS ASPSSEMVTLEEFLEESNRSSPTHDTPSCRDDLLSDYF RKASDPPAIGGQPGPPAKKEGAKMPTNFVAPTVKMA APTSEGRPLKPGQYVKPNFRLTEAEAPPSVAPRQAQP PQSLSLGRPRQAPEALGGRETGSHTLQSPAPPSSHSLA RERTPLVGKAGSSCQGPGPRSRPLDTRRFSLAPPKEER LAPLHQSATAPAIATAGAGAAAAGSGSNSQLLHFSPA AAPAARTKPKAPPRSGEVATITPVRAGLSLSEGDGVP GQGCSEGLPAKSPGRSPDLAPHLGRALEDCSRGSVSK SSPASPEPGGDPQTVWYEYGCV |
| 25 | DNA | Synthetic | CAGTAGAACACTCATTTGCAA |
| 26 | DNA | Synthetic | AGGCACCTGCCTTCCTAGATT |
| 27 | Protein | Human | SPSSEMVTLEEFLEESNRSSPTHDTPSCRDDL |

| SEQ ID NO | TYPE | SOURCE | SEQUENCE |
|---|---|---|---|
| 28 | Protein | Human | LDTRRFSLAPPKEERLAPLHQSATAPAIATAGAGAAA AGSGSNSQLLHFSPAAAPAARTKPKAPPRSGEVATITP VRAGLSLSEGDGVPGQGCSEGLPAKSPGRSPDLAPHL GRALEDCSRGSVSKSSPASPEPGGDPQTVWYE |
| 29 | Protein | Human | YGCV |
| 30 | Protein | Human | RHHKIKTGSPGSEVVTLQQFLEESNKLTSVQIK |
| 31 | Protein | Mouse | RAHHKMKAGSPGSEVVTLQQFLEESNKLTSIQLK |
| 32 | Protein | Rat | QAHHKMNAGSPGSEVVTLQQFLEESNKLTSIQLK |
| 33 | Protein | Chicken | CGRQIKTDSPGSEVVTLQQFLEESNKSTSSEMK |
| 34 | Protein | Anole | QGTRRIKTDSPGSEVVTLQQFLEESNTVTSTEIK |
| 35 | Protein | African clawed frog | SLQSKLMPGSPGSEMVSLKQFLEESNKLTVSQIRS |
| 36 | Protein | Zebrafish | STGSDVVSLQQFLEENTHTAEDPPSAP |
| 37 | Protein | Human | PPYVGVRPCSASPSSEMVTLEEFLEESNRSSPTHD |
| 38 | Protein | Mouse | STHTGVRPHSASPSSEMVTLEEFLEESNRGGSPTHDT |
| 39 | Protein | Rat | SAHTGVRPHSASPSSEMVTLEEFLEESNRGSPTH |
| 40 | Protein | Chicken | QSYVGRQRSASPGSEMVTLEEFLEESNRLSPPSDT |
| 41 | Protein | Anole | QARSVRHRPASPGSEMVTLEEFLEESNKLSPANET |
| 42 | Protein | African clawed frog | SLNDSELITLHQFLLEAETLNPSSQSPS |
| 43 | Protein | Zebrafish | QRPASRRPSSPGSEMVTLEEFLQESNALSPPTVQT |
| 44 | Protein | Human | EMVTLEEFLEESNRSS |
| 45 | Protein | Human | EVVTLQQFLEESNKLT |
| 46 | Protein | Rat | RLVTLEEFLASTQRKE |
| 47 | Protein | Rat | RLVTLEEFLRATEKKE |
| 48 | Protein | Synthetic | SRVTWYDFLMEDTKSR |
| 49 | Protein | Synthetic | KRLTVWEFLALPSST |

What is claimed is:

1. A method for inhibiting growth, self-renewal, and/or metastatic behavior of a cancer cell comprising selectively inhibiting expression or function of the full-length isoform of DAPLE (DAPLE-fl) in said cancer cell by administering to the cell an effective amount of a shRNA comprising a nucleic acid sequence CAGTAGAACACTCATTTGCAA (SEQ ID NO: 25) or AGGCACCTGCCTTCCTAGATT (SEQ ID NO: 26).

2. The method of claim 1, wherein the cancer cell is a circulating tumor cell (CTC).

3. The method of claim 1, wherein the cancer cell is a cancer initiating stem cell (CISC).

4. The method of claim 1, wherein the cancer cell is a metastatic cancer cell.

5. The method of any one of claims 1-4, wherein the cancer cell is characterized by Wnt signaling disturbances.

6. A method for treating a cancer in a subject in need thereof, said method comprising administering to said patient an effective amount of a selective inhibitor of expression or function of the full-length isoform of DAPLE (DAPLE-fl) in cancer cells of said subject, wherein the inhibitor is a shRNA comprising a nucleic acid sequence CAGTAGAACACTCATTTGCAA (SEQ ID NO: 25) or AGGCACCTGCCTTCCTAGATT (SEQ ID NO: 26).

7. The method of claim 6, wherein the cancer is a metastatic cancer.

8. A method for inhibiting and/or preventing cancer metastasis and/or recurrence in a subject in need thereof, comprising administering to said patient an effective amount of a selective inhibitor of expression or function of the full-length isoform of DAPLE (DAPLE-fl) in cancer cells of said subject, wherein the inhibitor is a shRNA comprising a nucleic acid CAGTAGAACACTCATTTGCAA (SEQ ID NO: 25) or AGGCACCTGCCTTCCTAGATT (SEQ ID NO: 26).

9. The method of any one of claims 6-8, wherein expression or function of DAPLE-fl is inhibited in circulating tumor cells (CTCs).

10. The method of any one of claims 6-8, wherein expression or function of DAPLE-fl is inhibited in cancer initiating stem cell (CISC).

11. The method of any one of claims 1-4 and 6-8, wherein the cancer is characterized by Wnt signaling disturbances.

12. The method of any one of claims 1-4 and 6-8, wherein the cancer is leukemia.

13. The method of any one of claims 1-4 and 6-8, wherein the cancer is selected from the group consisting of gastric cancer, small bowel cancer, colon cancer, and colorectal cancer.

14. The method of any one of claims 1-4 and 6-8, wherein the subject is human.

15. A pharmaceutical composition comprising a selective inhibitor of expression or a function of the full-length isoform of DAPLE (DAPLE-fl) in a cancer cell, wherein said inhibitor does not inhibit expression or a function of the short isoform of DAPLE (DAPLE-V2), wherein said inhibitor is a shRNA and wherein said shRNA comprises a nucleic acid sequence CAGTAGAACACTCATTTGCAA (SEQ ID NO:25) or AGGCACCTGCCTTCCTAGATT (SEQ ID NO:26); and
a pharmaceutically acceptable carrier and/or excipient.

* * * * *